(12) United States Patent
Mortensen et al.

(10) Patent No.: US 8,383,634 B2
(45) Date of Patent: Feb. 26, 2013

(54) METHODS OF TREATMENT USING HETEROARYL COMPOUNDS AND COMPOSITIONS THEREOF

(75) Inventors: Deborah Sue Mortensen, San Diego, CA (US); Maria Mercedes Delgado Mederos, San Diego, CA (US); John Joseph Sapienza, Chula Vista, CA (US); Ronald J. Albers, San Diego, CA (US); Steven Spencer Clareen, San Diego, CA (US); Kimberly Lyn Schwarz, San Diego, CA (US); Jason Simon Parnes, San Diego, CA (US); Jennifer R. Riggs, Cardiff, CA (US); Patrick William Papa, Carlsbad, CA (US); Sayee Gajanan Hegde, San Diego, CA (US); Jeffrey Mark McKenna, Horsham (GB)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/113,135

(22) Filed: May 23, 2011

(65) Prior Publication Data

US 2011/0224217 A1    Sep. 15, 2011

Related U.S. Application Data

(62) Division of application No. 11/975,657, filed on Oct. 18, 2007, now Pat. No. 7,968,556.

(60) Provisional application No. 60/853,135, filed on Oct. 19, 2006.

(51) Int. Cl.
| | | |
|---|---|---|
| A61P 11/06 | (2006.01) | |
| A61P 3/10 | (2006.01) | |
| A61P 31/04 | (2006.01) | |
| C07D 473/28 | (2006.01) | |
| C07D 473/18 | (2006.01) | |
| C07D 519/00 | (2006.01) | |
| C07D 487/04 | (2006.01) | |
| A61K 31/522 | (2006.01) | |

(52) U.S. Cl. ............. 514/263.2; 514/263.22; 514/263.3; 514/263.23

(58) Field of Classification Search ............... 514/263.3, 514/263.22, 263.2, 263.23; 544/264, 268, 544/269, 270, 276
See application file for complete search history.

(56) References Cited

U.S. PATENT DOCUMENTS

| | | | | |
|---|---|---|---|---|
| 2,852,506 | A | * | 9/1958 | Goldman et al. ........... 536/27.23 |
| 3,325,495 | A | * | 6/1967 | Alburn et al. ................ 544/277 |
| 5,424,311 | A | | 6/1995 | Billhardt-Troughton et al. |
| 2004/0023921 | A1 | | 2/2004 | Hong et al. |
| 2004/0063658 | A1 | | 4/2004 | Roberts et al. |
| 2004/0097485 | A1 | | 5/2004 | Burkitt et al. |
| 2005/0009737 | A1 | | 1/2005 | Clark |
| 2008/0214580 | A1 | | 9/2008 | Neagu et al. |
| 2009/0069289 | A1 | | 3/2009 | Neagu et al. |
| 2009/0163545 | A1 | | 6/2009 | Goldfarb |
| 2009/0281075 | A1 | | 11/2009 | Roughton et al. |
| 2010/0144738 | A1 | | 6/2010 | Bornmann |
| 2010/0249122 | A1 | | 9/2010 | Kalman |

FOREIGN PATENT DOCUMENTS

| | | |
|---|---|---|
| JP | 2002100363 | 4/2002 |
| WO | WO 02/076954 | 10/2002 |
| WO | WO 03/093290 | 11/2003 |
| WO | WO 2005/003147 | 1/2005 |
| WO | WO 2006/050076 | 5/2006 |
| WO | WO 2006/087530 A1 | 8/2006 |
| WO | WO 2007/114848 | 10/2007 |
| WO | WO 2008/030744 | 3/2008 |

OTHER PUBLICATIONS

Booth, et al., 1994, "Synthesis of 4- and 5-Disubstituted 1-Benzylimidazoles, Important Precursors of Purine Analogs," J. of Heterocyclic of Chemistry, vol. 31(2):345-50.
Booth et al., 2001, "The Reactions of Diaminomaleonitrile with Isocyanates and Either Aldehydes or Ketones Revisited," J. Org Chem, vol. 66:8436-8441.
Booth et al., 1995, "Synthesis of [1α, 2β, 3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Cohen, P. 2001, "The role of protein phosphorylation in human health and disease," Eur. J. Biochem,vol. 268:5001-5010.
Cohen, P. 2002, "Protein kinases—the major drug targets of the twenty-first century?" Nature Reviews-Drug Discovery, vol. 1:309-315.
Coish, et al., 2006, "Small molecule inhibitors of IKK kinase activity," Expert Opin. Ther. Patents, vol. 16(1):1-12.

(Continued)

*Primary Examiner* — Mark Berch
(74) *Attorney, Agent, or Firm* — Jones Day

(57) ABSTRACT

Provided herein are Heteroaryl Compounds having the following structure:

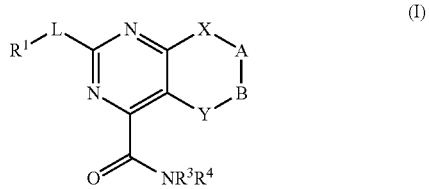

(I)

wherein $R^1$, $R^3$, $R^4$, L, X, Y, A and B are as defined herein, compositions comprising an effective amount of a Heteroaryl Compound and methods for treating or preventing cancer, inflammatory conditions, immunological conditions, metabolic conditions and conditions treatable or preventable by inhibition of a kinase pathway comprising administering an effective amount of a Heteroaryl Compound to a patient in need thereof.

4 Claims, No Drawings

OTHER PUBLICATIONS

Dang et al., 1999, "Efficient synthesis of purines and purine nucelosides via an inverse electron demand diels—alder reaction," J. Am Chem Soc., vol. 121(24):5833-5834.

Fabbro et al., 2002, "Protein kinasesas targets for anticancer agents: from inhibitors to useful drugs," Pharm & Therapeutics, vol. 93:79-98.

Farhadi et al., 2006, "The role of protein kinase C isoforms in modulatinginjuty and repairof the intestinal barrier," J. Pharm Exp. Ther., vol. 316(1):1-7.

Georgakis and Younes, 2006, "From rapi nui to rapamycin: targeting PI3K/Akt/mTOR for cancer therapy," Expert Rev. Anticancer Ther., vol. 6(1):131-140.

Irie et al., 2005, "Toward the development of new medicinal leads with selectivity for protein kinase C isozymes," The Chemical Record, vol. 5:185-195.

Hamad, 2001, "" Journal of Heterocyclic Chemistry, vol. 38(4):939-944.

Park et al., 2000, "A novel mechanism of TRAF signaling revealed by structural and functionalanalyses of the TRADD-TRAF2 interaction," Cell, vol. 101(7):777-787.

Seela et al., 2004, "Product Class 17: Purines," Science of Synthesis, vol. 16, pp. 945-1108.

Sridhar et al., 2000, "Proteinkinases as therapeutic targets," Pharm Research, vol. 17(11):1345-1353.

Westover et al., 1981, "Synthesis and antiviral activity of certain 9-β - D-Riofuranoaylpurine-6-carboxamides," J.Med. Chem., vol. 24(8):941-46.

Zaki et al., 2007, "The synthesis of imidazol[4,5-d]pyridines from a substituted imidazole and acyl or sulfonyl acetonitrile," Tetrahedron, vol. 63(18):3745-3753.

Ambinter Chemical Library as of Sep. 2006.

Interchem Chemical Library as of Sep. 2006.

Registry File Document for RN 863501-03-5, 863502-39-0.

* cited by examiner

METHODS OF TREATMENT USING HETEROARYL COMPOUNDS AND COMPOSITIONS THEREOF

This application is a divisional of U.S. non-provisional application Ser. No. 11/975,657, filed Oct. 18, 2007 now U.S. Pat. No. 7,968,556, currently allowed, which claims the benefit of U.S. provisional application No. 60/853,135, filed Oct. 19, 2006, which is incorporated by reference herein in its entirety.

1. FIELD

Provided herein are certain heteroaryl compounds, compositions comprising an effective amount of one or more such compounds and methods for treating or preventing cancer, inflammatory conditions, immunological conditions, metabolic conditions and conditions treatable or preventable by inhibition of a kinase pathway, comprising administering an effective amount of a heteroaryl compound to a patient in need thereof.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11): 1345-1353 (2000). Viral infections and the conditions related thereto have also been associated with the regulation of protein kinases. Park et al. *Cell* 101 (7): 777-787 (2000). Protein kinases can be divided into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs).

The IκB kinases (IKKs), are key regulatory signaling molecules coordinating the activation of NF-κB. IKK-1 and IKK-2 are structurally unique kinases containing an N-terminal kinase domain with a dual serine activation loop, a leucine zipper domain, and a C-terminal helix-loop-helix domain and serine cluster. Many immune and inflammatory mediators including TNFα, lipopolysaccharide (LPS), IL-1, anti-CD28, CD40L, FasL, viral infection, and oxidative stress have been shown to lead to NF-κB activation. Although the receptor complexes that transduce these diverse stimuli appear very different in their protein components, it is understood that each of these stimulation events leads to activation of the IKKs and NF-κB.

Data suggests that small molecule IKK-2 inhibitors have anti-inflammatory properties. Catley et al. *Mol. Pharmacol.* 70: 697-705 (2006). IKK-2 is activated in response to multiple inflammatory stimuli and signaling pathways, many of which play an important role in respiratory disease including IL-1β, LPS, TNFα, CD3/CD28 (antigen presentation), CD40L, viral infection, and oxidative stress. The ubiquitous expression of NF-κB, along with its response to multiple stimuli means that almost all cell types present in the lung are potential target for anti-NF-κB/IKK-2 therapy. This includes alveolar epithelium, mast cells, fibroblasts, vascular endothelium, and infiltrating leukocytes; neutrophils, macrophages, lymphocytes, eosinophils and basophils. By inhibiting the expression of genes such as cyclooxygenase-2 and 12-lipoxygenase (synthesis of inflammatory mediators), TAP-1 peptide transporter (antigen processing), MHC class I H-2K and class II invariant chains (antigen presentation), E-selectin and vascular cell adhesion molecule (leukocyte recruitment), interleukins-1, 2, 6, 8 (cytokines), RANTES, eotaxin, GM-CSF (chemokines), and superoxide dismutase and NADPH quinone oxidoreductase (reactive oxygen species), inhibitors of IKK-2 are believed to display broad anti-inflammatory activity.

mTOR (mammalian target of rapamycin), which is also called FRAP, RAFTI or SEPT), is a 2549-amino acid Ser/Thr protein kinase, which has been shown to be one of the most critical proteins in the PI3K/Akt pathway that regulates cell growth and proliferation. Georgakis and Younes, 2006, *Expert Rev. Anticancer Ther.* 6(1):131-140. Because PI3K and Akt are involved in the regulation of several cellular functions, there may be toxicities associated with inhibiting these kinases, making inhibition of mTOR the more promising approach. Id. Three mTOR inhibitors are currently in clinical trials for the treatment of cancer. These are CCI-779 (renal cancer, breast cancer, mantle cell lymphoma, glioblastoma multiforme and metastatic melanoma), RAD001 (refractory solid tumors, advanced hematologic tumors, GIST and advanced non-small cell lung cancer) and AP23573 (solid tumors, hematologic malignancy and sarcoma). Id. The preclinical success of these compounds demonstrates the usefulness of mTOR inhibitors in the treatment of cancer and the need for additional compounds with mTOR inhibitory activity.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

Citation or identification of any reference in Section 2 of this application is not to be construed as an admission that the reference is prior art to the present application.

3. SUMMARY

Provided herein are compounds having the following formula (I):

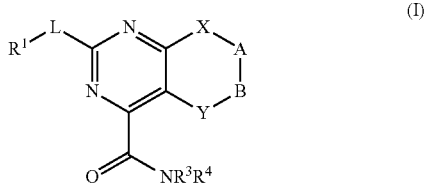

(I)

and pharmaceutically acceptable salts, polymorphs, clathrates, solvates, hydrates, stereoisomers and prodrugs thereof, wherein $R^1$, $R^3$, $R^4$, L, X, Y, A and B are as defined herein.

Compounds of formula (I), or pharmaceutically acceptable salts, clathrates, solvates, hydrates, stereoisomers or prodrugs thereof (each being referred to herein as "Heteroaryl Compounds"), are useful for treating or preventing cancer, inflammatory conditions, immunological conditions, metabolic conditions and conditions treatable or preventable by inhibition of a kinase pathway. In one embodiment, the kinase pathway is the IKK-2, mTOR, PI3K, SYK or TYK2 pathway. In another embodiment, the kinase pathway is the PI3Kα, PI3Kβ, PI3Kδ, Aurora, Abl, KDR, MLK1, CaMKIV, GSK3α, GSK3β, ATM, ATX or DNA-PK pathway.

Further provided herein are compositions comprising an effective amount of a Heteroaryl Compound and compositions comprising an effective amount of a Heteroaryl Compound and a pharmaceutically acceptable carrier or vehicle. The compositions are useful for treating or preventing cancer, inflammatory conditions, immunological conditions, metabolic conditions and conditions treatable or preventable by inhibition of a kinase pathway, in one embodiment, the IKK-2, mTOR, PI3K, SYK or TYK2 pathway. Further provided herein are methods for treating or preventing cancer, inflammatory conditions, immunological conditions, metabolic conditions and conditions treatable or preventable by inhibition of a kinase pathway, in one embodiment, the IKK-2, mTOR, PI3K, SYK or TYK2 pathway, comprising administering an effective amount of a Heteroaryl Compound to a patient in need of the treating or preventing.

The present embodiments can be understood more fully by reference to the detailed description and examples, which are intended to exemplify non-limiting embodiments.

4. DETAILED DESCRIPTION

4.1 Definitions

A "$C_{1-8}$alkyl" group is a saturated straight chain or branched non-cyclic hydrocarbon having from 1 to 8 carbon atoms. Representative —($C_{1-8}$alkyls) include -methyl, -ethyl, -n-propyl, -n-butyl, -n-pentyl, -n-hexyl, -n-heptyl and -n-octyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. A -($C_{1-8}$alkyl) group can be substituted or unsubstituted. For example, a $C_{1-8}$alkyl group can be substituted with phenyl to form a benzyl group.

A "$C_{2-8}$alkenyl" group is a straight chain or branched non-cyclic hydrocarbon having from 2 to 8 carbon atoms and including at least one carbon-carbon double bond. Representative straight chain and branched ($C_2$-$C_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "$C_{2-8}$alkynyl" group is a straight chain or branched non-cyclic hydrocarbon having from 2 to 8 carbon atoms and including at lease one carbon-carbon triple bond. Representative straight chain and branched —($C_2$-$C_8$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, and the like. An alkynyl group can be unsubstituted or substituted.

The terms "halogen" and "halo" mean fluorine, chlorine, bromine and iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like. An aryl group can be substituted or unsubstituted.

A "heteroaryl" group is an aryl ring system having one to four heteroatoms (e.g., O, S or N) as ring atoms in a heteroaromatic ring system, wherein the remainder of the atoms are carbon atoms. Suitable heteroatoms include oxygen, sulfur and nitrogen. In certain embodiments, the heterocyclic ring system is monocyclic or bicyclic. Non-limiting examples include aromatic groups selected from the following:

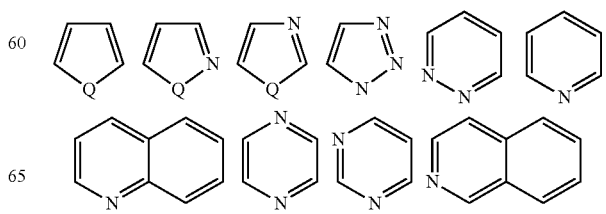

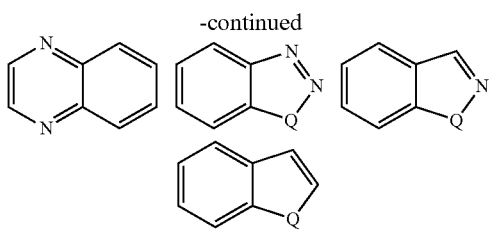

wherein Q is CH₂, CH=CH, O, S or NH. Further representative examples of heteroaryl groups include, but are not limited to, benzofuranyl, benzothienyl, indolyl, benzopyrazolyl, coumarinyl, furanyl, isothiazolyl, imidazolyl, isoxazolyl, thiazolyl, triazolyl, tetrazolyl, thiophenyl, pyrimidinyl, isoquinolinyl, quinolinyl, pyridinyl, pyrrolyl, pyrazolyl, 1H-indolyl, 1H-indazolyl, benzo[d]thiazolyl and pyrazinyl. Further representative examples of heteroaryl groups include those of the compounds disclosed herein. Heteroaryls can be bonded at any ring atom (i.e., at any carbon atom or heteroatom of the heteroaryl ring). A heteroaryl group can be substituted or unsubstituted. In one embodiment, the heteroaryl group is a $C_{3-10}$heteroaryl group.

A "cycloalkyl" group is a saturated or unsaturated non-aromatic carbocyclic ring. Representative cycloalkyl groups include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. A cycloalkyl group can be substituted or unsubstituted. In one embodiment, the cycloalkyl group is a $C_{3-8}$cycloalkyl group.

A "heterocycloalkyl" group is a non-aromatic cycloalkyl in which one to four of the ring carbon atoms are independently replaced with a heteroatom from the group consisting of O, S and N. Representative examples of a heterocycloalkyl group include, but are not limited to, morpholinyl, pyrrolyl, pyrrolidinyl, thienyl, furanyl, thiazolyl, imidazolyl, pyrazolyl, triazolyl, piperizinyl, isothiazolyl, isoxazolyl, (1,4)-dioxane, (1,3)-dioxolane, 4,5-dihydro-1H-imidazolyl and tetrazolyl. Heterocycloalkyls can also be bonded at any ring atom (i.e., at any carbon atom or heteroatom of the Heteroaryl ring). A heterocycloalkyl group can be substituted or unsubstituted. In one embodiment, the heterocycloalkyl is a 3-7 membered heterocycloalkyl.

When the groups described herein are said to be "substituted or unsubstituted," when substituted, they may be substituted with one or more of any substituent. Examples of substituents are those found in the exemplary compounds and embodiments disclosed herein, as well as halo (e.g., chloro, iodo, bromo, or fluoro); $C_{1-8}$alkyl; $C_{2-8}$ alkenyl; $C_{2-8}$ alkynyl; hydroxyl; $C_{1-8}$ alkoxyl; amino; nitro; thiol; thioether; imine; cyano; amido; phosphonato; phosphine; carboxyl; carbamoyl; carbamate; acetal; urea; thiocarbonyl; sulfonyl; sulfonamide; ketone; aldehyde; ester; acetyl; acetoxy; oxygen (=O); haloalkyl (e.g., trifluoromethyl); substituted aminoacyl and aminoalkyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, furanyl, or thiazinyl); carbocyclic or heterocyclic, monocyclic or fused or non-fused polycyclic aryl (e.g., phenyl, naphthyl, pyrrolyl, indolyl, furanyl, thienyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothienyl, or benzofuranyl); amino (primary, secondary, or tertiary); —O-lower alkyl; —O-aryl; aryl; aryl-lower alkyl; $CO_2CH_3$; $CONH_2$; $OCH_2CONH_2$; $NH_2$; $N(C_{1-4}alkyl)_2$; $NHC(O)C_{1-4}$ alkyl; $SO_2NH_2$; $SO_2C_{1-4}$alkyl; $OCHF_2$; $CF_3$; $OCF_3$; and such moieties may also be optionally substituted by a fused-ring structure or bridge, for example —OCH₂O— or —O-lower alkylene-O—. These substituents may optionally be further substituted with a substituent selected from such groups.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Heteroaryl Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein, the term "polymorph(s)" and related terms herein refer to solid forms of the Heteroaryl Compounds having different physical properties as a result of the order of the molecules in the crystal lattice. The differences in physical properties exhibited by solid forms affect pharmaceutical parameters such as storage stability, compressibility and density (important in formulation and product manufacturing), and dissolution rates (an important factor in determining bioavailability). Differences in stability can result from changes in chemical reactivity (e.g., differential oxidation, such that a dosage form discolors more rapidly when comprised of one solid form than when comprised of another solid form) or mechanical changes (e.g., tablets crumble on storage as a kinetically favored polymorph converts to thermodynamically more stable solid form) or both (e.g., tablets of one solid form are more susceptible to breakdown at high humidity). As a result of solubility/dissolution differences, in the extreme case, some solid form transitions may result in lack of potency or, at the other extreme, toxicity. In addition, the physical properties of the crystal may be important in processing, for example, one solid form might be more likely to form solvates or might be difficult to filter and wash free of impurities (i.e., particle shape and size distribution might be different between one solid form relative to the other).

As used herein and unless otherwise indicated, the term "clathrate" means a Heteroaryl Compound, or a salt thereof, in the form of a crystal lattice that contains spaces (e.g., channels) that have a guest molecule (e.g., a solvent or water) trapped within or a crystal lattice wherein a Heteroaryl Compound is a guest molecule. As used herein and unless otherwise indicated, the term "hydrate" means a Heteroaryl Compound, or a salt thereof, that further includes a stoichiometric or non-stoichiometric amount of water bound by non-covalent intermolecular forces.

As used herein and unless otherwise indicated, the term "solvate" means a Heteroaryl Compound, or a salt thereof, that further includes a stoichiometric or non-stoichiometric amount of a solvent bound by non-covalent intermolecular forces.

As used herein and unless otherwise indicated, the term "prodrug" means a Heteroaryl Compound derivative that can hydrolyze, oxidize, or otherwise react under biological conditions (in vitro or in vivo) to provide an active compound, particularly a Heteroaryl Compound. Examples of prodrugs include, but are not limited to, derivatives and metabolites of a Heteroaryl Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6$^{th}$ ed. (Donald J. Abraham ed., 2001, Wiley) and Design and Application of Prodrugs (H. Bundgaard ed., 1985, Harwood Academic Publishers Gmfh).

As used herein and unless otherwise indicated, the term "stereoisomer" or "stereomerically pure" means one stereoisomer of a Heteroaryl Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Heteroaryl Compounds can have chiral centers and can occur as racemates, individual enantiomers or diastereomers, and mixtures thereof. All such isomeric forms are included within the embodiments disclosed herein, including mixtures thereof.

Various Heteroaryl Compounds contain one or more chiral centers, and can exist as racemic mixtures of enantiomers, mixtures of diastereomers or enantiomerically or optically pure compounds. The use of stereomerically pure forms of such Heteroaryl Compounds, as well as the use of mixtures of those forms are encompassed by the embodiments disclosed herein. For example, mixtures comprising equal or unequal amounts of the enantiomers of a particular Heteroaryl Compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, N.Y., 1962); and Wilen, S. H., Tables of Resolving Agents and Optical Resolutions p. 268 (E. L. Eliel, Ed., Univ. of Notre Dame Press, Notre Dame, Ind., 1972).

It should also be noted the Heteroaryl Compounds can include E and Z isomers, or a mixture thereof, and cis and trans isomers or a mixture thereof. In certain embodiments, the Heteroaryl Compounds are isolated as either the E or Z isomer. In other embodiments, the Heteroaryl Compounds are a mixture of the E and Z isomers.

The term "effective amount" in connection with an Heteroaryl Compound can mean an amount capable of treating or preventing a disease disclosed herein, such as cancer, inflammatory conditions, immunological conditions, metabolic conditions or conditions treatable or preventable by inhibition of a kinase pathway, in one embodiment, the IKK-2, mTOR or PI3K pathway.

The term "patient" includes an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

4.2 Heteroaryl Compounds

Provided herein are Heteroaryl Compounds having the following formula (I):

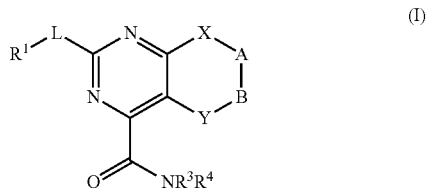

and pharmaceutically acceptable salts, polymorphs, clathrates, solvates, hydrates, stereoisomers, enantiomers and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;

—X-A-B—Y— taken together form —N($R^1$)$CH_2$C(O)NH—, —N($R^2$)C(O)$CH_2$NH—, —N($R^2$)C(O)NH—, —N($R^2$)C=N—, or —C($R^2$)=CHNH—;

L is a direct bond, NH or O;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl; and $R^3$ and $R^4$ are independently H or $C_{1-8}$alkyl.

In one embodiment, the Heteroaryl Compounds of formula (I) are those wherein —X-A-B—Y— taken together form —N($R^2$)$CH_2$C(O)NH—.

In another embodiment, the Heteroaryl Compounds of formula (I) are those wherein —X-A-B—Y— taken together form —N($R^2$)C(O)$CH_2$NH—.

In another embodiment, the Heteroaryl Compounds of formula (I) are those wherein —X-A-B—Y— taken together form —N($R^2$)C(O)NH—.

In another embodiment, the Heteroaryl Compounds of formula (I) are those wherein —X-A-B—Y— taken together form —N($R^2$)C=N—.

In another embodiment, the Heteroaryl Compounds of formula (I) are those wherein —X-A-B—Y— taken together form —C(R$^2$)=CHNH—.

In another embodiment, the Heteroaryl Compounds of formula (I) are those wherein L is a direct bond.

In another embodiment, the Heteroaryl Compounds of formula (I) are those wherein R$^1$ is substituted aryl, such as substituted phenyl.

In another embodiment, the Heteroaryl Compounds of formula (I) are those wherein R$^1$ is substituted or unsubstituted heteroaryl, such as substituted or unsubstituted pyridine, substituted or unsubstituted indole or substituted or unsubstituted quinoline.

In another embodiment, the Heteroaryl Compounds of formula (I) are those wherein R$^1$ is substituted or unsubstituted cycloalkyl, such as substituted or unsubstituted cyclopentyl.

In another embodiment, the Heteroaryl Compounds of formula (I) are those wherein —X-A-B—Y— taken together form —N(R$^2$)C(O)NH— and R$^1$ is substituted aryl, such as phenyl.

In another embodiment, the Heteroaryl Compounds of formula (I) are those wherein —X-A-B—Y— taken together form —N(R$^2$)C(O)NH— and R$^1$ is substituted or unsubstituted heteroaryl, such as substituted or unsubstituted pyridine, substituted or unsubstituted indole or substituted or unsubstituted quinoline.

In another embodiment, the Heteroaryl Compounds of formula (I) are those wherein —X-A-B—Y— taken together form —N(R$^2$)C(O)NH— and R$^1$ is substituted or unsubstituted cycloalkyl, such as substituted or unsubstituted cyclopentyl.

In another embodiment, the Heteroaryl Compounds of formula (I) are those wherein R$^2$ is substituted C$_{1-8}$alkyl, such as —CH$_2$C$_6$H$_5$.

In another embodiment, the Heteroaryl Compounds of formula (I) are those wherein R$^2$ is unsubstituted C$_{1-8}$alkyl, such as unsubstituted methyl.

In another embodiment, the Heteroaryl Compounds of formula (I) are those wherein R$^2$ is substituted or unsubstituted aryl, such as substituted or unsubstituted phenyl.

In another embodiment, the Heteroaryl Compounds of formula (I) are those wherein R$^2$ is substituted aryl, such as halo, haloalkyl or alkoxy substituted phenyl.

In another embodiment, the Heteroaryl Compounds of formula (I) are those wherein R$^2$ is substituted or unsubstituted cycloalkyl, such as substituted or unsubstituted cyclohexyl or substituted or unsubstituted cycloheptyl.

In another embodiment, the Heteroaryl Compounds of formula (I) are those wherein R$^2$ is substituted heterocycloalkyl, such as substituted piperidine.

In another embodiment, the Heteroaryl Compounds of formula (I) are those wherein R$^3$ and R$^4$ are H.

In another embodiment, the Heteroaryl Compounds of formula (I) are those wherein —X-A-B—Y— taken together form —N(R$^2$)C(O)NH— and R$^2$ is unsubstituted aryl, such as unsubstituted phenyl.

In another embodiment, the Heteroaryl Compounds of formula (I) are those wherein —X-A-B—Y— taken together form —N(R$^2$)C(O)NH—, R$^1$ is substituted or unsubstituted heteroaryl, such as substituted or unsubstituted pyridine, and R$^2$ is substituted or unsubstituted aryl, such as substituted or unsubstituted phenyl.

In another embodiment, the Heteroaryl Compounds of formula (I) are those wherein —X-A-B—Y— taken together form —N(R$^2$)C(O)NH—, R$^1$ is substituted or unsubstituted heteroaryl, such as substituted or unsubstituted pyridine, R$^2$ is substituted or unsubstituted aryl, such as substituted or unsubstituted phenyl, and R$^3$ and R$^4$ are H.

In another embodiment, the Heteroaryl Compounds of formula (I) are those wherein —X-A-B—Y— taken together form —N(R$^2$)C(O)NH—, L is a direct bond, R$^1$ is substituted or unsubstituted heteroaryl, such as substituted or unsubstituted pyridine, R$^2$ is substituted or unsubstituted aryl, such as substituted or unsubstituted phenyl, and R$^3$ and R$^4$ are H.

In another embodiment, the Heteroaryl Compounds of formula (I) are those wherein —X-A-B—Y— taken together form —N(R$^2$)C(O)NH—, R$^1$ is substituted or unsubstituted aryl, such as substituted or unsubstituted phenyl, and R$^2$ is substituted or unsubstituted aryl, such as substituted or unsubstituted phenyl.

In another embodiment, the Heteroaryl Compounds of formula (I) are those wherein —X-A-B—Y— taken together form —N(R$^2$)C(O)NH—, R$^1$ is substituted or unsubstituted aryl, such as substituted or unsubstituted phenyl, R$^2$ is substituted or unsubstituted aryl, such as substituted or unsubstituted phenyl, and R$^3$ and R$^4$ are H.

In another embodiment, the Heteroaryl Compounds of formula (I) are those wherein —X-A-B—Y— taken together form —N(R$^2$)C(O)NH—, L is a direct bond, R$^1$ is substituted or unsubstituted aryl, such as substituted or unsubstituted phenyl, R$^2$ is substituted or unsubstituted aryl, such as substituted or unsubstituted phenyl, and R$^3$ and R$^4$ are H.

In another embodiment, the Heteroaryl Compounds of formula (I) are those wherein —X-A-B—Y— taken together form —N(R$^2$)C(O)NH—, R$^1$ is substituted or unsubstituted heteroaryl, L is a direct bond and R$^2$ is substituted or unsubstituted C$_{1-8}$alkyl or substituted or unsubstituted cycloalkyl.

In another embodiment, the Heteroaryl Compounds of formula (I) are those wherein —X-A-B—Y— taken together form —N(R$^2$)C(O)NH—, R$^1$ is substituted or unsubstituted aryl, L is a direct bond and R$^2$ is substituted or unsubstituted C$_{1-8}$alkyl or substituted or unsubstituted cycloalkyl.

In another embodiment, the Heteroaryl Compounds of formula (I) do not include 8,9-dihydro-8-oxo-9-phenyl-2-(3-pyridinyl)-7H-purine-6-carboxamide, 8,9-dihydro-8-oxo-9-phenyl-2-(3-pyridinyl)-7H-purine-6-carboxamide, 8,9-dihydro-8-oxo-9-phenyl-2-(3-pyridinyl)-7H-purine-6-carboxamide, 2-(4-cyanophenyl)-8-oxo-9-phenyl-8,9-dihydro-7H-purine-6-carboxamide, 2-(4-nitrophenyl)-8-oxo-9-phenyl-8,9-dihydro-7H-purine-6-carboxamide, 9-benzyl-2-(4-methoxyphenyl)-8-oxo-8,9-dihydro-7H-purine-6-carboxamide, 2-methyl-8-oxo-9-phenyl-8,9-dihydro-7H-purine-6-carboxamide, 9-benzyl-9H-purine-2,6-dicarboxamide, 9-[2,3-bis[(benzoyloxy)methyl]cyclobutyl]-2-methyl-9H-Purine-6-carboxamide, 9-benzyl-2-methyl-9H-purine-6-carboxamide, 9-(2-hydroxyethyl)-2-methyl-9H-purine-6-carboxamide, 9-(2-hydroxyethyl)-2-(trifluoromethyl)-9H-purine-6-carboxamide, 9-(2-hydroxyethyl)-2-(prop-1-enyl)-9H-purine-6-carboxamide, 9-(2-hydroxyethyl)-2-phenyl-9H-purine-6-carboxamide, 9-(3-hydroxypropyl)-2-methyl-9H-purine-6-carboxamide, 9-(3-hydroxypropyl)-2-(trifluoromethyl)-9H-purine-6-carboxamide, 2-methyl-9-phenylmethyl-9H-purine-6-carboxamide or 2-methyl-9-β-D-ribofuranosyl-9H-purine-6-carboxamide.

In another embodiment, the Heteroaryl Compounds of formula (I) do not include compounds wherein R$^2$ is a substituted furanoside.

In another embodiment, the Heteroaryl Compounds of formula (I) do not include compounds wherein R$^2$ is a substituted or unsubstituted furanoside.

In another embodiment, the Heteroaryl Compounds of formula (I) do not include (2'R)-2'-deoxy-2'-fluoro-2'-C-methyl nucleosides.

In a further embodiment, provided herein are Heteroaryl Compounds having the following formula (II):

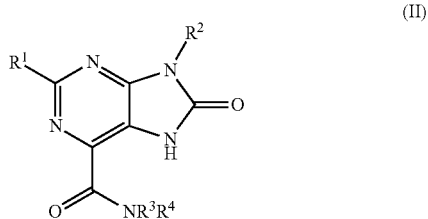

(II)

and pharmaceutically acceptable salts, polymorphs, clathrates, solvates, hydrates, stereoisomers, enantiomers and prodrugs thereof,
wherein:
$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;
$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl; and
$R^3$ and $R^4$ are independently H or $C_{1-8}$alkyl.

In one embodiment, the Heteroaryl Compounds of formula (II) are those wherein $R^1$ is substituted aryl, substituted or unsubstituted heteroaryl, such as substituted phenyl.

In another embodiment, the Heteroaryl Compounds of formula (II) are those wherein $R^1$ is substituted or unsubstituted heteroaryl, such as substituted or unsubstituted pyridine, substituted or unsubstituted indole or substituted or unsubstituted quinoline.

In another embodiment, the Heteroaryl Compounds of formula (II) are those wherein $R^1$ is substituted or unsubstituted cycloalkyl, such as substituted or unsubstituted cyclopentyl.

In another embodiment, the Heteroaryl Compounds of formula (II) are those wherein $R^2$ is substituted $C_{1-8}$alkyl, such as —$CH_2C_6H_5$.

In another embodiment, the Heteroaryl Compounds of formula (II) are those wherein $R^2$ is unsubstituted $C_{1-8}$alkyl, such as unsubstituted methyl.

In another embodiment, the Heteroaryl Compounds of formula (II) are those wherein $R^2$ is substituted or unsubstituted aryl, such as substituted or unsubstituted phenyl.

In another embodiment, the Heteroaryl Compounds of formula (II) are those wherein $R^2$ is substituted aryl, such as halo, haloalkyl or alkoxy substituted phenyl.

In another embodiment, the Heteroaryl Compounds of formula (II) are those wherein $R^2$ is substituted or unsubstituted cycloalkyl, such as substituted or unsubstituted cyclohexyl or substituted or unsubstituted cycloheptyl.

In another embodiment, the Heteroaryl Compounds of formula (II) are those wherein $R^2$ is substituted heterocycloalkyl, such as substituted piperidine.

In another embodiment, the Heteroaryl Compounds of formula (II) are those wherein $R^3$ and $R^4$ are H.

In another embodiment, the Heteroaryl Compounds of formula (II) do not include 8,9-dihydro-8-oxo-9-phenyl-2-(3-pyridinyl)-7H-Purine-6-carboxamide, 8,9-dihydro-8-oxo-9-phenyl-2-(3-pyridinyl)-7H-Purine-6-carboxamide, 8,9-dihydro-8-oxo-9-phenyl-2-(3-pyridinyl)-7H-Purine-6-carboxamide, 2-(4-cyanophenyl)-8-oxo-9-phenyl-8,9-dihydro-7H-purine-6-carboxamide, 2-(4-nitrophenyl)-8-oxo-9-phenyl-8,9-dihydro-7H-purine-6-carboxamide, 9-benzyl-2-(4-methoxyphenyl)-8-oxo-8,9-dihydro-7H-purine-6-carboxamide, 9-phenylmethyl-9H-purine-2,6-dicarboxamide, or 2-methyl-8-oxo-9-phenyl-8,9-dihydro-7H-purine-6-carboxamide.

In another embodiment, the Heteroaryl Compounds of formula (II) do not include compounds wherein $R^2$ is a substituted furanoside.

In another embodiment, the Heteroaryl Compounds of formula (II) do not include compounds wherein $R^2$ is a substituted or unsubstituted furanoside.

In another embodiment, the Heteroaryl Compounds of formula (II) do not include (2'R)-2'-deoxy-2'-fluoro-2'-C-methyl nucleosides.

In a further embodiment, provided herein are Heteroaryl Compounds having the following formula (III):

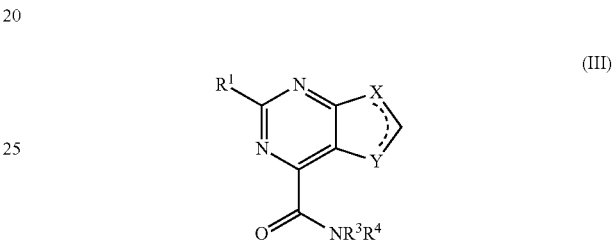

(III)

and pharmaceutically acceptable salts, polymorphs, clathrates, solvates, hydrates, stereoisomers, enantiomers and prodrugs thereof,
wherein:

is —C($R^2$)=CH—NH— or —N($R^2$)—CH=N—;
$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;
$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl; and
$R^3$ and $R^4$ are independently H or $C_{1-8}$alkyl.

In one embodiment, the Heteroaryl Compounds of formula (III) are those wherein $R^1$ is substituted aryl, such as substituted phenyl.

In another embodiment, the Heteroaryl Compounds of formula (III) are those wherein $R^1$ is substituted or unsubstituted heteroaryl, such as substituted or unsubstituted pyridine, substituted or unsubstituted indole or substituted or unsubstituted quinoline.

In another embodiment, the Heteroaryl Compounds of formula (III) are those wherein $R^1$ is substituted or unsubstituted cycloalkyl, such as substituted or unsubstituted cyclopentyl.

In another embodiment, the Heteroaryl Compounds of formula (III) are those wherein $R^2$ is substituted $C_{1-8}$alkyl, such as —$CH_2C_6H_5$.

In another embodiment, the Heteroaryl Compounds of formula (III) are those wherein $R^2$ is unsubstituted $C_{1-8}$alkyl, such as unsubstituted methyl.

In another embodiment, the Heteroaryl Compounds of formula (III) are those wherein $R^2$ is substituted or unsubstituted aryl, such as substituted or unsubstituted phenyl.

In another embodiment, the Heteroaryl Compounds of formula (III) are those wherein $R^2$ is substituted aryl, such as halo, haloalkyl or alkoxy substituted phenyl.

In another embodiment, the Heteroaryl Compounds of formula (III) are those wherein $R^2$ is substituted or unsubstituted cycloalkyl, such as substituted or unsubstituted cyclohexyl or substituted or unsubstituted cycloheptyl.

In another embodiment, the Heteroaryl Compounds of formula (III) are those wherein $R^2$ is substituted heterocycloalkyl, such as substituted piperidine.

In another embodiment, the Heteroaryl Compounds of formula (III) are those wherein $R^3$ and $R^4$ are H.

In another embodiment, the Heteroaryl Compounds of formula (III) are those wherein

is —C($R^2$)=CH—NH— and $R^2$ is substituted aryl, such as substituted phenyl.

In another embodiment, the Heteroaryl Compounds of formula (III) are those wherein

is —N($R^2$)—CH=N— and $R^2$ is substituted aryl, such as substituted phenyl.

In another embodiment, the Heteroaryl Compounds of formula (III) are those wherein $R^1$ is substituted aryl, such as phenyl, and $R^2$ is substituted aryl, such as substituted phenyl.

In another embodiment, the Heteroaryl Compounds of formula (III) do not include 9-benzyl-9H-purine-2,6-dicarboxamide, 9-[2,3-bis[(benzoyloxy)methyl]cyclobutyl]-2-methyl-9H-Purine-6-carboxamide, 9-benzyl-2-methyl-9H-purine-6-carboxamide, 9-(2-hydroxyethyl)-2-methyl-9H-purine-6-carboxamide, 9-(2-hydroxyethyl)-2-(trifluoromethyl)-9H-purine-6-carboxamide, 9-(2-hydroxyethyl)-2-(prop-1-enyl)-9H-purine-6-carboxamide, 9-(2-hydroxyethyl)-2-phenyl-9H-purine-6-carboxamide, 9-(3-hydroxypropyl)-2-methyl-9H-purine-6-carboxamide, 9-(3-hydroxypropyl)-2-(trifluoromethyl)-9H-purine-6-carboxamide, 9-phenylmethyl-9H-purine-2,6-dicarboxamide, 2-methyl-9-phenylmethyl-9H-purine-6-carboxamide or 2-methyl-9-β-D-ribofuranosyl-9H-purine-6-carboxamide.

In another embodiment, the Heteroaryl Compounds of formula (III) do not include compounds wherein $R^2$ is substituted cyclobutyl when

is —N($R^2$)—CH=N—.

In another embodiment, the Heteroaryl Compounds of formula (III) do not include compounds wherein $R^2$ is a substituted furanoside when

is —N($R^2$)—CH=N—.

In another embodiment, the Heteroaryl Compounds of formula (III) do not include compounds wherein $R^2$ is substituted pyrimidine when

is —C($R^2$)=CH—NH—.

In another embodiment, the Heteroaryl Compounds of formula (III) do not include compounds wherein $R^2$ is substituted oxetane when

is —N($R^2$)—CH=N—.

In another embodiment, the Heteroaryl Compounds of formula (III) do not include compounds wherein $R^2$ is substituted cyclopentyl or a heterocyclopentyl when

is —N($R^2$)—CH=N—.

In a further embodiment, provided herein are Heteroaryl Compounds having the following formula (IV):

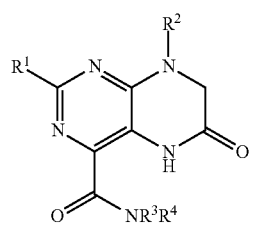

and pharmaceutically acceptable salts, polymorphs, clathrates, solvates, hydrates, stereoisomers, enantiomers and prodrugs thereof,
wherein:
$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;
$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl; and
$R^3$ and $R^4$ are independently H or $C_{1-8}$alkyl.

In one embodiment, the Heteroaryl Compounds of formula (IV) are those wherein $R^1$ is substituted aryl, such as substituted phenyl.

In another embodiment, the Heteroaryl Compounds of formula (IV) are those wherein R¹ is substituted or unsubstituted heteroaryl, such as substituted or unsubstituted pyridine, substituted or unsubstituted indole or substituted or unsubstituted quinoline.

In another embodiment, the Heteroaryl Compounds of formula (IV) are those wherein R¹ is substituted or unsubstituted cycloalkyl, such as substituted or unsubstituted cyclopentyl.

In another embodiment, the Heteroaryl Compounds of formula (IV) are those wherein R² is substituted $C_{1-8}$alkyl, such as —$CH_2C_6H_5$.

In another embodiment, the Heteroaryl Compounds of formula (IV) are those wherein R² is unsubstituted $C_{1-8}$alkyl, such as unsubstituted methyl.

In another embodiment, the Heteroaryl Compounds of formula (IV) are those wherein R² is substituted or unsubstituted aryl, such as substituted or unsubstituted phenyl.

In another embodiment, the Heteroaryl Compounds of formula (IV) are those wherein R² is substituted aryl, such as halo, haloalkyl or alkoxy substituted phenyl.

In another embodiment, the Heteroaryl Compounds of formula (IV) are those wherein R² is substituted or unsubstituted cycloalkyl, such as substituted or unsubstituted cyclohexyl or substituted or unsubstituted cycloheptyl.

In another embodiment, the Heteroaryl Compounds of formula (IV) are those wherein R² is substituted heterocycloalkyl, such as substituted piperidine.

In another embodiment, the Heteroaryl Compounds of formula (IV) are those wherein R³ and R⁴ are H.

In a further embodiment, provided herein are Heteroaryl Compounds having the following formula (V):

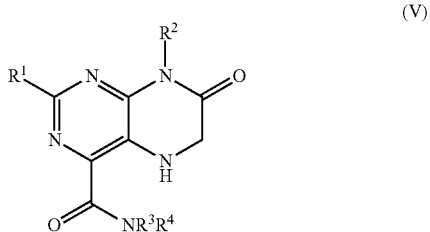

and pharmaceutically acceptable salts, polymorphs, clathrates, solvates, hydrates, stereoisomers, enantiomers and prodrugs thereof, wherein:

R¹ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;

R² is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl; and R³ and R⁴ are independently H or $C_{1-8}$alkyl.

In one embodiment, the Heteroaryl Compounds of formula (V) are those wherein R¹ is substituted aryl, such as substituted phenyl.

In another embodiment, the Heteroaryl Compounds of formula (V) are those wherein R¹ is substituted or unsubstituted heteroaryl, such as substituted or unsubstituted pyridine, substituted or unsubstituted indole or substituted or unsubstituted quinoline.

In another embodiment, the Heteroaryl Compounds of formula (V) are those wherein R¹ is substituted or unsubstituted cycloalkyl, such as substituted or unsubstituted cyclopentyl.

In another embodiment, the Heteroaryl Compounds of formula (V) are those wherein R² is substituted $C_{1-8}$alkyl, such as —$CH_2C_6H_5$.

In another embodiment, the Heteroaryl Compounds of formula (V) are those wherein R² is unsubstituted $C_{1-8}$alkyl, such as unsubstituted methyl.

In another embodiment, the Heteroaryl Compounds of formula (V) are those wherein R² is substituted or unsubstituted aryl, such as substituted or unsubstituted phenyl.

In another embodiment, the Heteroaryl Compounds of formula (V) are those wherein R² is substituted aryl, such as halo, haloalkyl or alkoxy substituted phenyl.

In another embodiment, the Heteroaryl Compounds of formula (V) are those wherein R² is substituted or unsubstituted cycloalkyl, such as substituted or unsubstituted cyclohexyl or substituted or unsubstituted cycloheptyl.

In another embodiment, the Heteroaryl Compounds of formula (V) are those wherein R² is substituted heterocycloalkyl, such as substituted piperidine.

In another embodiment, the Heteroaryl Compounds of formula (V) are those wherein R³ and R⁴ are H.

Representative Heteroaryl Compounds are set forth in Table 1, below.

TABLE 1

| Compound | Compound |
| --- | --- |
| 9-benzyl-8-oxo-2-(pyridin-3-yl)-8,9-dihydro-7H-purine-6-carboxamide<br>1 | N-methyl-8-oxo-9-phenyl-2-(pyridin-3-yl)-8,9-dihydro-7H-purine-6-carboxamide<br>2 |
| 8-oxo-9-phenyl-2-(pyridin-2-yl)-8,9-dihydro-7H-purine-6-carboxamide<br>3 | 2-(2-chloropyridin-3-yl)-8-oxo-9-phenyl-8,9-dihydro-7H-purine-6-carboxamide<br>4 |
| 2-(2-methoxypyridin-3-yl)-8-oxo-9-phenyl-8,9-dihydro-7H-purine-6-carboxamide<br>5 | N,N-dimethyl-8-oxo-9-phenyl-2-(pyridin-3-yl)-8,9-dihydro-7H-purine-6-carboxamide<br>6 |
| 9-methyl-8-oxo-2-(pyridin-3-yl)-8,9-dihydro-7H-purine-6-carboxamide<br>7 | 2-(4-hydroxyphenyl)-9-(2-methoxyphenyl)-8-oxo-8,9-dihydro-7H-purine-6-carboxamide<br>8 |

TABLE 1-continued

| Compound | Compound |
| --- | --- |
| 2-(3-hydroxyphenyl)-8-oxo-9-o-tolyl-8,9-dihydro-7H-purine-6-carboxamide<br>9 | 2-(1H-indol-4-yl)-9-(2-methoxyphenyl)-8-oxo-8,9-dihydro-7H-purine-6-carboxamide<br>10 |
| 2-(1H-indol-6-yl)-9-(2-methoxyphenyl)-8-oxo-8,9-dihydro-7H-purine-6-carboxamide<br>11 | 2-(3-hydroxyphenyl)-9-(4-methoxyphenyl)-8-oxo-8,9-dihydro-7H-purine-6-carboxamide<br>12 |
| 2-(2-hydroxypyridin-4-yl)-9-(2-methoxyphenyl)-8-oxo-8,9-dihydro-7H-purine-6-carboxamide<br>13 | 9-(2-chlorophenyl)-2-(3-hydroxyphenyl)-8-oxo-8,9-dihydro-7H-purine-6-carboxamide<br>14 |
| 9-(2-fluorophenyl)-2-(3-hydroxyphenyl)-8-oxo-8,9-dihydro-7H-purine-6-carboxamide<br>15 | 9-(2,6-difluorophenyl)-2-(3-hydroxyphenyl)-8-oxo-8,9-dihydro-7H-purine-6-carboxamide<br>16 |
| 9-cycloheptyl-8-oxo-2-(pyridin-3-yl)-8,9-dihydro-7H-purine-6-carboxamide<br>17 | 9-(2-methoxyphenyl)-8-oxo-2-(quinolin-5-yl)-8,9-dihydro-7H-purine-6-carboxamide<br>18 |
| 2-cyclopentyl-9-(2-methoxyphenyl)-8-oxo-8,9-dihydro-7H-purine-6-carboxamide<br>19 | 9-(2-methoxyphenyl)-8-oxo-2-(3-(trifluoromethyl)phenyl)-8,9-dihydro-7H-purine-6-carboxamide<br>20 |
| 9-(2-methoxyphenyl)-2-(6-methoxypyridin-3-yl)-8-oxo-8,9-dihydro-7H-purine-6-carboxamide<br>21 | 2-(3-hydroxyphenyl)-8-oxo-9-(4-(trifluoromethyl)phenyl)-8,9-dihydro-7H-purine-6-carboxamide<br>22 |
| 9-benzyl-2-(3-hydroxyphenyl)-8-oxo-8,9-dihydro-7H-purine-6-carboxamide<br>23 | 2-(3-hydroxyphenyl)-8-oxo-9-(2-(trifluoromethoxy)phenyl)-8,9-dihydro-7H-purine-6-carboxamide<br>24 |
| 9-(2,4-dichlorophenyl)-2-(3-hydroxyphenyl)-8-oxo-8,9-dihydro-7H-purine-6-carboxamide<br>25 | 9-(2-methoxyphenyl)-2-(3-nitrophenyl)-8-oxo-8,9-dihydro-7H-purine-6-carboxamide<br>26 |
| 2-(3-cyanophenyl)-8-oxo-9-phenyl-8,9-dihydro-7H-purine-6-carboxamide<br>27 | 9-(3-fluorophenyl)-2-(3-hydroxyphenyl)-8-oxo-8,9-dihydro-7H-purine-6-carboxamide<br>28 |
| 9-(2-methoxyphenyl)-8-oxo-2-(2-(trifluoromethyl)phenyl)-8,9-dihydro-7H-purine-6-carboxamide<br>29 | 2-(5-fluoropyridin-3-yl)-9-(2-methoxyphenyl)-8-oxo-8,9-dihydro-7H-purine-6-carboxamide<br>30 |
| 2-(1-benzylpiperidin-4-yl)-9-(2-methoxyphenyl)-8-oxo-8,9-dihydro-7H-purine-6-carboxamide<br>31 | benzyl 4-(6-carbamoyl-8-oxo-2-(pyridin-3-yl)-7H-purin-9(8H)-yl)piperidine-1-carboxylate<br>32 |
| 9-cyclohexyl-2-(3-hydroxyphenyl)-8-oxo-8,9-dihydro-7H-purine-6-carboxamide<br>33 | 9-(2-methoxyphenyl)-8-oxo-2-(3-(trifluoromethoxy)phenyl)-8,9-dihydro-7H-purine-6-carboxamide<br>34 |
| 9-phenyl-2-(pyridin-3-yl)-9H-purine-6-carboxamide<br>35 | 6-oxo-8-phenyl-2-(pyridin-3-yl)-5,6,7,8-tetrahydropteridine-4-carboxamide<br>36 |
| 6-oxo-8-phenyl-2-(pyridin-4-yl)-5,6,7,8-tetrahydropteridine-4-carboxamide<br>37 | 2-(3-aminophenyl)-9-(2-methoxyphenyl)-8-oxo-8,9-dihydro-7H-purine-6-carboxamide<br>38 |
| 2-(3-hydroxyphenyl)-9-(2-methoxyphenyl)-9H-purine-6-carboxamide<br>39 | 9-Cyclopentyl-2-(3-hydroxyphenyl)-8-oxo-8,9-dihydro-7H-purine-6-carboxamide<br>40 |
| 9-tert-Butyl-2-(3-hydroxy-phenyl)-8-oxo-8,9-dihydo-7H-purine-6-carboxamide<br>41 | [2-(3-Hydroxyphenyl)-9-(2-methoxyphenyl)-8-oxo(7-hydropurin-6-yl)]-N-methylcarbox-amide<br>42 |
| 2-phenyl-5H-pyrrolo[3,2-d]pyrimidine-4-carboxamide<br>43 | [2-(3-Hydroxyphenyl)-9-(2-methoxyphenyl)-8-oxo(7-hydropurin-6-yl)]-N,N-dimethyl carboxamide<br>44 |
| 2-(3-Hydroxyphenylamino)-9-(2-methoxyphenyl)-8-oxo-8,9-dihydro-7H-purine-6-carboxamide<br>45 | 2-(4-Hydroxyphenylamino)-9-(2-methoxyphenyl)-8-oxo-8,9-dihydro-7H-purine-6-carboxamide<br>46 |

TABLE 1-continued

| Compound | Compound |
|---|---|
| 9-(trans-4-Hydroxycyclohexyl)-2-(3-hydroxyphenyl)-8-oxo-8,9-dihydro-7H-purine-6-carboxamide<br>47 | 9-(trans-4-Hydroxycyclohexyl)-8-oxo-2-(pyridin-3-yl)-8,9-dihydro-7H-purine-6-carboxamide<br>48 |
| 9-(trans-4-Hydroxycyclohexyl)-2-(3-hydroxyphenyl)-8-oxo-8,9-dihydro-7H-purine-6-carboxamide<br>49 | 9-(trans-4-Hydroxycyclohexyl)-8-oxo-2-(pyridin-3-yl)-8,9-dihydro-7H-purine-6-carboxamide<br>50 |
| 2-(3-Hydroxyphenylamino)-9-(2-methoxyphenyl)-9H-purine-6-carboxamide<br>51 | 9-Isopropyl-2-(3-hydroxy-phenyl)-8-oxo-8,9-dihydo-7H-purine-6-carboxamide<br>52 |
| Methyl 4-(6-carbamoyl-9-(2-methoxyphenyl)-8-oxo-8,9-dihydro-7H-purin-2-yl) benzoate<br>53 | 2-(2-Chloro-3-hydroxyphenyl)-9-(2-methoxyphenyl)-8-oxo-7-hydropurine-6-carbox amide<br>54 |
| 2-(3-Cyanophenyl)-9-(2-methoxyphenyl)-8-oxo-8,9-dihydro-7H-purine-6-carboxamide<br>55 | 2-(2-Hydroxyphenylamino)-9-(2-methoxyphenyl)-8-oxo-8,9-dihydro-7H-purine-6-carboxamide<br>56 |
| 2-(3-Hydroxyphenyl)-9-(4-methoxy-2-methylphenyl)-8-oxo-8,9-dihydro-7H-purine-6-carboxamide<br>57 | 2-(3-Hydroxyphenyl)-8-oxo-9-(2-(trifluoromethyl)phenyl)-8,9-dihydro-7H-purine-6-carboxamide<br>58 |
| 2-(4-Cyano-phenyl)-9-(2-methoxy-phenyl)-8-oxo-8,9-dihydro-7H-purine-6-carboxamide<br>59 | 4-[6-Carbamoyl-9-(2-methoxy-phenyl)-8-oxo-8,9-dihydro-7H-purin-2-yl]-benzoic acid<br>60 |
| Methyl 3-(6-carbamoyl-9-(2-methoxyphenyl)-8-oxo-8,9-dihydro-7H-purin-2-yl)benzoate<br>61 | 3-(6-Carbamoyl-9-(2-methoxyphenyl)-8-oxo-8,9-dihydro-7H-purin-2-yl)benzoic acid<br>62 |
| 2-(3-Hydroxyphenyl)-9-(2-isopropylphenyl)-8-oxo-8,9-dihydro-7H-purine-6-carboxamide<br>63 | 2-(1H-Indazol-6-yl)-9-(2-methoxyphenyl)-8-oxo-7-hydropurine-6-carboxamide<br>64 |
| 2-(4-Carbamoylphenyl)-9-(2-methoxyphenyl)-8-oxo-8,9-dihydro-7H-purine-6-carboxamide<br>65 | 9-(2-Ethylphenyl)-2-(3-hydroxyphenyl)-8-oxo-8,9-dihydro-7H-purine-6-carboxamide<br>66 |
| 9-(2,5-Dichlorophenyl)-2-(3-hydroxyphenyl)-8-oxo-7-hydropurine-6-carboxamide<br>67 | 2-(3-Carbamoylphenyl)-9-(2-methoxyphenyl)-8-oxo-8,9-dihydro-7H-purine-6-carbox amide<br>68 |
| 9-(2,6-Dichlorophenyl)-2-(3-hydroxyphenyl)-8-oxo-7-hydropurine-6-carboxamide<br>69 | 2-(2-Hydroxyphenyl)-9-(2-methoxyphenyl)purine-6-carboxamide<br>70 |
| 2-(1H-Indazol-5-yl)-9-(2-methoxyphenyl)-8-oxo-7-hydropurine-6-carboxamide<br>71 | 9-(2,3-Dichlorophenyl)-2-(3-hydroxyphenyl)-8-oxo-7-hydropurine-6-carboxamide<br>72 |
| 2-[4-(Hydroxymethyl)phenyl]-9-(2-methoxyphenyl)-8-oxo-7-hydropurine-6-carbox-amide<br>73 | 2-[3-(Hydroxymethyl)phenyl]-9-(2-methoxyphenyl)-8-oxo-7-hydropurine-6-carbox-amide<br>74 |
| 9-(2-Methoxyphenyl)-8-oxo-2-(pyridin-4-yl)-8,9-dihydro-7H-purine-6-carboxamide<br>75 | 2-(4-Fluoro-3-hydroxyphenyl)-9-(2-methoxyphenyl)-8-oxo-7-hydropurine-6-carbox-amide<br>76 |
| 2-(2-Fluoro-3-hydroxyphenyl)-9-(2-methoxyphenyl)-8-oxo-7-hydropurine-6-carbox-amide<br>77 | 2-[4-(1-Hydroxy-isopropyl)phenyl]-9-(2-methoxyphenyl)-8-oxo-7-hydropurine-6-carboxamide<br>78 |
| 2-[3-(1-Hydroxy-isopropyl)phenyl]-9-(2-methoxyphenyl)-8-oxo-7-hydropurine-6-carboxamide<br>79 | 9-(2-Methoxyphenyl)-2-(2-nitrophenyl)-8-oxo-7-hydropurine-6-carboxamide<br>80 |
| 9-(2-Methoxyphenyl)-2-(4-nitrophenyl)-8-oxo-7-hydropurine-6-carboxamide<br>81 | 9-(2-Methoxyphenyl)-2-(2-nitrophenyl)-8-oxo-7-hydropurine-6-carboxamide<br>82 |
| 9-(2,4-Difluorophenyl)-2-(3-hydroxyphenyl)-8-oxo-7-hydropurine-6-carboxamide<br>83 | 9-(2-Methoxyphenyl)-2-{3-[(methylsulfonyl)amino]phenyl}-8-oxo-7-hydropurine-6-carboxamide<br>84 |

TABLE 1-continued

| Compound | Compound |
| --- | --- |
| 9-(4-Chloro-2-fluorophenyl)-2-(3-hydroxyphenyl)-8-oxo-7-hydropurine-6-carboxamide<br>85 | 9-(2-Chlorophenyl)-8-oxo-2-(3-pyridyl)-7-hydropurine-6-carboxamide<br>86 |
| 8-Oxo-2-(3-pyridyl)-9-[2-(trifluoromethyl)phenyl]-7-hydropurine-6-carboxamide<br>87 | 9-(3-Chloro-2-fluorophenyl)-2-(3-hydroxyphenyl)-8-oxo-7-hydropurine-6-carboxamide<br>88 |
| 9-(2-Fluoro-3-trifluoromethylphenyl)-2-(3-hydroxyphenyl)-8-oxo-7-hydropurine-6-carboxamide<br>89 | 9-(2,3,4-Trifluorophenyl)-2-(3-hydroxyphenyl)-8-oxo-7-hydropurine-6-carboxamide<br>90 |
| 2-(1H-Benzo[d]imidazol-6-yl)-9-(2-methoxyphenyl)-8-oxo-8,9-dihydro-7H-purine-6-carboxamide<br>91 | 2-[3-(Acetylamino)phenyl]-9-(2-methoxyphenyl)-8-oxo-7-hydropurine-6-carboxamide<br>92 |
| 2-(3-hydroxyphenyl)-8-(2-methoxyphenyl)-6-oxo-5,6,7,8-tetrahydropteridine-4-carboxamide<br>93 | 9-(2-Methoxyphenyl)-8-oxo-2-pyrazol-4-yl-7-hydropurine-6-carboxamide<br>94 |
| 9-(2-Methoxyphenyl)-8-oxo-2-pyrazol-3-yl-7-hydropurine-6-carboxamide<br>95 | 9-(4-Aminocyclohexyl)-2-(3-hydroxyphenyl)-8-oxo-7-hydropurine-6-carboxamide<br>96 |
| 2-[3-(Difluoromethyl)phenyl]-9-(2-methoxyphenyl)-8-oxo-7-hydropurine-6-carbox-amide<br>97 | 2-[5-(Difluoromethyl)-2-fluorophenyl]-9-(2-methoxyphenyl)-8-oxo-7-hydropurine-6-carboxamide<br>98 |
| 2-(1H-benzo[d]imidazol-4-yl)-9-(2-methoxyphenyl)-8-oxo-8,9-dihydro-7H-purine-6-carboxamide<br>99 | 2-(6-Hydroxypyridin-3-yl)-8-oxo-9-(2-(trifluoromethyl)phenyl)-8,9-dihydro-7H-purine-6-carboxamide<br>100 |
| 2-(1H-benzo[d]imidazol-6-yl)-9-(2-fluorophenyl)-8-oxo-8,9-dihydro-7H-purine-6-carboxamide<br>101 | 2-Benzimidazol-6-yl-8-oxo-9-[2-(trifluoromethyl)phenyl]-7-hydropurine-6-carboxamide<br>102 |
| 2-(5-Chloropyridin-3-yl)-8-oxo-9-(2-(trifluoromethyl)phenyl)-8,9-dihydro-7H-purine-6-carboxamide<br>103 | trans-4-(6-Carbamoyl-9-(2-methoxyphenyl)-8-oxo-8,9-dihydro-7H-purin-2-ylamino) cyclohexyl carbamate<br>104 |
| (R)-9-(2-Methoxyphenyl)-8-oxo-2-(pyrrolidin-3-ylamino)-8,9-dihydro-7H-purine-6-carboxamide<br>105 | (S)-9-(2-Methoxyphenyl)-8-oxo-2-(pyrrolidin-3-ylamino)-8,9-dihydro-7H-purine-6-carboxamide<br>106 |
| (cis)-4-(6-Carbamoyl-9-(2-methoxyphenyl)-8-oxo-8,9-dihydro-7H-purin-2-ylamino) cyclohexyl carbamate<br>107 | 2-(trans-4-Hydroxycyclohexylamino)-9-(2-methoxyphenyl)-8-oxo-8,9-dihydro-7H-purine-6-carboxamide<br>108 |
| 2-(4-Chloropyridin-3-yl)-8-oxo-9-(2-(trifluoromethyl)phenyl)-8,9-dihydro-7H-purine-6-carboxamide<br>109 | 2-(cis-4-Hydroxycyclohexylamino)-9-(2-methoxyphenyl)-8-oxo-8,9-dihydro-7H-purine-6-carboxamide<br>110 |
| 2-(4-((1H-Imidazol-1-yl)methyl)phenylamino)-9-(2-methoxyphenyl)-8-oxo-8,9-dihydro-7H-purine-6-carboxamide<br>111 | 2-(4-Hydroxypyridin-3-yl)-8-oxo-9-(2-(trifluoromethyl)phenyl)-8,9-dihydro-7H-purine-6-carboxamide<br>112 |
| (R)-9-(2-Methoxyphenyl)-8-oxo-2-(pyrrolidin-2-ylmethylamino)-8,9-dihydro-7H-purine-6-carboxamide<br>113 | (S)-9-(2-Methoxyphenyl)-8-oxo-2-(pyrrolidin-2-ylmethylamino)-8,9-dihydro-7H-purine-6-carboxamide<br>114 |
| 2-(4-(1H-1,2,4-Triazol-3-yl)phenyl)-9-(2-methoxyphenyl)-8-oxo-7-hydropurine-6-carboxamide<br>115 | 2-(2-Hydroxyethylamino)-9-(2-methoxyphenyl)-8-oxo-8,9-dihydro-7H-purine-6-carboxamide<br>116 |
| 9-(2-Methoxyphenyl)-8-oxo-2-(2-(trifluoromethyl)-1H-benzo[d]imidazol-6-yl)-8,9-dihydro-7H-purine-6-carboxamide<br>117 | 2-(3-(1H-1,2,4-Triazol-3-yl)phenyl)-9-(2-methoxyphenyl)-8-oxo-7-hydropurine-6-carboxamide<br>118 |
| 9-(Biphenyl-2-yl)-2-(3-hydroxyphenyl)-8-oxo-8,9-dihydro-7H-purine-6-carboxamide<br>119 | 2-(4-(1H-1,2,4-Triazol-3-yl)phenyl)-9-(2-fluorophenyl)-8-oxo-7-hydropurine-6-carboxamide<br>120 |
| 2-(4-(1H-1,2,4-Triazol-3-yl)phenyl)-9-(2-isopropylphenyl)-8-oxo-8,9-dihydro-7H-purine-6-carboxamide<br>121 | 9-(2-Methoxyphenyl)-2-(2-methyl-1H-benzo[d]imidazol-6-yl)-8-oxo-8,9-dihydro-7H-purine-6-carboxamide<br>122 |

TABLE 1-continued

| Compound | Compound |
|---|---|
| 2-(3-(Hydroxymethyl)phenylamino)-9-(2-methoxyphenyl)-8-oxo-8,9-dihydro-7H-purine-6-carboxamide<br>123 | 2-(2-(Hydroxymethyl)phenylamino)-9-(2-methoxyphenyl)-8-oxo-8,9-dihydro-7H-purine-6-carboxamide<br>124 |
| 9-(2-tert-Butylphenyl)-2-(3-hydroxyphenyl)-8-oxo-8,9-dihydro-7H-purine-6-carboxamide<br>125 | 2-(3-Hydroxyphenyl)-8-oxo-9-(2-phenoxyphenyl)-8,9-dihydro-7H-purine-6-carboxamide<br>126 |
| 2-(1H-Benzo[d]imidazol-6-yl)-9-(2-isopropylphenyl)-8-oxo-8,9-dihydro-7H-purine-6-carboxamide<br>127 | 2-(1H-Indazol-4-yl)-9-(2-methoxyphenyl)-8-oxo-8,9-dihydro-7H-purine-6-carboxamide<br>128 |
| 2-(2-Hydroxypyridin-3-yl)-8-oxo-9-(2-(trifluoromethyl)phenyl)-8,9-dihydro-7H-purine-6-carboxamide<br>129 | 2-(1H-Imidazo[4,5-b]pyridin-6-yl)-9-(2-methoxyphenyl)-8-oxo-8,9-dihydro-7H-purine-6-carboxamide<br>130 |
| 2-(4-(1H-Imidazol-1-yl)phenyl)-9-(2-isopropylphenyl)-8-oxo-8,9-dihydro-7H-purine-6-carboxamide<br>131 | 9-(2-Cyclohexylphenyl)-2-(3-hydroxyphenyl)-8-oxo-8,9-dihydro-7H-purine-6-carboxamide<br>132 |
| 2-(4-(1H-Imidazol-2-yl)phenyl)-9-(2-isopropylphenyl)-8-oxo-8,9-dihydro-7H-purine-6-carboxamide<br>133 | 2-(1H-Benzo[d]imidazol-1-yl)-9-(2-methoxyphenyl)-8-oxo-8,9-dihydro-7H-purine-6-carboxamide<br>134 |
| 2-(1H-Imidazo[4,5-b]pyridin-6-yl)-9-(2-isopropylphenyl)-8-oxo-8,9-dihydro-7H-purine-6-carboxamide<br>135 | 9-(2-Isopropylphenyl)-8-oxo-2-(1H-pyrrolo[2,3-b]pyridin-5-yl)-8,9-dihydro-7H-purine-6-carboxamide<br>136 |
| 2-(1H-Imidazo[4,5-b]pyridin-6-yl)-8-oxo-9-(2-(trifluoromethyl)phenyl)-8,9-dihydro-7H-purine-6-carboxamide<br>137 | 9-(2-Methoxyphenyl)-2-(2-(methylthio)-1H-benzo[d]imidazol-5-yl)-8-oxo-8,9-dihydro-7H-purine-6-carboxamide<br>138 |
| 2-(1H-Indol-5-yl)-9-(2-isopropylphenyl)-8-oxo-8,9-dihydro-7H-purine-6-carboxamide<br>139 | 9-(Cyclohexylmethyl)-2-(3-hydroxyphenyl)-8-oxo-8,9-dihydro-7H-purine-6-carboxamide<br>140 |
| 9-(2,3-Dihydro-1H-inden-1-yl)-2-(3-hydroxyphenyl)-8-oxo-8,9-dihydro-7H-purine-6-carboxamide<br>141 | 2-(3-Hydroxyphenyl)-9-isobutyl-8-oxo-8,9-dihydro-7H-purine-6-carboxamide<br>142 |
| 9-(trans-4-Methoxycyclohexyl)-2-(3-hydroxyphenyl)-8-oxo-8,9-dihydro-7H-purine-6-carboxamide<br>143 | 9-(cis-4-Methoxycyclohexyl)-2-(3-hydroxyphenyl)-8-oxo-8,9-dihydro-7H-purine-6-carboxamide<br>144 |
| 2-(3-Hydroxyphenyl)-8-oxo-9-(5,6,7,8-tetrahydronaphthalen-1-yl)-8,9-dihydro-7H-purine-6-carboxamide<br>145 | 2-(4-(1H-1,2,4-Triazol-3-yl)phenyl)-9-cyclohexyl-8-oxo-8,9-dihydro-7H-purine-6-carboxamide<br>146 |
| 2-(3-Hydroxyphenyl)-9-(1H-indol-4-yl)-8-oxo-8,9-dihydro-7H-purine-6-carboxamide<br>147 | 9-(2-Fluoro-3-methoxyphenyl)-2-(3-hydroxyphenyl)-8-oxo-8,9-dihydro-7H-purine-6-carboxamide<br>148 |
| 9-(2-Fluoro-5-methoxyphenyl)-2-(3-hydroxyphenyl)-8-oxo-8,9-dihydro-7H-purine-6-carboxamide<br>149 | 9-Cyclohexyl-2-(1H-imidazo[4,5-b]pyridin-6-yl)-8-oxo-8,9-dihydro-7H-purine-6-carboxamide<br>150 |
| 2-(3-Hydroxyphenyl)-8-oxo-9-(tetrahydro-2H-pyran-4-yl)-8,9-dihydro-7H-purine-6-carboxamide<br>151 | 2-(3-Hydroxyphenyl)-8-oxo-9-((tetrahydro-2H-pyran-4-yl)methyl)-8,9-dihydro-7H-purine-6-carboxamide<br>152 |
| 9-(2-Cyclopentylphenyl)-2-(3-hydroxyphenyl)-8-oxo-8,9-dihydro-7H-purine-6-carboxamide<br>153 | 2-(3-Hydroxyphenyl)-8-oxo-9-(piperidin-4-yl)-8,9-dihydro-7H-purine-6-carboxamide<br>154 |
| 9-(2-Fluoro-4-methoxyphenyl)-2-(3-hydroxyphenyl)-8-oxo-8,9-dihydro-7H-purine-6-carboxamide<br>155 | 2-(1H-benzo[d]imidazol-6-yl)-9-cyclohexyl-8-oxo-8,9-dihydro-7H-purine-6-carboxamide<br>156 |
| 2-Benzimidazol-6-yl-9-(trans-4-methoxycyclohexyl)-8-oxo-7-hydropurine-6-carboxamide<br>157 | 2-(4-(Aminomethyl)phenyl)-9-(2-methoxyphenyl)-8-oxo-8,9-dihydro-7H-purine-6-carboxamide<br>158 |
| 2-(3-Hydroxyphenyl)-9-(cis-4-(methoxymethyl)cyclohexyl)-8-oxo-8,9-dihydro-7H-purine-6-carboxamide<br>159 | 9-(trans-4-Aminocyclohexyl)-2-(3-hydroxyphenyl)-8-oxo-8,9-dihydro-7H-purine-6-carboxamide<br>160 |

TABLE 1-continued

| Compound | Compound |
|---|---|
| 2-(3-Hydroxyphenyl)-9-(2-isobutylphenyl)-8-oxo-8,9-dihydro-7H-purine-6-carboxamide 161 | (R)-2-(3-Hydroxyphenyl)-8-oxo-9-(tetrahydrofuran-3-yl)-8,9-dihydro-7H-purine-6-carboxamide 162 |
| (S)-2-(3-Hydroxyphenyl)-8-oxo-9-(tetrahydrofuran-3-yl)-8,9-dihydro-7H-purine-6-carboxamide 163 | 2-(3-(Aminomethyl)phenyl)-9-(2-methoxyphenyl)-8-oxo-8,9-dihydro-7H-purine-6-carboxamide 164 |
| 2-(4-(1H-1,2,3-Triazol-5-yl)phenyl)-9-(2-isopropylphenyl)-8-oxo-8,9-dihydro-7H-purine-6-carboxamide 165 | 2-(4-(1H-1,2,4-Triazol-3-yl)phenyl)-9-(cis-4-methoxycyclohexyl)-8-oxo-8,9-dihydro-7H-purine-6-carboxamide 166 |
| 2-(1H-Benzo[d]imidazol-6-yl)-9-(cis-4-methoxycyclohexyl)-8-oxo-8,9-dihydro-7H-purine-6-carboxamide 167 | 2-(1H-Imidazo[4,5-b]pyridin-6-yl)-9-(cis-4-methoxycyclohexyl)-8-oxo-8,9-dihydro-7H-purine-6-carboxamide 168 |
| 2-(3-Hydroxyphenyl)-9-((1r,4r)-4-(methoxymethyl)cyclohexyl)-8-oxo-8,9-dihydro-7H-purine-6-carboxamide 169 | 9-(2-Isopropylphenyl)-2-(4-(5-methyl-4H-1,2,4-triazol-3-yl)phenyl)-8-oxo-8,9-dihydro-7H-purine-6-carboxamide 170 |

4.3 Methods for Making Heteroaryl Compounds

The Heteroaryl Compounds can be made by one skilled in the art using conventional organic syntheses and commercially available materials. By way of example and not limitation, a Heteroaryl Compound can be prepared as outlined in Schemes 1-8 shown below, as well as in the examples set forth in Section 5.1. It should be noted that one skilled in the art can modify the procedures set forth in the illustrative schemes and examples to arrive at the desired product.

Scheme 1:

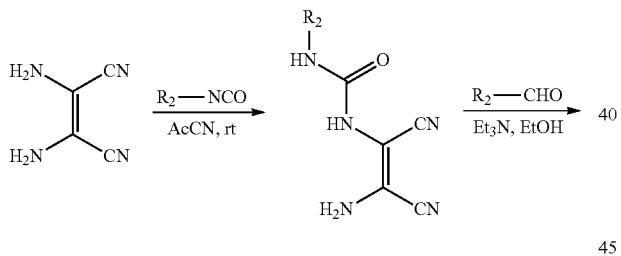

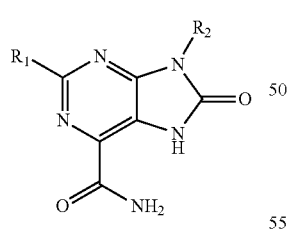

Scheme 2:

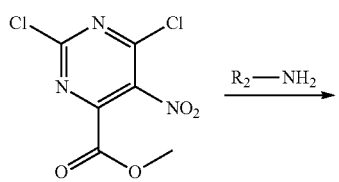

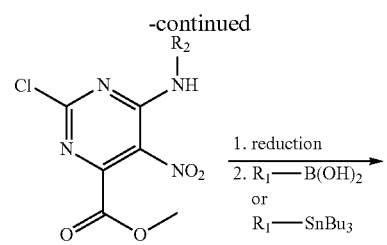

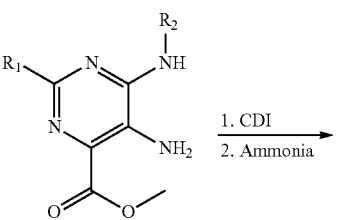

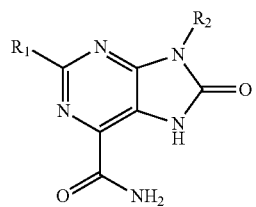

Scheme 3:

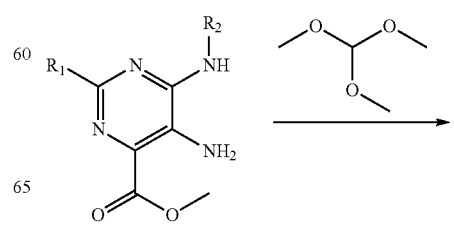

-continued
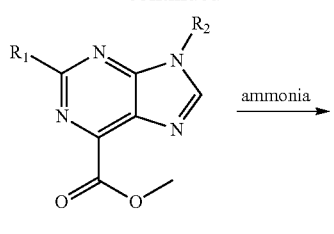
ammonia →
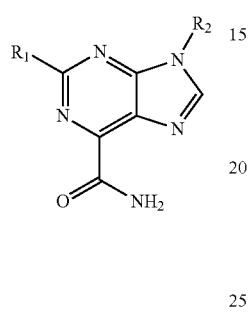
Scheme 4:
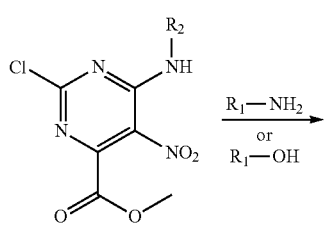
$R_1$—$NH_2$ or $R_1$—OH →
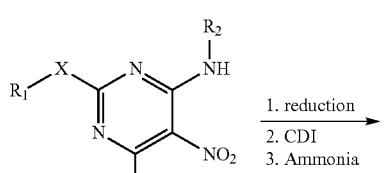
1. reduction
2. CDI
3. Ammonia
→
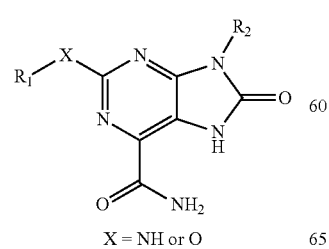
X = NH or O
Scheme 5:
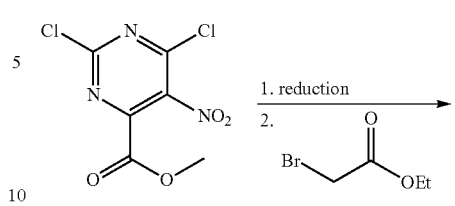
1. reduction
2. Br—CH$_2$—C(O)—OEt
→
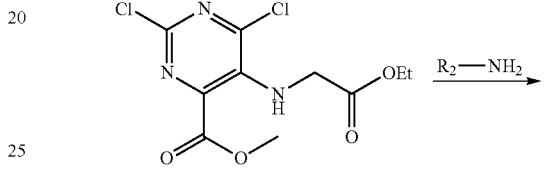
$R_2$—$NH_2$ →
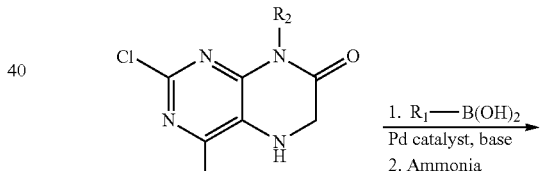
1. $R_1$—B(OH)$_2$, Pd catalyst, base
2. Ammonia
→
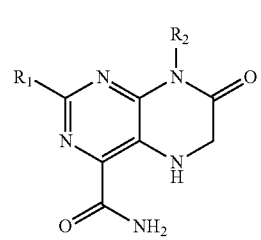

Scheme 6:

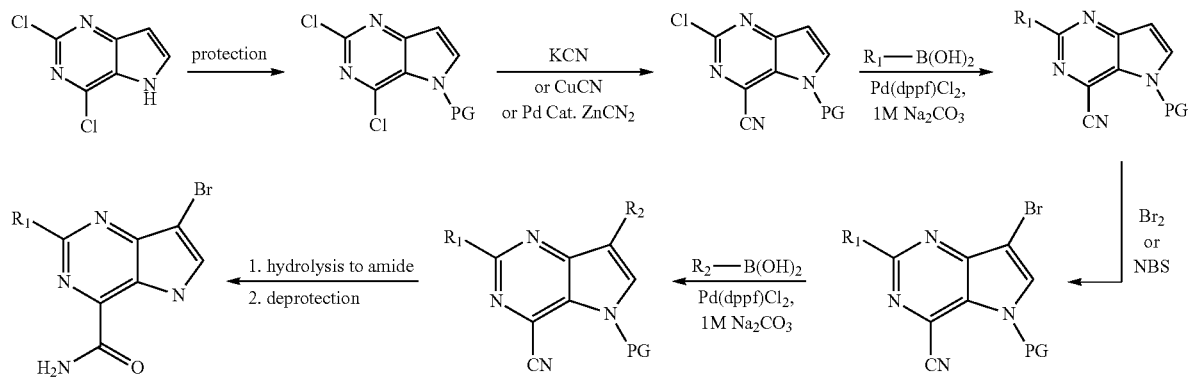

Scheme 7:

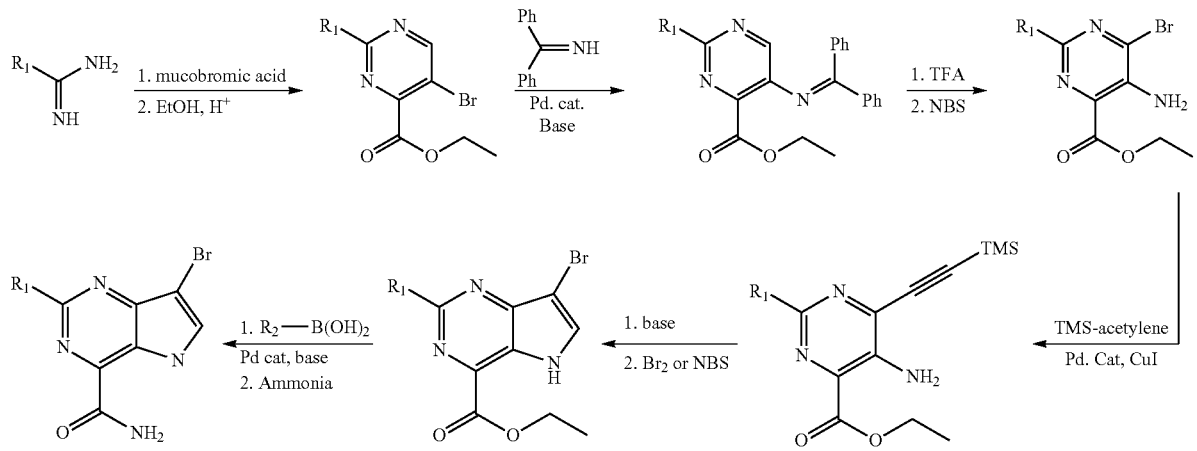

Scheme 8:

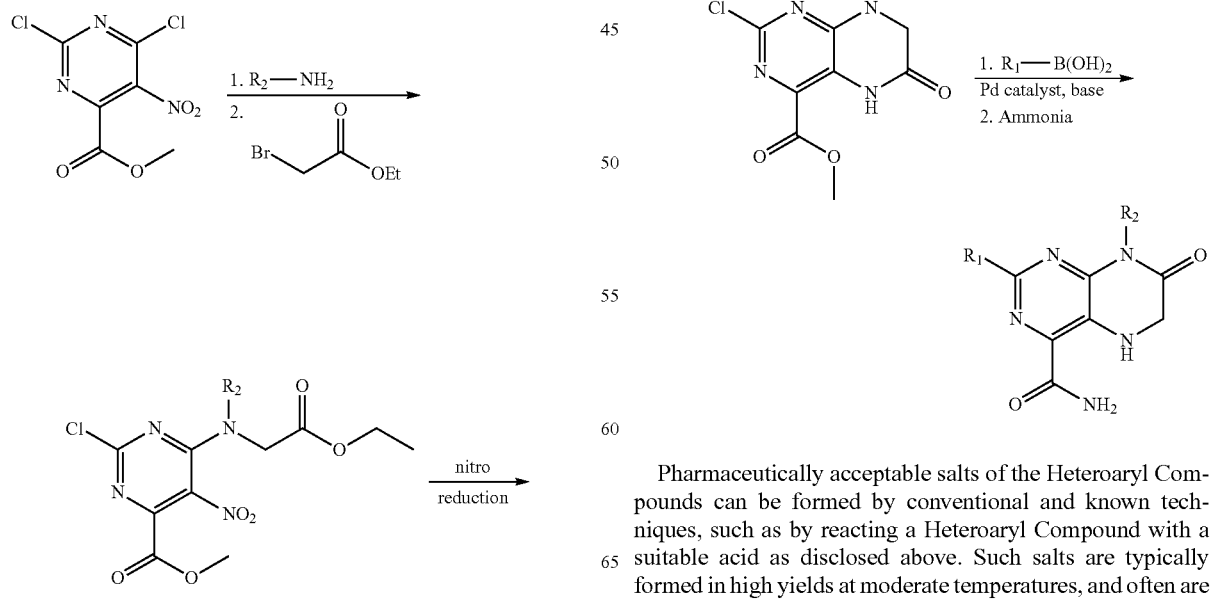

Pharmaceutically acceptable salts of the Heteroaryl Compounds can be formed by conventional and known techniques, such as by reacting a Heteroaryl Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Heteroaryl Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

4.4 Methods of Use

Heteroaryl Compounds described herein have utility as pharmaceuticals to treat or prevent disease in animals or humans. Further, Heteroaryl Compounds described herein are active against kinases (e.g., protein kinases), including those involved in cancer, inflammatory conditions, immunological conditions, neurodegenerative diseases, cardiovascular diseases and metabolic conditions. Without being limited by theory, it is thought the Heteroaryl Compounds are effective for treating and preventing cancer, inflammatory conditions, immunological conditions, neurodegenerative diseases, cardiovascular diseases and metabolic conditions due to their ability to modulate (e.g., inhibit) kinases which are involved in the etiology of these conditions. Accordingly, provided herein are many uses of the Heteroaryl Compounds, including the treatment or prevention of those diseases set forth below. The methods provided herein comprise the administration of an effective amount of one or more Heteroaryl Compounds to a patient in need thereof.

Representative immunological conditions that Heteroaryl Compounds are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Grave's disease and diabetes (e.g., Type I diabetes).

Representative inflammatory conditions that Heteroaryl Compounds are useful for treating or preventing include, but are not limited to, psoriasis, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, diabetes (e.g., Type I diabetes and Type II diabetes) and obesity.

Representative cardiovascular diseases that Heteroaryl Compounds are useful for treating or preventing include, but are not limited to, restenosis, stroke, myocardial infarction or ischemic damage to the heart, lung, gut, kidney, liver, pancreas, spleen or brain.

Representative metabolic conditions that Heteroaryl Compounds are useful for treating or preventing include, but are not limited to, obesity and diabetes (e.g., Type II diabetes).

Representative neurodegenerative diseases that Heteroaryl Compounds are useful for treating or preventing include, but are not limited to, Huntington's disease, Alzheimer's disease and HIV-associated encephalitis.

In a particular embodiment, provided herein are methods for the treatment or prevention of insulin resistance. In certain embodiments, provided herein are methods for the treatment or prevention of insulin resistance that leads to diabetes (e.g., Type II diabetes).

In another embodiment, provided herein are methods for the treatment or prevention of syndrome X or metabolic syndrome.

In another embodiment, provide herein are methods for the treatment or prevention of diabetes.

In another embodiment, provide herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, prediabetes (e.g., impaired glucose metabolism), cystic fibrosis related diabetes, hemochromatosis and ketosis-resistant diabetes.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

Representative cancers that Heteroaryl Compounds are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. Heteroaryl Compounds are also useful for treating or preventing solid tumors and blood born tumors.

Particular cancers within the scope of the methods provided herein include those associated with IKK-2, mTOR, PI3K, SYK or TYK2 kinases and mutants or isoforms thereof. Other cancers within the scope of the methods provided herein include those associated with the pathways of the following kinases: PI3Kα, PI3Kβ, PI3Kδ, Aurora, Abl, KDR, MLK1, CaMKIV, GSK3α, GSK3β, ATM, ATX or DNA-PK kinases and mutants or isoforms thereof.

More particularly, cancers and related disorders that can be treated or prevented by methods and compositions provided herein include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia ($R^{14}$), $R^{14}$ with ringed sideroblasts (RARS), $R^{14}$ with excess blasts (RAEB), RAEB in transformation (RAEB-T), preleukemia and chronic myelomonocytic leukemia (CMML), chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Accordingly, the methods and compositions provided herein are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions disclosed herein. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, kidney or uterus. In other specific embodiments, sarcoma, melanoma, or leukemia is treated or prevented.

In a particular embodiment, the methods and compositions provided herein are also useful for treating, preventing or managing various types of lymphomas (i.e., a heterogenous group of neoplasms arising in the reticuloendothelial and lymphatic systems), such as Non-Hodgkin's lymphoma (NHL) (i.e., a malignant monoclonal proliferation of lymphoid cells in sites of the immune system, including lymph nodes, bone marrow, spleen, liver and gastrointestinal tract). NHLs that the Heteroaryl Compounds are useful for treating or preventing include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma).

In another embodiment, the methods and compositions provided herein are also useful for administration to patients in need of a bone marrow transplant to treat a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., patients suffering from hematologic disorders, congenital immunodeficiences, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In another embodiment, provided herein are methods for the treatment of myeloproliferative disorders or myelodysplastic syndromes, comprising administering to a patient in need thereof an effective amount of a Heteroaryl Compound or a composition thereof. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibro-erythroleukemia; or agnogenic myeloid metaplasia.

In another embodiment, provided herein are methods for the treatment of cancer or tumors resistant to other kinase inhibitors such as imatinib mesylate (STI-571 or Gleevec™) treatment, comprising administering to a patient in need thereof an effective amount of a Heteroaryl Compound or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a patient in need thereof an effective amount of a Heteroaryl Compound or a composition thereof.

In a particular embodiment, provided herein are methods for the treatment or prevention of a disease or disorder associated with the inhibition of IKK-2, mTOR, PI3K, SYK or TYK2. Particular diseases which are treatable or preventable by inhibiting IKK-2, mTOR, PI3K, SYK or TYK2 include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative dieseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

In a specific embodiment, provided herein are methods for treating or preventing leukemia (i.e., malignant neoplasms of the blood-forming tissues) including, but not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

The various types of the cancers are described in U.S. provisional application No. 60/380,842, filed May 17, 2002, the entireties of which are incorporated herein by reference (see, e.g., Section 2.2. Types of Cancers). Specific cancers include, but are not limited to, leukemias such as chronic lymphocytic leukemia, chronic myelocytic leukemia, acute lymphoblastic leukemia, acute myelogenous leukemia, and acute myeloblastic leukemia; advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage 1V non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In one embodiment, the cancer is primary or metastatic. In another embodiment, the cancer is relapsed, refractory or resistance to chemotherapy or radiation; in particular, refractory to thalidomide.

Further provide herein are methods for treating patients who have been previously treated for cancer, but are non-responsive to standard therapies, as well as those who have not previously been treated. Also provided herein are methods for treating patients regardless of patient's age, although some cancers are more common in certain age groups. Still further provided herein are methods for treating patients who have undergone surgery in an attempt to treat the cancer at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In another embodiment, provided herein are methods for the treatment or prevention of a disease or disorder (e.g., a cancer or tumor) associated with the inhibition of PI3Kα, PI3Kβ, PI3Kδ, Aurora, Abl, KDR, MLK1, CaMKIV, GSK3α, GSK3β, ATM, ATX or DNA-PK.

In a particular embodiment, provide herein are methods for the treatment or prevention of a disease or disorder associated with the inhibition of mTOR including, but not limited to, tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (neurofibromin 1), AMPK (AMP-dependent protein kinase STK11, serine/threonine kinase 11), and LKB1. Without being limited by theory, it is thought that genetic defects associated with these proteins results in hyperactivation of the mTOR pathway. Particular diseases which are treatable or preventable through inhibition of the mTOR pathway include, but are not limited to, Cowden's disease, Cowden syndrome, Cowden-like syndrome, Bannayan-Zonana syndrome, Bannayan-Riley-Ruvalcaba syndrome, Lhermitte-Duclos disease, Endometrial carcinoma, Prostate carcinoma and Malignant melanoma, Tuberous sclerosis complex, Lymphangioleiomyomatosis, Neurofibromatosis 1, Familial hypertrophic cardiomyopathy, Peutz-jeghers syndrome, Renal Cell Carcinoma and polycystic kidney disease.

In a particular embodiment, provided herein are methods for the treatment or prevention of a disease or disorder associated with the modulation, for example inhibition, of a kinase, including, but are not limited to, tyrosine-protein kinase (ZAP-70), protein tyrosine kinase 2 beta (PYK2), focal adhesion kinase 1 (FAK), B lymphocyte kinase (BLK), hemopoietic cell kinase (HCK), v-yes-1 Yamaguchi sarcoma viral related oncogene homolog (LYN), T cell-specific protein-tyrosine kinase (LCK), proto-oncogene tyrosine-protein kinase (YES), proto-oncogene tyrosine-protein kinase (SRC), proto-oncogene tyrosine-protein kinase (FYN), proto-oncogene tyrosine-protein kinase (FGR), proto-oncogene tyrosine-protein kinase (FER), proto-oncogene tyrosine-protein kinase (FES), C-SRC kinase, protein-tyrosine kinase (CYL), tyrosine protein kinase (CSK), megakaryocyte-associated tyrosine-protein kinase (CTK), tyrosine-protein kinase receptor (EPH), Ephrin type-A receptor 1, Ephrin type-A receptor 4 (EPHA4), Ephrin type-B receptor 3 (EPHB3), Ephrin type-A receptor 8 (EPHA8), neurotrophic tyrosine kinase receptor, type 1 (NTRK1), protein-tyrosine kinase (PTK2), syk-related tyrosine kinase (SRK), protein tyrosine kinase (CTK), tyro3 protein tyrosine kinase (TYRO3), bruton agammaglobulinemia tyrosine kinase (BTK), leukocyte tyrosine kinase (LTK), protein-tyrosine kinase (SYK), protein-tyrosine kinase (STY), tek tyrosine kinase (TEK), elk-related tyrosine kinase (ERK), tyrosine kinase with immunoglobulin and egf factor homology domains (TIE), protein tyrosine kinase (TKF), neurotrophic tyrosine kinase, receptor, type 3 (NTRK3), mixed-lineage protein kinase-3 (MLK3), protein kinase, mitogen-activated 4 (PRKM4), protein kinase, mitogen-activated 1 (PRKM1), protein tyrosine kinase (PTK7), protein tyrosine kinase (EEK), minibrain (drosophila) homolog (MNBH), bone marrow kinase, x-linked (BMX), eph-like tyrosine kinase 1 (ETK1), macrophage stimulating 1 receptor (MST1R), btk-associated protein, 135 kd, lymphocyte-specific protein tyrosine kinase (LCK), fibroblast growth factor receptor-2 (FGFR2), protein tyrosine kinase-3 (TYK3), protein tyrosine kinase (TXK), tec protein tyrosine kinase (TEC), protein tyrosine kinase-2 (TYK2), eph-related receptor tyrosine kinase ligand 1 (EPLG1), t-cell tyrosine kinase (EMT), eph tyrosine kinase 1 (EPHT1), zona pellucida receptor tyrosine kinase, 95 kd (ZRK), protein kinase, mitogen-activated, kinase 1 (PRKMK1), eph tyrosine kinase 3 (EPHT3), growth arrest-specific gene-6 (GAS6), kinase insert domain receptor (KDR), axl receptor tyrosine kinase (AXL), fibroblast growth factor receptor-1 (FGFR1), v-erb-b2 avian erythroblastic leukemia viral oncogene homolog 2 (ERBB2), fins-like tyrosine kinase-3 (FLT3), neuroepithelial tyrosine kinase (NEP), neurotrophic tyrosine kinase receptor-related 3 (NTRKR3), eph-related receptor tyrosine kinase ligand 5 (EPLG5), neurotrophic tyrosine kinase, receptor, type 2 (NTRK2), receptor-like tyrosine kinase (RYK), tyrosine kinase, b-lymphocyte specific (BLK), eph tyrosine kinase 2 (EPHT2), eph-related receptor tyrosine kinase ligand 2 (EPLG2), glycogen storage disease VIII, eph-related receptor tyrosine kinase ligand 7 (EPLG7), janus kinase 1 (JAK1), fins-related tyrosine kinase-1 (FLT1), protein kinase, camp-dependent, regulatory, type I, alpha (PRKAR1A), wee-1 tyrosine kinase (WEE1), eph-like tyrosine kinase 2 (ETK2), receptor tyrosine kinase musk, insulin receptor (INSR), janus kinase 3 (JAK3), fins-related tyrosine kinase-3 ligand protein kinase c, beta 1 (PRKCB1), tyrosine kinase-type cell surface receptor (HER3), janus kinase 2 (JAK2), lim domain kinase 1 (LIMK1), dual specificity phosphatase 1 (DUSP1), hemopoietic cell kinase (HCK), tyrosine 3-monooxygenase/tryptophan 5-monooxygenase activation protein, eta polypeptide (YWHAH), ret proto-oncogene (RET), tyrosine 3-monooxygenase/tryptophan 5-monooxygenase activation protein, zeta polypeptide (YWHAZ), tyrosine 3-monooxygenase/tryptophan 5-monooxygenase activation protein, beta polypeptide (YWHAB), hepatoma transmembrane kinase (HTK), map kinase 6, phosphatidylinositol 3-kinase, catalytic, alpha polypeptide (PIK3CA), cyclin-dependent kinase inhibitor 3 (CDKN3), diacylglycerol kinase, delta, 130 kd, protein-tyrosine phosphatase, nonreceptor type, 13 (PTPN13), abelson murine leukemia viral oncogene homolog 1 (ABLI), diacylglycerol kinase, alpha (DAGK1), focal adhesion kinase 2, epithelial discoidin domain receptor 1 (EDDR1), anaplastic lymphoma kinase (ALK), phosphatidylinositol 3-kinase, catalytic, gamma polypeptide (PIK3CG), phosphatidylinositol 3-kinase regulatory subunit, (PIK3R1), eph homology kinase-1 (EHK1), v-kit hardy-zuckerman 4 feline sarcoma viral oncogene homolog (KIT), fibroblast growth factor receptor-3 (FGFR3), vascular endothelial growth factor c (VEGFC), epidermal growth factor receptor (EGFR), oncogene (TRK), growth factor receptor-bound protein-7 (GRB7), ras p21 protein activator (RASA2), met proto-oncogene (MET), src-like adapter (SLA), vascular endothelial growth factor (VEGF), vascular endothelial growth factor receptor (VEGFR), nerve growth factor receptor (NGFR), platelet derived growth factor receptor (PDGFR), platelet derived growth factor receptor beta (PDGFRB), dual-specificity tyrosine-(Y)-phosphorylation regulated kinase 2 (DYRK2), dual-specificity tyrosine-(Y)-phosphorylation regulated kinase 3 (DYRK3), dual-specificity tyrosine-(Y)-phosphorylation regulated kinase 4 (DYRK4), dual-specificity tyrosine-(Y)-phosphorylation regulated kinase 1A (DYRK1A), dual-specificity tyrosine-(Y)-phosphorylation regulated kinase 1B (DYRK1B), CDC-like kinase 1 (CLK1), protein tyrosine kinase STY, CDC-like kinase 4 (CLK4), CDC-like kinase 2 (CLK2) or CDC-like kinase 3 (CLK3).

In another embodiment, provided herein are methods for the treatment or prevention of a disease or disorder associated with the modulation, for example inhibition, of serine/threonine kinases or related molecules, including, but not limited to, Akt/protein kinase B, protein kinase A (PKA), CK2, cyclin-dependent kinase 7 (CDK7), rac serine/threonine protein kinase, serine-threonine protein kinase n (PKN), serine/threonine protein kinase 2 (STK2), zipper protein kinase (ZPK), protein-tyrosine kinase (STY), bruton agammaglobulinemia tyrosine kinase (BTK), mkn28 kinase, protein kinase, x-linked (PRKX), elk-related tyrosine kinase (ERK), ribosomal protein s6 kinase, 90 kd, polypeptide 3 (RPS6KA3), glycogen storage disease VIII, death-associated protein kinase 1 (DAPK1), pctaire protein kinase 1 (PCTK1), protein kinase, interferon-inducible double-stranded ma (PRKR), activin a receptor, type II-like kinase 1 (ACVRLK1), protein kinase, camp-dependent, catalytic, alpha (PRKACA), protein kinase, y-linked (PRKY), G protein-coupled receptor kinase 2 (GPRK21), protein kinase c, theta form (PRKCQ), lim domain kinase 1 (LIMK1), phosphoglycerate kinase 1 PGK1), lim domain kinase 2 (LIMK2), c-jun kinase, activin a receptor, type II-like kinase 2 (ACVRLK2), janus kinase 1 (JAK1), elkl motif kinase (EMK1), male germ cell-associated kinase (MAK), casein kinase 2, alpha-prime subunit (CSNK2A2), casein kinase 2, beta polypeptide (CSNK2B), casein kinase 2, alpha 1 polypeptide (CSNK2A1), ret proto-oncogene (RET), hematopoietic progenitor kinase 1, conserved helix-loop-helix ubiquitous kinase (CHUK), casein kinase 1, delta (CSNK1D), casein kinase 1, epsilon (CSNK1E), v-akt murine thyrnoma viral oncogene homolog 1 (AKT1), tumor protein p53 (TP53), protein phosphatase 1, regulatory (inhibitor) subunit 2 (PPP1R2), oncogene pim-1 (PIM1), transforming growth factor-beta receptor, type II (TGFBR2), transforming growth factor-beta receptor, type I (TGFBR1), v-raf murine sarcoma viral oncogene homolog b1 (BRAF), bone morphogenetic receptor type II (BMPR2), v-raf murine sarcoma 3611 viral oncogene homolog 1 (ARAF1), v-raf murine sarcoma 3611 viral oncogene homolog 2 (ARAF2), protein kinase C (PKC), v-kit hardy-zuckerman 4 feline sarcoma viral oncogene homolog (KIT) or c-KIT receptor (KITR).

In another embodiment, provided herein are methods for the treatment or prevention of a disease or disorder associated with the modulation, for example inhibition, of a MAP kinase, including, but not limited to, mitogen-activated protein kinase 3 (MAPK3), p44erk1, p44mapk, mitogen-activated protein kinase 3 (MAP kinase 3; p44), ERK1, PRKM3, P44ERK1, P44MAPK, mitogen-activated protein kinase 1 (MAPK1), mitogen-activated protein kinase kinase 1 (MEK1), MAP2K1protein tyrosine kinase ERK2, mitogen-activated protein kinase 2, extracellular signal-regulated kinase 2, protein tyrosine kinase ERK2, mitogen-activated protein kinase 2, extracellular signal-regulated kinase 2, ERK, p38, p40, p41, ERK2, ERT1, MAPK2, PRKM1, PRKM2, P42MAPK, p41mapk, mitogen-activated protein kinase 7 (MAPK7), BMK1 kinase, extracellular-signal-regulated kinase 5, BMK1, ERK4, ERK5, PRKM7, nemo-like kinase (NLK), likely ortholog of mouse nemo like kinase, mitogen-activated protein kinase 8 (MAPK8), protein kinase JNK1, JNK1 beta protein kinase, JNK1 alpha protein kinase, c-Jun N-terminal kinase 1, stress-activated protein kinase JNK1, JNK, JNK1, PRKM8, SAPK1, JNK1A2, JNK21B1/2, mitogen-activated protein kinase 10 (MAPK10), c-Jun kinase 3, JNK3 alpha protein kinase, c-Jun N-terminal kinase 3, stress activated protein kinase JNK3, stress activated protein kinase beta, mitogen-activated protein kinase 9 (MAPK9), MAP kinase 9, c-Jun kinase 2, c-Jun N-terminal kinase 2, stress-activated protein kinase JNK2, JNK2, JNK2A, JNK2B, PRKM9, JNK-55, JNK2BETA, p54aSAPK, JNK2ALPHA, mitogen-activated protein kinase 14 (MAPK14), p38 MAP kinase, MAP kinase Mxi2, Csaids binding protein, MAX-interacting protein 2, stress-activated protein kinase 2A, p38 mitogen activated protein kinase, cytokine suppressive anti-inflammatory drug binding protein, $R^{1K}$, p38, EXIP, Mxi2, CSBP1, CSBP2, CSPB1, PRKM14, PRKM15, SAPK2A, p38ALPHA, mitogen-activated protein kinase 11 (MAPK11), stress-activated protein kinase-2, stress-activated protein kinase-2b, mitogen-activated protein kinase p38-2, mitogen-activated protein kinase p38beta, P38B, SAPK2, p38-2, PRKM11, SAPK2B, p38Beta, P38BETA2, mitogen-activated protein kinase 13 (MAPK13), stress-activated protein kinase 4, mitogen-activated protein kinase p38 delta, SAPK4, PRKM13, p38delta, mitogen-activated protein kinase 12 (MAPK12), p38gamma, stress-activated protein kinase 3, mitogen-activated protein kinase 3, ERK3, ERK6, SAPK3, PRKM12, SAPK-3, P38GAMMA, mitogen-activated protein kinase 6 (MAPK6), MAP kinase isoform p97, mitogen-activated 5 protein kinase, mitogen-activated 6 protein kinase, extracellular signal-regulated kinase 3, extracellular signal-regulated kinase, p97, ERK3, PRKM6, p97MAPK, mitogen-activated protein kinase 4 (MAPK4), Erk3-related protein kinase, mitogen-activated 4 protein kinase (MAP kinase 4; p63), PRKM4, p63MAPK, ERK3-RELATED or Extracellular signal-regulated kinase 8 (ERK7).

A Heteroaryl Compound can be combined with other pharmacologically active compounds ("second active agents") in methods and compositions described herein. It is believed that certain combinations may work synergistically in the treatment of particular types diseases or disorders, and conditions and symptoms associated with such diseases or disorders. A Heteroaryl Compound can also work to alleviate adverse effects associated with certain second active agents, and vice versa.

One or more second active ingredients or agents can be used in the methods and compositions described herein. Second active agents can be large molecules (e.g., proteins) or small molecules (e.g., synthetic inorganic, organometallic, or organic molecules).

Examples of large molecule second active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with a Heteroaryl Compound vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin;

ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleeve®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), bortezomib, statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Similarly, examples of specific second agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483, 213, 10/411,656, 10/693,794, 10/699,154, and 10/981,189; and U.S. provisional application Nos. 60/554,923, 60/565, 172, 60/626,975, 60/630,599, 60/631,870, and 60/533,862.

Examples of additional second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®g), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of additional second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2ÿ, pentoxifylline, tin etiopurpurin, motexafin lutetium, 9-fluoro-11, 21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of additional second active agents include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of additional second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of additional second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of additional second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interfereon gamma, itraconazole, a combination of dead promastigotes and BCG, leucovorin, corticosteroids, sulfonamide, spiramycin, IgG (serology), trimethoprim, and sulfamethoxazole.

Examples of additional second active agents include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-ÿ), antibodies (e.g., anti-CD40 and IgM), oligonucleotides containing unmethylated CpG motifs, and vaccines (e.g., viral and tumor peptide vaccines).

Examples of additional second active agents include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, diclofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioperazine, tropisetron, and a mixture thereof.

Examples of additional second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises l-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of additional second active agents include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiarrythmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and a mixture thereof.

Examples of additional second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-1a, and interferon gamma-1b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a Heteroaryl Compound and a second active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for Heteroaryl Compounds is oral. Preferred routes of administration for the second active agents or ingredients of the invention are known to those of ordinary skill in the art. See, e.g., *Physicians' Desk Reference*, 1755-1760 (56th ed., 2002).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of a Heteroaryl Compound and any optional additional active agents concurrently administered to the patient.

Further provided herein are methods of reducing, treating and/or preventing adverse or undesired effects associated with conventional therapy including, but not limited to, surgery, chemotherapy, radiation therapy, hormonal therapy, biological therapy and immunotherapy. Heteroaryl Compounds and other active ingredients can be administered to a patient prior to, during, or after the occurrence of the adverse effect associated with conventional therapy.

4.5 Pharmaceutical Compositions and Routes of Administration

The Heteroaryl Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Heteroaryl Compound in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a Heteroaryl Compound to be administered to a patient is rather widely variable and can be subject to the judgment of a health-care practitioner. In general, the Heteroaryl Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the Heteroaryl Compound administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Heteroaryl Compound to a patient in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Heteroaryl Compound to a patient in need thereof. In a particular embodiment, the methods disclosed herein comprise the administration of 400 mg/day, 600 mg/day or 800 mg/day of a Heteroaryl Compound to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Heteroaryl Compound.

In a particular embodiment, provided herein are unit dosage formulation comprising about 100 mg or 400 mg of a Heteroaryl Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Heteroaryl Compound.

A Heteroaryl Compound can be administered once, twice, three, four or more times daily. In a particular embodiment, doses of 600 mg or less are administered as a once daily dose and doses of more than 600 mg are administered twice daily in an amount equal to one half of the total daily dose.

A Heteroaryl Compound can be administered orally for reasons of convenience. In one embodiment, when administered orally, a Heteroaryl Compound is administered with a meal and water. In another embodiment, the Heteroaryl Compound is dispersed in water or juice (e.g., apple juice or orange juice) and administered orally as a suspension.

The Heteroaryl Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Heteroaryl Compound without an additional carrier, excipient or vehicle.

In another embodiment, provided herein are compositions comprising an effective amount of a Heteroaryl Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Heteroaryl Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Heteroaryl Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Heteroaryl Compound can be delayed or prolonged by proper formulation. For example, a slowly soluble pellet of the Heteroaryl Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made longacting, by dissolving or suspending the Heteroaryl Compound in oily or emulsified vehicles that allow it to disperse slowly in the serum.

5. EXAMPLES

The following Examples are presented by way of illustration, not limitation.

5.1 Synthetic Examples

General Procedure A. In a round bottom flask, 2,3-diaminomaleonitrile was dissolved in acetonitrile and stirred at room temperature. The desired isocyanate was added and the reaction was stirred at room temperature overnight. The resulting product was collected by filtration, washed with a small amount of acetonitrile followed by diethyl ether. The filtered material was dried under high vacuum at 60° C. overnight to yield the desired urea.

General Procedure B. The urea starting material was dissolved in methanol and stirred at room temperature until homogeneous. The desired aldehyde and triethylamine were added sequentially. The reaction solution was stirred at room temperature overnight. The resulting heterogeneous mixture was filtered, washed with acetonitrile and diethyl ether to give the desired product.

General Procedure C. In a round bottom flask, ethyl 2,6-dichloro-5-nitropyrimidine-4-carboxylate was dissolved in tetrahydrofuran and stirred at room temperature. The desired amine was added to the reaction at −78° C. under an inert atmosphere. Diisopropylethylamine was then added dropwise over several minutes. The reaction was stirred overnight. The resulting product was concentrated under reduced pressure and purified using appropriate chromatographic techniques.

General Procedure D. The substituted 5-nitropyrimidine and tin (II) chloride dihydrate were dissolved in a mixture of ethanol and DMF. The reaction mixture was allowed to stir for 24 to 48 h. The resulting heterogeneous mixture was concentrated under reduced pressure and triturated with ethyl acetate to give the resulting product.

General Procedure D2. The substituted 5-nitropyrimidine, acetic acid and iron(s) were combined and heated to 65° C. The reaction mixture was monitored via thin layer chromatography. The resulting heterogeneous mixture was concentrated under reduced pressure and partitioned between ethyl acetate and aqueous potassium carbonate solution. The organics were dried over magnesium sulfate, filtered and removed under reduced pressure to afford the title compound.

General Procedure E. The substituted 5-aminopyrimidine, boronic acid, potassium phosphate, dicyclohexyl(2',6'-dimethoxybiphenyl-2-yl)phosphine and palladium (II) acetate were added to tetrahydrofuran and water in a microwave flask. The reaction mixture was heated at 120° C. for 30 min in a Biotage Emrys Optimizer microwave reactor. The reaction mixture was filtered and the solvent was removed under reduced pressure. The crude material was purified using appropriate chromatographic techniques. Fractions containing product were neutralized with potassium carbonate (saturated aqueous solution), extracted with ethyl acetate and dried over magnesium sulfate to provide the title compound.

General Procedure F. The diamine was dissolved in methylene chloride and 1,1'-carbonyldiimidazole was added. The reaction mixture was heated thermally to reflux for 2 to 48 hours or using a Biotage Emrys Optimizer microwave reactor at 120° C. for 30 min. The solvent was removed under reduced pressure and the crude material was purified by appropriate chromatographic techniques to give the title compound.

General Procedure G. A solution of the desired carboxylate was added to anhydrous methanol and cooled to −78° C. The solution was then saturated with ammonia gas. The reaction vessel was sealed at −78° C. and gradually allowed to warm to room temperature. After 24 hours the reaction was chilled to −78° C. and opened to the atmosphere. The volatiles were evaporated and the resulting material was suspended in methanol and filtered. The precipitate was dried under high vacuum to provide the title compound, which was further purified using the appropriate chromatographic techniques.

5.1.1 Example 1

Synthesis of 9-BENZYL-8-OXO-2-(PYRIDIN-3-YL)-8,9-DIHYDRO-7H-PURINE-6-CARBOXAMIDE A. 1-((Z)-2-Amino-1,2-dicyano-vinyl)-3-benzyl-urea. Benzyl isocyanate (1.3 g, 9.7 mmol) and 2,3-diaminomaleonitrile (1.0 g, 9.3 mmol) were reacted in acetonitrile according to General Procedure A. The material was triturated from acetonitrile/diethyl ether. The resultant solid was filtered and dried to give the title compound as an orange solid (0.83 g, 4.4 mmol, 37% yield); MS (ESI) m/z 242.1 [M+1]$^+$.

B. 9-Benzyl-8-oxo-2-(pyridin-3-yl)-8,9-dihydro-7H-purine-6-carboxamide. 1-((Z)-2-Amino-1,2-dicyano-vinyl)-3-benzyl-urea (0.1 g, 0.4 mmol) and 3-pyridine carboxaldehyde (0.1 g, 0.9 mmol) were reacted according to General Procedure B. Product was purified using reverse-phase semi-preparatory HPLC (5-60% acetonitrile+0.1% TFA in H$_2$O+0.1% TFA, over 39 min). Fractions containing the desired material were combined and concentrated under reduced pressure before being passed through a Strata-XC ion exchange column with water, methanol, and 5% ammonium hydroxide in methanol. The resulting solid was dried under high vacuum at 60° C. to afford the title compound as a white solid (0.082 g, 0.24 mmol, 59% yield). $^1$H NMR (400 MHz, DMSO-d$_6$) δ 11.76 (s, 1H), 9.70 (d, J=1.6, 1H), 8.86 (dt, J=8.2, 2.0, 1H), 8.67 (dd, J=4.7, 1.6, 1H), 8.58 (s, 1H), 7.96 (s, 1H), 7.53 (dd, J=7.8, 5.1, 1H), 7.44 (d, J=7.0, 2H), 7.35 (t, J=7.4, 2H), 7.26-7.31 (m, 1H), 5.12 (s, 2H); MS (ESI) m/z 347.1 [M+1]$^+$; mp 334-335° C.

5.1.2 Example 2

Synthesis of 2-(4-HYDROXYPHENYL)-9-(2-METHOXYPHENYL)-8-OXO-8,9-DIHYDRO-7H-PURINE-6-CARBOXAMIDE A. (Z)-1-(2-Amino-1,2-dicyanovinyl)-3-(2-methoxyphenyl)urea In a round bottom flask, 2,3-diaminomaleonitrile (3.41 g, 31.62 mmol) was dissolved in acetonitrile (60 mL) and stirred at room temperature. 2-Methoxyphenylisocyanate (5.0 g, 33.5 mmol) was added and the solution was stirred at room temperature for 16 hours. The resultant urea product was collected by filtration, washed with small portions of acetonitrile, followed by diethyl ether. The filtered material was dried under high vacuum at 60° C. overnight to yield the title compound (4.10 g, 51%). MS (ESI) m/z 258.0 [M+1]$^+$.

B. 2-(4-Hydroxyphenyl)-9-(2-methoxyphenyl)-8-oxo-8,9-dihydro-7H-purine-6-carbox-amide. (Z)-1-(2-Amino-1,2-dicyanovinyl)-3-(2-methoxyphenyl)urea (0.200 g, 0.778 mmol) was dissolved in methanol (15 ml) and stirred at room temperature until homogeneous. Triethylamine (0.15 mL)

and 4-hydroxybenzaldehyde (0.208 g, 1.71 mmol) were then added sequentially. The solution was allowed to stir at ambient temperature for 16 h. The resultant heterogeneous mixture was filtered, washed with additional acetonitrile followed by diethyl ether to afford the title compound (0.091 g, 31%). $^1$H NMR (400 MHz, DMSO-d$_6$) δ 11.61 (s, 1H), 9.79 (s, 1H), 8.42 (s, 1H), 8.18 (d, J=8.7, 2H), 7.94 (s, 1H), 7.53 (t, J=7.99, 1H), 7.47 (d, J=7.59, 1H), 7.28 (d, J=7.9, 1H), 7.15 (t, J=7.59, 1H), 6.78 (d, J=8.79, 2H); MS (ESI) m/z 378.1 [M+1]$^+$; mp 362-363° C.

5.1.3 Example 3

Synthesis of 2-(3-HYDROXYPHENYL)-8-OXO-9-O-TOLYL-8,9-DIHYDRO-7H-PURINE-6-CARBOXAMIDE A. (Z)-1-(2-Amino-1,2-dicyanovinyl)-3-(2-methoxyphenyl)urea. Diaminomaleonitrile (600 mg, 5.55 mmol) and o-tolyl isocyanate (0.729 mL, 5.88 mmol) were reacted in acetonitrile according to General Procedure A to give the title compound (604.8 mg, 42%). MS (ESI) m/z 242.2 [M+1]$^+$.

B. 2-(3-Hydroxyphenyl)-8-oxo-9-o-tolyl-8,9-dihydro-7H-purine-6-carboxamide. (Z)-1-(2-Amino-1,2-dicyanovinyl)-3-(2-methoxyphenyl)urea (0.2 g, 0.83 mmol), 3-hydroxybenzaldehyde (0.221 g, 1.81 mmol) and triethylamine (0.1 mL) were reacted according to General Procedure B. The resulting precipitate was dissolved in DMF and water was added to induce precipitation. This precipitate was filtered off and dried under vacuum to provide the title compound in 95% purity (0.188 g, 63%). $^1$H NMR (400 MHz, DMSO-d$_6$) δ 11.79 (s, 1H), 9.47 (s, 1H), 8.40 (s, 1H), 7.98 (s, 1H), 7.89 (d, J=8.00, 1H), 7.67 (s, 1H), 7.49-7.43 (overlapping m, 4H), 7.22 (t, J=8.00, 1H), 6.81 (d, J=6.05, 1H), 2.16 (s, 3H). MS (ESI) m/z 362.1 [M+1]$^+$; mp 366-367° C.

5.1.4 Example 4

Synthesis of 2-(1H-INDOL-4-YL)-9-(2-METHOXYPHENYL)-8-OXO-8,9-DIHYDRO-7H-PURINE-6-CARBOXAMIDE A. 2-(1H-Indol-4-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (see Example 2.A) (0.2 g, 0.78 mmol), indole-4-carboxaldehyde (0.246 g, 1.7 mmol) and triethylamine (0.1 mL) were reacted according to General Procedure B. The resulting precipitate was dissolved in DMF and water was added to induce precipitation. This precipitate was filtered off and dried under vacuum to provide the title compound in 98.8% purity (0.122 g, 39%). $^1$H NMR (400 MHz, DMSO-d$_6$) δ 11.68 (s, 1H), 11.19 (s, 1H), 8.23 (m, 2H), 8.02 (s, 1H), 7.57 (m, 2H), 7.48 (d, J=8.20, 1H), 7.31 (m, 2H), 7.17 (m, 2H), 7.01 (s, 1H), 3.76 (s, 3H); MS (ESI) m/z 401.3 [M+1]$^+$; mp 312-313° C.

5.1.5 Example 5

Synthesis of 2-(1H-INDOL-6-YL)-9-(2-METHOXYPHENYL)-8-OXO-8,9-DIHYDRO-7H-PURINE-6-CARBOXAMIDE A. 2-(1H-Indol-6-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (see Example 2.A) (0.2 g, 0.78 mmol), indole-6-carboxaldehyde (0.246 g, 1.7 mmol) and triethylamine (0.1 mL) were reacted according to General Procedure B. The resulting precipitate was dissolved in DMF and water was added to induce precipitation. This precipitate was filtered off and dried under vacuum to provide the title compound in 97.5% purity (0.116 g, 37%). $^1$H NMR (400 MHz, DMSO-d$_6$) δ 11.62 (s, 1H), 11.18 (s, 1H), 8.41 (s, 1H), 8.32 (s, 1H), 8.17 (dd, J=9.76, 1.37, 1H), 7.97 (s, 1H), 7.55 (m, 3H), 7.41 (t, J=2.6, 1H), 7.31 (d, J=8.2, 1H), 7.18 (t, J=7.7, 1H), 6.43 (s, 1H), 3.76 (s, 3H); MS (ESI) m/z 401.3 [M+1]$^+$; mp 203-204° C.

5.1.6 Example 6

Synthesis of 2-(3-HYDROXYPHENYL)-9-(4-METHOXYPHENYL)-8-OXO-8,9-DIHYDRO-7H-PURINE-6-CARBOXAMIDE A. (Z)-1-(2-Amino-1,2-dicyanovinyl)-3-(4-methoxyphenyl)urea. In a round bottom flask, 2,3-diaminomaleonitrile (2.0 g, 18.50 mmol) was dissolved in acetonitrile (25 mL) and stirred at room temperature. 4-Methoxyphenylisocyanate (2.92 g, 19.61 mmol) was added and the solution was stirred at room temperature for 16 hours. The resultant urea product was collected by filtration, washed with small portions of acetonitrile followed by diethyl ether. The filtered material was dried under high vacuum at 60° C. overnight to yield the title compound (4.39 g, 92%). MS (ESI) m/z 258.3 [M+1]$^+$.

B. 2-(3-Hydroxyphenyl)-9-(4-methoxyphenyl)-8-oxo-8,9-dihydro-7H-purine-6-carbox-amide. (Z)-1-(2-Amino-1,2-dicyanovinyl)-3-(2-methoxyphenyl)urea (0.250 g, 0.972 mmol) was dissolved in methanol (15 ml) and stirred at room temperature until homogeneous. Triethylamine (0.2 mL) and 3-hydroxybenzaldehyde (0.261 g, 2.13 mmol) were then added sequentially. The solution was allowed to stir for 16 hours at ambient temperature. The resultant heterogeneous mixture was filtered, washed with additional acetonitrile followed by diethyl ether to afford the crude cyclized product. The resultant solid was triturated with dimethylformamide/water while sonicating. This solid was again triturated with methanol/water while sonicating to afford the title compound (0.087 g, 23%). $^1$H NMR (400 MHz, DMSO-d$_6$) δ 11.69 (s, 1H), 9.47 (s, 1H), 8.36 (s, 1H), 7.75 (s, 1H), 7.58 (d, J=7.99, 1H), 7.25 (t, J=7.99, 1H), 7.15 (t, J=7.99, 2H), 6.83 (d, J=7.99, 1H); MS (ESI) m/z 378.5 [M+1]$^+$; mp 386-388° C.

5.1.7 Example 7

Synthesis of 2-(2-HYDROXYPYRIDIN-4-YL)-9-(2-METHOXYPHENYL)-8-OXO-8,9-DIHYDRO-7H-PURINE-6-CARBOXAMIDE A. 2-(2-Hydroxypyridin-4-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (See Example 2.A) (0.2 g, 0.78 mmol), 2-hydroxyisonicotinaldehyde (0.209 g, 1.7 mmol) and triethylamine (0.1 mL) were reacted according to General Procedure B. The resulting precipitate was dissolved in DMF and water was added to induce precipitation. This precipitate was filtered off and dried under vacuum to provide the title compound in 97.6% purity (0.2 g, 68%). $^1$H NMR (400 MHz, DMSO-d$_6$) δ 11.91 (s, 1H), 11.64 (s, 1H), 8.57 (s, 1H), 7.98 (s, 1H), 7.55 (t, J=7.9, 1H), 7.49 (d, J=7.8, 1H), 7.40 (d, J=6.4, 1H), 7.29 (m, 2H), 7.14 (m, 2H), 3.74 (s, 3H); MS (ESI) m/z 379.4 [M+1]$^+$; mp 360-362° C.

5.1.8 Example 8

Synthesis of 9-(2-CHLOROPHENYL)-2-(3-HYDROXYPHENYL)-8-OXO-8,9-DIHYDRO-7H-PURINE-6-CARBOXAMIDE A. (Z)-1-(2-amino-1,2-dicyanovinyl)-3-(2-chlorophenyl) urea. 2-Chlorophenyl-isocyanate (1.0 g, 9.2 mmol) and 2,3-diaminomaleonitrile (1.5 g, 9.7 mmol) were reacted in acetonitrile according to General Procedure A. The resulting solid was filtered and dried under high vacuum (1.1 g, 4.2 mmol, 45% yield); MS (ESI) m/z 262.1 [M+1]$^+$.

B. 9-(2-Chlorophenyl)-2-(3-hydroxyphenyl)-8-oxo-8,9-dihydro-7H-purine-6-carboxamide. (Z)-1-(2-Amino-1,2-dicyanovinyl)-3-(2-chlorophenyl)urea (0.25 g, 1.0 mmol) and 3-hydroxy benzaldehyde (0.13 g, 1.1 mmol) were reacted according to General Procedure B. Product was purified using reverse-phase semi-preparatory HPLC (5-60% acetonitrile+ 0.1% TFA in H$_2$O+0.1% TFA, over 39 min). Fractions containing the desired material were combined and concentrated under reduced pressure before being passed through a Strata-XC ion exchange column with water, methanol, and 5% ammonium hydroxide in methanol. The resultant solid was dried under high vacuum at 60° C. to afford the title compound as a white solid (0.030 g, 0.079 mmol, 8% yield). $^1$H NMR (400 MHz, DMSO-d$_6$) δ 11.90 (s, 1H), 9.48 (s, 1H), 8.43 (s, 1H), 8.02 (s, 1H), 7.89 (d, J=7.8, 1H), 7.79 (dd, J=7.4, 2.0, 1H), 7.74 (dd, J=7.0, 2.3, 1H), 7.59-7.68 (m, 3H), 7.23 (t, J=8.0, 1H), 6.82 (dd, J=8.0, 2.5, 1H); MS (ESI) m/z 382.0 [M+1]$^+$; mp 360-364° C.

5.1.9 Example 9

Synthesis of 9-(2-FLUOROPHENYL)-2-(3-HYDROXYPHENYL)-8-OXO-7-HYDROPURINE-6-CARBOXAMIDE A. (Z)-1-(2-Amino-1,2-dicyanovinyl)-3-(2-fluorophenyl) urea. Diamino-maleonate (1.0 g, 9.25 mmol) and 2-fluorophenyl isocyanate (1.10 mL, 9.71 mmol) were reacted in acetonitrile (20 mL) according to General Procedure A. Material was dried in the vacuum oven overnight to give the title compound as a solid (0.34 g, 19%). MS (ESI) m/z 234.2 [M+1]$^+$.

B. 9-(2-Fluorophenyl)-2-(3-hydroxyphenyl)-8-oxo-7-hydropurine-6-carboxamide. A solution of (Z)-1-(2-amino-1,2-dicyanovinyl)-3-(2-fluorophenyl)urea (0.25 g, 1.24 mmol), 3-hydroxybenzaldehyde (0.33 g, 2.72 mmol), and triethylamine (0.2 mL) in methanol (15 mL) were reacted according to General Procedure B. The resulting product was taken up in DMF (3 mL) and triturated with deionized water. The resulting precipitate was filtered, washed with deionized water, and dried under high vacuum at 60° C. to provide the title compound (0.18 g, 39%). $^1$H NMR (400 MHz, DMSO-d$_6$) δ 11.89 (s, 1H), 9.48 (s, 1H), 8.41 (s, 1H), 8.00 (s, 1H), 7.91 (d, J=7.8, 1H), 7.69-7.74 (m, 2H), 7.61-7.68 (m, 1H), 7.55 (td, J=9.3, 1.0, 1H), 7.46 (td, J=7.6, 1.2, 1H), 7.24 (t, J=7.8, 1H), 6.85 (d, J=1.6, 1H), 6.83 (dd, J=2.7, 0.8, 1H); MS (ESI) m/z 366.3 [M+1]$^+$.

5.1.10 Example 10

Synthesis of 9-(2,6-DIFLUOROPHENYL)-2-(3-HYDROXYPHENYL)-8-OXO-8,9-DIHYDRO-7H-PURINE-6-CARBOXAMIDE A. (Z)-1-(2-Amino-1,2-dicyanovinyl)-3-(2,6-difluorophenyl)urea. Diaminomaleonitrile (600 mg, 5.55 mmol) and 2,6-difluorophenyl isocyanate (0.912 mL, 5.88 mmol) were reacted in acetonitrile according to General Procedure A to give the title compound (550 mg, 38%); MS (ESI) m/z 264.2 [M+1]$^+$.

B. 9-(2,6-Difluorophenyl)-2-(3-hydroxyphenyl)-8-oxo-8,9-dihydro-7H-purine-6-carbox-amide. (Z)-1-(2-Amino-1,2-dicyanovinyl)-3-(2,6-difluorophenyl)urea (0.2 g, 0.76 mmol), 3-hydroxybenzaldehyde (0.202 g, 1.66 mmol) and triethylamine (0.1 mL) were reacted according to General Procedure B. The resulting precipitate was dissolved in DMF and water was added to induce precipitation. This precipitate was filtered off and dried under vacuum to provide the title compound in 99.7% purity (0.135 g, 46%). $^1$H NMR (400 MHz, DMSO-d$_6$) δ 12.09 (s, 1H), 9.49 (s, 1H), 8.43 (s, 1H), 8.04 (s, 1H), 7.91 (d, J=7.81, 1H), 7.76 (m, 1H), 7.71 (s, 1H), 7.49 (t, J=8.0, 2H), 7.25 (t, J=8.00, 1H), 6.84 (d, J=8.2, 1H); MS (ESI) m/z 384.4 [M+1]$^+$; mp 355-358° C.

5.1.11 Example 11

Synthesis of 9-CYCLOHEPTYL-8-OXO-2-(3-PYRIDYL)-7-HYDROPURINE-6-CARBOXAMIDE

A. (Z)-1-(2-amino-1,2-dicyanovinyl)-3-cycloheptylurea. 2,3-Diaminomaleonitrile (1.0 g, 9.25 mmol) and cycloheptyl isocyanate (1.29 mL, 9.71 mmol) were reacted in acetonitrile (20 mL) at 50° C. according to General Procedure A. Material was dried under high vacuum at 60° C. overnight to give the title compound as a solid (0.80 g, 35%). MS (ESI) m/z 248.4 [M+1]$^+$.

B. 9-Cycloheptyl-8-oxo-2-(3-pyridyl)-7-hydropurine-6-carboxamide. A solution of (Z)-1-(2-amino-1,2-dicyanovinyl)-3-cycloheptylurea (0.25 g, 1.01 mmol), 3-hydroxy benzaldehyde (0.21 g, 2.22 mmol), and triethylamine (0.2 mL) in methanol (15 mL) were reacted according to General Procedure B. The resulting product was taken up in DMF (3 mL) and triturated with deionized water. This precipitate was filtered, washed with deionized H$_2$O, and dried under high vacuum at 60° C. to provide the title compound (0.02 g, 7%). $^1$H NMR (400 MHz, DMSO-d$_6$) δ 11.56 (s, 1H), 9.70 (d, J=1.2, 1H), 8.86 (dt, J=8.1, 1.8, 1H), 8.68 (d, J=3.5, 1H), 8.54 (s, 1H), 7.91 (s, 1H), 7.55 (dd, J=7.8, 4.7, 1H), 4.43-4.51 (m, 1H), 2.33-2.45 (m, 2H), 1.86-1.93 (m, 3H), 1.81-1.85 (m, 1H), 1.61-1.72 (m, 4H), 1.49-1.60 (m, 2H); MS (ESI) m/z 353.5 [M+1]$^+$.

5.1.12 Example 12

Synthesis of 9-(2-METHOXYPHENYL)-8-OXO-2-(QUINOLIN-5-YL)-8,9-DIHYDRO-7H-PURINE-6-CARBOXAMIDE A. 9-(2-Methoxyphenyl)-8-oxo-2-(quinolin-5-yl)-8,9-dihydro-7H-purine-6-carboxamide. (Z)-1-(2-Amino-1,2-dicyanovinyl)-3-(2-methoxyphenyl)urea (See Example 2.A) (0.250 g, 0.972 mmol) was dissolved in methanol (15 ml) and stirred at room temperature until homogeneous. Triethylamine (0.2 mL) and quinoline-5-carboxaldehyde (0.305 g, 1.945 mmol) were then added and the solution was allowed to stir for 16 hours. The resultant heterogeneous mixture was filtered, washed with additional acetonitrile, followed by diethyl ether, to afford the crude cyclized product. The solid was triturated with dimethylformamide/water while sonicating. This solid was again triturated with methanol/water while sonicating to afford the title compound (0.184 g, 46%). $^1$H NMR (400 MHz, DMSO-d$_6$) δ 11.88 (s, 1H), 9.00 (d, J=8.79, 1H), 8.90 (m, 1H), 8.21 (m, 2H), 8.10 (d, J=8.39, 1H), 8.00 (s, 1H), 7.83 (t, J=7.59, 1H), 7.51 (m, 3H), 7.28 (d, J=7.59, 1H), 7.12 (t, J=7.60, 1H); MS (ESI) m/z 413.0 [M+1]$^+$; mp 335-337° C.

5.1.13 Example 13

Synthesis of 2-CYCLOPENTYL-9-(2-METHOX-YPHENYL)-8-OXO-8,9-DIHYDRO-7H-PURINE-6-CARBOXAMIDE A. 2-Cyclopentyl-9-(2-methoxyphenyl)-8-oxo-8,9-dihydro-7H-purine-6-carboxamide. To a solution containing (Z)-1-(2-amino-1,2-dicyanovinyl)-3-(2-methoxyphenyl)urea (See Example 2.A) (0.250 g, 0.972 mmol) in methanol (15 ml) and triethylamine (0.2 mL) was added cyclopentanecarboxaldehyde (0.190 g, 1.94 mmol). The solution was allowed to stir for 16 hours at ambient temperature. The resultant heterogeneous mixture was filtered, washed with additional acetonitrile followed by diethyl ether to afford the crude cyclized product. The solid was triturated with dimethylformamide/water while sonicating. The solid was then washed with additional water followed by a small portion of methanol to afford the title compound after drying (0.146 g, 42%). $^1$H NMR (400 MHz, DMSO-d$_6$) δ 11.52 (s, 1H), 8.01 (s, 1H), 7.89 (s, 1H), 7.51 (t, J=7.19, 1H), 7.41 (d, J=7.99, 1H), 7.23 (d, J=8.39, 1H), 7.10 (t, J=7.19, 1H), 3.72 (s, 3H), 3.14 (m, 1H), 1.90 (m, 2H), 1.80 (m, 2H), 1.69 (m, 2H), 1.56 (m, 2H); MS (ESI) m/z 354.0 [M+1]$^+$; mp 244-246° C.

5.1.14 Example 14

Synthesis of 9-(2-METHOXYPHENYL)-8-OXO-2-(3-(TRIFLUOROMETHYL)PHENYL)-8,9-DIHYDRO-7H-PURINE-6-CARBOXAMIDE A. 9-(2-Methoxyphenyl)-8-oxo-2-(3-(trifluoromethyl)phenyl)-8,9-dihydro-7H-purine-6-carboxamide. (Z)-1-(2-Amino-1,2-dicyanovinyl)-3-(2-methoxyphenyl)urea (See Example 2.A) (0.40 g, 1.6 mmol) and 3-(trifluoromethyl)benzaldehyde (0.28 g, 1.6 mmol) were reacted according to General Procedure B. The resultant heterogeneous mixture was filtered, and then triturated with dimethylformamide/water while sonicating. The resultant solid was washed with diethyl ether and then dried under high vacuum at 60° C. to afford the title compound as a white solid (0.047 g, 0.11 mmol, 7% yield). $^1$H NMR (400 MHz, DMSO-d$_6$) δ 11.90 (s, 1H), 9.48 (s, 1H), 8.43 (s, 1H), 8.02 (s, 1H), 7.89 (d, J=7.8, 1H), 7.79 (dd, J=7.4, 2.0, 1H), 7.74 (dd, J=7.0, 2.3, 1H), 7.59-7.68 (m, 3H), 7.23 (t, J=8.0, 1H), 6.82 (dd, J=8.0, 2.5, 1H); MS (ESI) m/z 430.0 [M+1]$^+$; mp 271-275° C.

5.1.15 Example 15

Synthesis of 2-(6-METHOXY(3-PYRIDYL))-9-(2-METHOXYPHENYL)-8-OXO-7-HYDROPURINE-6-CARBOXAMIDE A. 2-(6-Methoxy(3-pyridyl))-9-(2-methoxyphenyl)-8-oxo-7-hydropurine-6-carboxamide. A solution of (Z)-1-(2-amino-1,2-dicyanovinyl)-3-(2-methoxyphenyl)urea (see Example 2.A) (0.25 g, 0.97 mmol), 6-methoxy-3-pyridine carboxaldehyde (0.30 g, 2.14 mmol), and triethylamine (0.2 mL) in methanol (10 mL) were reacted according to General Procedure B. The resulting product was taken up in DMF (3 mL) and triturated with deionized water. This precipitate was filtered, stirred in refluxing methanol for 15 min, and hot filtered. This precipitate was subsequently dried in the vacuum oven to yield the title compound (0.22 g, 58%). $^1$H NMR (400 MHz, DMSO-d$_6$) δ 11.73 (s, 1H), 9.15 (d, J=2.3, 1H), 8.53-8.57 (m, 2H), 7.96 (s, 1H), 7.53-7.58 (m, 1H), 7.49 (dd, J=7.6, 1.8, 1H), 7.29 (dd, J=8.4, 1.0, 1H), 7.15 (td, J=7.6, 1.2, 1H), 6.87 (d, J=9.0, 1H), 3.90 (s, 3H), 3.75 (s, 3H); MS (ESI) m/z 393.2 [M+1]$^+$.

5.1.16 Example 16

Synthesis of 2-(3-HYDROXYPHENYL)-8-OXO-9-(4-(TRIFLUOROMETHYL)PHENYL)-8,9-DIHYDRO-7H-PURINE-6-CARBOXAMIDE A. 1-((Z)-2-Amino-1,2-dicyano-vinyl)-3-trifluoromethyl-phenyl)-urea. 4-(Trifluoromethyl)phenyl-isocyanate (1.0 g, 9.2 mmol) and 2,3-diaminomaleonitrile (1.5 g, 9.7 mmol) were reacted according to General Procedure A. The resulting yellow/green compound was filtered and dried under high vacuum (1.1 g, 4.2 mmol, 45% yield). MS (ESI) m/z 262.1 [M+1]$^+$.

B. 2-(3-Hydroxyphenyl)-8-oxo-9-(4-(trifluoromethyl)phenyl)-8,9-dihydro-7H-purine-6-carboxamide. 1-((Z)-2-Amino-1,2-dicyano-vinyl)-3-trifluoromethyl-phenyl)-urea (0.30 g, 1.0 mmol) and 3-hydroxybenzaldehyde (0.13 g, 1.1 mmol) were reacted according to General Procedure B. The crude residue was triturated with dimethylformamide/water while sonicating. The resulting product was dried under high vacuum at 60° C. to afford the title compound as a yellow solid (146 mg, 0.352 mmol, 35% yield). $^1$H NMR (400 MHz, DMSO-d$_6$) δ 1.90 (s, 1H), 9.51 (s, 1H), 8.44 (s, 1H), 8.00-8.07 (m, 5H), 7.98 (d, J=8.2, 1H), 7.80-7.82 (m, 1H), 7.27 (t, J=8.0, 1H), 6.86 (dd, J=7.6, 2.9, 1H); MS (ESI) m/z 382.0 [M+1]$^+$; mp 360-364° C.

5.1.17 Example 17

Synthesis of 9-BENZYL-2-(3-HYDROXYPHE-NYL)-8-OXO-8,9-DIHYDRO-7H-PURINE-6-CARBOXAMIDE A. 9-Benzyl-2-(3-hydroxyphenyl)-8-oxo-8,9-dihydro-7H-purine-6-carboxamide. 1-((Z)-2-Amino-1,2-dicyano-vinyl)-3-benzyl-urea (See Example 1.A) (0.50 g, 2.1 mmol) and 3-hydroxybenzaldehyde (0.27 g, 2.2 mmol) were reacted according to General Procedure B. The resultant heterogeneous mixture was filtered, and then washed with additional acetonitrile and diethyl ether to afford the crude crystallized product. The solid was triturated with dimethylformamide/water while sonicating. The product was filtered and dried under high vacuum at 60° C. to afford the title compound as a white solid (0.082 g, 0.24 mmol, 59% yield). $^1$H NMR (400 MHz, DMSO-d$_6$) δ 11.66 (s, 1H), 9.53 (s, 1H), 8.35 (s, 1H), 8.02 (d, J=7.8, 1H), 7.95 (s, 1H), 7.90-7.92 (m, 1H), 7.43 (s, 1H), 7.41 (s, 1H), 7.35 (t, J=7.4, 2H), 7.28 (td, J=7.5, 2.9, 2H), 6.87 (dd, J=7.4, 2.0, 1H), 5.09 (s, 2H); MS (ESI) m/z 362.1 [M+1]$^+$; mp 362-366° C.

5.1.18 Example 18

Synthesis of 2-(3-HYDROXYPHENYL)-8-OXO-9-[2-(TRIFLUOROMETHOXY)PHENYL]-7-HY-DROPURINE-6-CARBOXAMIDE A. (Z)-1-(2-Amino-1,2-dicyanovinyl)-3-(2-(trifluoromethoxy)phenyl)urea. Diamino-maleonate (0.5 g, 4.63 mmol) and 2-(trifluoromethyl)-phenyl isocyanate (0.73 mL, 4.86 mmol) were reacted in acetonitrile (15 mL) according to General Procedure A. Material was dried under high vacuum at 60° C. overnight to give the title compound as a solid (0.94 g, 57%). MS (ESI) m/z 312.2 [M+1]⁺.

B. 2-(3-Hydroxyphenyl)-8-oxo-9-[2-(trifluoromethoxy) phenyl]-7-hydropurine-6-carbox-amide A solution of (Z)-1-(2-amino-1,2-dicyanovinyl)-3-(2-(trifluoromethoxy)phenyl) urea (0.25 g, 0.80 mmol), 3-hydroxybenzaldehyde (0.22 g, 1.78 mmol), and triethylamine (0.2 mL) in methanol (15 mL) were reacted according to General Procedure B. The resulting product was taken up in DMF (3 mL) and triturated with deionized water. The resulting precipitate was filtered and dried in the vacuum oven to yield the title compound (0.22 g, 64%). $^1$H NMR (400 MHz, DMSO-$d_6$) δ 11.92 (s, 1H), 9.49 (s, 1H), 8.44 (s, 1H), 8.03 (s, 1H), 7.90 (d, J=7.8, 1H), 7.80 (dd, J=7.8, 1.6, 1H), 7.64-7.76 (m, 4H), 7.23 (t, J=8.0, 1H), 6.83 (ddd, J=6.6, 1.6, 1.2, 1H); MS (ESI) m/z 432.4 [M+1]⁺.

5.1.19 Example 19

Synthesis of 9-(2,4-DICHLOROPHENYL)-2-(3-HYDROXYPHENYL)-8-OXO-8,9-DIHYDRO-7H-PURINE-6-CARBOXAMIDE A. (Z)-1-(2-Amino-1,2-dicyanovinyl)-3-(2,4-dichlorophenyl)urea. In a round bottom flask, 2,3-diaminomaleonitrile (1.0 g, 9.26 mmol) was dissolved in acetonitrile (20 mL) and stirred at room temperature. 2,4-Dichlorophenylisocyanate (1.82 g, 9.72 mmol) was added and the solution was stirred at room temperature for 16 hours. The resultant urea product was collected by filtration, washed with small portions of acetonitrile followed by diethyl ether. The filtered material was dried under high vacuum at 60° C. overnight to yield the title compound (2.15 g, 79%). $^1$H NMR (300 MHz, DMSO-$d_6$) δ 8.41 (d, J=4.8, 2H), 8.14 (d, 8.7, 1H), 7.63 (d, J=2.1, 1H), 7.39 (dd, 1H), 7.32 (bs, 2H).

B. 9-(2,4-Dichlorophenyl)-2-(3-hydroxyphenyl)-8-oxo-8,9-dihydro-7H-purine-6-carbox-amide. To a solution containing (Z)-1-(2-amino-1,2-dicyanovinyl)-3-(2,4-dichlorophenyl)urea (0.500 g, 1.69 mmol) in methanol (25 ml) and triethylamine (0.33 mL) was added 3-hydroxybenzaldehyde (0.413 g, 3.38 mmol). The solution was allowed to stir for 16 hours. The resultant heterogeneous mixture was filtered, washed with additional acetonitrile followed by diethyl ether to afford the crude cyclized product. The solid was triturated with dimethylformamide/water while sonicating to afford the title compound after drying (0.207 g, 29%). $^1$H NMR (400 MHz, DMSO-$d_6$) δ 11.94 (s, 1H), 9.47 (s, 1H), 8.43 (s, 1H), 8.01 (m, 2H), 8.10 (d, J=7.99, 1H), 7.79 (d, J=8.79, 1H), 7.72 (dd, 1H), 7.68 (m, 1H), 7.23 (d, J=7.99, 1H), 6.82 (dd, 1H); MS (ESI) m/z 418.0 [M+2]⁺; mp 375-377° C.

5.1.20 Example 20

Synthesis of 9-(2-METHOXYPHENYL)-2-(3-NITROPHENYL)-8-OXO-8,9-DIHYDRO-7H-PURINE-6-CARBOXAMIDE A. 9-(2-Methoxyphenyl)-2-(3-nitrophenyl)-8-oxo-8,9-dihydro-7H-purine-6-carboxamide. (Z)-1-(2-Amino-1,2-dicyanovinyl)-3-(2-methoxyphenyl)urea (See Example 2.A) (0.2 g, 0.78 mmol), 3-nitrobenzaldehyde (0.256 g, 1.7 mmol) and triethylamine (0.1 mL) were reacted according to General Procedure B. The resulting precipitate was dissolved in DMF and water was added to induce precipitation. This precipitate was filtered off and dried under vacuum to provide the title compound in 99.7% purity (0.118 g, 37%). $^1$H NMR (400 MHz, DMSO-$d_6$) δ 11.91 (s, 1H), 9.02 (s, 1H), 8.88 (d, J=7.8, 1H), 8.69 (s, 1H), 8.29 (d, J=8.0, 1H), 8.04 (s, 1H), 7.75 (t, J=8.0, 1H), 7.58 (t, J=7.9, 1H), 7.52 (d, J=7.8, 1H), 7.32 (d, J=8.2, 1H), 7.17 (t, J=7.6, 1H), 3.76 (s, 3H); MS (ESI) m/z 407.3 [M+1]⁺; mp 295-296° C.

5.1.21 Example 21

Synthesis of 9-(3-FLUOROPHENYL)-2-(3-HYDROXYPHENYL)-8-OXO-8,9-DIHYDRO-7H-PURINE-6-CARBOXAMIDE A. 1-((Z)-2-Amino-1,2-dicyano-vinyl)-3-(-fluoro-phenyl)-urea. 3-Fluoro-phenyl-isocyanate (1.0 g, 9.3 mmol) and 2,3-diaminomaleonitrile (1.3 g, 9.7 mmol) were reacted according to General Procedure A. The resulting brown solid was filtered and dried under high vacuum (2.0 g, 8.2 mmol, 89% yield). MS (ESI) m/z 246.1 [M+1]⁺.

B. 9-(3-Fluorophenyl)-2-(3-hydroxyphenyl)-8-oxo-8,9-dihydro-7H-purine-6-carboxamide. 1-((Z)-2-Amino-1,2-dicyano-vinyl)-3-(-fluoro-phenyl)-urea (0.50 g, 2.0 mmol) and 3-hydroxybenzaldehyde (0.26 g, 2.1 mmol) were reacted according to General Procedure B. The resultant heterogeneous mixture was filtered, and triturated with dimethylformamide/water while sonicating. The solid was triturated a second time using dimethylformamide/diethyl ether. The resulting solid was dried under high vacuum at 95° C. overnight to afford the title compound as a white solid (0.27 g, 0.74 mmol, 37% yield). $^1$H NMR (400 MHz, DMSO-$d_6$) δ 11.83 (s, 1H), 9.50 (s, 1H), 8.40 (s, 1H), 7.98 (s, 1H), 7.95 (ddd, J=8.0, 1.2, 1.0, 1H), 7.78 (dd, J=2.3, 1.6, 1H), 7.62-7.70 (m, 3H), 7.33-7.38 (m, 1H), 7.26 (t, J=8.0, 1H), 6.85 (ddd, J=8.0, 2.5, 0.8, 1H); MS (ESI) m/z 366.0 [M+1]⁺; mp>375° C.

5.1.22 Example 22

Synthesis of 9-(2-METHOXYPHENYL)-8-OXO-2-(2-(TRIFLUOROMETHYL)PHENYL)-8,9-DIHYDRO-7H-PURINE-6-CARBOXAMIDE A. 9-(2-Methoxyphenyl)-8-oxo-2-(2-(trifluoromethyl)phenyl)-8,9-dihydro-7H-purine-6-carboxamide. (Z)-1-(2-Amino-1,2-dicyanovinyl)-3-(2-methoxyphenyl)urea (See Example 2.A) (0.50 g, 1.9 mmol) and 2-(trifluoromethyl)benzaldehyde (0.36 g, 2.0 mmol) were reacted according to General Procedure B. Product was purified using reverse-phase semi-preparatory HPLC (5-60% acetonitrile+0.1% TFA in H$_2$O+0.1% TFA, over 39 min). Fractions containing the desired material were combined and concentrated under reduced pressure before being passed through a Strata-XC ion exchange column with water, methanol, and 5% ammonium hydroxide in methanol. The resultant solid was dried under high vacuum at 95° C. to afford the title compound as a white solid (0.079 g, 0.18 mmol, 9% yield). $^1$H NMR (400 MHz, DMSO-$d_6$) δ 11.89 (s, 1H), 8.02 (s, 1H), 7.95 (s, 1H), 7.72-7.83 (m, 3H), 7.65 (t, J=7.2, 1H), 7.50 (dd, J=7.0, 1.2, 1H), 7.44 (dd, J=7.8, 1.6, 1H), 7.24 (dd, J=8.4, 1.0, 1H), 7.09 (td, J=7.6, 1.2, 1H), 3.73 (s, 3H); MS (ESI) m/z 430.0 [M+1]⁺; mp 237-240° C.

5.1.23 Example 23

Synthesis of 2-(5-FLUORO(3-PYRIDYL))-9-(2-METHOXYPHENYL)-8-OXO-7-HYDROPURINE-6-CARBOXAMIDE A. 2-(5-Fluoro(3-pyridyl))-9-(2-methoxyphenyl)-8-oxo-7-hydropurine-6-carboxamide. A solution of (Z)-1-(2-

Amino-1,2-dicyanovinyl)-3-(2-methoxyphenyl)urea (See Example 2.A) (0.25 g, 1.00 mmol), 3-fluoro-5-formylpyridine (0.27 g, 2.14 mmol), and triethylamine (0.2 mL) in methanol (10 mL) were reacted according to General Procedure B. The resulting product was taken up in DMF (3 mL) and triturated with deionized water. The resulting precipitate was filtered, stirred with refluxing methanol for 15 min, and hot filtered. The product was taken up in DMSO and heated to become a homogeneous solution, and then allowed to sit overnight. The crystals were filtered and washed with ice cooled DMSO to yield to title compound. (0.01 g, 2%). $^1$H NMR (400 MHz, DMSO-$d_6$) δ 11.92 (s, 1H), 9.29 (t, J=1.6, 1H), 8.74 (s, 1H), 8.68 (dd, J=2.9, 1.8, 1H), 8.64-8.67 (m, 1H), 8.02 (s, 1H), 7.57 (ddd, J=8.7, 7.3, 1.6, 1H), 7.51 (dd, J=7.8, 1.6, 1H), 7.31 (dd, J=8.4, 1.0, 1H), 7.16 (td, J=7.6, 1.2, 1H), 3.76 (s, 3H); MS (ESI) m/z 381.1 [M+1]$^+$.

5.1.24 Example 24

Synthesis of 9-(2-METHOXYPHENYL)-8-OXO-2-[1-BENZYL(4-PIPERIDYL)]-7-HYDROPURINE-6-CARBOXAMIDE A. 9-(2-Methoxyphenyl)-8-oxo-2-[1-benzyl(4-piperidyl)]-7-hydropurine-6-carboxamide. A solution of (Z)-1-(2-Amino-1,2-dicyanovinyl)-3-(2-methoxyphenyl)urea (see Example 2.A) (0.5 g, 1.95 mmol), N-benzylpiperidine-4-carboxaldehyde (0.85 mL, 4.28 mmol), and triethylamine (0.5 mL) in methanol (20 mL) were reacted according to General Procedure B. The resulting product was taken up in DMF (3 mL) and triturated with deionized water. This precipitate was filtered, stirred with refluxing methanol for 15 min, and hot filtered to yield to title compound. (0.08 g, 10%). $^1$H NMR (400 MHz, DMSO-$d_6$) δ 7.90 (s, 1H), 7.49-7.55 (m, 1H), 7.41 (dd, J=7.8, 1.6, 1H), 7.21-7.32 (m, 6H), 7.11 (t, J=7.2, 1H), 3.72 (s, 3H), 3.44 (s, 2H), 2.81-2.87 (m, 2H), 2.61-2.70 (m, 1H), 1.94-1.99 (m, 1H), 1.80 (d, J=2.0, 2H), 1.78 (s, 2H); MS (ESI) m/z 459.6 [M+1]$^+$.

5.1.25 Example 25

Synthesis of BENZYL 4-(6-CARBAMOYL-8-OXO-2-(PYRIDIN-3-YL)-7H-PURIN-9(8H)-YL)PIPERIDINE-1-CARBOXYLATE A. (Z)-Benzyl-4-(3-(2-amino-1,2-dicyanovinyl)ureido)piperidine-1-carboxylate. 2,3-Diaminomaleonitrile (0.28 g, 2.60 mmol) and benzyl-4-isocyanato-tetrahydropyridine carboxylate (0.7 g, 2.69 mmol) were reacted in acetonitrile (15 mL) according to General Procedure A. Material was dried under high vacuum at 60° C. overnight to give the title compound as a solid (0.36 g, 37%). MS (ESI) m/z 369.3 [M+1]$^+$.

B. Benzyl-4-(6-carbamoyl-8-oxo-2-(pyridin-3-yl)-7H-purin-9(8H)-yl)piperidine-1-carboxylate A solution of (Z)-benzyl 4-(3-(2-amino-1,2-dicyanovinyl)ureido)piperidine-1-carboxylate (0.35 g, 0.95 mmol), 3-pyridinecarboxaldehyde (0.2 mL, 2.09 mmol), and triethylamine (0.3 mL) in methanol (15 mL) were reacted according to General Procedure B. The resulting product was taken up in methanol, heated for 10 minutes, allowed to cool to room temperature, and filtered, and dried under high vacuum to yield the title compound (0.20 g, 44%). $^1$H NMR (400 MHz, DMSO-$d_6$) δ 11.68 (s, 1H), 9.69 (d, J=1.6, 1H), 8.83 (dt, J=7.8, 2.0, 1H), 8.69 (dd, J=4.9, 1.8, 1H), 8.57 (s, 1H), 7.95 (s, 1H), 7.52 (dd, J=8.2, 5.1, 1H), 7.30-7.42 (m, 5H), 4.58 (tt, J=12.1, 4.1, 1H), 4.19 (d, J=12.9, 2H), 3.04 (s, 2H), 2.45 (s, 2H), 1.83 (d, J=10.9, 2H); MS (ESI) m/z 474.4 [M+1]$^+$.

5.1.26 Example 26

Synthesis of 9-CYCLOHEXYL-2-(3-HYDROXYPHENYL)-8-OXO-8,9-DIHYDRO-7H-PURINE-6-CARBOXAMIDE A. (Z)-1-(2-Amino-1,2-dicyanovinyl)-3-cyclohexylurea. 2,3-Diaminomaleonitrile (1.00 g, 9.25 mmol) and cyclohexylisocyanate (1.33 mL, 9.71 mmol) were reacted in acetonitrile (20 mL) according to General Procedure A. The reaction required heating at 50° C. overnight to convert roughly 70% (monitor LC-MS) of the starting material to the desired product. Work-up follows General Procedure A. Material was dried in vacuum oven overnight to give the title compound as a solid (1.17 g, 55%). MS (ESI) m/z 234.4 [M+1]$^+$.

B. 9-Cyclohexyl-2-(3-hydroxyphenyl)-8-oxo-8,9-dihydro-7H-purine-6-carboxamide. A solution of (Z)-1-(2-amino-1,2-dicyanovinyl)-3-cyclohexylurea (0.25 g, 1.08 mmol), 3-hydroxybenzaldehyde (0.28 mL, 2.36 mmol), and triethylamine (0.3 mL) in methanol (10 mL) were reacted according to General Procedure B. The resulting product was taken up in a mixture of ethyl acetate:methanol (3:1), heated for 10 minutes, filtered, and dried under high vacuum to yield the title compound (0.08 g, 21%). $^1$H NMR (400 MHz, DMSO-$d_6$) δ 11.50 (s, 1H), 9.56 (s, 1H), 8.33 (s, 1H), 8.01 (d, J=7.8, 1H), 7.92 (s, 1H), 7.89-7.91 (m, 1H), 7.29 (t, J=7.8, 1H), 6.86-6.90 (m, 1H), 4.26 (tt, J=12.3, 3.8, 1H), 2.32-2.43 (m, 2H), 1.89 (d, J=12.9, 2H), 1.80 (d, J=10.5, 2H), 1.73 (d, J=12.1, 1H), 1.35-1.45 (m, 2H); MS (ESI) m/z 354.4 [M+1]$^+$.

5.1.27 Example 27

Synthesis of 9-(2-METHOXYPHENYL)-8-OXO-2-(3-(TRIFLUOROMETHOXY)PHENYL)-8,9-DIHYDRO-7H-PURINE-6-CARBOXAMIDE A. 9-(2-Methoxyphenyl)-8-oxo-2-(3-(trifluoromethylphenyl)-8,9-dihydro-7H-purine-6-carboxamide. (Z)-1-(2-Amino-1,2-dicyanovinyl)-3-(2-methoxyphenyl)urea (See Example 2.A) (0.50 g, 1.9 mmol) and 3-(trifluoromethoxy)benzaldehyde (0.52 g, 2.0 mmol) were reacted according to General Procedure B. The resultant heterogeneous mixture was filtered, and triturated with methanol/diethyl ether while sonicating. The brown solid, recovered by filtration, was triturated a second time using methanol/diethyl ether to afford a yellow powder that was subsequently dried under high vacuum at 60° C. to afford the title compound (0.19 g, 0.43 mmol, 22% yield). $^1$H NMR (400 MHz, DMSO-$d_6$) δ 11.83 (s, 1H), 8.66 (s, 1H), 8.40 (s, 1H), 8.34 (d, J=8.2, 1H), 8.01 (s, 1H), 7.53-7.60 (m, 2H), 7.50 (dd, J=7.6, 1.4, 1H), 7.44 (d, J=8.2, 1H), 7.30 (d, J=8.2, 1H), 7.16 (t, J=7.4, 1H), 3.75 (s, 3H); MS (ESI) m/z 446.1 [M+1]$^+$; mp 269-272° C.

5.1.28 Example 28

Synthesis of 9-PHENYL-2-(3-PYRIDYL)PURINE-6-CARBOXAMIDE

A. Methyl 2,6-dihydroxy-5-nitropyrimidine-4-carboxylate. This compound can be prepared as described in *J. Med. Chem.*, 42(11), 1951-1964, 1999, which is incorporated herein by reference in its entirety.

B. Methyl 2,6-dichloro-5-nitropyrimidine-4-carboxylate. This compound can be prepared as described in *J. Med. Chem.*, 42(11), 1951-1964, 1999, which is incorporated herein by reference in its entirety.

C. Methyl 2-chloro-5-nitro-6-(phenylamino)pyrimidine-4-carboxylate. A solution of Methyl 2,6-dichloro-5-nitropyrimidine-4-carboxylate (0.72 g, 2.87 mmol) in anhydrous THF (14 mL) was chilled to −78° C. under nitrogen. A solution of aniline (0.288 mL, 3.16 mmol) and diisopropylethylamine (1.50 mL, 8.61 mmol) in anhydrous THF (10 mL) was then added drop wise with stirring over 10 minutes. The reaction was stirred at −78° C. for 1 hour and then allowed to warm to room temperature. After 90 minutes, the solvent was evaporated and the resulting residue purified using chromatography on a normal phase silica gel column (0-10% ethyl acetate in hexanes). Fractions containing product were combined and the solvent evaporated to provide the title compound (0.545 g, 1.76 mmol, 61% yield). MS (ESI) m/z 309.4 [M+1]$^+$.

D. Methyl 5-amino-2-chloro-6-(phenylamino)pyrimidine-4-carboxylate. To a solution of methyl 2-chloro-5-nitro-6-(phenylamino)pyrimidine-4-carboxylate (0.259 g, 0.839 mmol) in DMF (3.0 mL) and ethanol (13 mL) was added tin(II) chloride dihydrate (0.568 g, 2.52 mmol). The mixture was stirred at room temperature for 70 minutes, filtered, and the volatiles evaporated. The resulting residue was purified using chromatography on a normal phase silica gel column (1-10% methanol in dichloromethane). Fractions containing product were combined and the solvent evaporated to provide the title compound (0.190 g, 0.683 mmol, 82% yield). MS (ESI) m/z 279.3 [M+1]$^+$.

E. Methyl 5-amino-6-(phenylamino)-2-(3-pyridyl)pyrimidine-4-carboxylate. To a solution of methyl 5-amino-2-chloro-6-(phenylamino)pyrimidine-4-carboxylate (0.189 g, 0.68 mmol) in anhydrous DMF (3.5 mL) was added 3-(tributylstannyl)pyridine (1.252 g, 3.4 mmol), and dichlorobis(triphenylphosphine) palladium(II) (0.239 g, 0.34 mmol). The solution was purged with nitrogen then heated in an Emrys Optimizer microwave reactor for 30 minutes at 120° C. The volatiles were evaporated and the resulting residue was purified using chromatography on a normal phase silica gel column (1-10% methanol in dichloromethane). Fractions containing product were combined and the solvent evaporated. The material was re-purified using reverse-phase preparatory HPLC (30-80% acetonitrile+0.1% TFA in H$_2$O+0.1% TFA, over 30 minutes). Fractions containing the desired material were combined and concentrated under reduced pressure before being passed through a Strata-XC ion exchange column with water, methanol, and 5% ammonium hydroxide in methanol. The resulting solid was dried under high vacuum at 60° C. to afford the title compound (0.125 g, 0.389 mmol, 57% yield). MS (ESI) m/z 322.4 [M+1]$^+$.

F. 5-Amino-6-(phenylamino)-2-(3-pyridyl)pyrimidine-4-carboxamide. A solution of methyl 5-amino-6-(phenylamino)-2-(3-pyridyl)pyrimidine-4-carboxylate (0.123 g, 0.383 mmol) in anhydrous methanol (15 mL) was chilled to −78° C. The solution was then saturated with ammonia gas. The reaction vessel was sealed at −78° C. and allowed to warm to room temperature. After 18 hours the reaction was chilled to −78° C. and opened to atmosphere. The volatiles were evaporated and the resulting solids dried under vacuum to provide the title compound (0.117 g, 0.383 mmol, 100% yield). $^1$H NMR (400 MHz, DMSO-d$_6$) δ 9.50 (d, J=1.6, 1H), 8.93 (s, 1H), 8.67 (dt, J=8.0, 2.0, 1H), 8.58 (dd, J=4.8, 1.6, 1H), 8.43 (s, 1H), 7.85 (d, J=8.4, 2H), 7.63 (s, 1H), 7.42-7.47 (m, 3H) 7.23 (s, 2H), 7.11 (t, J=7.6, 1H); MS (ESI) m/z 307.3 [M+1]$^+$; mp 285-288° C.

G. 9-Phenyl-2-(3-pyridyl)purine-6-carboxamide. A suspension of 5-Amino-6-(phenylamino)-2-(3-pyridyl)pyrimidine-4-carboxamide (0.061 g, 0.199 mmol) in triethyl orthoformate (6 mL) was stirred at 130° C. for 3 hours. The reaction was then cooled to room temperature and diluted with ethyl ether. The resulting solids were collected by filtration, rinsed with ethyl ether, and dried under vacuum at 60° C. to provide the title compound (0.056 g, 0.177 mmol, 89% yield). $^1$H NMR (400 MHz, DMSO-d$_6$) δ 9.70 (d, J=1.6, 1H), 9.20 (s, 1H), 8.84 (dt, J=8.0, 2.0, 1H), 8.72 (dd, J=4.8, 1.6, 1H), 8.61 (s, 1H), 8.12 (s, 1H), 8.05 (d, J=8.4, 2H), 7.71 (t, J=6.4, 2H), 7.54-7.61 (m, 2H); MS (ESI) m/z 317.4 [M+1]$^+$; mp 298-299° C.

5.1.29 Example 29

Synthesis of 6-OXO-8-PHENYL-2-(3-PYRIDYL)-5,7,8-TRIHYDROPTERIDINE-4-CARBOXAMIDE

A. Ethyl 2-{[2-chloro-6-(ethoxycarbonyl)-5-nitropyrimidin-4-yl]phenylamino}acetate. A solution of ethyl 2,6-dichloro-5-nitropyrimidine-4-carboxylate (1.5 g, 5.67 mmol) in anhydrous THF (20 mL) was chilled to −78° C. under nitrogen. A solution of ethyl 2-(phenylamino)acetate (1.11 g, 6.22 mmol) and diisopropylethylamine (3.0 mL, 17.01 mmol) in anhydrous THF (10 mL) was then added drop wise with stirring over 10 min. The reaction was stirred at −78° C. for 6 hours followed by addition of aqueous sodium bicarbonate solution (saturated, 10 mL). The mixture was extracted with ethyl acetate (3×10 mL). The organic phase was dried over sodium sulfate and concentrated to a residue which was purified by chromatography on a normal phase silica gel column (0-10% ethyl acetate in hexanes). Fractions containing product were combined and the solvent evaporated to provide the title compound (1.1 g, 2.89 mmol, 41% yield). MS (ESI) m/z 409.5 [M+1]$^+$.

B. Ethyl 2-chloro-6-oxo-8-phenyl-5,7,8-trihydropteridine-4-carboxylate. To a solution of ethyl 2-{[2-chloro-6-(ethoxycarbonyl)-5-nitropyrimidin-4-yl]phenylamino}acetate (1.7 g, 4.16 mmol) in glacial acetic acid (20.0 mL) was added iron powder (1.2 g, 20.8 mmole). The grey suspension was heated to 60° C. for 12 hours. Additional iron powder (total of 3.4 g) was added over the next 24 hours. The acetic acid was removed under reduced pressure and the residue was suspended in methanol, filtered through a short Celite pad and concentrated under reduced pressure to a residue. The resulting residue was purified by chromatography on a normal phase silica gel column (20-40% ethyl acetate in hexanes). Fractions containing product were combined and the solvent evaporated to provide the title compound (0.595 g, 1.78 mmol, 43% yield); MS (ESI) m/z 333.2 [M+1]$^+$.

C. Ethyl 6-oxo-8-phenyl-2-(3-pyridyl)-5,7,8-trihydropteridine-4-carboxylate. To a solution of 2-chloro-6-oxo-8-phenyl-5,7,8-trihydropteridine-4-carboxylate (0.150 g, 0.45 mmol) in anhydrous DMF (3.0 mL) was added 3-(tributylstannyl)pyridine (0.828 g, 2.25 mmol), and dichlorobis(triphenylphosphine) palladium(II) (0.158 g, 0.225 mmol). The solution was purged with nitrogen then heated in an Emrys Optimizer microwave reactor for 30 minutes at 120° C. The volatiles were evaporated and the resulting residue was purified by chromatography on a normal phase silica gel column (1-10% methanol in dichloromethane). Fractions containing product were combined and the solvent evaporated. The material was re-purified using reverse-phase preparatory HPLC (10-70% acetonitrile+0.1% TFA in H$_2$O+0.1% TFA, over 30 min). Fractions containing the desired material were combined and concentrated under reduced pressure to a residue. The residue was dissolved in methylene chloride (100 mL) which was washed with aqueous potassium carbonate solution (saturated, 10 mL) and dried over sodium sulfate.

The organic phase was concentrated and the resulting solid was dried under high vacuum at 60° C. to afford the title compound (0.082 g, 0.12 mmol, 48% yield). MS (ESI) m/z 376.4 [M+1]+.

D. 6-Oxo-8-phenyl-2-(3-pyridyl)-5,7,8-trihydropteridine-4-carboxamide. A solution of ethyl 6-oxo-8-phenyl-2-(3-pyridyl)-5,7,8-trihydropteridine-4-carboxylate (0.038 g, 0.101 mmol) in anhydrous methanol (15 mL) was chilled to −78° C. The solution was then saturated with ammonia gas. The reaction vessel was sealed at −78° C. and allowed to warm to room temperature. After 18 hours the reaction was chilled to −78° C. and opened to atmosphere. The volatiles were evaporated and the resulting solids dried under vacuum to provide the title compound (0.027 g, 0.078 mmol, 76% yield). $^1$H NMR (300 MHz, DMSO-$d_6$) δ 11.4 (s, 1H), 9.33 (d, J=1.2, 1H), 8.83 (s, 1H), 8.59 (dd, J=4.9, 1.6, 1H), 8.52 (dt, J=8.0, 3.9, 1H), 8.23 (s, 1H), 7.59-7.49 (m, 4H), 7.45-7.33 (m, 2H), 4.67 (s, 2H); MS (ESI) m/z 347.4 [M+1]+; mp 294-296° C.

5.1.30 Example 30

Synthesis of 2-(3-HYDROXYPHENYL)-9-(2-METHOXYPHENYL)-9H-PURINE-6-CARBOXAMIDE

A. Ethyl 2-chloro-6-(2-methoxyphenylamino)-5-nitropyrimidine-4-carboxylate. In a 250 mL round-bottomed flask was placed ethyl 2,6-dichloro-5-nitropyrimidine-4-carboxylate (2 g, 7.52 mmol) in tetrahydrofuran (50 mL) and the mixture was cooled down to −78° C. A solution of 2-methoxyaniline (0.763 mL, 6.77 mmol) and diisopropylethyl amine (1.313 mL, 7.52 mmol) in 4 mL of tetrahydrofuran was added dropwise and the reaction was allowed to warm to room temperature overnight. Solvent was removed under reduced pressure and the crude material was purified by column chromatography (SiO$_2$, 90% nHexanes in ethyl acetate) to provide the title compound as an orange solid (2.42 g, 6.86 mmol, 91% yield). MS (ESI) m/z 353.3 [M+1]+.

B. Ethyl 5-amino-2-chloro-6-(2-methoxyphenylamino)pyrimidine-4-carboxylate. Ethyl 2-chloro-6-(2-methoxyphenylamino)-5-nitropyrimidine-4-carboxylate (622 mg, 1.763 mmol) was suspended in a mixture of ethanol (13 mL) and DMF (3 mL) and tin (II) chloride dihydrate (1.19 g, 5.29 mmol) was added. The reaction was stirred at room temperature overnight, filtered, and the volatiles evaporated. The resulting residue was purified by chromatography on a normal phase silica gel column (50% nHexanes in ethyl acetate). Fractions containing product were combined and the solvent evaporated to provide the title compound (0.465 g, 1.441 mmol, 82% yield) as a yellow solid. MS (ESI) m/z 323.3 [M+1]+.

C. Ethyl 5-amino-2-(3-hydroxyphenyl)-6-(2-methoxyphenylamino)pyrimidine-4-carboxylate. In a microwave flask was placed ethyl 5-amino-2-chloro-6-(2-methoxyphenylamino)pyrimidine-4-carboxylate (404 mg, 1.252 mmol), 3-hydroxyphenylboronic acid (259 mg, 1.878 mmol), potassium phosphate (531 mg, 2.504 mmol), dicyclohexyl(2',6'-dimethoxybiphenyl-2-yl)phosphine (77 mg, 0.188 mmol) and palladium (II) acetate (42.2 mg, 0.188 mmol) in tetrahydrofuran (20 mL) and water (2 mL) and the reaction mixture was heated at 120° C. for 20 min in the microwave. The reaction mixture was filtered and the solvent was removed under reduced pressure. The crude material was purified by column chromatography (SiO$_2$, 80-60% n-hexanes in ethyl acetate) and semi prep HPLC (20-100% acetonitrile+0.1% TFA in H$_2$O+0.1% TFA, over 30 min). Fractions containing product were neutralized with potassium carbonate (saturated aqueous solution), extracted with ethyl acetate and dried over magnesium sulfate to provide the title compound (57.8 mg, 0.152 mmol, 12% yield). MS (ESI) m/z 381.4 [M+1]+.

D. 5-Amino-2-(3-hydroxyphenyl)-6-(2-methoxyphenylamino)pyrimidine-4-carboxamide. A solution of ethyl 5-amino-2-(3-hydroxyphenyl)-6-(2-methoxyphenylamino)pyrimidine-4-carboxylate. (57.8 mg, 0.152 mmol) in anhydrous methanol (5 mL) was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting material was purified by column chromatography (SiO$_2$, 2% to 5% methanol in methylene chloride) to provide the title compound in 98.3% purity (53 mg, 0.151 mmol, 99% yield). $^1$H NMR (400 MHz, CD$_3$OD) δ 8.41 (m, 1H), 7.79 (dt, J=8.00, 1.20, 1H), 7.73 (m, 1H), 7.21 (t, J=8.00, 1H), 7.06 (m, 3H), 6.79 (ddd, J=8.00, 2.54, 0.98, 1H), 3.94 (s, 3H); MS (ESI) m/z 352.2 [M+1]+; mp: 230-231° C.

E. 2-(3-Hydroxyphenyl)-9-(2-methoxyphenyl)-9H-purine-6-carboxamide. 5-Amino-2-(3-hydroxyphenyl)-6-(2-methoxyphenylamino)pyrimidine-4-carboxamide (30 mg, 0.085 mmol) was suspended in triethyl orthoformate (3 mL) and stirred at 130° C. for 2 h. The reaction was then cooled to room temperature and diluted with ethyl ether. The resulting solids were collected by filtration, rinsed with ethyl ether, and dried under vacuum at 60° C. to provide the title compound in 98.3% purity (20 mg, 0.054 mmol, 64% yield). $^1$H NMR (400 MHz, DMSO-$d_6$) δ 9.59 (s, 1H), 8.85 (s, 1H), 8.48 (s, 1H), 8.12 (s, 1H), 7.90 (d, J=7.81, 1H), 7.84 (s, 1H), 7.69 (d, J=7.81, 1H), 7.61 (t, J=8.20, 1H), 7.39 (d, J=8.20, 1H), 7.31-7.223 (overlapping m, 2H), 6.87 (d, J=7.61, 1H), 3.81 (s, 3H); MS (ESI) m/z 362.0 [M+1]+; mp 257-259° C.

5.1.31 Example 31

Synthesis of 9-CYCLOPENTYL-2-(3-HYDROXYPHENYL)-8-OXO-8,9-DIHYDRO-7H-PURINE-6-CARBOXAMIDE A. Ethyl 2-chloro-6-(cyclopentylamino)-5-nitropyrimidine-4-carboxylate. In a 250 mL round-bottomed flask was placed ethyl 2,6-dichloro-5-nitropyrimidine-4-carboxylate (1.5 g, 5.64 mmol) in tetrahydrofuran (30 mL) and the mixture was cooled down to −78° C. A solution of cyclopentylamine (0.501 mL, 5.07 mmol) and diisopropylethyl amine (0.985 mL, 5.64 mmol) in 4 mL of tetrahydrofuran was added dropwise and the reaction was allowed to warm to room temperature overnight. Solvent was removed under reduced pressure and the crude material was purified by column chromatography (0-2% ethyl acetate in hexanes) to provide the title compound (1.26 g, 4.00 mmol, 71% yield). MS (ESI) m/z 315.2 [M+1]+.

B. Ethyl 5-amino-2-chloro-6-(cyclopentylamino)pyrimidine-4-carboxylate. Ethyl 2-chloro-6-(cyclopentylamino)-5-nitropyrimidine-4-carboxylate (283 mg, 0.899 mmol) was suspended in a mixture of ethanol (8 mL) and DMF (1.85 mL) and tin (II) chloride dihydrate (609 mg, 2.70 mmol) was added. The reaction was stirred at room temperature overnight, filtered, and the volatiles evaporated. The resulting residue was purified by chromatography on a normal phase silica gel column (50% ethyl acetate in hexanes). Fractions containing product were combined and the solvent evaporated to provide the title compound (212.7 mg, 0.747 mmol, 83% yield) as a white solid. MS (ESI) m/z 285.2 [M+1]+.

C. Ethyl 5-amino-6-(cyclopentylamino)-2-(3-hydroxyphenyl)pyrimidine-4-carboxylate. In a microwave flask was placed ethyl 5-amino-2-chloro-6-(cyclopentylamino)pyrimidine-4-carboxylate (212 mg, 0.745 mmol), 3-hydroxyphenylboronic acid (154 mg, 1.12 mmol), potassium phosphate (316 mg, 1.49 mmol), dicyclohexyl(2',6'-dimethoxybiphenyl-2-yl)phosphine (45.8 mg, 0.112 mmol) and palladium (II) acetate (25.1 mg, 0.112 mmol) in tetrahydrofuran (3 mL) and water (0.3 mL) and the reaction mixture was heated at 120° C. for 30 min in the microwave. The reaction mixture was filtered and the solvent was removed under reduced pressure. The crude material was purified by column chromatography (25-43% ethyl acetate in hexanes and a second chromatography using 0-2% methanol in methylene chloride) to provide the title compound (76.3 mg, 0.223 mmol, 30% yield). MS (ESI) m/z 343.2 [M+1]$^+$.

D. Ethyl 9-cyclopentyl-2-(3-hydroxyphenyl)-8-oxo-8,9-dihydro-7H-purine-6-carboxylate. Ethyl 5-amino-6-(cyclopentylamino)-2-(3-hydroxyphenyl)pyrimidine-4-carboxylate (76.3 mg, 0.223 mmol) was dissolved in methylene chloride (5 ml) and 1,1'-carbonyldiimidazole (361.6 mg, 2.23 mmol) was added. The reaction was refluxed for 1H and then stirred at room temperature for 5 days. The solvent was removed under reduced pressure and the crude material was purified by column chromatography (50% ethyl acetate in hexanes) to provide the title compound (49.7 mg, 0.135 mmol, 60% yield). MS (ESI) m/z 369.4 [M+1]$^+$.

E. 9-Cyclopentyl-2-(3-hydroxyphenyl)-8-oxo-8,9-dihydro-7H-purine-6-carboxamide. A solution of ethyl 9-cyclopentyl-2-(3-hydroxyphenyl)-8-oxo-8,9-dihydro-7H-purine-6-carboxylate (49.7 mg, 0.135 mmol) in anhydrous methanol (5 mL) was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting material was resuspended in methanol and filtered. The precipitate was dried under high vacuum to provide the title compound in 100% purity (33 mg, 0.151 mmol, 72% yield). $^1$H NMR (400 MHz, DMSO-d$_6$) δ 11.48 (s, 1H), 9.52 (s, 1H), 8.31 (s, 1H), 7.99 (d, J=7.81, 1H), 7.89 (d, J=12.88, 1H), 7.28 (t, J=8.00, 1H), 6.87 (dd, J=8.00, 1.66, 1H), 4.83 (m, 1H), 2.22 (m, 2H), 2.01 (m, 4H), 1.69 (m, 2H); MS (ESI) m/z 340.0 [M+1]$^+$; mp 360-361° C.

5.1.32 Example 32

Synthesis of 9-TERT-BUTYL-2-(3-HYDROXY-PHENYL)-8-OXO-8,9-DIHYDRO-7H-PURINE-6-CARBOXAMIDE A. 6-tert-Butylamino-2-chloro-5-nitro-pyrimidine-4-carboxylate. tert-Butylamine (0.26 g, 3.6 mmol), 2,6-dichloro-5-nitropyrimidine-4-carboxylate (1.0 g, 3.8 mmol) and diisopropylethylamine (1.5 g, 11 mmol) were reacted according to General Procedure C and purified using Biotage silica gel chromatography (0-35% ethyl acetate in hexanes) to afford the title compound (0.73 g, 2.4 mmol, 91% yield). MS (ESI) m/z 303.5 [M+1]$^+$, 304.5 [M+2]$^+$.

B. 5-Amino-6-tert-butylamino-2-chloro-pyrimidine-4-carboxylate. 6-tert-Butylamino-2-chloro-5-nitro-pyrimidine-4-carboxylate (0.73 g, 2.4 mmol) was suspended in ethanol (40 mL) and DMF (4 mL) and reacted with tin (II) chloride dihydrate (1.6 g, 7.5 mmol) according to General Procedure D. The crude residue (0.46 g, 1.69 mmol, 70% yield) was taken on to the next step without further purification. MS (ESI) m/z 273.4 [M+1]$^+$.

C. 5-Amino-6-tert-butylamino-2-(3-hydroxy-phenyl)-pyrimidine-4-carboxylate. In a microwave flask was placed 5-amino-6-tert-butylamino-2-chloro-pyrimidine-4-carboxylate (0.46 g, 1.69 mmol), 3-hydroxyphenylboronic acid (0.35 g, 2.53 mmol), potassium phosphate (0.72 g, 3.4 mmol), dicyclohexyl(2',6'-dimethoxybiphenyl-2-yl)phosphine (0.10 g, 0.25 mmol) and palladium (II) acetate (0.06 g, 0.25 mmol) in tetrahydrofuran (17 mL) and water (1.7 mL). The mixture was reacted according to General Procedure E. The crude residue was purified using Biotage silica gel chromatography (0-35% ethyl acetate in hexanes) to afford the title compound (0.26 g, 0.79 mmol, 36% yield). MS (ESI) m/z 331.4 [M+1]$^+$.

D. 9-tert-Butyl-2-(3-hydroxy-phenyl)-8-oxo-8,9-dihydro-7H-purine-6-carboxylate. 5-Amino-6-tert-butylamino-2-(3-hydroxy-phenyl)-pyrimidine-4-carboxylate (0.26 g, 0.79 mmol) and 1,1'-carbonyldiimidazole (0.64 g, 4.0 mmol) were reacted according to General Procedure F. The crude residue was purified using Biotage silica gel chromatography (0-50% ethyl acetate in hexanes) to afford the title compound (0.13 g, 0.36 mmol, 46% yield). MS (ESI) m/z 357.4 [M+1]$^+$.

E. 9-tert-Butyl-2-(3-hydroxy-phenyl)-8-oxo-8,9-dihydro-7H-purine-6-carboxamide. 9-tert-Butyl-2-(3-hydroxy-phenyl)-8-oxo-8,9-dihydro-7H-purine-6-carboxylate (0.13 g, 0.36 mmol) and ammonia gas were reacted according to General Procedure G. The crude residue was purified using reverse-phase semi-preparatory HPLC (10-70% acetonitrile+0.1% TFA in H$_2$O+0.1% TFA, over 39 min). Fractions containing the desired material were combined and concentrated under reduced pressure before being passed through a Strata-XC ion exchange column with water, methanol and 5% ammonium hydroxide in methanol. The resulting residue was dried under high vacuum at 60° C. to afford the title compound as a white solid in 100% purity (0.013 g, 0.040 mmol, 11% yield). $^1$H NMR (400 MHz, DMSO-d$_6$) δ 11.33 (s, 1H), 9.53 (s, 1H), 8.31 (s, 1H), 7.97 (d, 1H), 7.89 (s, 1H), 7.82-7.87 (m, 1H), 7.28 (t, J=8.0, 1H), 6.82-6.90 (m, 1H), 1.82 (s, 9H); MS (ESI) m/z 328.1 [M+1]$^+$.

5.1.33 Example 33

Synthesis of [2-(3-HYDROXYPHENYL)-9-(2-METHOXYPHENYL)-8-OXO(7-HYDROPURIN-6-YL)]-N-METHYLCARBOXAMIDE A. Methyl 2-(3-hydroxyphenyl)-9-(2-methoxyphenyl)-8-oxo-7-hydropurine-6-carboxylate. 2-(3-Hydroxyphenyl)-9-(2-methoxyphenyl)-8-oxo-7-hydropurine-6-carboxamide (0.49 g, 1.27 mmol) was dissolved in a mixture of ethanol (20 mL) and DMSO (10 mL). To this reaction mixture 1N NaOH (10 mL) was added and heated for 2 days at 90° C. The reaction was cooled to room temperature, volatiles removed, and the residue was dissolved in a mixture of ethanol and Et$_2$O, and adjusted the pH ~4 with 3N HCl. Organics were removed by vacuum filtration and the solid collected. Product was purified using reverse-phase semi-preparatory HPLC (30-70% acetonitrile+0.1% TFA in H$_2$O+0.1% TFA, over 39 min). Fractions containing the desired material were combined and concentrated under reduced pressure before being passed through a Strata-XC ion exchange column with water, methanol, and 5% ammonium hydroxide in methanol. The resultant solid was dried under high vacuum at 60° C. to afford 2-(3-Hydroxyphenyl)-9-(2-methoxyphenyl)-8-oxo-7-hydropurine-6-carboxylic acid as a white solid (0.005 g, 0.01 mmol, 1% yield). $^1$H NMR (400 MHz, DMSO-d$_6$) δ 7.68 (s, 1H), 7.61 (d, J=7.6, 1H), 7.53 (t, J=8.0, 1H), 7.46 (d, J=6.8, 1H), 7.28 (s, J=8.4, 1H), 7.20-7.12 (m, 2H), 6.75 (d, J=6.4, 1H), 3.74 (s, 3H); MS (ESI) m/z 379.4 [M+1]$^+$; mp 229-230° C. 2-(3-Hydroxyphenyl)-9-(2-methoxyphenyl)-8-oxo-7-hydropurine-6-carboxylic acid (0.6 g, 1.6 mmol) was dissolved in MeOH (20 mL) and a 30% solution H₂O₂ (0.75 mL) was added and allowed to stir at room temperature overnight. Upon consumption of starting material, the reaction's volatiles were removed, and the remaining mixture was neutralized with sat. NaHCO₃. The formed precipitate was filtered and washed with deionized H₂O. The product was purified by silica gel chromatography using a gradient of methanol in dichloromethane (0% to 7% MeOH). Clean fractions were combined and condensed to afford the title compound (0.275 g, 43%). MS (ESI) m/z 379.4 [M+1]⁺.

B. [2-(3-Hydroxyphenyl)-9-(2-methoxyphenyl)-8-oxo(7-hydropurin-6-yl)]-N-methylcarbox-amide. Methyl 2-(3-hydroxyphenyl)-9-(2-methoxyphenyl)-8-oxo-7-hydropurine-6-carboxylate (0.15 g, 0.38 mmol) and potassium cyanide (0.025 g, 0.38 mmol) were dissolved in methanol (10 mL). Methylamine (1.0 mL) was added and the reaction was sealed and heated at 60° C. overnight. The reaction was cooled to room temperature, volatiles removed, and product was purified using reverse-phase semi-preparatory HPLC (30-70% acetonitrile+0.1% TFA in H₂O+0.1% TFA, over 39 min). Fractions containing the desired material were combined and concentrated under reduced pressure before being passed through a Strata-XC ion exchange column with water, methanol, and 5% ammonium hydroxide in methanol. The resultant solid was dried under high vacuum at 60° C. to afford the title compound as a white solid (0.005 g, 0.01 mmol, 1% yield). ¹H NMR (400 MHz, CD₃OD-d₄) δ 11.74 (s, 1H), 9.49 (s, 1H), 8.96 (d, J=5.2, 1H), 7.89 (d, J=7.6, 1H), 7.69 (m, 1H), 7.55 (dt, J=8.4, 2.0, 1H), 7.49 (dd, J=8.0, 2.0, 1H), 7.30 (d, J=7.6, 1H), 7.23 (t, J=7.6, 1H), 7.15 (dt, J=7.6, 1.2, 1H), 6.82 (dd, J=8.0, 2.4, 1H), 3.75 (s, 3H), 3.92 (d, J=4.8, 3H); MS (ESI) m/z 392.3 [M+1]⁺; mp 339° C.

5.1.34 Example 34

Synthesis of 9-(2-ISOPROPYLPHENYL)-2-(4-(5-METHYL-4H-1,2,4-TRIAZOL-3-YL)PHENYL)-8-OXO-8,9-DIHYDRO-7H-PURINE-6-CARBOXAMIDE A. 4-(Diethoxymethyl)benzonitrile. 4-Formylbenzonitrile (1.00 g, 7.63 mmol) and triethyl orthoformate (2.54 ml, 15.3 mmol) were added to a suspension of perchloric acid on silica gel (prepared by stirring 1 mL perchloric acid (60%) with 12 g silica gel in 50 mL ether for 30 min and then removing ether under reduced pressure) (0.100 g) in ethanol (7.6 mL). The mixture was stirred at room temperature for 30 min and then solvents were removed under reduced pressure yielding a clear, pale yellow oil (1.57 g, 100%). As the product quickly hydrolyzes back to the starting material, it was quickly carried on to the next step without further purification. MS (ESI) m/z 206.1 [M+1]⁺.

B. 3-(4-(Diethoxymethyl)phenyl)-5-methyl-4H-1,2,4-triazole. 4-(Diethoxymethyl)benzonitrile (500 mg, 2.44 mmol), acetohydrazide (361 mg, 4.87 mmol) and potassium carbonate (673 mg, 4.87 mmol) were added to 1-butanol (2.4 mL) in a thick-wall borosilicate glass vial (20 mL). The solution was then heated in a Biotage Emrys Optimizer microwave reactor at 150° C. for 7 h. The reaction mixture was filtered and then concentrated under reduced pressure. The crude product was purified by Biotage chromatography (0-10% methanol in dicholoromethane) to provide the desired product (135 mg, 21%) as a pale, yellow solid. MS (ESI) m/z 262.0 [M+1]⁺.

C. 4-(5-Methyl-4H-1,2,4-triazol-3-yl)benzaldehyde. 3-(4-(Diethoxymethyl)phenyl)-5-(130 mg, 0.497 mmol) was added to a suspension of perchloric acid on silica gel (100 mg) in 1:1 methanol:water (1 mL). The reaction mixture was stirred for 1 h at room temperature. Upon filtration of the silica gel, a white solid precipitated from the filtrate. The solid was collected and determined to be the desired product (80 mg, 86%). ¹H NMR (400 MHz, DMSO-d₆) δ 13.88 (br s, 1H), 10.04 (s, 1H), 8.19 (d, J=8.20, 2H), 7.98 (d, J=8.59, 2H), 2.44 (s, 3H).

D. 9-(2-Isopropylphenyl)-2-(4-(5-methyl-4H-1,2,4-triazol-3-yl)phenyl)-8-oxo-8,9-dihydro-7H-purine-6-carboxamide. (Z)-1-(2-Amino-1,2-dicyanovinyl)-3-(2-isopropylphenyl)urea (216 mg, 0.801 mmol), 4-(5-methyl-4H-1,2,4-triazol-3-yl)benzaldehyde (75 mg, 0.401 mmol) and triethylamine (0.112 ml, 0.801 mmol) were stirred in methanol (7 mL) for 24 h. The resulting heterogeneous mixture was filtered. The precipitate was collected and recrystallized by dissolving in warm DMF (1 mL) and adding water dropwise. The solid was collected and dried under vacuum at 60° C. for 48 h yielding an off-white solid (30 mg, 16%). ¹H NMR (400 MHz, CD₃OD) δ 8.55-8.39 (m, 2H), 8.08-7.91 (m, 2H), 7.64-7.54 (m, 2H), 7.46-7.33 (m, 2H), 2.78 (spt, J=6.64, 1H), 2.49 (s, 2H), 2.40 (br s, 1H), 1.22 (d, J=6.64, 3H), 1.17 (d, J=6.64, 3H); MS (ESI) m/z 455.1 [M+1]⁺.

5.1.35 Example 35

Synthesis of [2-(3-HYDROXYPHENYL)-9-(2-METHOXYPHENYL)-8-OXO(7-HYDROPURIN-6-YL)]-N,N-DIMETHYLCARBOXAMIDE A. [2-(3-Hydroxyphenyl)-9-(2-methoxyphenyl)-8-oxo(7-hydropurin-6-yl)]-N,N-dimethyl carboxamide. Methyl 2-(3-hydroxyphenyl)-9-(2-methoxyphenyl)-8-oxo-7-hydropurine-6-carboxylate (0.13 g, 0.32 mmol) (see example 33.A) and potassium cyanide (0.025 g, 0.38 mmol) were dissolved in methanol (10 mL). Dimethylamine (1.0 mL) was added and the reaction was sealed and heated at 60° C. overnight. The reaction was cooled to room temperature, volatiles removed, and product was purified using reverse-phase semi-preparatory HPLC (5-60% acetonitrile+0.1% TFA in H₂O+0.1% TFA, over 39 min). Fractions containing the desired material were combined and concentrated under reduced pressure before being passed through a Strata-XC ion exchange column with water, methanol, and 5% ammonium hydroxide in methanol. The resultant solid was dried under high vacuum at 60° C. to afford the title compound as a white solid (0.005 g, 0.01 mmol, 1% yield). ¹H NMR (300 MHz, CD₃OD-d₄) δ 11.84 (s, 1H), 9.51 (s, 1H), 7.60-7.48 (m, 4H), 7.30 (d, J=8.1, 1H), 7.25-7.13 (m, 2H), 6.80 (d, J=7.8, 1H), 3.77 (s, 3H), 3.19 (s, 3H), 3.10 (s, 3H); MS (ESI) m/z 406.0 [M+1]⁺; mp 290-292° C.

5.1.36 Example 36

Synthesis of 2-(3-HYDROXYPHENYLAMINO)-9-(2-METHOXYPHENYL)-8-OXO-8,9-DIHYDRO-7H-PURINE-6-CARBOXAMIDE A. Ethyl 2-(3-hydroxyphenylamino)-6-(2-methoxyphenylamino)-5-nitropyrimidine-4-carboxylate. To a solution of ethyl 2-chloro-6-(2-methoxyphenylamino)-5-nitropyrimidine-4-carboxylate (See Example 30.A) (200 mg, 0.567 mmol) in DMF (3 mL) was added 3-aminophenol (74.3 mg, 0.680 mmol) and N,N-diisopropylethylamine (0.149 mL, 0.851 mmol). The reaction was stirred at room temperature overnight. Solvent was removed under reduced pressure and the resulting residue was purified by chromatography on a normal phase silica gel column (25-43% ethyl acetate in hexanes). Fractions containing product were combined and the solvent evaporated to provide the title compound (227 mg, 0.534 mmol, 94% yield) as an orange solid. MS (ESI) m/z 426.2 [M+1]+.

B. Ethyl 5-amino-2-(3-hydroxyphenylamino)-6-(2-methoxyphenylamino)pyrimidine-4-carboxylate. Ethyl 2-(3-hydroxyphenylamino)-6-(2-methoxyphenylamino)-5-nitropyrimidine-4-carboxylate (227 mg, 0.534 mmol) was dissolved in ethanol (15 mL) and 10% palladium on carbon (56.8 mg, 0.053 mmol) was added. The reaction mixture was stirred at room temperature under an atmosphere of hydrogen overnight. The reaction was then filtered through Celite, solvent was removed under reduced pressure and purified by column chromatography (2% methanol in methylene chloride). A second chromatographic purification was necessary (50% ethyl acetate in hexanes). Fractions containing product were combined and the solvent evaporated to provide the title compound (186.8 mg, 0.472 mmol, 89% yield). MS (ESI) m/z 396.2 [M+1]+.

C. 2-(3-Hydroxyphenylamino)-9-(2-methoxyphenyl)-8-oxo-8,9-dihydro-7H-purine-6-carboxamide. Ethyl 5-amino-2-(3-hydroxyphenylamino)-6-(2-methoxyphenylamino)pyrimidine-4-carboxylate (110.4 mg, 0.279 mmol) was dissolved in methylene chloride (5 mL) and 1,1'-carbonyldiimidazole (453 mg, 2.79 mmol) was added. The reaction was refluxed for 1H and then stirred at room temperature overnight. Solvent was removed under reduced pressure and the crude material was passed through a plug of silica gel using 5% methanol/ethyl acetate as eluent to yield a mixture of ethyl 2-(3-hydroxyphenylamino)-9-(2-methoxyphenyl)-8-oxo-8,9-dihydro-7H-purine-6-carboxylate and ethyl 2-(3-(1H-imidazole-1-carbonyloxy)phenyl amino)-9-(2-methoxyphenyl)-8-oxo-8,9-dihydro-7H-purine-6-carboxylate. This mixture was dissolved in anhydrous methanol (5 mL) and was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting material was purified by column chromatography (5% methanol in methylene chloride) to provide the title compound in 99.4% purity (38.1 mg, 0.097 mmol, 35% yield). $^1$H NMR (400 MHz, DMSO-$d_6$) δ 11.25 (s, 1H), 9.32 (s, 1H), 9.27 (s, 1H), 8.05 (s, 1H), 7.54-7.48 (m, 2H), 7.44 (d, J=7.42, 1H), 7.35 (s, 1H), 7.23 (d, J=8.20, 1H), 7.10 (t, J=8.20, 1H), 6.97 (m, 2H), 6.28 (m, 1H), 3.75 (s, 3H); MS (ESI) m/z 393.1 [M+1]+; mp 190-191° C.

5.1.37 Example 37

Synthesis of 2-(4-HYDROXYPHENYLAMINO)-9-(2-METHOXYPHENYL)-8-OXO-8,9-DIHYDRO-7H-PURINE-6-CARBOXAMIDE A. Ethyl 2-(4-hydroxyphenylamino)-6-(2-methoxyphenylamino)-5-nitropyrimidine-4-carboxylate. To a solution of ethyl 2-chloro-6-(2-methoxyphenylamino)-5-nitropyrimidine-4-carboxylate (See Example 30.A) (200 mg, 0.567 mmol) in DMF (3 mL) was added 4-aminophenol (74.3 mg, 0.680 mmol) and N,N-diisopropylethylamine (0.149 mL, 0.851 mmol). The reaction was stirred at room temperature overnight. Solvent was removed under reduced pressure and the resulting residue was purified by chromatography on a normal phase silica gel column (50% ethyl acetate in hexanes). Fractions containing product were combined and the solvent evaporated to provide the title compound (220 mg, 0.517 mmol, 91% yield) as an orange solid. MS (ESI) m/z 426.2 [M+1]+.

B. Ethyl 5-amino-2-(4-hydroxyphenylamino)-6-(2-methoxyphenylamino)pyrimidine-4-carboxylate. Ethyl 2-(4-hydroxyphenylamino)-6-(2-methoxyphenylamino)-5-nitropyrimidine-4-carboxylate (220 mg, 0.517 mmol) was dissolved in ethanol (10 mL) and 10% palladium on carbon (55 mg, 0.052 mmol) was added. The reaction mixture was stirred at room temperature under an atmosphere of hydrogen overnight. The reaction was then filtered through Celite, solvent was removed under reduced pressure and purified by column chromatography (60-100% ethyl acetate in hexanes). Fractions containing product were combined and the solvent evaporated to provide the title compound (201.3 mg, 0.509 mmol, 98% yield). MS (ESI) m/z 396.2 [M+1]+.

C. 2-(4-Hydroxyphenylamino)-9-(2-methoxyphenyl)-8-oxo-8,9-dihydro-7H-purine-6-carboxamide. Ethyl 5-amino-2-(4-hydroxyphenylamino)-6-(2-methoxyphenylamino)pyrimidine-4-carboxylate (156.8 mg, 0.397 mmol) was dissolved in methylene chloride (5 mL) and 1,1'-carbonyldiimidazole (643 mg, 3.97 mmol) was added. The reaction was refluxed for 1 h and then stirred at room temperature overnight. Solvent was removed under reduced pressure and the crude material was passed through a plug of silica gel using 6:4 ethyl acetate/nHexanes as eluent to yield a mixture of ethyl 2-(4-hydroxyphenylamino)-9-(2-methoxyphenyl)-8-oxo-8,9-dihydro-7H-purine-6-carboxylate and ethyl 2-(4-(1H-imidazole-1-carbonyloxy)phenyl amino)-9-(2-methoxyphenyl)-8-oxo-8,9-dihydro-7H-purine-6-carboxylate. This mixture was dissolved in anhydrous methanol (5 mL) and was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting material was purified by column chromatography (5% methanol in methylene chloride and a second chromatography using 100% ethyl acetate) to provide the title compound in 98.8% purity (12.6 mg, 0.097 mmol, 8% yield). $^1$H NMR (400 MHz, DMSO-$d_6$) δ 11.17 (s, 1H), 9.09 (s, 1H), 8.94 (s, 1H), 7.93 (s, 1H), 7.50 (m, 2H), 7.42 (m, 3H), 7.23 (d, J=8.20, 1H), 7.10 (t, J=8.20, 1H), 6.64 (d, J=8.79, 2H), 3.75 (s, 3H); MS (ESI) m/z 393.1 [M+1]+; mp 223-224° C.

5.1.38 Example 38

Synthesis of N-METHYL-8-OXO-9-PHENYL-2-(PYRIDIN-3-YL)-8,9-DIHYDRO-7H-PURINE-6-CARBOXAMIDE A. 8-Oxo-9-phenyl-2-(pyridin-3-yl)-8,9-dihydro-7H-purine-6-carboxylic acid. 8-Oxo-9-phenyl-2-(pyridin-3-yl)-8,9-dihydro-7H-purine-6-carboxamide (0.2 g, 0.55 mmol) was dissolved in a mixture of DMSO (3 mL) and aqueous 6N hydrochloric acid solution (1.2 mL). The mixture was heated to 90° C. for 24 h and then poured into an ice/water slurry. The pH was adjusted to 5 and the resulting precipitate was filtered and dried to afford the title compound as a solid (0.108 g, 0.323 mmol, 54% yield), which was used directly in the next step. MS (ESI) m/z 334.1 [M+1]+.

B. N-Methyl-8-oxo-9-phenyl-2-(pyridin-3-yl)-8,9-dihydro-7H-purine-6-carboxamide. To a solution of 8-oxo-9-phenyl-2-(pyridin-3-yl)-8,9-dihydro-7H-purine-6-carboxylic acid (0.150 g, 0.45 mmole) in DMSO (2.0 mL) was added diisopropylamine (0.17 g, 1.35 mmole), methylamine (0.280 g, 4.5 ml of 2.0 M solution in tetrahydrofuran, 9 mmole) and then benzotriazol-1-yloxy-tris(dimethylamino)-phosphonium hexafluorophosphate (0.298 g, 0.68 mmole).

The mixture was sonicated for 5 min to dissolve all components of the mixture. After stirring 10 min starting material was consumed (monitored by LCMS). Solvent was removed and the product was purified using reverse-phase semi-preparatory HPLC (10-40% acetonitrile+0.1% TFA in H$_2$O+ 0.1% TFA, over 30 min). Fractions containing the desired material were neutralized with aqueous sodium carbonate solution and then concentrated to a smaller volume. The resulting precipitate was filtered and washed with water. The resulting solid was dried under high vacuum at 60° C. to afford the title compound as a solid (0.070 g, 0.20 mmol, 44% yield). $^1$H NMR (400 MHz, DMSO-d$_6$) δ 12.0 (s, 1H), 9.73 (s, 1H), 9.29-9.20 (brs, 1H), 8.81-8.76 (m, 1H), 8.76-8.72 (m, 1H), 7.86-7.57 (m, 6H), 3.01 (d, J=4.9, 3H); MS (ESI) m/z 347.2 [M+1]$^+$; mp>330° C.

5.1.39 Example 39

9-(TRANS-4-HYDROXYCYCLOHEXYL)-2-(3-HYDROXYPHENYL)-8-OXO-8,9-DIHYDRO-7H-PURINE-6-CARBOXAMIDE

A. 1-((Z)-2-Amino-1,2-dicyanovinyl)-3-(trans-4-hydroxycyclohexyl)urea. cis-4-Hydroxycyclohexane carboxylic acid (2.0 g, 13.87 mmol), triethylamine (1.40 g, 13.87 mmol) and diphenylphosphorylazide (3.81 g, 13.87 mmol) were combined in toluene and stirred at room temperature. The reaction was monitored via thin layer chromatography (50% ethyl acetate in hexanes, KMnO$_4$ stain). After 30 min the solution was condensed under reduced pressure and the oil diluted with acetonitrile (30 mL) followed by the addition of diaminomaleonitrile (1.57 g, 14.56 mmol). The solution was heated to 65° C. for 16 h. The solution was condensed under reduced pressure and partitioned between water and ethyl acetate (3×), organics combined, dried over magnesium sulfate, filtered and solvent removed to afford the crude product. The crude oil was purified using Biotage silica gel chromatography (70-100% ethyl acetate in hexanes followed by 10% methanol in ethyl acetate) to afford the title compound (1.90 g, 37%). MS (ESI) m/z 250.1 [M+1]$^+$.

B. 9-(trans-4-Hydroxycyclohexyl)-2-(3-hydroxyphenyl)-8-oxo-8,9-dihydro-7H-purine-6-carboxamide. 1-((Z)-2-Amino-1,2-dicyanovinyl)-3-(trans-4-hydroxycyclohexyl) urea (1.0 g, 4.01 mmol), 3-hydroxybenzaldehyde (1.02 g, 8.02 mmol) and triethylamine (1.2 mL) in methanol (35 mL) were reacted according to General Procedure B and purified using reverse-phase-preparative HPLC (5-55% acetonitrile+ 0.1% TFA in H$_2$O+0.1% TFA, over 39 min) to afford the title compound (0.047 g, 3.2%). $^1$H NMR (400 MHz, DMSO-d$_6$) δ 11.47 (s, 1H), 9.48 (s, 1H), 8.31 (s, 1H), 8.01 (d, J=8.0, 1H), 7.91 (m, 1H), 7.27 (t, J=8.0, 1H), 6.87 (d, J=8.0, 1H), 4.47 (s, 1H), 4.26 (m, 1H), 3.92 (s, 1H), 2.80 (q, J=12.4, 2H), 1.84 (d, J=13.2, 2H), 1.57 (t, J=13.6, 2H), 1.49 (d, J=10.4, 2H); MS (ESI) m/z 370.1[M+1]$^+$; mp 366-368° C.

5.1.40 Example 40

9-(TRANS-4-HYDROXYCYCLOHEXYL)-8-OXO-2-(PYRIDIN-3-YL)-8,9-DIHYDRO-7H-PURINE-6-CARBOXAMIDE

A. 9-(trans-4-Hydroxycyclohexyl)-8-oxo-2-(pyridin-3-yl)-8,9-dihydro-7H-purine-6-carboxamide. 1-((Z)-2-Amino-1,2-dicyanovinyl)-3-(trans-4-hydroxycyclohexyl) urea (See Example 3.A) (0.900 g, 3.61 mmol) and 3-pyridylcarboxaldehyde (0.774 g, 7.22 mmol) and triethylamine (1.2 mL) were reacted according to General Procedure B. The crude was purified using reverse-phase preparative HPLC (10-40% acetonitrile+0.1% TFA in H$_2$O+0.1% TFA, over 30 min) to afford the title compound (0.037 g, 2.8%). $^1$H NMR (300 MHz, DMSO-d$_6$) δ 10.80 (s, 1H), 9.72 (d, J=1.8, 1H), 8.89 (dd, J=8.1, 1H), 8.67 (d, J=5.1, 1H), 8.57 (s, 1H), 7.91 (s, 1H), 7.52 (m, 1H), 4.52 (dd, J=2.1, 1H), 4.27 (m, 1H), 3.92 (s, 1H), 2.84 (q, J=9.6, 2H), 1.84 (d, J=13.8, 2H), 1.54 (m, 5H); MS (ESI) m/z 355.4[M+1]$^+$; mp 331-333° C.

5.1.41 Example 41

9-(TRANS-4-HYDROXYCYCLOHEXYL)-2-(3-HYDROXYPHENYL)-8-OXO-8,9-DIHYDRO-7H-PURINE-6-CARBOXAMIDE

A. 1-((Z)-2-Amino-1,2-dicyanovinyl)-3-(trans-4-hydroxycyclohexyl)urea. Trans-4-hydroxycyclohexane carboxylic acid (3.0 g, 20.80 mmol), triethylamine (2.10 g, 20.80 mmol) and diphenylphosphorylazide (5.72 g, 20.80 mmol) were combined in toluene and stirred at room temperature. The reaction was monitored via thin layer chromatography (50% ethyl acetate in hexanes, KMnO$_4$ stain). After 30 min, the solution was condensed under reduced pressure and the oil diluted with acetonitrile (30 mL) followed by the addition of diaminomaleonitrile (2.24 g, 21.84 mmol). The solution was heated to 65° C. for 16 h. The resultant heterogeneous mixture was triturated with water. The resultant precipitate was filtered and dried under vacuum to afford the title compound (1.60 g, 31%). MS (ESI) m/z 250.1[M+1]$^+$.

B. 9-(trans-4-Hydroxycyclohexyl)-2-(3-hydroxyphenyl)-8-oxo-8,9-dihydro-7H-purine-6-carboxamide. 1-((Z)-2-Amino-1,2-dicyanovinyl)-3-(trans-4-hydroxycyclohexyl) urea (0.800 g, 3.21 mmol), 3-hydroxybenzaldehyde (0.612 g, 4.81 mmol) and triethylamine (1.2 mL) in methanol (35 mL) were reacted according to General Procedure B and purified using reverse-phase preparative HPLC (5-55% acetonitrile+ 0.1% TFA in H$_2$O+0.1% TFA, over 30 min) to afford the title compound (0.082 g, 6.9%). $^1$H NMR (300 MHz, DMSO-d$_6$) δ 11.51 (s, 1H), 9.56 (s, 1H), 8.33 (s, 1H), 8.00 (d, J=8.1, 1H), 7.89 (d, J=7.2, 2H), 7.29 (t, J=7.5, 1H), 6.87 (d, J=7.5, 1H), 4.72 (d, J=4.2, 1H), 4.23 (m, 1H), 3.60 (m, 1H), 1.97 (d, J=10.4, 2H), 1.77 (d, J=10.4, 2H), 1.35 (m, 2H); MS (ESI) m/z 370.1[M+1]$^+$; mp 373-375° C.

5.1.42 Example 42

9-(TRANS-4-HYDROXYCYCLOHEXYL)-8-OXO-2-(PYRIDIN-3-YL)-8,9-DIHYDRO-7H-PURINE-6-CARBOXAMIDE

A. 9-(trans-4-Hydroxycyclohexyl)-8-oxo-2-(pyridin-3-yl)-8,9-dihydro-7H-purine-6-carboxamide. 1-((Z)-2-Amino-1,2-dicyanovinyl)-3-(trans-4-hydroxycyclohexyl) urea (See Example 41.A) (0.800 g, 3.21 mmol) and 3-pyridylcarboxaldehyde (0.516 g, 4.81 mmol) and triethylamine (1.2 mL) were reacted according to General Procedure B. The crude was purified using reverse-phase preparative HPLC (5-40% acetonitrile+0.1% TFA in H$_2$O+0.1% TFA, over 30 min) to afford the title compound (0.060 g, 5.3%). $^1$H NMR (300 MHz, DMSO-d$_6$) δ 11.61 (s, 1H), 9.70 (s, 1H), 8.85 (d, 1H), 8.85 (d, J=7.8 1H), 8.68 (d, J=4.8, 1H), 8.56 (s, 1H), 7.93 (s, 1H), 7.54 (dd, J=6.0, J=8.1, 1H), 4.71 (d, J=4.2, 1H), 4.27 (m, 1H), 3.59 (m, 1H), 2.0 (d, J=11.5, 2H), 1.78 (d, J=11.7, 2H), 1.35 (q, J=11.7, 2H); MS (ESI) m/z 355.4[M+ 1]$^+$; mp 343-345° C.

5.1.43 Example 43

Synthesis of 2-(3-HYDROXYPHENYLAMINO)-9-(2-METHOXYPHENYL)-9H-PURINE-6-CARBOXAMIDE A. 5-Amino-2-(3-hydroxyphenylamino)-6-(2-methoxyphenylamino)pyrimidine-4-carbox-amide. In a sealed tube, ethyl 5-amino-2-(3-hydroxyphenylamino)-6-(2-methoxyphenyl-amino)pyrimidine-4-carboxylate (See example 36.B) (76.4 mg, 0.193 mmol) was dissolved in anhydrous methanol (5 mL) and was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting material was purified by column chromatography (100% ethyl acetate) to provide the title compound (61.5 mg, 0.168 mmol, 87% yield). MS (ESI) m/z 367.2 [M+1]$^+$.

B. 2-(3-Hydroxyphenylamino)-9-(2-methoxyphenyl)-9H-purine-6-carboxamide. 5-Amino-2-(3-hydroxyphenylamino)-6-(2-methoxyphenylamino)pyrimidine-4-carboxamide (61.5 mg, 0.168 mmol) was suspended in triethyl orthoformate (5 mL) and stirred at 130° C. for 1H. The reaction was then cooled to room temperature and solvent was removed under reduced pressure. The crude material was purified by column chromatography (5% methanol in methylene chloride) and a second chromatography (0-10% methanol in ethyl acetate) to provide the title compound in 99.6% purity (48.2 mg, 0.128 mmol, 76% yield). $^1$H NMR (400 MHz, DMSO-d$_6$) δ 9.74 (s, 1H), 9.18 (s, 1H), 8.49 (s, 1H), 8.29 (s, 1H), 8.09 (s, 1H), 7.63 (dd, J=7.81, 1.56, 1H), 7.56 (t, J=8.60, 1H), 7.33 (d, J=8.59, 1H), 7.26 (d, J=8.59, 1H), 7.20-7.16 (m, 2H), 6.97 (t, J=8.10, 1H), 6.33 (d, J=9.76, 1H), 3.81 (s, 3H); MS (ESI) m/z 377.1 [M+1]$^+$; mp 155-157° C.

5.1.44 Example 44

Synthesis of 9-ISOPROPYL-2-(3-HYDROXY-PHENYL)-8-OXO-8,9-DIHYDRO-7H-PURINE-6-CARBOXAMIDE A. 6-Isopropylamino-2-chloro-5-nitro-pyrimidine-4-carboxylate. Isopropylamine (0.34 g, 5.7 mmol) and 2,6-dichloro-5-nitropyrimidine-4-carboxylate (1.6 g, 6.0 mmol) were reacted according to General Procedure C and purified using Biotage silica gel chromatography (0-35% ethyl acetate in hexanes) to afford the title compound (1.8 g, 4.0 mmol, 68% yield). MS (ESI) m/z 289.7 [M+1]$^+$, 290.5 [M+2]$^+$.

B. 5-Amino-6-isopropylamino-2-chloro-pyrimidine-4-carboxylate. 6-isopropylamino-2-chloro-5-nitro-pyrimidine-4-carboxylate (1.2 g, 4.2 mmol) was suspended in ethanol (80 mL) and DMF (16 mL) and reacted with tin (II) chloride dihydrate (2.8 g, 12.3 mmol) according to General Procedure D. The crude residue (0.46 g, 1.69 mmol, 70% yield) was taken on to the next step without further purification. MS (ESI) m/z 259.1 [M+1]$^+$, 260.1 [M+2]$^+$.

C. 5-Amino-6-isopropylamino-2-(3-hydroxy-phenyl)-pyrimidine-4-carboxylate. In a microwave flask was placed 5-amino-6-isopropylamino-2-chloro-pyrimidine-4-carboxylate (1.2 g, 4.6 mmol), 3-hydroxyphenylboronic acid (0.96 g, 7.0 mmol), potassium phosphate (3.0 g, 14.0 mmol), dicyclohexyl(2',6'-dimethoxybiphenyl-2-yl)phosphine (0.28 g, 0.68 mmol) and palladium (II) acetate (0.16 g, 0.71 mmol) in tetrahydrofuran (25 mL) and water (4 mL). The mixture was reacted according to General Procedure E. The crude residue was purified using Biotage silica gel chromatography (0-35% ethyl acetate in hexanes) to afford the title compound (0.43 g, 1.4 mmol, 29% yield). MS (ESI) m/z 317.1 [M+1]$^+$.

D. 9-Isopropyl-2-(3-hydroxy-phenyl)-8-oxo-8,9-dihydro-7H-purine-6-carboxylate. 5-Amino-6-isopropylamino-2-(3-hydroxy-phenyl)-pyrimidine-4-carboxylate (0.43 g, 1.4 mmol) and 1,1'-carbonyldiimidazole (1.1 g, 6.8 mmol) were reacted according to General Procedure F. The crude residue was triturated with methylene chloride and cold hexanes to afford the title compound as a white solid (0.29 g, 0.85 mmol, 63% yield). MS (ESI) m/z 343.4 [M+1]$^+$.

E. 9-Isopropyl-2-(3-hydroxy-phenyl)-8-oxo-8,9-dihydro-7H-purine-6-carboxamide. 9-Isopropyl-2-(3-hydroxy-phenyl)-8-oxo-8,9-dihydro-7H-purine-6-carboxylate (0.29 g, 0.85 mmol) and ammonia gas were reacted according to General Procedure G. The crude residue was triturated with boiling methanol and diethyl ether. The resulting white solid was dried under high vacuum at 60° C. to afford the title compound as a white solid in 95.8% purity (0.029 g, 0.093 mmol, 11% yield). $^1$H NMR (400 MHz, DMSO-d$_6$) δ 11.48 (s, 1H), 9.52 (s, 1H), 8.33 (s, 1H), 8.01 (d, J=6.6, 1H), 7.91 (s, 1H), 7.18-7.35 (m, 1H), 6.87 (d, J=8.6, 1H), 4.55-4.83 (m, 1H), 1.57 (d, J=6.2, 6H); MS (ESI) m/z 314.2 [M+1]$^+$; mp 338-342° C.

5.1.45 Example 45

Synthesis of METHYL 4-(6-CARBAMOYL-9-(2-METHOXYPHENYL)-8-OXO-8,9-DIHYDRO-7H-PURIN-2-YL)BENZOATE A. Methyl 4-(6-carbamoyl-9-(2-methoxyphenyl)-8-oxo-8,9-dihydro-7H-purin-2-yl)benzoate. (Z)-1-(2-Amino-1,2-dicyanovinyl)-3-(2-methoxyphenyl)urea (See Example 2.A) (0.65 g, 2.53 mmol), 4-acetoxybenzaldehyde (0.44 g, 2.65 mmol) and triethylamine (3.0 mL) were reacted according to General Procedure B. The crude residue was purified using Biotage silica gel chromatography (0-100% ethyl acetate in hexanes) to afford the title compound in 98.9% purity (0.129 g, 0.069 mmol, 51% yield). $^1$H NMR (400 MHz, DMSO-d$_6$) δ 11.87 (s, 1H), 8.58 (s, 1H), 8.51-8.53 (m, J=1.2, 1H), 8.49-8.51 (m, J=3.5, 1H), 8.02 (dd, J=8.4, 4.1, 1H), 7.50-7.60 (m, 1H), 7.31 (dd, J=7.4, 3.5, 1H), 7.15-7.20 (m, 1H), 3.88 (s, 1H), 3.76 (s, 1H); MS (ESI) m/z 420.1 [M+1]$^+$; mp 286-290° C.

5.1.46 Example 46

Synthesis of 2-(2-CHLORO-3-HYDROXYPHENYL)-9-(2-METHOXYPHENYL)-8-OXO-7-HYDROPURINE-6-CARBOXAMIDE A. 2-(2-Chloro-3-hydroxyphenyl)-9-(2-methoxyphenyl)-8-oxo-7-hydropurine-6-carbox amide. N-(1-Amino-2,2-dicyanovinyl)[(2-methoxyphenyl)amino]carboxamide (0.25 g, 1.0 mmol), 2-chloro-3-hydroxybenzaldehyde (0.33 g, 2.1 mmol), and triethylamine (0.25 mL) were reacted according to General Procedure B. Product was purified using reverse-phase semi-preparatory HPLC (20-70% acetonitrile+0.1% TFA in H$_2$O+0.1% TFA, over 39 min). Fractions containing the desired material were combined and concentrated under reduced pressure before being passed through a Strata-XC ion exchange column with water, methanol, and 5% ammonium hydroxide in methanol. The resultant solid was dried under high vacuum at 60° C. to afford the title compound as a white solid (0.082 g, 0.19 mmol, 20% yield). $^1$H NMR (300 MHz, DMSO-d$_6$) δ 11.82 (s, 1H), 10.22 (s, 1H), 8.00 (d, J=16, 2H), 7.51 (dt, J=7.8, 0.9, 1H), 7.45 (dd, J=7.8, 1.2, 1H), 7.25-7.00 (m, 5H), 3.73 (s, 3H); MS (ESI) m/z 412.2 [M+1]$^+$; mp 331-334° C.

5.1.47 Example 47

Synthesis of 2-(3-CYANOPHENYL)-9-(2-METHOXYPHENYL)-8-OXO-8,9-DIHYDRO-7H-PURINE-6-CARBOXAMIDE A. 2-(3-Cyanophenyl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (See Example 2.A) (0.2 g, 0.78 mmol), 3-formylbenzonitrile (0.222 g, 1.7 mmol) and triethylamine (0.1 mL) were reacted according to General Procedure B. The resulting precipitate was dissolved in DMF and crashed out by the addition of water. This precipitate was filtered off and dried under vacuum to provide the title compound in 96.3% purity (0.174 g, 0.451 mmol, 58% yield). $^1$H NMR (300 MHz, DMSO-d$_6$) δ 11.87 (s, 1H), 8.99 (s, 1H), 8.76 (s, 1H), 8.52 (d, J=7.97, 1H), 8.03 (s, 1H), 7.90 (d, J=7.69, 1H), 7.67-7.49 (m, 3H), 7.30 (d, J=7.69, 1H), 7.16 (t, J=7.55, 1H), 3.75 (s, 3H); MS (ESI) m/z 387.3 [M+1]$^+$; mp 316-318° C.

5.1.48 Example 48

Synthesis of 2-(2-HYDROXYPHENYLAMINO)-9-(2-METHOXYPHENYL)-8-OXO-8,9-DIHYDRO-7H-PURINE-6-CARBOXAMIDE A. Ethyl 2-(2-hydroxyphenylamino)-6-(2-methoxyphenylamino)-5-nitropyrimidine-4-carboxylate. To a solution of ethyl 2-chloro-6-(2-methoxyphenylamino)-5-nitropyrimidine-4-carboxylate (See Example 30.A) (300 mg, 0.851 mmol) in DMF (5 mL) was added 2-aminophenol (111 mg, 1.021 mmol) and N,N-diisopropylethylamine (0.223 mL, 1.276 mmol). The reaction was stirred at room temperature overnight. Solvent was removed under reduced pressure and the resulting residue was purified by chromatography on a normal phase silica gel column (50% ethyl acetate in hexanes). Fractions containing product were combined and the solvent evaporated to provide the title compound (362 mg, 0.851 mmol, 100% yield). MS (ESI) m/z 426.2 [M+1]$^+$.

B. Ethyl 5-amino-2-(2-hydroxyphenylamino)-6-(2-methoxyphenylamino)pyrimidine-4-carboxylate. Ethyl 2-(2-hydroxyphenylamino)-6-(2-methoxyphenylamino)-5-nitropyrimidine-4-carboxylate (362 mg, 0.851 mmol) was dissolved in ethanol (20 mL) and 10% palladium on carbon (91 mg, 0.085 mmol) was added. The reaction mixture was stirred at room temperature under an atmosphere of hydrogen overnight. The reaction was then filtered through Celite, solvent was removed under reduced pressure and purified by column chromatography (50% ethyl acetate in hexanes). Fractions containing product were combined and the solvent evaporated to provide the title compound (272.6 mg, 0.689 mmol, 81% yield). MS (ESI) m/z 396.2 [M+1]$^+$.

C. Ethyl 5-amino-2-(2-(tert-butyldimethylsilyloxy)phenylamino)-6-(2-methoxyphenyl amino)pyrimidine-4-carboxylate. Ethyl 5-amino-2-(2-hydroxyphenylamino)-6-(2-methoxy phenylamino)pyrimidine-4-carboxylate (184 mg, 0.465 mmol) was dissolved in methylene chloride (5 mL) and tert-butyldimethylsilyl chloride (77 mg, 0.512 mmol) and imidazole (38.0 mg, 0.558 mmol) were added. The reaction mixture was stirred overnight at room temperature. Solvent was removed under reduced pressure and crude was purified by column chromatography (20% ethyl acetate in hexanes). Fractions containing product were combined and the solvent evaporated to provide the title compound (232.6 mg, 0.456 mmol, 98% yield) as a yellow solid. MS (ESI) m/z 510.5 [M+1]$^+$.

D. Ethyl 2-(2-(tert-butyldimethylsilyloxy)phenylamino)-9-(2-methoxyphenyl)-8-oxo-8,9-dihydro-7H-purine-6-carboxylate. Ethyl 5-amino-2-(2-(tert-butyldimethylsilyloxy) phenyl amino)-6-(2-methoxyphenylamino)pyrimidine-4-carboxylate (232.6 mg, 0.456 mmol) was dissolved in methylene chloride (5 mL) and 1,1'-carbonyldiimidazole (740 mg, 4.56 mmol) was added. The reaction was refluxed for 1H and then stirred at room temperature overnight. Solvent was removed under reduced pressure and crude was purified by column chromatography (50% ethyl acetate in hexanes). Fractions containing product were combined and the solvent evaporated to provide the title compound (235.2 mg, 0.439 mmol, 96% yield) as a yellow solid. MS (ESI) m/z 536.4 [M+1]$^+$.

E. 2-(2-Hydroxyphenylamino)-9-(2-methoxyphenyl)-8-oxo-8,9-dihydro-7H-purine-6-carboxamide. Ethyl 2-(2-(tert-butyldimethylsilyloxy)phenylamino)-9-(2-methoxyphenyl)-8-oxo-8,9-dihydro-7H-purine-6-carboxylate (235.2 mg, 0.439 mmol) was dissolved in anhydrous methanol (8 mL) and was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting material was resuspended in methylene chloride. The precipitate was filtered and washed with methylene chloride and 5% methanol in methylene chloride and dried under high vacuum to provide the title compound in 97.4% purity (125 mg, 0.319 mmol, 73% yield). $^1$H NMR (300 MHz, DMSO-d$_6$) δ 11.28 (s, 1H), 9.81 (s, 1H), 7.94-7.91 (m, 2H), 7.81 (s, 2H), 7.53 (t, J=7.00, 1H), 7.45 (dd, J=7.69, 1.65, 1H), 7.26 (d, J=7.42, 1H), 7.12 (t, J=7.42, 1H), 6.82-6.66 (m, 3H), 3.76 (s, 3H); MS (ESI) m/z 393.2 [M+1]$^+$; mp 314-315° C.

5.1.49 Example 49

2-(3-HYDROXYPHENYL)-9-(4-METHOXY-2-METHYLPHENYL)-8-OXO-8,9-DIHYDRO-7H-PURINE-6-CARBOXAMIDE

A. (Z)-1-(2-Amino-1,2-dicyanovinyl)-3-(4-methoxy-2-methylphenyl)urea. 4-Methoxy-2-methylphenyl isocyanate (1.51 g, 9.25 mmol) and diaminomaleonitrile (1.0 g, 9.25 mmol) were reacted according to General Procedure A. The resultant heterogeneous mixture was filtered and washed with acetonitrile followed by diethyl ether to afford the title compound (0.435 g, 17%). MS (ESI) m/z 272.4[M+1]$^+$.

B. 2-(3-Hydroxyphenyl)-9-(4-methoxy-2-methylphenyl)-8-oxo-8,9-dihydro-7H-purine-6-carboxamide. (Z)-1-(2-Amino-1,2-dicyanovinyl)-3-(4-methoxy-2-methylphenyl) urea (0.435 g, 1.60 mmol), 3-hydroxybenzaldehyde (0.390 g, 3.2 mmol) and triethylamine (0.6 mL) were reacted according to General Procedure B. The precipitate was triturated with dimethylformamide and water to afford the title compound (0.310 g, 49%). $^1$H NMR (300 MHz, DMSO-d$_6$) δ 11.73 (s, 1H), 9.47 (s, 1H), 8.38 (s, 1H), 7.97 (s, 1H), 7.90 (d, J=8.4, 1H), 7.68 (s, 1H), 7.36 (d, J=8.4, 1H), 7.27 (t, J=8.4, 1H), 7.03 (d, J=3.0, 1H), 6.95 (dd, J=2.7, J=9.0, 1H), 6.81 (dd, J=8.1, 1H), 3.84 (s, 3H), 2.1 (s, 3H); MS (ESI) m/z 392.4[M+1]$^+$; mp 355-357° C.

5.1.50 Example 50

2-(3-HYDROXYPHENYL)-8-OXO-9-(2-(TRIFLUOROMETHYL)PHENYL)-8,9-DIHYDRO-7H-PURINE-6-CARBOXAMIDE

A. (Z)-1-(2-Amino-1,2-dicyanovinyl)-3-(2-(trifluoromethyl)phenyl)urea. α,α,α-Trifluoro-o-tolyl isocyanate (1.73 g, 9.24 mmol) and diaminomaleonitrile (2.5 g, 23.12 mmol) were reacted according to General Procedure A. The resultant heterogeneous mixture was filtered and washed with acetonitrile followed by diethyl ether to afford the title compound (0.410 g, 15%). MS (ESI) m/z 296.4[M+1]$^+$.

B. 2-(3-Hydroxyphenyl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl)urea (0.403 g, 1.36 mmol), 3-hydroxybenzaldehyde (0.333 g, 2.73 mmol) and triethylamine (0.6 mL) were reacted according to General Procedure B. The precipitate was triturated with dimethylformamide and water to afford the title compound (0.206 g, 36%). $^1$H NMR (300 MHz, DMSO-d$_6$) δ 11.89 (s, 1H), 9.45 (s, 1H), 8.42 (s, 1H), 8.0 (m, 3H) 7.84 (m, 3H), 7.62 (s, 1H), 7.21 (t, J=8.1, 1H), 6.81 (dd, J=7.2, 1.5, 1H); MS (ESI) m/z 416.4[M+1]$^+$; mp 363-365° C.

5.1.51 Example 51

Synthesis of 2-(4-CYANO-PHENYL)-9-(2-METHOXY-PHENYL)-8-OXO-8,9-DIHYDRO-7H-PURINE-6-CARBOXAMIDE A. 2-(4-Cyano-phenyl)-9-(2-methoxy-phenyl)-8-oxo-8,9-dihydro-7H-purine-6-carboxamide. (Z)-1-(2-Amino-1,2-dicyanovinyl)-3-(2-methoxyphenyl)urea (See Example 2.A) (0.30 g, 1.2 mmol), 4-formylbenzonitrile (0.16 g, 1.22 mmol) and triethylamine (1.5 mL) were reacted according to General Procedure B. The crude residue was triturated with DMF and water to afford a light brown solid. This solid was dried under vacuum at 60° C. to give the title compound in 98.4% purity (0.051 g, 0.13 mmol, 11% yield). $^1$H NMR (300 MHz, DMSO-d$_6$) δ 11.91 (s, 1H), 8.64 (s, 1H), 8.56 (d, J=8.2, 1H), 8.03 (s, 1H), 7.92 (d, J=8.2, 1H), 7.48-7.61 (m, 1H), 7.30 (d, J=8.5, 1H), 7.16 (t, J=7.6, 1H), 3.75 (s, 1H); MS (ESI) m/z 387.1 [M+1]$^+$; mp 335-338° C.

5.1.52 Example 52

Synthesis of 4-[6-CARBAMOYL-9-(2-METHOXYPHENYL)-8-OXO-8,9-DIHYDRO-7H-PURIN-2-YL]-BENZOIC ACID METHYL ESTER A. 4-[6-Carbamoyl-9-(2-methoxy-phenyl)-8-oxo-8,9-dihydro-7H-purin-2-yl]-benzoic acid. (Z)-1-(2-Amino-1,2-dicyanovinyl)-3-(2-methoxyphenyl)urea (See Example 2.A) (0.30 g, 1.2 mmol), 4-formylbenzoic acid (0.44 g, 2.65 mmol) and triethylamine (3.0 mL) were reacted according to General Procedure B. The crude residue was purified using Biotage silica gel chromatography (0-100% ethyl acetate in hexanes) to afford the title compound in 99.4% purity (0.129 g, 0.069 mmol, 51% yield). $^1$H NMR (300 MHz, DMSO-d$_6$) δ 11.85 (s, 1H), 8.56 (s, 1H), 8.48 (d, J=8.2, 1H), 8.03 (s, 1H), 7.99 (d, J=8.5, 1H), 7.49-7.61 (m, 1H), 7.31 (d, J=8.5, 1H), 7.17 (td, J=7.7, 1.1, 1H), 3.76 (s, 1H); MS (ESI) m/z 420.1 [M+1]$^+$; mp 328-332° C.

5.1.53 Example 53

Synthesis of METHYL 3-(6-CARBAMOYL-9-(2-METHOXYPHENYL)-8-OXO-8,9-DIHYDRO-7H-PURIN-2-YL)BENZOATE A. Methyl 3-(6-carbamoyl-9-(2-methoxyphenyl)-8-oxo-8,9-dihydro-7H-purin-2-yl)benzoate. (Z)-1-(2-Amino-1,2-dicyanovinyl)-3-(2-methoxyphenyl)urea (See Example 2.A) (0.4 g, 1.56 mmol), methyl 3-formylbenzoate (0.556 g, 3.39 mmol) and triethylamine (0.2 mL) were reacted according to General Procedure B. The resulting precipitate was dissolved in DMF and crashed out by the addition of water. This precipitate was filtered off and dried under vacuum to provide the title compound in 98.7% purity (0.426 g, 1.02 mmol, 65% yield). $^1$H NMR (300 MHz, DMSO-d$_6$) δ 11.83 (s, 1H), 8.77-8.74 (m, 2H), 8.53 (s, 1H), 8.03-8.00 (m, 2H), 7.64-7.51 (m, 3H), 7.32 (d, J=7.69, 1H), 7.17 (t, J=7.69, 1H), 3.86 (s, 3H), 3.77 (s, 3H); MS (ESI) m/z 420.1 [M+1]$^+$; mp 265-266° C.

5.1.54 Example 54

Synthesis of 2-(3-AMINOPHENYL)-9-(2-METHOXYPHENYL)-8-OXO-8,9-DIHYDRO-7H-PURINE-6-CARBOXAMIDE A. 2-(3-Aminophenyl)-9-(2-methoxyphenyl)-8-oxo-8,9-dihydro-7H-purine-6-carboxamide. 9-(2-Methoxyphenyl)-2-(3-nitrophenyl)-8-oxo-8,9-dihydro-7H-purine-6-carboxamide (See Example 20.A) (68 mg, 0.167 mmol) was dissolved in ethanol (10 ml) and 10% palladium on carbon catalyst (17.81 mg, 0.017 mmol) was added. The reaction mixture was stirred at room temperature under an atmosphere of hydrogen overnight. The crude reaction was filtered through Celite and purified by column chromatography (SiO$_2$, 2% methanol in dichloromethane) to yield the title product in 98.8% purity (15 mg, 24%). $^1$H NMR (400 MHz, DMSO-d$_6$) δ 11.70 (s, 1H), 8.27 (s, 1H), 8.02 (s, 1H), 7.55 (m, 2H), 7.49 (m, 2H), 7.29 (d, J=8.2, 1H), 7.15 (t, J=7.4, 1H), 7.07 (t, J=7.7, 1H), 6.62 (d, J=7.8, 1H), 5.10 (s, 2H), 3.75 (s, 3H); MS (ESI) m/z 377.1 [M+1]$^+$; mp 284-285° C.

5.1.55 Example 55

Synthesis of 3-(6-CARBAMOYL-9-(2-METHOXYPHENYL)-8-OXO-8,9-DIHYDRO-7H-PURIN-2-YL)BENZOIC ACID A. 3-(6-Carbamoyl-9-(2-methoxyphenyl)-8-oxo-8,9-dihydro-7H-purin-2-yl)benzoic acid. Methyl 3-(6-carbamoyl-9-(2-methoxyphenyl)-8-oxo-8,9-dihydro-7H-purin-2-yl)benzoate (50 mg, 0.119 mmol) was dissolved in DMF (2 mL) and 1 mL of a 5M solution of sodium hydroxide in water was added. The reaction mixture was stirred at room temperature overnight. The solvents were removed under reduced pressure and the residue neutralized with 1N HCl. The precipitate was filtered off, washed with water and dried under high vacuum to provide the title compound in 97.9% purity (48.3 mg, 0.119 mmol, 100% yield). $^1$H NMR (300 MHz, DMSO-d$_6$) δ 11.81 (s, 1H), 8.76-8.74 (m, 2H), 8.51 (s, 1H), 8.01-7.98 (m, 2H), 7.61-7.50 (m, 3H), 7.31 (d, J=8.24, 1H), 7.17 (t, J=7.69, 1H), 3.76 (s, 3H); MS (ESI) m/z 406.5 [M+1]$^+$; mp 348-350° C.

5.1.56 Example 56

2-(3-HYDROXYPHENYL)-9-(2-ISOPROPYLPHENYL)-8-OXO-8,9-DIHYDRO-7H-PURINE-6-CARBOXAMIDE

A. (Z)-1-(2-Amino-1,2-dicyanovinyl)-3-(2-isopropylphenyl)urea. 2-Isopropylphenyl isocyanate (1.49 g, 9.25 mmol) and diaminomaleonitrile (1.0 g, 9.25 mmol) were reacted according to General Procedure A. The resultant heterogeneous mixture was filtered and washed with acetonitrile followed by diethyl ether to afford the title compound (0.338 g, 14%). MS (ESI) m/z 270.4[M+1]$^+$.

B. 2-(3-Hydroxyphenyl)-9-(2-isopropylphenyl)-8-oxo-8,9-dihydro-7H-purine-6-carboxamide. (Z)-1-(2-Amino-1,2-dicyanovinyl)-3-(2-isopropylphenyl)urea (0.338 g, 1.25 mmol), 3-hydroxybenzaldehyde (0.306 g, 2.51 mmol) and triethylamine (0.6 mL) were reacted according to General Procedure B. The resultant heterogeneous mixture was filtered and washed with methanol followed by diethyl ether to afford the title compound (0.137 g, 28%). $^1$H NMR (300 MHz, DMSO-d$_6$) δ 11.80 (s, 1H), 9.48 (s, 1H), 8.40 (s, 1H), 7.99 (s, 1H), 7.88 (d, J=8.1, 1H), 7.66 (s, 1H), 7.57 (m, 2H), 7.41 (d, J=4.2, 2H), 7.21 (t, J=7.8, 1H), 6.80 (d, J=7.8, 1H), 2.73 (m, 1H), 1.11 (t, J=7.2, 6H); MS (ESI) m/z 390.4[M+1]$^+$; mp 322-324° C.

5.1.57 Example 57

Synthesis of 2-(1H-INDAZOL-6-YL)-9-(2-METHOXYPHENYL)-8-OXO-7-HYDROPURINE-6-CARBOXAMIDE A. 2-(1H-Indazol-6-yl)-9-(2-methoxyphenyl)-8-oxo-7-hydropurine-6-carboxamide. (Z)-1-(2-Amino-1,2-dicyanovinyl)-3-(2-methoxyphenyl)urea (See Example 2.A) (0.23 g, 0.89 mmol) and 1H-indazole-6-carbaldehyde (0.29 g, 1.95 mmol) were reacted according to General Procedure B. The solution was allowed to stir at room temperature for 18 h. The resultant heterogeneous mixture was filtered and purified using reverse-phase semi-preparatory HPLC (20-100% MeCN+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (42 mg, 0.11 mmol, 12%) as an off-white solid. $^1$H NMR (300 MHz, DMSO-d$_6$) δ 8.64 (s, 1H), 8.52 (s, 1H), 8.36 (dd, J=8.4, 1.5, 1H), 8.16 (s, 1H), 8.09 (s, 1H), 7.86 (d, J=8.4, 1H), 7.63 (m, 2H), 7.40 (dd, J=7.2, 1.0, 1H), 7.26 (ddd, J=8.7, 7.5, 1.2, 1H), 3.84 (s, 3H); MS (ESI) m/z 402.1[M+1]$^+$; mp 309-310° C.

5.1.58 Example 58

Synthesis of 2-(4-CARBAMOYLPHENYL)-9-(2-METHOXYPHENYL)-8-OXO-8,9-DIHYDRO-7H-PURINE-6-CARBOXAMIDE A. 2-(4-Carbamoylphenyl)-9-(2-methoxyphenyl)-8-oxo-8,9-dihydro-7H-purine-6-carboxamide. Methyl 4-(6-carbamoyl-9-(2-methoxyphenyl)-8-oxo-8,9-dihydro-7H-purin-2-yl)benzoate (See Example 45.A) (0.15 g, 0.36 mmol) was dissolved in 30 mL of methanol. The temperature of the solution was brought to −78° C. and NH$_{3(g)}$ was bubbled into the reaction vessel for 15 min. The reaction vessel was sealed and stirred for 6 h. After 6 h, KCN (0.05, 0.77 mmol) was added and the reaction was heated at 50° C. for 24 hours. The crude residue was purified using Biotage silica gel chromatography (0-20% methanol in DCM) and rinsed with boiling methanol (100 mL) to give the desired compound (0.020 g, 0.049 mmol, 14% yield). $^1$H NMR (400 MHz, DMSO-d$_6$) δ 12.56 (s, 1H), 8.58 (s, 1H), 8.51-8.53 (m, J=1.2, 1H), 8.49-8.51 (m, 1H), 8.02 (dd, J=8.4, 4.1, 1H), 7.50-7.59 (m, 1H), 7.31 (dd, J=7.4, 3.5, 1H), 7.15-7.22 (m, 1H), 3.81 (s, 1H); MS (ESI) m/z 405.1 [M+1]$^+$; mp>350° C.

5.1.59 Example 59

9-(2-ETHYLPHENYL)-2-(3-HYDROXYPHENYL)-8-OXO-8,9-DIHYDRO-7H-PURINE-6-CARBOXAMIDE

A. (Z)-1-(2-Amino-1,2-dicyanovinyl)-3-(2-ethylphenyl)urea. 2-Isopropylphenyl isocyanate (1.36 g, 9.25 mmol) and diaminomaleonitrile (1.0 g, 9.25 mmol) were reacted according to General Procedure A. The resultant heterogeneous mixture was filtered and washed with acetonitrile followed by diethyl ether to afford the title compound (1.05 g, 45%). MS (ESI) m/z 256.4[M+1]$^+$.

B. 9-(2-Ethylphenyl)-2-(3-hydroxyphenyl)-8-oxo-8,9-dihydro-7H-purine-6-carboxamide. (Z)-1-(2-Amino-1,2-dicyanovinyl)-3-(2-ethylphenyl)urea (1.05 g, 4.11 mmol), 3-hydroxybenzaldehyde (1.0 g, 8.22 mmol) and triethylamine (1.2 mL) were reacted according to General Procedure B. The resultant heterogeneous mixture was filtered and washed with methanol followed by diethyl ether to afford the crude compound. The solid was purified using preparative HPLC (0.202 g, 13%). $^1$H NMR (300 MHz, DMSO-d$_6$) δ 11.80 (s, 1H), 9.47 (s, 1H), 8.40 (s, 1H), 7.99 (s, 1H), 7.88 (d, J=8.1, 1H), 7.65 (s, 1H), 7.51 (m, 2H), 7.43 (d, J=4.2, 2H), 7.22 (t, J=7.8, 1H), 6.80 (d, J=7.8, 1H), 2.46 (q, J=7.5, 1H), 1.05 (t, J=7.8, 6H); MS (ESI) m/z 390.4[M+1]$^+$; mp 355-357° C.

5.1.60 Example 60

Synthesis of 9-(2,5-DICHLOROPHENYL)-2-(3-HYDROXYPHENYL)-8-OXO-7-HYDROPURINE-6-CARBOXAMIDE A. N-((1Z)-2-Amino-1,2-dicyanovinyl)[(2,5-dichlorophenyl)amino]carboxamide. 2,5-Dichlorobenzenisocyanate (1.83 g, 9.71 mmol) and 2,3-diaminomaleonitrile (1.0 g, 9.3 mmol) were reacted in acetonitrile according to General Procedure A. The material was filtered and suspended acetonitrile/diethyl ether. The resultant solid was filtered and dried to give the title compound as a tan solid (2.38 g, 8.07 mmol, 87% yield); MS (ESI) m/z 296.1 [M+1]$^+$.

B. 9-(2,5-Dichlorophenyl)-2-(3-hydroxyphenyl)-8-oxo-7-hydropurine-6-carboxamide. N-((1Z)-2-Amino-1,2-dicyanovinyl)[(2,5-dichlorophenyl)amino]carboxamide (0.440 g, 1.49 mmol), 3-hydroxybenzaldehyde (0.409 g, 3.36 mmol), and triethyl amine (0.291 mL, 2.08 mmol) in MeOH (15 mL) were reacted according to General Procedure B. The resultant heterogeneous mixture was filtered, washed with additional acetonitrile followed by MeOH to afford the title compound (0.365 g, 59%). $^1$H NMR (300 MHz, DMSO-d$_6$) δ 11.90 (s, 1H), 9.49 (s, 1H), 8.42 (s, 1H), 8.06 (s, 1H), 7.90 (d, J=2.3, 1H), 7.81-7.88 (m, 1H), 7.65-7.75 (m, 1H), 7.23 (t, J=7.6, 1H), 6.82 (dd, J=7.5, 2.2, 1H); MS (ESI) m/z 416.1 [M+1]$^+$; mp 358-360° C.

5.1.61 Example 61

Synthesis of 2-(3-CARBAMOYLPHENYL)-9-(2-METHOXYPHENYL)-8-OXO-8,9-DIHYDRO-7H-PURINE-6-CARBOXAMIDE A. 2-(3-Carbamoylphenyl)-9-(2-methoxyphenyl)-8-oxo-8,9-dihydro-7H-purine-6-carbox amide. Methyl 3-(6-carbamoyl-9-(2-methoxyphenyl)-8-oxo-8,9-dihydro-7H-purin-2-yl)benzoate (96 mg, 0.229 mmol) and potassium cyanide (7.45 mg, 0.114 mmol) were dissolved in dry methanol and cooled to −78° C. The solution was saturated with ammonia gas and the reaction was capped and stirred at 50° C. for 48 h. LCMS showed that reaction was incomplete, additional potassium cyanide (7.45 mg, 0.114 mmol) was added, the solution was cooled to −78° C. and saturated again with ammonia gas. Reaction was stirred at 60° C. for three days. After cooling down a precipitate formed that was filtered off and purified by column chromatography (10% methanol in methylene chloride). Fractions containing product were combined to provide the title compound in 97.2% purity (44 mg, 0.109 mmol, 47% yield). $^1$H NMR (300 MHz, DMSO-d$_6$) δ 11.83 (s, 1H), 8.80 (s, 1H), 8.60 (s, 1H), 8.41 (d, J=7.97, 1H), 8.12-8.08 (m, 2H), 7.93 (d, J=7.42, 1H), 7.58-7.49 (m, 4H), 7.30 (d, J=7.69, 1H), 7.16 (t, J=7.69, 1H), 3.75 (s, 3H); MS (ESI) m/z 405.1 [M+1]$^+$; mp 338-339° C.

5.1.62 Example 62

Synthesis of 9-(2,6-DICHLOROPHENYL)-2-(3-HYDROXYPHENYL)-8-OXO-7-HYDROPURINE-6-CARBOXAMIDE A. N-((1Z)-2-Amino-1,2-dicyanovinyl)[(2,6-dichlorophenyl)amino]carboxamide. 2,6-Dichlorobenzenisocyanate (1.83 g, 9.71 mmol) and 2,3-diaminomaleonitrile (1.0 g, 9.3 mmol) were reacted in acetonitrile according to General Procedure A. The material was filtered and suspended acetonitrile/diethyl ether. The resultant solid was filtered and dried to give the title compound as a tan solid (1.74 g, 5.87 mmol, 64% yield); MS (ESI) m/z 296.1 [M+1]$^+$.

B. 9-(2,6-Dichlorophenyl)-2-(3-hydroxyphenyl)-8-oxo-7-hydropurine-6-carboxamide. N-((1Z)-2-Amino-1,2-dicyanovinyl)[(2,6-dichlorophenyl)amino]carboxamide (0.3 g, 1.02 mmol), 3-hydroxybenzaldehyde (0.278 g, 2.28 mmol), and triethyl amine (0.199 mL, 1.43 mmol) in MeOH (15 mL) were reacted according to General Procedure B. Product was purified using reverse-phase semi-preparatory HPLC (30-70% acetonitrile+0.1% TFA in H$_2$O+0.1% TFA, over 39 min). Fractions containing the desired material were combined and concentrated under reduced pressure to a minimal amount of water. Ammonium hydroxide (2 mL) was added and the resulting slurry was sonicated and extracted with EtOAc. The organic layer was dried and concentrated to afford the title compound as a white solid (0.07 g, 0.17 mmol, 17% yield). $^1$H NMR (300 MHz, DMSO-d$_6$) δ 12.2 (s, 1H), 9.50 (s, 1H), 8.47 (s, 1H), 8.07 (s, 1H), 7.89 (d, J=8.0, 1H), 7.78-7.86 (m, 1H), 7.63-7.76 (m, 1H), 7.24 (t, J=7.8, 1H), 6.84 (dd, J=7.6, 2.1, 1H); MS (ESI) m/z 416.1 [M+1]$^+$; mp 290-292° C.

5.1.63 Example 63

Synthesis of 2-(2-HYDROXYPHENYL)-9-(2-METHOXYPHENYL)PURINE-6-CARBOXAMIDE

A. Ethyl 5-amino-2-(2-hydroxyphenyl)-6-[(2-methoxyphenyl)amino]pyrimidine-4-carboxylate. In a microwave flask was placed ethyl 5-amino-2-chloro-6-(2-methoxyphenylamino)pyrimidine-4-carboxylate (400 mg, 1.24 mmol), 3-hydroxyphenylboronic acid (260 mg, 1.86 mmol), potassium phosphate (531 mg, 2.504 mmol), dicyclohexyl(2′,6′-dimethoxybiphenyl-2-yl)phosphine (77 mg, 0.188 mmol) and palladium (II) acetate (42.2 mg, 0.188 mmol) in tetrahydrofuran (20 mL) and water (2 mL) and the reaction mixture was heated at 120° C. for 60 min in the microwave. The reaction mixture was filtered and the crude product adsorbed onto silica gel. Flash chromatography (40% EtOAc in hexanes) afforded the title compound (235 mg, 0.62 mmol, 50%) as a tan solid. MS (ESI) m/z 381.3[M+1]$^+$.

B. 5-Amino-2-(2-hydroxyphenyl)-6-[(2-methoxyphenyl)amino]pyrimidine-4-carboxamide. A solution of ethyl 5-amino-2-(2-hydroxyphenyl)-6-(2-methoxyphenylamino)pyrimidine-4-carboxylate (235 mg, 0.61 mmol) in anhydrous methanol (10 mL) was chilled to −78° C. The solution was then saturated with ammonia gas for 15 minutes. The reaction vessel was sealed at −78° C. and allowed to warm to room temperature. After 18 h the reaction was chilled to −78° C. and opened to atmosphere. The volatiles were removed under reduced pressure and the crude product was used in the next step without purification.

C. 2-(2-Hydroxyphenyl)-9-(2-methoxyphenyl)purine-6-carboxamide. 5-Amino-2-(2-hydroxyphenyl)-6-(2-methoxyphenylamino)pyrimidine-4-carboxamide (153 mg, 0.61 mmol) was suspended in triethyl orthoformate (15 mL) and stirred at 130° C. for 1H. The reaction was then cooled to room temperature and diluted with ethyl ether. The resulting solids were collected by filtration, rinsed with ethyl ether, and dried under vacuum at 60° C. to provide the title compound (120 mg, 0.33 mmol, 54% yield) as a tan solid. $^1$H NMR (300 MHz, DMSO-d$_6$) δ 9.06 (s, 1H), 8.57 (s, 1H), 8.54 (s, 1H), 8.29 (dd, J=7.8, 1.5, 1H), 7.73 (dd, J=7.5, 1.5, 1H), 7.63 (m, 1H), 7.39 (m, 2H), 7.26 (ddd, J=8.7, 7.8, 1.2, 1H), 6.95 (m, 2H), 3.87 (s, 3H); MS (ESI) m/z 362.1[M+1]$^+$; mp 278-280° C.

5.1.64 Example 64

Synthesis of 2-(1H-INDAZOL-5-YL)-9-(2-METHOXYPHENYL)-8-OXO-7-HYDROPURINE-6-CARBOXAMIDE A. 2-(1H-Indazol-5-yl)-9-(2-methoxyphenyl)-8-oxo-7-hydropurine-6-carboxamide. (Z)-1-(2-Amino-1,2-dicyanovinyl)-3-(2-methoxyphenyl)urea (See Example 2.A) (0.37 g, 3.51 mmol) and 1H-indazole-5-carbaldehyde (0.47 g, 3.21 mmol) were reacted according to General Procedure B. The solution was allowed to stir at room temperature for 18 h. The resultant heterogeneous mixture was filtered and purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (89 mg, 0.22 mmol, 15%) as an off-white solid. $^1$H NMR (400 MHz, DMSO-d$_6$) δ 13.14 (s, 1H), 11.66 (s, 1H), 8.80 (s, 1H), 8.52 (s, 1H), 8.40 (dd, J=9.2, 1.6, 1H), 8.15 (s, 1H), 7.98 (s, 1H), 7.55 (m, 3H), 7.31 (d, J=7.6, 1H), 7.17 (ddd, J=8.8, 7.6, 1.2, 1H), 3.76 (s, 3H); MS (ESI) m/z 402.1 [M+1]$^+$; mp 360° C.

5.1.65 Example 65

Synthesis of 9-(2,3-DICHLOROPHENYL)-2-(3-HYDROXYPHENYL)-8-OXO-7-HYDROPURINE-6-CARBOXAMIDE A. N-((1Z)-2-Amino-1,2-dicyanovinyl)[(2,3-dichlorophenyl)amino]carboxamide. 2,3-Dichlorobenzenisocyanate (0.91 g, 4.85 mmol) and 2,3-diaminomaleonitrile (0.5 g, 4.62 mmol) were reacted in acetonitrile according to General Procedure A. The material was triturated from acetonitrile/diethyl ether. The resultant solid was filtered and dried to give the title compound as an tan solid (0.68 g, 2.58 mmol, 28% yield); MS (ESI) m/z 297.1 [M+1]$^+$.

B. 9-(2,3-Dichlorophenyl)-2-(3-hydroxyphenyl)-8-oxo-7-hydropurine-6-carboxamide. N-((1Z)-2-Amino-1,2-dicyanovinyl)[(2,3-dichlorophenyl)amino]carboxamide (1.04 g, 3.51 mmol) and 3-hydroxy-benzaldehyde (0.94 g, 7.72 mmol) were reacted according to General Procedure B. The solution was allowed to stir at room temperature for 18 h. The resultant heterogeneous mixture was filtered and 200 mg of crude product was purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (104 mg, 0.25 mmol) as an off-white solid. $^1$H NMR (400 MHz, DMSO-d$_6$) 611.95 (s, 1H), 9.46 (s, 1H), 8.42 (s, 1H), 8.01 (s, 1H), 7.92 (dd, J=8.0, 1.2, 1H), 7.88 (dd, J=7.6, 1.0, 1H), 7.77 (d, J=8.0, 1H), 7.65 (m, 2H), 7.23 (t, J=7.6, 1H), 6.83 (dd, J=8.0, 2.4, 1H); MS (ESI) m/z 415.9 [M+1]$^+$; mp 352-353° C.

5.1.66 Example 66

Synthesis of 2-[4-(HYDROXYMETHYL)PHENYL]-9-(2-METHOXYPHENYL)-8-OXO-7-HYDROPURINE-6-CARBOXAMIDE A. 2-[4-(Hydroxymethyl)phenyl]-9-(2-methoxyphenyl)-8-oxo-7-hydropurine-6-carbox-amide. Methyl 4-(6-carbamoyl-9-(2-methoxyphenyl)-8-oxo-8,9-dihydro-7H-purin-2-yl)benzoate (See Example 45.A) (300 mg, 0.72 mmol) was dissolved in anhydrous tetrahydrofuran (20 mL). At -78° C. a solution of lithium aluminum hydride (2.0 M, 0.72 mL) was added and the reaction was allowed to warm to rt over 4 h. Reaction was quenched with methanol and volatiles were removed under reduced pressure. The crude material was purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (43 mg, 0.11 mmol, 15%) as an off-white solid. $^1$H NMR (400 MHz, DMSO-d$_6$) δ 11.71 (s, 1H), 8.48 (s, 1H), 8.31 (d, J=8.0, 1H), 7.98 (s, 1H), 7.55 (ddd, J=8.4, 8.0, 1.6, 1H), 7.50 (dd, J=8.0, 2.0, 1H), 7.36 (d, J=8.4, 1H), 7.29 (dd, J=8.4, 0.8, 1H), 7.17 (ddd, J=8.8, 7.6, 1.2. $^1$H), 5.25 (t, J=5.6, 1H), 4.53 (d, J=5.6, 2H), 3.74 (s, 3H); MS (ESI) m/z 392.1 [M+1]$^+$; mp 294-295° C.

5.1.67 Example 67

Synthesis of 2-[3-(HYDROXYMETHYL)PHENYL]-9-(2-METHOXYPHENYL)-8-OXO-7-HYDROPURINE-6-CARBOXAMIDE A. Methyl 3-[6-carbamoyl-9-(2-methoxyphenyl)-8-oxo-7-hydropurin-2-yl]benzoate. (Z)-1-(2-Amino-1,2-dicyanovinyl)-3-(2-methoxyphenyl)urea (See Example 2.A) (0.3 g, 1.17 mmol), methyl 3-formylbenzoate (0.431 g, 2.63 mmol) and triethyl amine (0.229 mL, 1.64 mmol) in MeOH (15 mL) were reacted according to General Procedure B. The resultant heterogeneous mixture was filtered, washed with additional acetonitrile to afford the title compound (0.400 g, 0.95 mmol, 82% yield); MS (ESI) m/z 420.4 [M+1]$^+$.

B. 2-[3-(Hydroxymethyl)phenyl]-9-(2-methoxyphenyl)-8-oxo-7-hydropurine-6-carbox-amide. Methyl 3-[6-carbamoyl-9-(2-methoxyphenyl)-8-oxo-7-hydropurin-2-yl]benzoate (0.128 g, 0.3 mmol) was dissolved in tetrahydrofuran and cooled to -78° C. Lithium aluminum hydride (2M in tetrahydrofuran, 0.301 mL, 0.601 mmol) was added and the reaction was allowed to warm to room temperature. After 10 hours, the reaction was quenched with MeOH, the salts were filtered, and the reaction was concentrated. The product was purified using reverse-phase preparatory HPLC (30-70% acetonitrile+0.1% TFA in H$_2$O+0.1% TFA, over 40 min). Fractions containing the desired material were combined and concentrated under reduced pressure to a minimal amount of water. EtOAc was added and the organic layer was washed 5 times with satd. NaHCO$_3$. The organic layer was dried and concentrated to afford the title compound as an off-white solid (0.03 g, 0.077 mmol, 26% yield). $^1$H NMR (400 MHz, DMSO-d$_6$) δ 11.75 (s, 1H), 8.46 (s, 1H), 8.30 (s, 1H), 8.19-8.26 (m, 1H), 8.02 (s, 1H), 7.53-7.59 (m, 1H), 7.50 (dd, J=7.8, 1.6, 1H), 7.35-7.42 (m, 1H), 7.30 (d, J=7.4, 1H), 7.16 (t, J=7.5, 1H), 5.20 (t, J=5.9, 1H), 4.53 (d, J=5.9, 1H), 3.75 (s, 1H); MS (ESI) m/z 392.3 [M+1]$^+$; mp 280-282° C.

5.1.68 Example 68

Synthesis of 9-(2-METHOXYPHENYL)-8-OXO-2-(PYRIDIN-4-YL)-8,9-DIHYDRO-7H-PURINE-6-CARBOXAMIDE A. 9-(2-Methoxyphenyl)-8-oxo-2-(pyridin-4-yl)-8,9-dihydro-7H-purine-6-carboxamide. (Z)-1-(2-Amino-1,2-dicyanovinyl)-3-(2-methoxyphenyl)urea (See Example 2.A) (0.25 g, 0.97 mmol), isonicotinaldehyde (0.156 mL, 1.65 mmol), and triethylamine (0.271 ml, 1.94 mmol) were reacted according to General Procedure B. The resulting material was dried under vacuum to give product as a tan solid (0.23 g, 0.64 mmol, 65% yield). $^1$H NMR (400 MHz, DMSO-d$_6$) δ 11.93 (s, 1H), 8.66 (AA'XX', J=6.05, 2H), 8.62 (bs, 1H), 8.27 (AA'XX', J$_{AX}$=6.05, 2H), 8.04 (bs, 1H), 7.56 (td, J=7.91, 1.76, 1H), 7.50 (dd, J=7.71, 1.67, 1H), 7.30 (d, J=7.61, 1H), 7.16 (td, J=7.71, 1.10, 1H), 3.75 (s, 3H); MS (ESI) m/z 363.1 [M+1]$^+$; mp 318-320° C.

5.1.69 Example 69

Synthesis of 2-(4-FLUORO-3-HYDROXYPHENYL)-9-(2-METHOXYPHENYL)-8-OXO-7-HYDROPURINE-6-CARBOXAMIDE A. 4-Fluoro-3-hydroxybenzaldehyde. 4-Fluoro-3-methoxybenzaldehyde (0.590 g, 3.83 mmol) was dissolved in CH$_2$Cl$_2$ and cooled to -78° C. Boron tribromide (1M in CH$_2$Cl$_2$, 9.58 mL, 9.58 mmol) was added slowly and the reaction was allowed to warm to rt overnight. An ice/water mixture was added to the resulting slurry and stirred for 30 min. The layers were separated and the organic layer was washed with NaHCO$_3$ (sat.) and 2N NaOH. The aqueous layer was acidified with conc. HCl and extracted with CH$_2$Cl$_2$. The organic layer was dried and concentrated to afford the title compound (0.220 g, 1.57 mmol, 41% yield).

B. 2-(4-Fluoro-3-hydroxyphenyl)-9-(2-methoxyphenyl)-8-oxo-7-hydropurine-6-carbox-amide. (Z)-1-(2-Amino-1,2-dicyanovinyl)-3-(2-methoxyphenyl)urea (See Example 2.A) (0.207 g, 0.698 mmol), 4-fluoro-3-hydroxybenzaldehyde (0.220 g, 1.57 mmol) and triethyl amine (0.136 mL, 0.977 mmol) in MeOH (15 mL) were reacted according to General Procedure B. The product was purified using reverse-phase preparatory HPLC (30-70% acetonitrile+0.1% TFA in H$_2$O+0.1% TFA, over 40 min). Fractions containing the desired material were combined and concentrated under reduced pressure to a minimal amount of water. Ammonium hydroxide (2 mL) was added and the resulting slurry was sonicated and filtered. The solid was dried and concentrated to afford the title compound as an off-white solid (0.106 g, 0.267 mmol, 38% yield). $^1$H NMR (400 MHz, DMSO-d$_6$) δ 11.73 (s, 1H), 9.93 (s, 1H), 8.42 (s, 1H), 7.90-8.04 (m, 1H), 7.85 (dd, J=9.0, 2.3, 1H), 7.52-7.62 (m, 1H), 7.49 (dd, J=7.6, 1.8, 1H), 7.30 (d, J=7.4, 1H), 7.09-7.23 (m, 1H), 3.74 (s, 1H); MS (ESI) m/z 396.4 [M+1]$^+$; mp 344-346° C.

5.1.70 Example 70

Synthesis of 2-(2-FLUORO-3-HYDROXYPHENYL)-9-(2-METHOXYPHENYL)-8-OXO-7-HYDROPURINE-6-CARBOXAMIDE A. 2-Fluoro-3-hydroxybenzaldehyde. 2-Fluoro-3-methoxybenzaldehyde (1.0 g, 6.49 mmol) was dissolved in CH$_2$Cl$_2$ and cooled to −78° C. Boron tribromide (1M in CH$_2$Cl$_2$, 16.22 mL, 16.22 mmol) was added slowly and the reaction was allowed to warm to rt overnight. An ice/water mixture was added to the resulting slurry and stirred for 30 min. The layers were separated and the organic layer was washed with NaHCO$_3$ (sat.) and 2N NaOH. The aqueous layer was acidified with conc. HCl and extracted with CH$_2$Cl$_2$. The organic layer was dried and concentrated to afford the title compound (0.190 g, 1.36 mmol, 21% yield).

B. 2-(2-Fluoro-3-hydroxyphenyl)-9-(2-methoxyphenyl)-8-oxo-7-hydropurine-6-carbox-amide. (Z)-1-(2-Amino-1,2-dicyanovinyl)-3-(2-methoxyphenyl)urea (See Example 2.A) (0.179 g, 0.603 mmol), 2-fluoro-3-hydroxybenzaldehyde (0.190 g, 1.36 mmol) and triethyl amine (0.117 mL, 0.844 mmol) in MeOH (15 mL) were reacted according to General Procedure B. The resultant heterogeneous mixture was filtered and washed with additional acetonitrile. The solid was further dissolved in DMF and precipitation was induced with the addition of water. The resulting solid was filtered and dried to afford the title compound as an off-white solid (0.157 g, 0.396 mmol, 66% yield). $^1$H NMR (400 MHz, DMSO-d$_6$) δ 9.86 (s, 1H), 8.12 (s, 1H), 8.01 (s, 1H), 7.44-7.61 (m, 1H), 7.32-7.41 (m, 1H), 7.27 (d, J=7.6, 1H), 7.14 (t, J=7.4, 1H), 6.99-7.05 (m, 1H), 3.74 (s, 1H); MS (ESI) m/z 396.4 [M+1]$^+$; mp>300° C.

5.1.71 Example 71

Synthesis of 2-[4-(1-HYDROXY-ISOPROPYL)PHENYL]-9-(2-METHOXYPHENYL)-8-OXO-7-HYDROPURINE-6-CARBOXAMIDE A. 2-[4-(1-Hydroxy-isopropyl)phenyl]-9-(2-methoxyphenyl)-8-oxo-7-hydropurine-6-carboxamide. Methyl 4-(6-carbamoyl-9-(2-methoxyphenyl)-8-oxo-8,9-dihydro-7H-purin-2-yl)benzoate (See Example 45.A) (500 mg, 1.19 mmol) was dissolved in anhydrous tetrahydrofuran (20 mL). Methyl magnesium bromide (1.4M, 2.2 mL, 2.97 mmol) was added via syringe and stirred at rt 3 days. Quenched reaction with methanol and removed volatiles under reduced pressure. The crude material was purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (150 mg, 0.36 mmol, 30%) as an off-white solid. $^1$H NMR (400 MHz, DMSO-d$_6$) δ 8.51 (s, 1H), 8.25 (s, 1H), 8.23 (s, 1H), 7.95 (s, 1H), 7.54 (m, 1H), 7.51 (s, 1H), 7.48 (m, 2H), 7.29 (dd, J=8.4, 1.2, 1H), 7.15 (ddd, J=8.8, 7.6, 1.2, 1H), 5.06 (s, 1H), 3.74 (s, 3H), 1.42 (s, 6H); MS (ESI) m/z 420.4 [M+1]$^+$; mp 293-294° C.

5.1.72 Example 72

Synthesis of 2-[3-(1-HYDROXY-ISOPROPYL)PHENYL]-9-(2-METHOXYPHENYL)-8-OXO-7-HYDROPURINE-6-CARBOXAMIDE A. Methyl 3-[6-carbamoyl-9-(2-methoxyphenyl)-8-oxo-7-hydropurin-2-yl]benzoate. (Z)-1-(2-Amino-1,2-dicyanovinyl)-3-(2-methoxyphenyl)urea (See Example 2.A) (0.3 g, 1.17 mmol), methyl 3-formylbenzoate (0.431 g, 2.63 mmol) and triethyl amine (0.229 mL, 1.64 mmol) in MeOH (15 mL) were reacted according to General Procedure B. The resultant heterogeneous mixture was filtered, washed with additional acetonitrile to afford the title compound (0.400 g, 0.95 mmol, 82% yield). MS (ESI) m/z 420.4 [M+1]$^+$.

B. 2-[3-(1-Hydroxy-isopropyl)phenyl]-9-(2-methoxyphenyl)-8-oxo-7-hydropurine-6-carboxamide. Methyl 3-[6-carbamoyl-9-(2-methoxyphenyl)-8-oxo-7-hydropurin-2-yl]benzoate (0.200 g, 0.477 mmol) was dissolved in tetrahydrofuran and methyl magnesium bromide (1.4M in tetrahydrofuran, 2.73 mL, 3.82 mmol) was added and the reaction was heated to reflux over 4 days. The reaction was quenched with MeOH, the salts were filtered, and the reaction was concentrated. The product was purified using reverse-phase preparatory HPLC (20-70% acetonitrile+0.1% TFA in H$_2$O+0.1% TFA, over 40 min). Fractions containing the desired material were combined and concentrated under reduced pressure to a minimal amount of water. EtOAc was added and the organic layer was washed 5 times with satd. NaHCO$_3$. The organic layer was dried and concentrated to afford the title compound as an off-white solid (0.040 g, 0.095 mmol, 20% yield). $^1$H NMR (400 MHz, DMSO-d$_6$) δ 11.74 (s, 1H), 8.42 (s, 1H), 8.18 (d, J=7.8, 1H), 8.04 (s, 1H), 7.43-7.67 (m, 1H), 7.23-7.43 (m, 1H), 7.16 (t, J=7.6, 1H), 5.05 (s, 1H), 3.76 (s, 1H), 1.40 (s, 6H); MS (ESI) m/z 420.4 [M+1]$^+$; mp 149-151° C.

5.1.73 Example 73

Synthesis of 9-(2-METHOXYPHENYL)-2-(2-NITROPHENYL)-8-OXO-7-HYDROPURINE-6-CARBOXAMIDE A. 9-(2-Methoxyphenyl)-2-(2-nitrophenyl)-8-oxo-7-hydropurine-6-carboxamide. (Z)-1-(2-Amino-1,2-dicyanovinyl)-3-(2-methoxyphenyl)urea (See Example 2.A) (0.3 g, 1.17 mmol), 2-nitrobenzaldehyde (0.397 g, 2.63 mmol) and triethyl amine (0.228 mL, 1.64 mmol) in 20 mL MeOH were reacted according to General Procedure B. The resultant heterogeneous mixture was filtered and washed with additional acetonitrile. The product was dissolved in CH$_2$Cl$_2$/MeOH and the precipitate filtered to afford the title compound as an off-white solid (0.090 g, 0.22 mmol, 19% yield). $^1$H NMR (400 MHz, DMSO-d$_6$) δ 11.96 (s, 1H), 8.01-8.18 (m, 1H), 7.93 (d, J=2.0, 1H), 7.85 (d, J=7.8, 1H), 7.75 (t, J=7.8, 1H), 7.67 (t, J=6.8, 1H), 7.53 (t, J=7.6, 1H), 7.41 (d, J=7.4, 1H), 7.25 (d, J=7.4, 1H), 7.10 (t, J=7.6, 1H), 3.76 (s, 1H); MS (ESI) m/z 407.4 [M+1]$^+$; mp 319-321° C.

5.1.74 Example 74

Synthesis of 9-(2-METHOXYPHENYL)-2-(4-NITROPHENYL)-8-OXO-7-HYDROPURINE-6-CARBOXAMIDE A. 9-(2-Methoxyphenyl)-2-(4-nitrophenyl)-8-oxo-7-hydropurine-6-carboxamide. (Z)-1-(2-Amino-1,2-dicyanovinyl)-3-(2-methoxyphenyl)urea (See Example 2.A) (0.3 g, 1.17 mmol), 4-nitrobenzaldehyde (0.397 g, 2.63 mmol) and triethyl amine (0.228 mL, 1.64 mmol) in 20 mL MeOH were reacted according to General Procedure B. The resultant heterogeneous mixture was filtered and washed with additional acetonitrile. The product was dissolved in $CH_2Cl_2$/MeOH and the precipitate filtered to afford the title compound as an off-white solid (0.060 g, 0.15 mmol, 13% yield). $^1$H NMR (400 MHz, DMSO-d$_6$) δ 11.94 (s, 1H), 8.63 (m, 1H), 8.28 (d, J=9.0, 1H), 8.06 (s, 1H), 7.58 (t, J=7.4, 1H), 7.51 (dd, J=7.8, 1.6, 1H), 7.31 (d, J=7.4, 1H), 7.17 (t, J=7.6, 1H), 3.76 (s, 1H); MS (ESI) m/z 407.4 [M+1]$^+$; mp 348-350° C.

5.1.75 Example 75

Synthesis of 2-(5-METHOXY-4-METHYL(3-PYRIDYL))-9-(2-METHOXYPHENYL)-8-OXO-7-HYDROPURINE-6-CARBOXAMIDE A. 9-(2-Methoxyphenyl)-2-(2-nitrophenyl)-8-oxo-7-hydropurine-6-carboxamide. (Z)-1-(2-Amino-1,2-dicyanovinyl)-3-(2-methoxyphenyl)urea (See Example 2.A) (0.124 g, 0.482 mmol), 5-methoxy-4-methylpyridine-3-carbaldehyde (0.164 g, 1.09 mmol) and triethyl amine (0.094 mL, 0.675 mmol) in 20 mL MeOH were reacted according to General Procedure B. The resultant heterogeneous mixture was filtered and washed with additional acetonitrile to afford the title compound as an off-white solid (0.115 g, 0.283 mmol, 59% yield). $^1$H NMR (400 MHz, DMSO-d$_6$) δ 11.85 (s, 1H), 8.52 (s, 1H), 8.31 (s, 1H), 8.21 (s, 1H), 7.97 (s, 1H), 7.49-7.58 (m, 1H), 7.47 (dd, J=7.8, 1.6, 1H), 7.26 (dd, J=8.4, 1.0, 1H), 7.11 (td, J=7.6, 1.2, 1H), 3.91 (s, 1H), 3.75 (s, 1H), 2.25 (s, 1H); MS (ESI) m/z 407.0 [M+1]$^+$; mp 278-280° C.

5.1.76 Example 76

Synthesis of 9-(2,4-DIFLUOROPHENYL)-2-(3-HYDROXYPHENYL)-8-OXO-7-HYDROPURINE-6-CARBOXAMIDE A. N-((1Z)-2-Amino-1,2-dicyanovinyl)[(2,4-difluorophenyl)amino]carboxamide. 2,4-Difluorobenzenisocyanate (1.15 mL, 9.71 mmol) and 2,3-diaminomaleonitrile (1.0 g, 9.25 mmol) were reacted in acetonitrile according to General Procedure A. The material was triturated from acetonitrile/diethyl ether. The resultant solid was filtered and dried to give the title compound as an tan solid (0.68 g, 2.58 mmol, 28% yield). MS (ESI) m/z 264.2 [M+1]$^+$.

B. 9-(2,4-Difluorophenyl)-2-(3-hydroxyphenyl)-8-oxo-7-hydropurine-6-carboxamide. N-((1Z)-2-Amino-1,2-dicyanovinyl) [(2,4-difluorophenyl)amino]carboxamide (500 mg, 1.9 mmol) and 3-hydroxy-benzaldehyde (510 mg, 4.18 mmol) were reacted according to General Procedure B. The solution was allowed to stir at room temperature for 18 h. The resultant heterogeneous mixture was filtered and 100 mg of crude product was purified using reverse-phase semi-preparatory HPLC (20-100% acetonitrile+0.1% TFA in $H_2O$+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (45 mg, 0.13 mmol) as a white solid. $^1$H NMR (400 MHz, DMSO-d$_6$) δ 11.91 (s, 1H), 9.48 (s, 1H), 8.42 (s, 1H), 8.01 (s, 1H), 7.91 (d, J=8.0, 1H), 7.80 (dd, J=8.4, 6.0, 1H), 7.16 (m, 1H), 7.65 (m, 1H), 7.38 (m, 1H), 7.23 (t, J=8.0, 1H), 6.83 (dd, J=7.6, 1.2, 1H); MS (ESI) m/z 384.1 [M+1]$^+$; mp 364° C.

5.1.77 Example 77

Synthesis of 9-(2-METHOXYPHENYL)-2-{3-[(METHYLSULFONYL)AMINO]PHENYL}-8-OXO-7-HYDROPURINE-6-CARBOXAMIDE A. Methyl 3-[(methylsulfonyl)amino]benzoate. Methyl 3-aminobenzoate was dissolved in anhydrous tetrahydrofuran (50 mL) followed by addition of triethylamine (2.8 mL, 19.8 mmol) and methanesulfonyl chloride (0.85 mL, 10.9 mmol). The reaction was stirred overnight. Water (100 mL) and ethyl acetate (100 mL) were added to the reaction mixture and the layers separated. The aqueous layer was extracted with ethyl acetate (2×50 mL), dried with sodium sulfate, and adsorbed onto silica gel. Flash Silica Gel Chromatography (40% EtOAc in Hexanes) afforded the title compound (1.3 g, 5.6 mmol, 57%) as a white solid. MS (ESI) m/z 230.1 [M+1]$^+$.

B. [3-(Hydroxymethyl)phenyl](methylsulfonyl)amine. Methyl 3-[(methylsulfonyl)amino]benzoate (1.2 g, 5.23 mmol) was dissolved in anhydrous tetrahydrofuran (40 mL) and cooled to −78° C. A solution of lithium aluminum hydride (2.0M, 5.23 mL, 10.46 mmol) was added via syringe and allowed to slowly warm to rt. The reaction was quenched with methanol and the crude product adsorbed onto silica gel. Flash chromatography (80% EtOAc in Hexanes) afforded the title compound (0.85 g, 4.22 mmol, 81%) as a white solid. MS (ESI) m/z 202.2.1 [M+1]$^+$.

C. 3-[(Methylsulfonyl)amino]benzaldehyde. [3-(Hydroxymethyl)phenyl](methylsulfonyl)amine (0.42 g, 2.08 mmol) was dissolved in dichloromethane (20 mL) followed by addition of pyridinium chlorochromate (0.67 g, 3.12 mmol). The reaction was stirred at rt for 1H. Filtered crude reaction through a plug of silica gel and washed with 60% EtOAc/Hex (250 mL), removed volatiles under reduced pressure to afford the title compound (0.40 g, 2.01 mmol, 97%) as a white solid. MS (ESI) m/z 200.2 [M+1]$^+$ D. 9-(2-Methoxyphenyl)-2-{3-[(methylsulfonyl)amino] phenyl}-8-oxo-7-hydropurine-6-carboxamide. (Z)-1-(2-Amino-1,2-dicyanovinyl)-3-(2-methoxyphenyl)urea (See Example 2.A) (154 mg, 0.60 mmol) and 3-[(methylsulfonyl) amino]benzaldehyde (260 mg, 1.31 mmol) were reacted according to General Procedure B. The solution was allowed to stir at room temperature for 16 h. The resultant heterogeneous mixture was filtered and purified using reverse-phase semi-preparatory HPLC (20-100% acetonitrile+0.1% TFA in $H_2O$+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (151 mg, 0.33 mmol, 55%) as a white solid. $^1$H NMR (400 MHz, DMSO-d$_6$) δ 11.80 (s, 1H), 9.78 (s, 1H), 8.32 (s, 1H), 8.20 (d, J=8.0, 1H), 8.06 (m, 2H), 7.55 (m, 1H), 7.50 (dd, J=8.0, 4.0, 1H), 7.41 (m, 1H), 7.31 (m, 2H), 7.15 (m, 1H), 3.73 (s, 3H), 2.96 (s, 3H); MS (ESI) m/z 455.1 [M+1]$^+$; mp 306° C.

5.1.78 Example 78

Synthesis of 9-(4-CHLORO-2-FLUOROPHENYL)-2-(3-HYDROXYPHENYL)-8-OXO-7-HYDROPURINE-6-CARBOXAMIDE A. N-((1Z)-2-Amino-1,2-dicyanovinyl)[(4-chloro-2-fluorophenyl)amino]carboxamide. 4-Chloro-2-fluorobenzenisocyanate (0.834 g, 4.86 mmol) and 2,3-diaminomaleonitrile (0.500 g, 4.63 mmol) were reacted in acetonitrile according to General Procedure A. The material was filtered and washed with acetonitrile. The resultant solid was dried to give the title compound as a tan solid.

B. 9-(4-Chloro-2-fluorophenyl)-2-(3-hydroxyphenyl)-8-oxo-7-hydropurine-6-carboxamide. N-((1Z)-2-Amino-1,2-dicyanovinyl)[(4-chloro-2-fluorophenyl)amino]carboxamide (1.29 g, 4.63 mmol), 3-hydroxybenzaldehyde (1.27 g, 10.42 mmol) and triethyl amine (0.903 mL, 6.48 mmol) in 10 mL MeOH were reacted according to General Procedure B. The resultant heterogeneous mixture was filtered and washed with additional acetonitrile. The product was dissolved in DMF and precipitation induced with water. The precipitate was filtered to afford the title compound as an off-white solid (0.400 g, 1.0 mmol, 22% yield over 2 steps). $^1$H NMR (400 MHz, DMSO-d$_6$) δ 11.94 (s, 1H), 9.48 (s, 1H), 8.43 (s, 1H), 8.02 (s, 1H), 7.92 (dt, J=7.8, 1.2, 1H), 7.85 (dd, J=10.0, 2.1, 1H), 7.77 (t, J=8.4, 1H), 7.71-7.74 (m, 1H), 7.56-7.62 (m, 1H), 7.24 (t, J=7.8, 1H), 6.84 (dd, J=8.2, 1.6, 1H); MS (ESI) m/z 400.1 [M+1]$^+$; mp>350° C.

5.1.79 Example 79

Synthesis of 9-(2-CHLOROPHENYL)-8-OXO-2-(3-PYRIDYL)-7-HYDROPURINE-6-CARBOXAMIDE

A. N-((1Z)-2-Amino-1,2-dicyanovinyl)[(2-chlorophenyl)amino]carboxamide. 2-Chloro-benzenisocyanate (0.744 g, 4.85 mmol) and 2,3-diaminomaleonitrile (0.500 g, 4.63 mmol) were reacted in acetonitrile according to General Procedure A. The material was filtered and washed with acetonitrile. The resultant solid was dried to give the title compound as a tan solid.

B. 9-(2-Chlorophenyl)-8-oxo-2-(3-pyridyl)-7-hydropurine-6-carboxamide. N-((1Z)-2-Amino-1,2-dicyanovinyl)[(5-chloro-2-fluorophenyl)amino]carboxamide (1.21 g, 4.63 mmol), pyridine-3-carbaldehyde (1.16 g, 10.42 mmol) and triethyl amine (0.903 mL, 6.48 mmol) in 10 mL MeOH were reacted according to General Procedure B. The resultant heterogeneous mixture was filtered and washed with additional acetonitrile. The product was purified using reverse-phase preparatory HPLC (10-40% acetonitrile+0.1% TFA in H$_2$O+0.1% TFA, over 30 min). Fractions containing the desired material were combined and concentrated under reduced pressure to a minimal amount of water. EtOAc was added and the organic layer was washed 5 times with NaHCO$_3$ (sat). The organic layer was dried and concentrated to afford the title compound as an off-white solid (0.018 g, 0.05 mmol, 11% yield over 2 steps). $^1$H NMR (400 MHz, DMSO-d$_6$) δ 12.02 (s, 1H), 9.54 (s, 1H), 8.58-8.70 (m, 1H), 8.04 (s, 1H), 7.77-7.82 (m, 1H), 7.74 (dd, J=7.4, 2.0, 1H), 7.55-7.68 (m, 1H), 7.47 (dd, J=8.4, 4.9, 1H), 5.76 (s, 1H); MS (ESI) m/z 367.4 [M+1]$^+$; mp 296-298° C.

5.1.80 Example 80

Synthesis of 8-OXO-2-(3-PYRIDYL)-9-[2-(TRIFLUOROMETHYL)PHENYL]-7-HYDROPURINE-6-CARBOXAMIDE 3

A. N-((1Z)-2-Amino-1,2-dicyanovinyl)[(2-trifluoromethylphenyl)amino]carboxamide. 2-Trifluoromethylbenzenisocyanate (0.909 g, 4.85 mmol) and 2,3-diaminomaleonitrile (0.500 g, 4.63 mmol) were reacted in acetonitrile according to General Procedure A. The material was filtered and washed with acetonitrile. The resultant solid was dried to give the title compound as a tan solid.

B. 8-Oxo-2-(3-pyridyl)-9-[2-(trifluoromethyl)phenyl]-7-hydropurine-6-carboxamide. N-((1Z)-2-Amino-1,2-dicyanovinyl)[(2-trifluoromethylphenyl)amino]carboxamide (1.37 g, 4.63 mmol), pyridine-3-carbaldehyde (1.16 g, 10.42 mmol) and triethyl amine (0.903 mL, 6.48 mmol) in 10 mL MeOH were reacted according to General Procedure B. The resultant reaction mixture was concentrated. The product was purified using reverse-phase preparatory HPLC (20-60% acetonitrile+0.1% TFA in H$_2$O+0.1% TFA, over 30 min). Fractions containing the desired material were combined and concentrated under reduced pressure to a minimal amount of water. EtOAc was added and the organic layer was washed 5 times with NaHCO$_3$ (sat.). The organic layer was dried and concentrated to afford the title compound as an off-white solid (0.072 g, 0.18 mmol, 39% yield over 2 steps). $^1$H NMR (400 MHz, DMSO-d$_6$) δ 12.01 (s, 1H), 9.51 (d, J=2.0, 1H), 8.65 (s, 1H), 8.62 (dd, J=4.9, 1.8, 1H), 8.58 (dt, J=8.2, 2.0, 1H), 8.01-8.08 (m, 1H), 7.97 (t, J=7.6, 1H), 7.81-7.89 (m, 1H), 7.46 (dd, J=8.2, 4.7, 1H); MS (ESI) m/z 400.9 [M+1]$^+$; mp 300-302° C.

5.1.81 Example 81

Synthesis of 9-(3-CHLORO-2-FLUOROPHENYL)-2-(3-HYDROXYPHENYL)-8-OXO-7-HYDROPURINE-6-CARBOXAMIDE A. N-((1Z)-2-Amino-1,2-dicyanovinyl) [(3-chloro-2-fluorophenyl)amino]carboxamide. 3-Chloro-2-fluorobenzenisocyanate (0.834 g, 4.86 mmol) and 2,3-diaminomaleonitrile (0.500 g, 4.63 mmol) were reacted in acetonitrile according to General Procedure A. The material was filtered and washed with acetonitrile. The resultant solid was dried to give the title compound as a tan solid.

B. 9-(3-Chloro-2-fluorophenyl)-2-(3-hydroxyphenyl)-8-oxo-7-hydropurine-6-carboxamide. N-((1Z)-2-Amino-1,2-dicyanovinyl)[(3-chloro-2-fluorophenyl)amino]carboxamide (1.29 g, 4.63 mmol), 3-hydroxybenzaldehyde (1.27 g, 10.42 mmol) and triethyl amine (0.903 mL, 6.48 mmol) in 10 mL MeOH were reacted according to General Procedure B. The resultant heterogeneous mixture was filtered and washed with additional acetonitrile. The product was purified using reverse-phase preparatory HPLC (30-70% acetonitrile+0.1% TFA in H$_2$O+0.1% TFA, over 35 min). Fractions containing the desired material were combined and concentrated under reduced pressure to a minimal amount of water. Ammonium hydroxide (2 mL) was added and the resulting slurry was sonicated and filtered. The solid was dried and concentrated to afford the title compound as an off-white solid (0.033 g, 0.08 mmol, 18% yield over 2 steps). $^1$H NMR (400 MHz, DMSO-d$_6$) δ 11.97 (s, 1H), 9.49 (s, 1H), 8.43 (s, 1H), 8.02 (s, 1H), 7.91 (d, J=7.8, 1H), 7.85 (t, J=7.6, 1H), 7.68-7.77 (m, 1H), 7.51 (t, J=8.2, 1H), 7.24 (t, J=8.0, 1H), 6.84 (dd, J=8.0, 1.8, 1H), 5.76 (s, 1H); MS (ESI) m/z 400.1 [M+1]$^+$; mp>350° C.

5.1.82 Example 82

Synthesis of 9-(2-FLUORO-3-TRIFLUOROMETH-YLPHENYL)-2-(3-HYDROXYPHENYL)-8-OXO-7-HYDROPURINE-6-CARBOXAMIDE A. N-((1Z)-2-Amino-1,2-dicyanovinyl)[(2-fluoro-3-trifluoromethylphenyl)amino]carbox-amide. 2-Fluoro-3-trifluoromethylbenzenisocyanate (0.991 g, 4.86 mmol) and 2,3-diaminomaleonitrile (0.500 g, 4.63 mmol) were reacted in acetonitrile according to General Procedure A. The material was filtered and washed with acetonitrile. The resultant solid was dried to give the title compound as a tan solid.

B. 9-(2-Fluoro-3-trifluoromethylphenyl)-2-(3-hydroxyphenyl)-8-oxo-7-hydropurine-6-carboxamide. N-((1Z)-2-Amino-1,2-dicyanovinyl)[(2-fluoro-3-trifluoromethylphenyl)amino]carboxamide (1.45 g, 4.63 mmol), 3-hydroxybenzaldehyde (1.27 g, 10.42 mmol) and triethyl amine (0.903 mL, 6.48 mmol) in 10 mL MeOH were reacted according to General Procedure B. The resultant heterogeneous mixture was filtered and washed with additional acetonitrile. The product was purified using reverse-phase preparatory HPLC (20-60% acetonitrile+0.1% TFA in H$_2$O+0.1% TFA, over 35 min). Fractions containing the desired material were combined and concentrated under reduced pressure to a minimal amount of water. Ammonium hydroxide (2 mL) was added and the resulting slurry was sonicated and filtered. The solid was dried and concentrated to afford the title compound as an off-white solid (0.053 g, 0.12 mmol, 27% yield over 2 steps). $^1$H NMR (400 MHz, DMSO-d$_6$) δ 12.00 (s, 1H), 9.48 (s, 1H), 8.44 (s, 1H), 8.10 (t, J=7.2, 1H), 7.97-8.06 (m, 1H), 7.90 (d, J=8.2, 1H), 7.60-7.77 (m, 1H), 7.24 (t, J=7.8, 1H), 6.84 (d, J=7.8, 1H), 5.76 (s, 1H); MS (ESI) m/z 434.3 [M+1]$^+$; mp>350° C.

5.1.83 Example 83

Synthesis of 9-(2,3,4-TRIFLUOROPHENYL)-2-(3-HYDROXYPHENYL)-8-OXO-7-HYDROPURINE-6-CARBOXAMIDE A. N-((1Z)-2-Amino-1,2-dicyanovinyl)[(2,3,4-trifluorophenyl)amino]carboxamide. 2,3,4-Trifluorobenzenisocyanate (0.836 g, 4.86 mmol) and 2,3-diaminomaleonitrile (0.500 g, 4.63 mmol) were reacted in acetonitrile according to General Procedure A. The material was filtered and washed with acetonitrile. The resultant solid was dried to give the title compound as a tan solid.

B. 9-(2,3,4-Trifluorophenyl)-2-(3-hydroxyphenyl)-8-oxo-7-hydropurine-6-carboxamide. N-((1Z)-2-Amino-1,2-dicyanovinyl)[(2,3,4-trifluorophenyl)amino]carboxamide (1.3 g, 4.63 mmol), 3-hydroxybenzaldehyde (1.27 g, 10.42 mmol) and triethyl amine (0.903 mL, 6.48 mmol) in 10 mL MeOH were reacted according to General Procedure B. The resultant heterogeneous mixture was filtered and washed with additional acetonitrile to afford the title compound as an off-white solid (0.030 g, 0.075 mmol, 16% yield over 2 steps). $^1$H NMR (400 MHz, DMSO-d$_6$) 11.98 (s, 1H), 9.49 (s, 1H), 8.44 (s, 1H), 8.02 (s, 1H), 7.92 (d, J=8.2, 1H), 7.70-7.79 (m, 1H), 7.59-7.70 (m, 1H), 7.25 (t, J=7.8, 1H), 6.85 (dd, J=7.6, 2.1, 1H); MS (ESI) m/z 402.0 [M+1]$^+$; mp>350° C.

5.1.84 Example 84

Synthesis of 2-(1H-BENZO[D]IMIDAZOL-6-YL)-9-(2-METHOXYPHENYL)-8-OXO-8,9-DIHYDRO-7H-PURINE-6-CARBOXAMIDE A. (1H-Benzo[d]imidazol-6-yl)methanol. Benzimidazole-6-carboxylic acid (2.0 g, 12.3 mmol) was suspended in anhydrous tetrahydrofuran (50 mL) and cooled −78° C. A solution of lithium aluminum hydride (2.0M, 12.3 mL, 26.6 mmol) was added via syringe and allowed to slowly warm to room temperature with stirring overnight. The reaction was quenched with methanol and the crude product adsorbed onto silica gel. Flash Chromatography (20% MeOH in EtOAc) afforded the title compound (1.42 g, 9.6 mmol, 78%) as a yellow foam. MS (ESI) m/z 149.1 [M+1]$^+$.

B. 1H-Benzo[d]imidazole-6-carbaldehyde. (1H-Benzo[d]imidazol-6-yl)methanol (1.0 g, 6.75 mmol) was dissolved in anhydrous dimethylsulfoxide (30 mL), sulfurtrioxide pyridine complex (3.21 g, 20.2 mmol) and diisopropylethylamine (3.5 mL, 20.2 mmol) was added via syringe. The reaction was heated to 55° C. for 3 days. The reaction was poured into water (100 mL), extracted with EtOAc (3×100 mL), dried combined organic layers with sodium sulfate and adsorbed onto silica gel. Flash chromatography (10% MeOH in EtOAc) afforded the title compound (0.11 g, 4.22 mmol, 11%) as a white solid. MS (ESI) m/z 147.1 [M+1]$^+$.

C. 2-(1H-Benzoldiimidazol-6-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (See Example 2.A) (88 mg, 0.34 mmol) and 1H-benzo[d]imidazole-6-carbaldehyde (110 mg, 0.75 mmol) were reacted according to General Procedure B. The solution was allowed to stir at room temperature for 16 h. The resultant heterogeneous mixture was filtered and purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (120 mg, 0.30 mmol, 88%) as a white solid. $^1$H NMR (400 MHz, DMSO-d$_6$) δ 11.69 (s, 1H), 8.59 (s, 1H), 8.55 (s, 1H), 8.43 (s, 1H), 8.37 (d, J=8.4, 1H), 7.98 (s, 1H), 7.62 (d, J=8.8, 1H), 7.57 (ddd, J=9.2, 7.6, 1.6, 1H), 7.52 (dd, J=7.6, 1.6, 1H), 7.31 (dd, J=7.2, 1.2, 1H), 7.18 (ddd, J=8.8, 7.6, 1.2, 1H), 3.76 (s, 3H); MS (ESI) m/z 402.1 [M+1]$^+$; mp 306° C.

5.1.85 Example 85

Synthesis of 2-[3-(ACETYLAMINO)PHENYL]-9-(2-METHOXYPHENYL)-8-OXO-7-HYDROPU-RINE-6-CARBOXAMIDE A. 2-[3-(Acetylamino)phenyl]-9-(2-methoxyphenyl)-8-oxo-7-hydropurine-6-carboxamide. 2-(3-Aminophenyl)-9-(2-methoxyphenyl)-8-oxo-7-hydropurine-6-carboxamide (100 mg, 0.27 mmol) was dissolved in anhydrous pyridine (4 mL) and cooled to 0° C. Acetic anhydride (0.10 mL, 0.29 mmol) was added via syringe and the reaction was allowed to warm to room temperature and stirred overnight. Removed solvent under reduced pressure. The residue was purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (20 mg, 0.048 mmol, 18%) as a white solid. $^1$H NMR (400 MHz, DMSO-d$_6$) δ 10.12 (s, 1H), 9.23 (s, 1H), 8.21 (s, 1H), 7.94 (d, J=8.0, 1H), 7.87 (d, J=8.0, 1H), 7.62 (s, 1H), 7.52 (ddd, J=9.6, 8.8, 1.6, 1H), 7.34 (m, 3H), 7.17 (ddd, J=8.8, 7.6, 1.2, 1H), 3.80 (s, 3H), 2.11 (s, 3H); MS (ESI) m/z 419.1 [M+1]$^+$; mp 265° C.

5.1.86 Example 86

Synthesis of 2-(3-HYDROXYPHENYL)-8-(2-METHOXYPHENYL)-6-OXO-5,6,7,8-TETRAHYDROPTERIDINE-4-CARBOXAMIDE A. Ethyl 2-(2-methoxyphenylamino)acetate. o-Anisidine (5.0 g, 40.60 mmol) and potassium carbonate (16.80 g, 121.80 mmol) were combined in dimethylformamide (120 mL) and allowed to stir at room temperature. Ethyl bromoacetate (6.78 g, 40.60 mmol) in dimethylformamide (10 mL) were added at once to the solution and the mixture heated to 55° C. The reaction was monitored by thin layer chromatography for the disappearance of starting materials. The solution was filtered through celite and washed with ethyl acetate. The filtrate was condensed under reduced pressure and the resultant crude oil was purified using Biotage silica gel chromatography (0-40% ethyl acetate in hexanes) to afford the title compound (6.3 g, 74%). MS (ESI) m/z 210.1 [M+1]$^+$.

B. Ethyl 2-chloro-6-((2-ethoxy-2-oxoethyl)(2-methoxyphenyl)amino)-5-nitro-5,6-dihydro-pyrimidine-4-carboxylate. Ethyl 2,6-dichloro-5-nitropyrimidine-4-carboxylate (3.0 g, 11.27 mmol), ethyl 2-(2-methoxyphenylamino)acetate (2.35 g, 11.27 mmol) and diisopropylethylamine (4.36 g, 33.81 mmol) were reacted according to General Procedure C and partitioned between water and ethyl acetate (3×) to afford the title compound without purification (2.05 g, 41%). MS (ESI) m/z 439.2 [M+1]$^+$, 441.4 [M+2]$^+$.

C. Ethyl 2-chloro-8-(2-methoxyphenyl)-6-oxo-4-a,5,6,7,8,8a-hexahydropteridine-4-carboxylate. Ethyl 2-chloro-6-((2-ethoxy-2-oxoethyl)(2-methoxyphenyl)amino)-5-nitro-5,6-dihydropyrimidine-4-carboxylate (2.07 g, 4.72 mmol), iron powder (5.27 g, 94.4 mmol) and acetic acid were combined and heated to 60° C. The reaction was monitored via thin layer chromatography for starting material consumption and product formation. After one hour, the solution was condensed under reduced pressure and diluted with methanol and filtered through celite. The filtrate was condensed under reduced pressure and the resultant oil purified using Biotage silica gel chromatography (5-75% ethyl acetate in hexanes) to afford the title compound (1.17 g, 69%). $^1$H NMR (300 MHz, DMSO-d$_6$) δ 10.28 (bs, 1H), 7.39 (m, 2H), 7.20 (d, J=8, 1H), 7.06 (t, J=7.5, 1H), 4.1 (bs, 1H), 4.45 (bs, 1H), 4.37 (q, J=7.2, 2H), 3.79 (s, 3H), 1.33 (t, J=6.9, 3H); MS (ESI) m/z 363.4 [M+1]$^+$.

D. Ethyl 2-(3-hydroxyphenyl)-8-(2-methoxyphenyl)-6-oxo-5,6,7,8-tetrahydropteridine-4-carboxylate. Ethyl 2-chloro-8-(2-methoxyphenyl)-6-oxo-4-a,5,6,7,8,8a-hexahydropteridine-4-carboxylate (0.500 g, 1.38 mmol), dichloro[1,1'-bis(diphenylphosphino)ferrocene]palladium (II) dichloromethane adduct (0.112 g, 0.138 mmol), potassium phosphate (0.877 g, 4.19 mmol) and tetrahydrofuran (15 mL) were combined and heated together in a Biotage Emrys Optimizer microwave reactor at 120° C. for 45 min. The solution was condensed under reduced pressure and partitioned between aqueous potassium carbonate and ethyl acetate (3×), filtered and solvent removed to afford the crude title compound. The crude was purified using reverse-phase preparative HPLC (30-70% acetonitrile+0.1% TFA in H$_2$O+ 0.1% TFA, over 30 min). Fractions containing clean product were passed through a Phenomenex Strata-X-C solid phase extraction column to remove TFA. The product was released from the column using 2M ammonia in methanol. The solution was concentrated under reduced pressure and dried under vacuum to give the title product (0.250 g, 43%). MS (ESI) m/z 421.2 [M+1]$^+$.

E. 2-(3-hydroxyphenyl)-8-(2-methoxyphenyl)-6-oxo-5,6,7,8-tetrahydropteridine-4-carbox-amide. Ethyl 2-(3-hydroxyphenyl)-8-(2-methoxyphenyl)-6-oxo-5,6,7,8-tetrahydropteridine-4-carboxylate (0.250 g, 0.59 mmol) and methanol (10 ml) were reacted according to General Procedure G and purified using reverse-phase preparative HPLC (30-70% acetonitrile+0.1% TFA in H$_2$O+0.1% TFA, over 30 min). Fractions that contained clean product by HPLC were combined and condensed under reduced pressure. The slurry was diluted with concentrated ammonium hydroxide (1 mL) to neutralize the trifluoroacetic acid. The resultant precipitate was filtered, washed with water and dried under vacuum oven to afford the title compound (0.026 g, 11%). $^1$H NMR (400 MHz, DMSO-d$_6$) δ 11.24 (s, 1H), 9.39 (s, 1H), 8.57 (s, 1H), 8.18 (s, 1H), 7.61 (d, J=7.99, 1H), 7.43 (m, 3H), 7.22 (d, J=7.59, 1H), 7.09 (m, 2H), 6.79 (d, J=7.59, 1H), 4.5 (bs, 2H), 3.76 (s, 3H). MS (ESI) m/z 392.4 [M+1]$^+$; mp 336-338° C.

5.1.87 Example 87

Synthesis of 9-(2-METHOXYPHENYL)-8-OXO-2-PYRAZOL-4-YL-7-HYDROPURINE-6-CARBOXAMIDE A. 9-(2-Methoxyphenyl)-8-oxo-2-pyrazol-4-yl-7-hydropurine-6-carboxamide. (Z)-1-(2-Amino-1,2-dicyanovinyl)-3-(2-methoxyphenyl)urea (See Example 2.A) (540 mg, 2.10 mmol) and pyrazole-4-carbaldehyde (400 mg, 4.16 mmol) were reacted according to General Procedure B. The solution was allowed to stir at room temperature for 21 h. The resultant heterogeneous mixture was filtered and purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (420 mg, 1.19 mmol, 57%) as a white solid. $^1$H NMR (400 MHz, DMSO-d$_6$) δ 13.04 (s, 1H), 11.58 (s, 1H), 8.43 (s, 1H), 8.34 (s, 1H), 8.03 (d, J=1.6, 1H), 7.94 (s, 1H), 7.53 (ddd, J=8.4, 8.0, 2.0, 1H), 7.45 (dd, J=7.6, 1.6, 1H), 7.27 (dd, J=8.8, 1.2, 1H), 7.12 (ddd, J=8.8, 7.6, 1.2, 1H), 3.78 (s, 3H); MS (ESI) m/z 352.0 [M+1]$^+$; mp 306° C.

5.1.88 Example 88

Synthesis of 9-(2-METHOXYPHENYL)-8-OXO-2-PYRAZOL-3-YL-7-HYDROPURINE-6-CARBOXAMIDE A. 9-(2-Methoxyphenyl)-8-oxo-2-pyrazol-3-yl-7-hydropurine-6-carboxamide. (Z)-1-(2-Amino-1,2-dicyanovinyl)-3-(2-methoxyphenyl)urea (See Example 2.A) (540 mg, 2.10 mmol) and pyrazole-3-carbaldehyde (400 mg, 4.16 mmol) were reacted according to General Procedure B. The solution was allowed to stir at room temperature for 21 h. The resultant heterogeneous mixture was filtered and purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (385 mg, 1.09 mmol, 52%) as a white solid. $^1$H NMR (400 MHz, DMSO-$d_6$) δ 13.65 (s, 1H), 11.85 (s, 1H), 8.77 (s, 1H), 8.00 (s, 1H), 7.45 (m, 3H), 7.28 (dd, J=8.4, 1.0, 1H), 7.15 (ddd, J=8.8, 8.0, 1.0, 1H), 3.74 (s, 3H); MS (ESI) m/z 352.0 [M+1]$^+$; mp 306° C.

5.1.89 Example 89

Synthesis of 9-(4-AMINOCYCLOHEXYL)-2-(3-HYDROXYPHENYL)-8-OXO-7-HYDROPURINE-6-CARBOXAMIDE A. Ethyl 6-({4-[(tert-butoxy)carbonylamino]cyclohexyl}amino)-2-chloro-5-nitro pyrimidine-4-carboxylate. Ethyl 2,6-dichloro-5-nitropyrimidine-4-carboxylate 2-(1.5 g, 5.64 mmol), N-(4-aminocyclohexyl)(tert-butoxy)carboxamide (1.09 g, 5.08 mmol), and diisopropylethylamine (0.982 mL, 5.64 mmol) were reacted in tetrahydrofuran (40 mL) according to General Procedure C. The reaction mixture was concentrated and the resulting oil was used directly without further purification. MS (ESI) m/z 444.4 [M+1]$^+$.

B. Ethyl 5-amino-6-({4-[(tert-butoxy)carbonylamino]cyclohexyl}amino)-2-chloropyrimidine-4-carboxylate. Ethyl 6-({4-[(tert-butoxy)carbonylamino]cyclohexyl}amino)-2-chloro-5-nitropyrimidine-4-carboxylate (2.51 g, 5.64 mmol) and tin (II) chloride dihydrate (3.82 g, 16.92 mmol) in Ethanol (35 mL) and DMF (10 mL) were reacted according to General Procedure D. The resultant heterogeneous mixture was filtered and concentrated. The product was purified by biotage silica gel chromatography (0-60% ethyl acetate in hexanes) to afford the title compound (1.08 g, 2.60 mmol, 46% yield over 2 steps). MS (ESI) m/z 414.4 [M+1]$^+$.

C. Ethyl 5-amino-6-({4-[(tert-butoxy)carbonylamino]cyclohexyl}amino)-2-(3-hydroxy-phenyl)pyrimidine-4-carboxylate. Ethyl 5-amino-6-({4-[(tert-butoxy)carbonylamino]cyclo-hexyl}amino)-2-chloropyrimidine-4-carboxylate (0.480 g, 1.16 mmol), 3-hydroxyphenylboronic acid (0.239 g, 1.73 mmol), potassium phosphate (0.499 g, 2.32 mmol), palladium (11) acetate (0.039 g, 0.174 mmol), and dicyclohexyl(2',6'-dimethoxybiphenyl-2-yl)phosphine (0.071 g, 0.174 mmol) were dissolved in tetrahydrofuran (12 mL) and water (1.2 mL) and reacted according to General Procedure E. The resultant reaction mixture was concentrated. The product was purified by biotage silica gel chromatography (0-70% ethyl acetate in hexanes) to afford the title compound as an off-white solid (0.100 g, 0.212 mmol, 18% yield). MS (ESI) m/z 472.5 [M+1]$^+$.

D. Ethyl 5-amino-6-({4-[(tert-butoxy)carbonylamino]cyclohexyl}amino)-2-(3-hydroxy-phenyl)pyrimidine-4-carboxylate. Ethyl 5-amino-6-({4-[(tert-butoxy)carbonylamino]cyclohexyl}amino)-2-(3-hydroxyphenyl)pyrimidine-4-carboxylate (0.100 g, 0.212 mmol) and 1,1'-carbonyldiimidazole (0.344 g, 2.12 mmol) were dissolved in tetrahydrofuran (8 mL) and reacted according to General Procedure F. The resultant reaction mixture was concentrated. The product was purified by biotage silica gel chromatography (0-60% ethyl acetate in hexanes) to afford the title compound as an off-white solid (0.100 g, 0.202 mmol, 95% yield). MS (ESI) m/z 498.5 [M+1]$^+$.

E. 9-{4-[(tert-Butoxy)carbonylamino]cyclohexyl}-2-(3-hydroxyphenyl)-8-oxo-7-hydro purine-6-carboxamide. Ethyl 5-amino-6-({4-[(tert-butoxy)carbonylamino]cyclohexyl}amino)-2-(3-hydroxyphenyl)pyrimidine-4-carboxylate (0.100 g, 0.201 mmol) was dissolved in MeOH (20 mL) and reacted according to General Procedure G. The resultant reaction mixture was concentrated and used directly in the next step without further purification or characterization. MS (ESI) m/z 469.4 [M+1]$^+$.

F. 9-(4-Aminocyclohexyl)-2-(3-hydroxyphenyl)-8-oxo-7-hydropurine-6-carboxamide. 9-{4-[(tert-Butoxy)carbonylamino]cyclohexyl}-2-(3-hydroxyphenyl)-8-oxo-7-hydropurine-6-carbox-amide (0.100 g, 0.212 mmol) was dissolved in $CH_2Cl_2$ (10 mL) and TFA (1 mL) was added. The reaction was stirred for 4 h and concentrated. The residue was dissolved in $CH_3CN$ and water and the resulting precipitate was filtered. The product was passed through a strata-XC ion exchange column with water, methanol and 5% ammonium hydroxide in methanol. The product was eluded with 15-20% ammonium hydroxide in water and the fractions were concentrated to afford the title compound as a white powder (0.032 g, 0.087 mmol, 41% yield over 2 steps). $^1$H NMR (400 MHz, DMSO-$d_6$) δ 8.54 (s, 1H), 7.94 (d, J=7.8, 1H), 7.87 (dd, J=2.3, 1.6, 1H), 7.78 (s, 1H), 7.27 (t, J=7.8, 1H), 6.83 (dd, J=7.6, 2.1, 1H), 4.14-4.32 (m, 1H), 2.81-2.89 (m, 1H), 2.52-2.56 (m, 1H), 2.41-2.47 (m, 1H), 1.97 (d, J=12.1, 1H), 1.75 (d, J=10.9, 1H), 1.22-1.38 (m, 1H); MS (ESI) m/z 369.5 [M+1]$^+$; mp 318-320° C.

5.1.90 Example 90

Synthesis of 2-[3-(DIFLUOROMETHYL)PHENYL]-9-(2-METHOXYPHENYL)-8-OXO-7-HYDROPURINE-6-CARBOXAMIDE A. 3-(Difluoromethyl)benzaldehyde. 3-(Difluoromethyl)-1-bromobenzene (1.0 g, 4.83 mmol) was dissolved in anhydrous tetrahydrofuran (20 mL) and cooled to −78° C. n-Butyl lithium (1.6M, 3.2 mL, 5.07 mmol) was added and the reaction stirred for 30 min. Dimethylformamide (1 mL) was added and the solution was allowed to warm to room temperature. The reaction was quenched with saturated sodium bicarbonate, extracted with diethyl ether (2×75 mL), and dried with sodium sulfate. Purification by flash chromatography (20% EtOAc in Hex) afforded a yellow oil (560 mg, 3.58 mmol, 74%). MS (ESI) m/z 157.1 [M+1]$^+$.

B. 2-[3-(Difluoromethyl)phenyl]-9-(2-methoxyphenyl)-8-oxo-7-hydropurine-6-carbox-amide. (Z)-1-(2-Amino-1,2-dicyanovinyl)-3-(2-methoxyphenyl)urea (See Example 2.A) (560 mg, 2.18 mmol), 3-(difluoromethyl)benzaldehyde (750 mg, 4.80 mmol), triethylamine (0.14 mL, 3.27 mmol) and methanol (30 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in $H_2O$+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (45 mg, 0.11 mmol, 5%) as a white solid. $^1$H NMR (400 MHz, DMSO-$d_6$) δ 11.82 (s, 1H), 8.28 (dd, J=7.2, 1.0, 1H), 8.21 (s, 1H), 8.06 (s, 1H), 7.70 (m, 1H), 7.53 (ddd, J=8.4, 7.6, 1.6, 1H), 7.47 (dd, J=8.0, 2.0, 1H), 7.42 (dd, J=10.8, 8.8, 1H), 7.27 (dd, J=8.4, 1.2, 1H), 7.12 (ddd, J=8.8, 7.6, 1.2, 1H), 7.07 (t, J=55.0, 1H), 3.78 (s, 3H); MS (ESI) m/z 412.0 [M+1]$^+$; mp 270° C.

5.1.91 Example 91

Synthesis of 2-[5-(DIFLUOROMETHYL)-2-FLUO-ROPHENYL]-9-(2-METHOXYPHENYL)-8-OXO-7-HYDROPURINE-6-CARBOXAMIDE A. 5-(Difluoromethyl)-2-fluorobenzaldehyde. 1-(Difluoromethyl)-4-fluorobenzene (1.0 g, 8.84 mmol) was dissolved in anhydrous tetrahydrofuran (20 mL) and cooled to −78° C. n-Butyl lithium (1.6M, 4.5 mL, 7.18 mmol) was added via syringe and the reaction stirred for 30 minutes. Dimethylformamide (1 mL) was added and the solution was allowed to warm to room temperature. The reaction was quenched with saturated sodium bicarbonate, extracted with diethyl ether (2×75 mL), and dried with sodium sulfate. Purification by flash chromatography (10% EtOAc in Hex) gave the product as a yellow oil (540 mg, 3.08 mmol, 45%). MS (ESI) m/z 175.0 [M+1]$^+$.

B. 2-[5-(Difluoromethyl)-2-fluorophenyl]-9-(2-methoxyphenyl)-8-oxo-7-hydropurine-6-carboxamide. (Z)-1-(2-Amino-1,2-dicyanovinyl)-3-(2-methoxyphenyl)urea (See Example 2.A) (510 mg, 2.00 mmol) and 5-(difluoromethyl)-2-fluorobenzaldehyde (680 mg, 4.38 mmol) were reacted according to General Procedure B. The solution was allowed to stir at room temperature for 16 h. The resultant heterogeneous mixture was filtered and purified using reverse-phase semi-preparatory HPLC (20-100% acetonitrile+0.1% TFA in $H_2O$+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (80 mg, 0.19 mmol, 10%) as a white solid. $^1$H NMR (400 MHz, DMSO-$d_6$) δ 11.85 (s, 1H), 8.28 (dd, J=7.2, 1.0, 1H), 8.23 (s, 1H), 8.06 (s, 1H), 7.70 (m, 1H), 7.53 (ddd, J=8.4, 7.6, 1.6, 1H), 7.47 (dd, J=8.0, 2.0, 1H), 7.42 (dd, J=10.8, 8.8, 1H), 7.27 (dd, J=8.4, 1.2, 1H), 7.12 (ddd, J=8.8, 7.6, 1.2, 1H), 7.07 (t, J=55.0, 1H), 3.78 (s, 3H); MS (ESI) m/z 430.0 [M+1]$^+$; mp 225° C.

5.1.92 Example 92

Synthesis of 2-(1H-BENZO[D]IMIDAZOL-4-YL)-9-(2-METHOXYPHENYL)-8-OXO-8,9-DIHYDRO-7H-PURINE-6-CARBOXAMIDE A. 1H-Benzo[d]imidazole-4-carboxylic acid. 2,3-Diaminobenzoic acid (1.0 g, 6.57 mmol) was suspended in triethylorthoformate (20 mL) and heated to 130° C. overnight. Diethyl ether (100 mL) was then added and the resulting precipitate filtered to give a white solid (1.04 g, 6.41 mmol, 98%). $^1$H NMR (400 MHz, DMSO-$d_6$) δ 8.22 (s, 1H), 7.91 (dd, J=8.0, 1.2, 1H), 7.82 (dd, J=8.0, 1.2, 1H), 7.29 (dd, J=8.0, 7.6, 1H); MS (ESI) m/z 163.0 [M+1]$^+$.

B. (1H-Benzo[d]imidazol-4-yl)methanol. 1H-Benzo[d]imidazole-4-carboxylic acid (1.04 g, 6.41 mmol) was suspended in anhydrous tetrahydrofuran (80 mL) and cooled to −78° C. A solution of lithium aluminum hydride in tetrahydrofuran (2.0M, 6.4 mL) was added via syringe. The reaction was allowed to warm to room temperature and stirred overnight. The reaction was quenched with methanol and adsorbed onto silica gel. Flash chromatography (20% MeOH in EtOAc) afforded a white solid (550 mg, 3.72 mmol, 58%). MS (ESI) m/z 149.0 [M+1]$^+$.

C. 1H-Benzo[d]imidazole-4-carbaldehyde. (1H-Benzo[d]imidazol-4-yl)methanol (550 mg, 3.72 mmol) was dissolved in dimethylsulfoxide (30 mL). Diisopropylethylamine (1.9 mL, 11.1 mmol) and sulfurtrioxide complex of pyridine (1.77 g, 11.1 mmol) was added and the solution allowed to stir overnight at room temperature. Poured reaction into water (50 mL) and extracted with ethyl acetate (3×150 mL), dried with sodium sulfate, and concentrated under reduced pressure to give a white solid (100 mg, 18%). MS (ESI) m/z 147.0 [M+1]$^+$.

D. 2-(1H-benzo[d]imidazol-4-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (See Example 2.A) (80 mg, 0.31 mmol), 1H-benzo[d]imidazole-4-carbaldehyde (80 mg, 0.54 mmol), triethylamine (0.06 mL, 0.41 mmol) and methanol (3 mL) were reacted according to General Procedure B. The solution was allowed to stir at room temperature overnight. The resultant heterogeneous mixture was filtered and washed with diethyl ether. The solid was dried in a vacuum oven at 60° C. overnight to afford the title compound (30 mg, 0.075 mmol, 24%) as a white solid. $^1$H NMR (400 MHz, DMSO-$d_6$) δ 11.91 (s, 1H), 11.75 (s, 1H), 8.57 (s, 1H), 8.32 (s, 1H), 8.13 (s, 1H), 8.09 (d, J=7.6, 1H), 7.77 (d, J=7.6, 1H), 7.56 (ddd, J=10.4, 9.8, 2.0, 1H), 7.54 (m, 1H), 7.32 (dd, J=2.0, 7.6, 1H), 7.26 (t, J=7.6, 1H), 7.18 (ddd, J=8.8, 7.6, 1.2, 1H), 3.76 (s, 3H); MS (ESI) m/z 402.1 [M+1]$^+$; mp 312° C.

5.1.93 Example 93

Synthesis of 2-(6-HYDROXYPYRIDIN-3-YL)-8-OXO-9-(2-(TRIFLUOROMETHYL)PHENYL)-8,9-DIHYDRO-7H-PURINE-6-CARBOXAMIDE A. 2-(6-Hydroxypyridin-3-yl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl)urea (See Example 50.A) (0.15 g, 0.51 mmol), 6-hydroxynicotinaldehyde (0.13 g, 1.0 mmol), and triethylamine (0.10 ml, 0.72 mmol) in methanol (7.0 mL) were reacted according to General Procedure B. The resulting material was precipitated from DMF/water and dried under house vacuum to provide the product as an off white solid (0.105 g, 0.25 mmol, 49% yield). $^1$H NMR (400 MHz, DMSO-$d_6$) δ 11.83 (overlapping bs, 2H), 8.66 (m, 1H), 8.30 (2, 2H), 8.02-7.92 (overlapping m, 3H), 7.85-7.78 (overlapping m, 2H), 6.39 (d, J=9.9, 2H); MS (ESI) m/z 417.0 [M+1]$^+$; mp 348-352° C. (dec).

5.1.94 Example 94

Synthesis of 2-(1H-BENZO[D]IMIDAZOL-6-YL)-9-(2-FLUOROPHENYL)-8-OXO-8,9-DIHYDRO-7H-PURINE-6-CARBOXAMIDE A. 2-(1H-benzo[d]imidazol-6-yl)-9-(2-fluorophenyl)-8-oxo-8,9-dihydro-7H-purine-6-carboxamide. N-((1Z)-2-Amino-1,2-dicyanovinyl)[(2-fluorophenyl)amino]carboxamide (See Example 9.A) (67 mg, 0.27 mmol), 1H-benzo[d]imidazole-6-carbaldehyde (See Example 84.B) (80 mg, 0.54 mmol), triethylamine (0.06 mL, 0.41 mmol) and methanol (3 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in $H_2O$+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (75 mg, 0.20 mmol, 74%) as a white solid. $^1$H NMR (400

MHz, DMSO-d$_6$) δ 12.53 (s, 1H), 11.84 (s, 1H), 8.37 (m, 1H), 8.27 (s, 1H), 8.00 (d, J=9.6, 1H), 7.74 (ddd, J=9.2, 8.0, 1.6, 1H), 7.65 (m, 1H), 7.57 (ddd, J=10.0, 8.4, 1.6, 1H), 7.48 (ddd, J=9.2, 8.0, 1.6, 1H); MS (ESI) m/z 390.1[M+1]$^+$; mp 278° C.

5.1.95 Example 95

Synthesis of 2-BENZIMIDAZOL-6-YL-8-OXO-9-[2-(TRIFLUOROMETHYL)PHENYL]-7-HYDRO-PURINE-6-CARBOXAMIDE A. 2-Benzimidazol-6-yl-8-oxo-9-[2-(trifluoromethyl)phenyl]-7-hydropurine-6-carboxamide. N-((1Z)-2-Amino-1,2-dicyanovinyl) {[2-(trifluoromethyl)phenyl]amino}carboxamide (150 mg, 0.51 mmol), benzimidazole-6-carbaldehyde (150 mg, 0.1.02 mmol), triethylamine (0.11 mL, 0.77 mmol) and methanol (8 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H$_2$O+0.1% TFA). The volatiles were removed under reduced pressure, the suspended solid treated with ammonium hydroxide with sonication, and filtered. The solid was washed with diethyl ether and dried in a vacuum oven at 60° C. overnight to afford the title compound (31 mg, 0.071 mmol, 14%) as a white solid. $^1$H NMR (400 MHz, DMSO-d$_6$) δ 12.53 (s, 1H), 12.46 (s, 1H), 8.71 (s, 1H), 8.61 (s, 1H), 8.54 (s, 1H), 8.38 (s, 1H), 8.32 (dd, J=1.6, 8.4, 1H), 8.25 (d, J=3.2, 1H), 7.99 (m, 1H), 7.86 (m, 1H), 7.65 (d, J=8.4, 1H), 7.51 (d, J=8.4, 1H); MS (ESI) m/z 440.1[M+1]$^+$; mp 258° C.

5.1.96 Example 96

Synthesis of 2-(5-CHLOROPYRIDIN-3-YL)-8-OXO-9-(2-(TRIFLUOROMETHYL)PHENYL)-8,9-DIHYDRO-7H-PURINE-6-CARBOXAMIDE A. 2-(5-Chloropyridin-3-yl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl) urea (See Example 50.A) (0.15 g, 0.51 mmol), 5-chloronicotinaldehyde (0.14 g, 0.99 mmol), and triethylamine (0.10 ml, 0.72 mmol) were combined in methanol (7.0 mL) and stirred at room temperature overnight. Excess solvent was removed under reduced pressure and the resulting residue was purified by reverse-phase preparatory HPLC (30-80% acetonitrile+0.1% TFA in H$_2$O+0.1% TFA, over 30 min). Clean fractions were neutralized with ammonium hydroxide and solvent removed under reduced pressure. The resulting material was taken up in ethyl acetate, washed successively with potassium carbonate, water, and brine. The solution was dried over sodium sulfate, filtered and solvent removed under reduced pressure to provide the product as an off white solid (0.035 g, 0.08 mmol, 16% yield). $^1$H NMR (400 MHz, DMSO-d$_6$) δ 12.07 (bs, 1H), 9.23 (s, 1H), 8.95 (s, 1H), 8.59 (m, 2H), 7.93 (m, 2H), 7.78 (m, 2H), 7.63 (bs, 1H); MS (ESI) m/z 435.0 [M+1]$^+$; mp 230-232° C.

5.1.97 Example 97

Synthesis of TRANS-4-(6-CARBAMOYL-9-(2-METHOXYPHENYL)-8-OXO-8,9-DIHYDRO-7H-PURIN-2-YLAMINO)CYCLOHEXYL CARBAMATE A. Ethyl 2-(trans-4-hydroxycyclohexylamino)-6-(2-methoxyphenylamino)-5-nitropyrimidine-4-carboxylate. Ethyl 2-chloro-6-(2-methoxyphenylamino)-5-nitropyrimidine-4-carboxylate (See Example 30.A) (0.300 g, 0.852 mmol), trans-4-aminocyclohexanol (0.117 g, 1.022 mmol) and diisopropylethylamine were reacted according to General Procedure C, except at room temperature and in dimethylformamide (5 ml). The crude reaction mixture was condensed and purified using Biotage chromatography (0-100% ethyl acetate in hexanes) to afford the title compound (0.303 g, 82%). MS (ESI) m/z 432.5 [M+1]$^+$.

B. Ethyl 5-amino-2-(trans-4-hydroxycyclohexylamino)-6-(2-methoxyphenylamino)pyrimidine-4-carboxylate. Ethyl 2-(trans-4-hydroxycyclohexylamino)-6-(2-methoxyphenyl amino)-5-nitropyrimidine-4-carboxylate (0.300 g, 0.852 mmol) was dissolved in ethanol (20 mL) and 10% palladium on carbon (0.073 g) was added to the flask and flushed with fresh hydrogen gas and allowed to stir at room temperature. After 16 h, the reaction was filtered through celite and the filtrate condensed under reduced pressure. The crude oil was purified using biotage chromatography (5% methanol in ethyl acetate) to afford the title compound (0.240 g, 70%). MS (ESI) m/z 402.4 [M+1]$^+$.

C. Ethyl 2-(trans-4-(1H-imidazole-1-carbonyloxy)cyclohexylamino)-9-(2-methoxyphenyl)-8-oxo-8,9-dihydro-7H-purine-6-carboxylate. Ethyl 5-amino-2-(trans-4-hydroxycyclohexyl amino)-6-(2-methoxyphenylamino)pyrimidine-4-carboxylate (0.240 g, 0.598 mmol) and 1,1'-1,1'-carbonyldiimidazole (0.968 g, 5.98 mmol) in dichloromethane (20 mL) were reacted according to general procedure F and purified using biotage chromatography (40-100% ethyl acetate in hexanes) to afford a mixture of the title product and the cleaved free hydroxyl product. MS (ESI) m/z 522.5 [M+1]$^+$.

D. trans-4-(6-Carbamoyl-9-(2-methoxyphenyl)-8-oxo-8,9-dihydro-7H-purin-2-ylamino)cyclohexyl carbamate. Ethyl 2-(trans-4-(1H-imidazole-1-carbonyloxy)cyclohexylamino)-9-(2-methoxyphenyl)-8-oxo-8,9-dihydro-7H-purine-6-carboxylate (0.250 g, 0.479 mmol) and ammonia gas were reacted in methanol (10 mL) according to General Procedure G and purified using reverse-phase preparative HPLC (10-80% acetonitrile+0.1% TFA in H$_2$O+0.1% TFA, over 30 min) to afford the title compound (0.135 g, 25%). $^1$H NMR (400 MHz, DMSO-d$_6$) δ 10.899 (s, 1H), 7.984 (s, 1H), 7.784 (s, 1H), 7.47 (t, J=7.19, 1H), 7.36 (d, J=7.99, 1H), 7.19 (d, J=7.59, 1H), 7.06 (t, J=6.39. $^1$H, 6.78 (d, J=6.79, 1H), 4.37 (s, 1H), 1.92 (s, 4H), 1.42 (m, 2H), 1.22 (m, 2H); MS (ESI) m/z 442.4 [M+1]$^+$; mp 187-189° C.

5.1.98 Example 98

Synthesis of (R)-9-(2-METHOXYPHENYL)-8-OXO-2-(PYRROLIDIN-3-YLAMINO)-8,9-DIHYDRO-7H-PURINE-6-CARBOXAMIDE A. (R)-Ethyl 2-(1-(tert-butoxycarbonyl)pyrrolidin-3-ylamino)-6-(2-methoxyphenylamino)-5-nitropyrimidine-4-carboxylate. Ethyl 2-chloro-6-(2-methoxyphenylamino)-5-nitro-pyrimidine-4-carboxylate (See Example 30.A) (0.300 g, 0.852 mmol), (R) 1-boc-3-aminopyrrolidine (0.190 g, 1.022 mmol) and diisopropylethylamine (0.164 g, 1.27 mmol) were reacted according to General Procedure C, except at room temperature and in dimethylformamide (5 ml). The crude reaction mixture was condensed and purified using Biotage chromatography (0-100% ethyl acetate in hexanes) to afford the title compound (0.403 g, 94%). MS (ESI) m/z 503 [M+1]$^+$.

B. (R)-Ethyl 5-amino-2-(1-(tert-butoxycarbonyl)pyrrolidin-3-ylamino)-6-(2-methoxy-phenylamino)pyrimidine-4- carboxylate. (R)-Ethyl 2-(1-(tert-butoxycarbonyl)pyrrolidin-3-ylamino)-6-(2-methoxyphenylamino)-5-nitropyrimidine-4-carboxylate (0.403 g, 0.802 mmol) was dissolved in ethanol (20 mL) and 10% palladium on carbon (0.080 g) were added to the flask and flushed with fresh hydrogen gas and allowed to stir at room temperature. After 16 hours, the reaction was filtered through celite and the filtrate condensed under reduced pressure. The crude oil was purified using biotage chromatography (0-100% ethyl acetate in hexanes) to afford the title compound (0.340 g, 89%). MS (ESI) m/z 473.5 [M+1]$^+$.

C. (R)-Ethyl 2-(1-(tert-butoxycarbonyl)pyrrolidin-3-ylamino)-9-(2-methoxyphenyl)-8-oxo-8,9-dihydro-7H-purine-6-carboxylate. (R)-Ethyl 5-amino-2-(1-(tert-butoxycarbonyl)pyrrolidin-3-ylamino)-6-(2-methoxyphenylamino)pyrimidine-4-carboxylater (0.34 g, 0.720 mmol) and carbonyldiimidazole (1.16 g, 7.20 mmol) in dichloromethane (20 mL) were reacted according to General Procedure F and purified using biotage chromatography (0-100% ethyl acetate in hexanes) to afford a mixture of the title product (0.333 g, 93%). MS (ESI) m/z 499.5 [M+1]$^+$.

D. (R)-Ethyl 9-(2-methoxyphenyl)-8-oxo-2-(pyrrolidin-3-ylamino)-8,9-dihydro-7H-purine-6-carboxylate. (R)-Ethyl 2-(1-(tert-butoxycarbonyl)pyrrolidin-3-ylamino)-9-(2-methoxy-phenyl)-8-oxo-8,9-dihydro-7H-purine-6-carboxylate (0.333 g, 0.668 mmol) were dissolved in dichloromethane (3 mL) and trifluoroacetic acid (1 mL). The solution was stirred for two hours and condensed under reduced pressure to afford the crude title compound (0.300 g, 100%). MS (ESI) m/z 399.3 [M+1]$^+$.

E. (R)-9-(2-Methoxyphenyl)-8-oxo-2-(pyrrolidin-3-ylamino)-8,9-dihydro-7H-purine-6-carboxamide. (R)-Ethyl 9-(2-methoxyphenyl)-8-oxo-2-(pyrrolidin-3-ylamino)-8,9-dihydro-7H-purine-6-carboxylate (0.300 g) and ammonia gas methanol (10 mL) were reacted according to General Procedure G and purified using reverse-phase preparative HPLC (5-60% acetonitrile+0.1% TFA in H$_2$O+0.1% TFA, over 30 min) to afford the title compound (0.076 g, 30%). $^1$H NMR (400 MHz, DMSO-d$_6$) δ 7.91 (s, 1H), 7.781 (s, 1H), 7.466 (m, 1H), 7.34 (d, J=7.59, 1H), 7.19 (d, J=7.99, 1H), 7.06 (t, J=7.19, 1H), 6.96 (d, J=6.39, 1H), 4.24 (s, 1H), 3.72 (s, 3H), 2.94 (m, 2H), 2.72 (m, 1H), 2.64 (m, 1H), 1.95 (m, 1H), 1.58 (m, 1H); MS (ESI) m/z 370.2 [M+1]$^+$; mp>400° C.

5.1.99 Example 99

Synthesis of (S)-9-(2-METHOXYPHENYL)-8-OXO-2-(PYRROLIDIN-3-YLAMINO)-8,9-DIHYDRO-7H-PURINE-6-CARBOXAMIDE A. (S)-Ethyl 2-(1-(tert-butoxycarbonyl)pyrrolidin-3-ylamino)-6-(2-methoxyphenylamino)-5-nitropyrimidine-4-carboxylate Ethyl 2-chloro-6-(2-methoxyphenylamino)-5-nitropyrimidine-4-carboxylate (See Example 30.A) (0.300 g, 0.852 mmol), (S) 1-boc-3-aminopyrrolidine (0.190 g, 1.022 mmol) and diisopropylethylamine (0.164 g., 1.27 mmol) were reacted according to General Procedure C, except at room temperature and in dimethylformamide (5 ml). The crude reaction mixture was condensed and purified using Biotage chromatography (0-100% ethyl acetate in hexanes) to afford the title compound (0.424 g, 99%). MS (ESI) m/z 503 [M+1]$^+$.

B. (S)-Ethyl 5-amino-2-(1-(tert-butoxycarbonyl)pyrrolidin-3-ylamino)-6-(2-methoxy-phenylamino)pyrimidine-4-carboxylate (S)-Ethyl 2-(1-(tert-butoxycarbonyl)pyrrolidin-3-ylamino)-6-(2-methoxyphenylamino)-5-nitropyrimidine-4-carboxylate (0.424 g, 0.844 mmol) was dissolved in ethanol (20 mL) and 10% palladium on carbon (0.085 g) were added to the flask and flushed with fresh hydrogen gas and allowed to stir at room temperature. After 16 h, the reaction was filtered through celite and the filtrate condensed under reduced pressure. The crude oil was purified using biotage chromatography (0-100% ethyl acetate in hexanes) to afford the title compound (0.357 g, 94%). MS (ESI) m/z 473.5 [M+1]$^+$.

C. (S)-Ethyl 2-(1-(tert-butoxycarbonyl)pyrrolidin-3-ylamino)-9-(2-methoxyphenyl)-8-oxo-8,9-dihydro-7H-purine-6-carboxylate (S)-Ethyl 5-amino-2-(1-(tert-butoxycarbonyl)pyrrolidin-3-ylamino)-6-(2-methoxyphenylamino)pyrimidine-4-carboxylate (0.357 g, 0.756 mmol) and carbonyldiimidazole (1.22 g, 7.56 mmol) in dichloromethane (20 mL) were reacted according to general procedure F and purified using biotage chromatography (0-100% ethyl acetate in hexanes) to afford a mixture of the title product (0.369 g, 98%). MS (ESI) m/z 499.5 [M+1]$^+$.

D. (S)-Ethyl 9-(2-methoxyphenyl)-8-oxo-2-(pyrrolidin-3-ylamino)-8,9-dihydro-7H-purine-6-carboxylate. (S)-Ethyl 2-(1-(tert-butoxycarbonyl)pyrrolidin-3-ylamino)-9-(2-methoxy-phenyl)-8-oxo-8,9-dihydro-7H-purine-6-carboxylate (0.369 g, 0.668 mmol) were dissolved in dichloromethane (3 mL) and trifluoroacetic acid (1 mL). The solution was stirred for two hours and condensed under reduced pressure to afford the crude title compound (0.300 g, 100%). MS (ESI) m/z 399.3 [M+1]$^+$.

E. (S)-9-(2-Methoxyphenyl)-8-oxo-2-(pyrrolidin-3-ylamino)-8,9-dihydro-7H-purine-6-carboxamide. (S)-Ethyl 9-(2-methoxyphenyl)-8-oxo-2-(pyrrolidin-3-ylamino)-8,9-dihydro-7H-purine-6-carboxylate (0.300 g) and ammonia gas in methanol (10 mL) were reacted according to General Procedure G and purified using reverse-phase preparative HPLC (5-60% acetonitrile+0.1% TFA in H$_2$O+0.1% TFA, over 30 min) to afford the title compound (0.105 g, 31%). $^1$H NMR (400 MHz, DMSO-d$_6$) δ 7.91 (s, 1H), 7.781 (s, 1H), 7.466 (m, 1H), 7.34 (d, J=7.59, 1H), 7.19 (d, J=7.99, 1H), 7.06 (t, J=7.19, 1H), 6.96 (d, J=6.39, 1H), 4.24 (s, 1H), 3.72 (s, 3H), 2.94 (m, 2H), 2.72 (m, 1H), 2.64 (m, 1H), 1.95 (m, 1H), 1.58 (m, 1H); MS (ESI) m/z 370.2 [M+1]$^+$; mp>400° C.

5.1.100 Example 100

Synthesis of (CIS)-4-(6-CARBAMOYL-9-(2-METHOXYPHENYL)-8-OXO-8,9-DIHYDRO-7H-PURIN-2-YLAMINO)CYCLOHEXYL CARBAMATE A. Ethyl 2-(cis-4-hydroxycyclohexylamino)-6-(2-methoxyphenylamino)-5-nitropyrimidine-4-carboxylate. Ethyl 2-chloro-6-(2-methoxyphenylamino)-5-nitropyrimidine-4-carboxylate (See Example 30.A) (0.300 g, 0.852 mmol), cis-4-aminocyclohexanol (0.155 g, 1.022 mmol) and diisopropylethylamine (0.274 g, 2.13 mmol) were reacted according to General Procedure C, except at room temperature and in dimethylformamide (5 ml). The crude reaction mixture was condensed and purified using Biotage chromatography (0-100% ethyl acetate in hexanes) to afford the title compound (0.342 g, 93%). MS (ESI) m/z 432.0 [M+1]$^+$.

B. Ethyl 5-amino-2-(cis-4-hydroxycyclohexylamino)-6-(2-methoxyphenylamino)pyrimidine-4-carboxylate. Ethyl 2-(cis-4-hydroxycyclohexylamino)-6-(2-methoxyphenylamino)-5-nitropyrimidine-4-carboxylate (0.340 g, 0.788 mmol) was dissolved in ethanol (20 mL) and 10% palladium on carbon (0.070 g) were added to the flask and flushed with fresh hydrogen gas and allowed to stir at room temperature.

After 16 h, the reaction was filtered through celite and the filtrate condensed under reduced pressure. The crude oil was purified using biotage chromatography (5% methanol in ethyl acetate) to afford the title compound (0.272 g, 70%). MS (ESI) m/z 402.4 [M+1]$^+$.

C. Ethyl 2-(cis-4-(1H-imidazole-1-carbonyloxy)cyclohexylamino)-9-(2-methoxyphenyl)-8-oxo-8,9-dihydro-7H-purine-6-carboxylate. Ethyl 5-amino-2-(cis-4-hydroxycyclohexylamino)-6-(2-methoxyphenylamino)pyrimidine-4-carboxylate (0.272 g, 0.678 mmol) and 1,1'-1,1'-carbonyldiimidazole (1.09 g, 6.78 mmol) in dichloromethane (20 mL) were reacted according to General Procedure F and purified using biotage chromatography (60-100% ethyl acetate in hexanes) to afford the title compound and the free hydroxyl derivative (0.250 g, 71%). MS (ESI) m/z 522.4 [M+1]$^+$.

D. (cis)-4-(6-Carbamoyl-9-(2-methoxyphenyl)-8-oxo-8,9-dihydro-7H-purin-2-ylamino)cyclohexyl carbamate. Ethyl 2-(cis-4-(1H-imidazole-1-carbonyloxy)cyclohexylamino)-9-(2-methoxyphenyl)-8-oxo-8,9-dihydro-7H-purine-6-carboxylate (0.250 g, 0.479 mmol) and ammonia gas were reacted in methanol (10 mL) according to General Procedure G and purified using purified using reverse-phase preparative HPLC (10-80% acetonitrile+0.1% TFA in H$_2$O+0.1% TFA, over 30 min) to afford the title compound (0.105 g, 24%). $^1$H NMR (400 MHz, DMSO-d$_6$) δ 10.888 (s, 1H), 7.777 (s, 1H), 7.47 (t, J=7.19, 1H), 7.36 (d, J=7.99, 1H), 7.19 (d, J=7.59, 1H), 7.07 (t, J=6.39. $^1$H), 6.86 (s, J=6.79, 1H), 6.33 (s, 1H) 4.47 (s, 1H), 3.85 (s, 1H), 3.70 (s, 3H), 1.60 (m, 7H); MS (ESI) m/z 442.4 [M+1]$^+$; mp 157-160° C.

5.1.101 Example 101

Synthesis of 2-(TRANS-4-HYDROXYCYCLOHEXYLAMINO)-9-(2-METHOXYPHENYL)-8-OXO-8,9-DIHYDRO-7H-PURINE-6-CARBOXAMIDE A. Ethyl 2-(trans-4-hydroxycyclohexylamino)-6-(2-methoxyphenylamino)-5-nitropyrimidine-4-carboxylate. Ethyl 2-chloro-6-(2-methoxyphenylamino)-5-nitropyrimidine-4-carboxylate (See Example 30.A) (0.300 g, 0.852 mmol), trans-4-aminocyclohexanol (0.117 g, 1.022 mmol) and diisopropylethylamine were reacted according to General Procedure C, except at room temperature and in dimethylformamide (5 mL). The crude reaction mixture was condensed and purified using Biotage chromatography (0-100% ethyl acetate in hexanes) to afford the title compound (0.303 g, 82%). MS (ESI) m/z 432.5 [M+1]$^+$.

B. Ethyl 5-amino-2-(trans-4-hydroxycyclohexylamino)-6-(2-methoxyphenylamino)pyrimidine-4-carboxylate. Ethyl 2-(trans-4-hydroxycyclohexylamino)-6-(2-methoxyphenylamino)-5-nitropyrimidine-4-carboxylate (0.300 g, 0.852 mmol) was dissolved in ethanol (20 mL) and 10% palladium on carbon (0.073 g) were added to the flask and flushed with fresh hydrogen gas and allowed to stir at room temperature. After 16 hours, the reaction was filtered through celite and the filtrate condensed under reduced pressure. The crude oil was purified using biotage chromatography (5% methanol in ethyl acetate) to afford the title compound (0.240 g, 70%). MS (ESI) m/z 402.4 [M+1]$^+$.

C. Ethyl 2-(trans-4-hydroxycyclohexylamino)-9-(2-methoxyphenyl)-8-oxo-8,9-dihydro-7H-purine-6-carboxylate and the imidazole ester. Ethyl 5-amino-2-(trans-4-hydroxycyclohexylamino)-6-(2-methoxyphenylamino)pyrimidine-4-carboxylate (0.240 g, 0.598 mmol) and 1,1'-1,1'-carbonyldiimidazole (0.968 g, 5.98 mmol) in dichloromethane (20 mL) were reacted according to general procedure F. A mixture of the title compound and the imidazole ester were formed and were taken on without further purification. MS (ESI) m/z 399 [M+1]$^+$ (title compound), 522 [M+1]$^+$ (imidazole urea).

D. 2-(trans-4-Hydroxycyclohexylamino)-9-(2-methoxyphenyl)-8-oxo-8,9-dihydro-7H-purine-6-carboxamide. Ethyl 2-(trans-4-hydroxycyclohexylamino)-9-(2-methoxyphenyl)-8-oxo-8,9-dihydro-7H-purine-6-carboxylate and the imidazole ester and ammonia gas were reacted in methanol according to General Procedure G and purified using reverse-phase preparative HPLC (10-80% acetonitrile+0.1% TFA in H$_2$O+0.1% TFA, over 30 min) to afford the title compound (0.050 g, 3% over 2 steps). $^1$H NMR (400 MHz, DMSO-d$_6$) δ 7.822 (s, 1H), 7.75 (s, 1H), 7.46 (t, J=8.69, 1H), 7.36 (d, J=7.99, 1H), 7.19 (d, J=8.39, 1H), 7.06 (t, J=7.99, 1H), 6.98 (s, 1H), 4.64 (s, 1H), 3.72 (s, 3H), 1.78 (t, J=15.99, 4H), 1.19 (m, 4H); MS (ESI) m/z 399.1 [M+1]$^+$; mp 165-167° C.

5.1.102 Example 102

Synthesis of 2-(4-CHLOROPYRIDIN-3-YL)-8-OXO-9-(2-(TRIFLUOROMETHYL)PHENYL)-8,9-DIHYDRO-7H-PURINE-6-CARBOXAMIDE A. 2-(4-Chloropyridin-3-yl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl) urea (See Example 50.A) (0.15 g, 0.51 mmol), 4-chloronicotinaldehyde (0.14 g, 0.99 mmol), and triethylamine (0.10 ml, 0.72 mmol) were combined in ethanol (7.0 mL) and stirred at room temperature overnight. Excess solvent was removed under reduced pressure and the resulting residue was purified by silica gel Biotage chromatography (0-20% methanol in dichloromethane). Clean fractions were combined and solvent removed under reduced pressure. The resulting material was dried under house vacuum to provide the product as an off white solid (0.075 g, 0.17 mmol, 34% yield). $^1$H NMR (400 MHz, DMSO-d$_6$) δ 12.11 (s, 1H), 8.93 (s, 1H), 8.56 (d, J=5.3, 1H), 8.25 (bs, 1H), 8.06 (bs, 1H), 8.01 (d, J=7.8, 1H), 7.93 (m, 1H), 7.82 (m, 2H), 7.61 (d, J=5.73, 1H); MS (ESI) m/z 435.0 [M+1]$^+$; mp 244-248° C. (dec).

5.1.103 Example 103

Synthesis of 2-(CIS-4-HYDROXYCYCLOHEXYLAMINO)-9-(2-METHOXYPHENYL)-8-OXO-8,9-DIHYDRO-7H-PURINE-6-CARBOXAMIDE A. Ethyl 2-(cis-4-hydroxycyclohexylamino)-6-(2-methoxyphenylamino)-5-nitropyrimidine-4-carboxylate. Ethyl 2-chloro-6-(2-methoxyphenylamino)-5-nitropyrimidine-4-carboxylate (See Example 30.A) (0.300 g, 0.852 mmol), cis-4-aminocyclohexanol (0.155 g, 1.022 mmol) and diisopropylethylamine (0.274 g, 2.13 mmol) were reacted according to General Procedure C, except at room temperature and in dimethylformamide (5 mL). The crude reaction mixture was condensed and purified using Biotage chromatography (0-100% ethyl acetate in hexanes) to afford the title compound (0.342 g, 93%). MS (ESI) m/z 432.0 [M+1]$^+$.

B. Ethyl 5-amino-2-(cis-4-hydroxycyclohexylamino)-6-(2-methoxyphenylamino)pyrimidine-4-carboxylate. Ethyl 2-(cis-4-hydroxycyclohexylamino)-6-(2-methoxyphenylamino)-5-nitropyrimidine-4-carboxylate (0.340 g, 0.788 mmol) was dissolved in ethanol (20 mL) and 10% palladium on carbon (0.070 g) were added to the flask and flushed with fresh hydrogen gas and allowed to stir at room temperature.

After 16 h, the reaction was filtered through celite and the filtrate condensed under reduced pressure. The crude oil was purified using Biotage chromatography (5% methanol in ethyl acetate) to afford the title compound (0.272 g, 70%). MS (ESI) m/z 402.4 [M+1]$^+$.

C. Ethyl 2-(cis-4-hydroxycyclohexylamino)-9-(2-methoxyphenyl)-8-oxo-8,9-dihydro-7H-purine-6-carboxylate. Ethyl 5-amino-2-(cis-4-hydroxycyclohexylamino)-6-(2-methoxyphenyl-amino)pyrimidine-4-carboxylate (0.272 g, 0.678 mmol) and 1,1'-1,1'-carbonyldiimidazole (1.09 g, 6.78 mmol) in dichloromethane (20 mL) were reacted according to General Procedure F. A mixture of the title compound and the imidazole ester were formed and were taken on without further purification. MS (ESI) m/z 399 [M+1]$^+$ (title compound), 522 [M+1]$^+$ (imidazole urea).

D. 2-(cis-4-Hydroxycyclohexylamino)-9-(2-methoxyphenyl)-8-oxo-8,9-dihydro-7H-purine-6-carboxamide. Ethyl 2-(cis-4-hydroxycyclohexylamino)-9-(2-methoxyphenyl)-8-oxo-8,9-dihydro-7H-purine-6-carboxylate and the imidazole ester and ammonia gas in methanol were reacted according to General Procedure G and purified using reverse-phase preparative HPLC (10-80% acetonitrile+0.1% TFA in H$_2$O+0.1% TFA, over 30 min) to afford the title compound (0.010 g, 5% over 2 steps). $^1$H NMR (400 MHz, DMSO-d$_6$) δ 7.75 (s, 1H), 7.4 (t, J=8.69, 1H), 7.36 (dd, J=7.99, 1H), 7.19 (d, J=8.39, 1H), 7.06 (t, J=7.99, 1H), 6.73 (s, 1H), 4.23 (d, J=3.19, 1H), 3.68 (s, 1H), 1.53 (m, 9H); MS (ESI) m/z 399.1 [M+1]$^+$; mp 295-297° C.

5.1.104 Example 104

Synthesis of 2-(4-((1H-IMIDAZOL-1-YL)METHYL)PHENYLAMINO)-9-(2-METHOXYPHENYL)-8-OXO-8,9-DIHYDRO-7H-PURINE-6-CARBOXAMIDE A. Ethyl 2-(4-(hydroxymethyl)phenylamino)-6-(2-methoxyphenylamino)-5-nitropyrimidine-4-carboxylate. Ethyl 2-chloro-6-(2-methoxyphenylamino)-5-nitropyrimidine-4-carboxylate (See Example 30.A) (0.250 g, 0.710 mmol), 4-aminobenzyl alcohol (0.104 g, 0.852 mmol) and diisopropylethylamine (0.137 g, 1.065 mmol) were reacted according to General Procedure C, except at room temperature and in dimethylformamide (5 mL). The crude reaction mixture was condensed and purified using Biotage chromatography (60-100% ethyl acetate in hexanes) to afford the title compound (0.374 g, >100%). MS (ESI) m/z 440.0 [M+1]$^+$.

B. Ethyl 5-amino-2-(4-(hydroxymethyl)phenylamino)-6-(2-methoxyphenylamino)pyrimidine-4-carboxylate. Ethyl 2-(4-(hydroxymethyl)phenylamino)-6-(2-methoxyphenylamino)-5-nitropyrimidine-4-carboxylate (0.374 g, 0.788 mmol) was dissolved in ethanol (20 mL) and 10% palladium on carbon (0.075 g) were added to the flask and flushed with fresh hydrogen gas and allowed to stir at room temperature. After 16 h, the reaction was filtered through celite and the filtrate condensed under reduced pressure. The crude oil was purified using Biotage chromatography (0-100% ethyl acetate in hexanes) to afford the title compound (0.180 g, 51%). MS (ESI) m/z 410.5 [M+1]$^+$.

C. Ethyl 2-(4-((1H-imidazol-1-yl)methyl)phenylamino)-9-(2-methoxyphenyl)-8-oxo-8,9-dihydro-7H-purine-6-carboxylate. Ethyl 5-amino-2-(4-(hydroxymethyl)phenylamino)-6-(2-methoxyphenylamino)pyrimidine-4-carboxylate (0.180 g, 0.440 mmol) and 1,1'-1,1'-carbonyldiimidazole (0.713 g, 4.44 mmol) in dichloromethane (20 mL) were reacted according to General Procedure F and purified using Biotage silica gel chromatography (10% methanol in ethyl acetate) to afford the title compound (0.700 g, >100%). MS (ESI) m/z 486.5 [M+1]$^+$.

D. 2-(4-((1H-Imidazol-1-yl)methyl)phenylamino)-9-(2-methoxyphenyl)-8-oxo-8,9-dihydro-7H-purine-6-carboxamide. Ethyl 2-(4-((1H-imidazol-1-yl)methyl)phenylamino)-9-(2-methoxyphenyl)-8-oxo-8,9-dihydro-7H-purine-6-carboxylate (0.700 g) and ammonia gas were reacted in methanol according to General Procedure G and purified using reverse-phase preparative HPLC (5-60% acetonitrile+0.1% TFA in H$_2$O+0.1% TFA, over 30 min) to afford the title compound (0.048 g, 24%) $^1$H NMR (400 MHz, DMSO-d$_6$) δ 11.24 (s, 1H), 9.44 (s, 1H), 7.93 (s, 1H), 7.70 (s, 1H), 7.646 (d, J=8.79, 2H), 7.59 (s, 1H), 7.50 (t, J=7.19, 1H), 7.43 (d, J=7.99, 1H), 7.23 (d, J=8.39, 1H), 7.15 (d, J=7.19, 2H), 7.09 (t, J=7.59, 2H), 6.87 (s, 1H), 5.07 (s, 2H), 3.74 (s, 3H); MS (ESI) m/z 457.3 [M+1]$^+$; mp 165-170° C.

5.1.105 Example 105

Synthesis of 2-(4-HYDROXYPYRIDIN-3-YL)-8-OXO-9-(2-(TRIFLUOROMETHYL)PHENYL)-8,9-DIHYDRO-7H-PURINE-6-CARBOXAMIDE A. 2-(4-Hydroxypyridin-3-yl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl) urea (See Example 50.A) (0.15 g, 0.51 mmol), 4-hydroxynicotinaldehyde (0.13 g, 1.06 mmol), and triethylamine (0.10 ml, 0.72 mmol) were combined in ethanol (7.0 mL) and stirred at room temperature overnight. Excess solvent was removed under reduced pressure and the resulting residue was purified by silica gel Biotage chromatography (0-40% methanol in dichloromethane). Clean fractions were combined and solvent removed under reduced pressure. The resulting material was dried under house vacuum to provide the product as an off white solid (0.07 g, 0.17 mmol, 33% yield). MS (ESI) m/z 417.0 [M+1]$^+$.

5.1.106 Example 106

Synthesis of (R)-9-(2-METHOXYPHENYL)-8-OXO-2-(PYRROLIDIN-2-YLMETHYLAMINO)-8,9-DIHYDRO-7H-PURINE-6-CARBOXAMIDE A. (R)-Ethyl 2-((1-(tert-butoxycarbonyl)pyrrolidin-2-yl) methylamino)-6-(2-methoxy-phenylamino)-5-nitropyrimidine-4-carboxylate. Ethyl 2-chloro-6-(2-methoxyphenylamino)-5-nitropyrimidine-4-carboxylate (See Example 30.A) (0.300 g, 0.852 mmol), (R) 1-boc-(aminomethyl)pyrrolidine (0.207 g, 1.02 mmol) and diisopropylethylamine (0.164 g, 1.27 mmol) were reacted according to General Procedure C, except at room temperature and in dimethylformamide (5 mL). The crude reaction mixture was condensed and purified using Biotage chromatography (0-100% ethyl acetate in hexanes) to afford the title compound (0.430 g, 97%). MS (ESI) m/z 517.5 [M+1]$^+$.

B. (R)-Ethyl 5-amino-2-((1-(tert-butoxycarbonyl)pyrrolidin-2-yl)methylamino)-6-(2-methoxyphenylamino)pyrimidine-4-carboxylate. (R)-Ethyl 2-((1-(tert-butoxycarbonyl)pyrrolidin-2-yl)methylamino)-6-(2-methoxyphenylamino)-5-nitropyrimidine-4-carboxylate (0.430 g, 0.802 mmol) was dissolved in ethanol (20 mL) and 10% palladium on carbon (0.086 g) were added to the flask and flushed with fresh hydrogen gas and allowed to stir at room temperature. After 16 h, the reaction was filtered through celite and the filtrate condensed under reduced pressure. The crude oil was purified using Biotage chromatography (0-100% ethyl acetate in hexanes) to afford the title compound (0.360 g, 89%). MS (ESI) m/z 487.2 [M+1]+.

C. (R)-Ethyl 2-((1-(tert-butoxycarbonyl)pyrrolidin-2-yl)methylamino)-9-(2-methoxy-phenyl)-8-oxo-8,9-dihydro-7H-purine-6-carboxylate. (R)-Ethyl 5-amino-2-((1-(tert-butoxy-carbonyl)pyrrolidin-2-yl)methylamino)-6-(2-methoxyphenylamino)pyrimidine-4-carboxylate (0.360 g, 0.740 mmol) and carbonyldiimidazole (1.19 g, 7.40 mmol) in dichloromethane (20 mL) were reacted according to General Procedure F and purified using Biotage chromatography (0-100% ethyl acetate in hexanes) to afford the title product (0.381 g, 100%). MS (ESI) m/z 513.0 [M+1]+.

D. (R)-Ethyl 9-(2-methoxyphenyl)-8-oxo-2-(pyrrolidin-2-ylmethylamino)-8,9-dihydro-7H-purine-6-carboxylate. (R)-Ethyl 2-((1-(tert-butoxycarbonyl)pyrrolidin-2-yl)methylamino)-9-(2-methoxyphenyl)-8-oxo-8,9-dihydro-7H-purine-6-carboxylate (0.381 g, 0.744 mmol) was dissolved in dichloromethane (3 mL) and trifluoroacetic acid (1 mL) was added. The solution was stirred for two h and condensed under reduced pressure to afford the crude title compound (0.420 g, >100%). MS (ESI) m/z 413.1 [M+1]+.

E. (R)-9-(2-Methoxyphenyl)-8-oxo-2-(pyrrolidin-2-ylmethylamino)-8,9-dihydro-7H-purine-6-carboxamide. (R)-Ethyl 9-(2-methoxyphenyl)-8-oxo-2-(pyrrolidin-2-ylmethylamino)-8,9-dihydro-7H-purine-6-carboxylate (0.420 g) and ammonia gas in methanol (10 mL) were reacted according to General Procedure G and purified using reverse-phase preparative HPLC (5-60% acetonitrile+0.1% TFA in H$_2$O+0.1% TFA, over 30 min) to afford the title compound (0.120 g, 30%). $^1$H NMR (400 MHz, DMSO-d$_6$) δ 7.73 (s, 1H), 7.45 (t, J=7.99, 3H), 7.31 (d, J=6.79, 1H), 7.19 (d, J=8.39, 1H), 7.05 (t, J=7.19, 1H), 6.76 (s, 1H), 3.71 (s, 3H), 3.23 (s, 2H), 2.88 (s, 1H), 1.70 (s, 3H); MS (ESI) m/z 384.4 [M+1]+; mp 155-157° C.

5.1.107 Example 107

Synthesis of (S)-9-(2-METHOXYPHENYL)-8-OXO-2-(PYRROLIDIN-2-YLMETHYLAMINO)-8,9-DIHYDRO-7H-PURINE-6-CARBOXAMIDE A. (S)-Ethyl 2-((1-(tert-butoxycarbonyl)pyrrolidin-2-yl)methylamino)-6-(2-methoxy-phenylamino)-5-nitropyrimidine-4-carboxylate. Ethyl 2-chloro-6-(2-methoxyphenylamino)-5-nitropyrimidine-4-carboxylate (See Example 30.A) (0.300 g, 0.852 mmol), (S) 1-boc-(aminomethyl)pyrrolidine (0.206 g, 1.02 mmol) and diisopropylethylamine (0.164 g, 1.27 mmol.) were reacted according to General Procedure C, except at room temperature and in dimethylformamide (5 mL). The crude reaction mixture was condensed and purified using Biotage chromatography (0-100% ethyl acetate in hexanes) to afford the title compound (0.416 g, 95%). MS (ESI) m/z 517.3 [M+1]+.

B. (S)-Ethyl 5-amino-2-((1-(tert-butoxycarbonyl)pyrrolidin-2-yl)methylamino)-6-(2-methoxyphenylamino)pyrimidine-4-carboxylate. (S)-Ethyl 2-((1-(tert-butoxycarbonyl)pyrrolidin-2-yl)methylamino)-6-(2-methoxyphenylamino)-5-nitropyrimidine-4-carboxylate (0.416 g, 0.802 mmol) was dissolved in ethanol (20 mL) and 10% palladium on carbon (0.083 g) were added to the flask and flushed with fresh hydrogen gas and allowed to stir at room temperature. After 16 h, the reaction was filtered through celite and the filtrate condensed under reduced pressure. The crude oil was purified using Biotage chromatography (0-100% ethyl acetate in hexanes) to afford the title compound (0.340 g, 84%). MS (ESI) m/z 487.6 [M+1]+.

C. (S)-Ethyl 2-((1-(tert-butoxycarbonyl)pyrrolidin-2-yl)methylamino)-9-(2-methoxy-phenyl)-8-oxo-8,9-dihydro-7H-purine-6-carboxylate. (S)-Ethyl 5-amino-2-((1-(tert-butoxy-carbonyl)pyrrolidin-2-yl)methylamino)-6-(2-methoxyphenylamino)pyrimidine-4-carboxylate (0.340 g, 0.740 mmol) and carbonyldiimidazole (1.13 g, 7.40 mmol) in dichloromethane (20 mL) were reacted according to general procedure F and purified using Biotage chromatography (0-100% ethyl acetate in hexanes) to afford the title product (0.352 g, 98%). MS (ESI) m/z 513.5 [M+1]+.

D. (S)-Ethyl 9-(2-methoxyphenyl)-8-oxo-2-(pyrrolidin-2-ylmethylamino)-8,9-dihydro-7H-purine-6-carboxylate. (S)-Ethyl 2-((1-(tert-butoxycarbonyl)pyrrolidin-2-yl)methylamino)-9-(2-methoxyphenyl)-8-oxo-8,9-dihydro-7H-purine-6-carboxylate (0.352 g, 0.687 mmol) was dissolved in dichloromethane (3 mL) and trifluoroacetic acid (1 mL) was added. The solution was stirred for two h and condensed under reduced pressure to afford the crude title compound (0.400 g, >100%). MS (ESI) m/z 413.1 [M+1]+.

E. (S)-9-(2-Methoxyphenyl)-8-oxo-2-(pyrrolidin-2-ylmethylamino)-8,9-dihydro-7H-purine-6-carboxamide. (S)-Ethyl 9-(2-methoxyphenyl)-8-oxo-2-(pyrrolidin-2-ylmethylamino)-8,9-dihydro-7H-purine-6-carboxylate (0.400 g) and ammonia gas in methanol (10 mL) were reacted according to General Procedure G and purified using reverse-phase preparative HPLC (5-60% acetonitrile+0.1% TFA in H$_2$O+0.1% TFA, over 30 min) to afford the title compound (0.140 g, 38%). $^1$H NMR (400 MHz, DMSO-d$_6$) δ 7.72 (s, 1H), 7.45 (t, J=7.99, 3H), 7.30 (d, J=6.79, 1H), 7.18 (d, J=8.39, 1H), 7.05 (t, J=7.19, 1H), 6.76 (s, 1H), 3.71 (s, 3H), 3.22 (s, 2H), 2.88 (s, 1H), 1.70 (m, 3H); MS (ESI) m/z 384.4 [M+1]+; mp 160-165° C.

5.1.108 Example 108

Synthesis of 2-(4-(1H-1,2,4-TRIAZOL-3-YL)PHENYL)-9-(2-METHOXYPHENYL)-8-OXO-7-HYDROPURINE-6-CARBOXAMIDE A. (4-(1H-1,2,4-Triazol-3-yl)phenyl)methanol. 4-(1H-1,2,4-Triazol-3-yl)benzoic acid (1.79 g, 9.46 mmol) was suspended in anhydrous tetrahydrofuran (50 mL) and cooled −78° C. A solution of lithium aluminum hydride (2.0M, 23.0 mL, 46.0 mmol) was added and the reaction was allowed to slowly warm to room temperature with stirring overnight. The reaction was quenched with methanol and the crude product adsorbed onto silica gel. Flash Chromatography (10% MeOH in EtOAc) afforded the title compound (1.60 g, 9.14 mmol, 97%) as a white solid. MS (ESI) m/z 176.1 [M+1]+.

B. 4-(1H-1,2,4-Triazol-3-yl)benzaldehyde. (4-(1H-1,2,4-Triazol-3-yl)phenyl)methanol (92 mg, 0.53 mmol) was dissolved in anhydrous dimethylsulfoxide (1.5 mL) and methylene chloride (5 mL). Pyridiniumchlorochromate (0.23 g, 1.06 mmol) was added to the solution and stirred at room temperature overnight. The reaction mixture was filtered through silica gel and washed with ethyl acetate. Organics were poured into water (100 mL), extracted with EtOAc (3×100 mL), combined organic layers were dried with sodium sulfate, and concentrated under reduced pressure to afford the title compound (70 mg, 0.27 mmol, 51%) as a white solid. MS (ESI) m/z 174.1 [M+1]+.

C. 2-(4-(1H-1,2,4-Triazol-3-yl)phenyl)-9-(2-methoxyphenyl)-8-oxo-7-hydropurine-6-carboxamide. (Z)-1-(2-Amino-1,2-dicyanovinyl)-3-(2-methoxyphenyl)urea (See Example 2.A) (70 mg, 0.27 mmol), 4-(1H-1,2,4-triazol-3-yl)benzaldehyde (110 mg, 0.53 mmol), triethylamine (0.1 mL, 0.72 mmol) and methanol (4 mL) were reacted according to General Procedure B. The solution was allowed to stir at room temperature overnight. The resultant heterogeneous mixture was filtered, washed with diethyl ether, and dried under reduced pressure to afford the title compound (68 mg, 0.16 mmol, 59%) as a white solid. $^1$H NMR (400 MHz, DMSO-$d_6$) δ 11.78 (s, 1H), 8.55 (s, 1H), 8.47 (m, 2H), 8.07 (d, J=8.4, 2H), 8.01 (s, 1H), 7.57 (ddd, J=9.2, 7.6, 2.0, 1H), 7.51 (dd, J=7.6, 1.6, 1H), 7.31 (dd, J=8.4, 1.2, 1H), 7.17 (ddd, J=8.8, 7.6, 1.2, 1H), 3.76 (s, 3H); MS (ESI) m/z 429.1 [M+1]$^+$; mp 358° C.

5.1.109 Example 109

Synthesis of 2-(2-HYDROXYETHYLAMINO)-9-(2-METHOXYPHENYL)-8-OXO-8,9-DIHYDRO-7H-PURINE-6-CARBOXAMIDE A. Ethyl 2-(2-hydroxyethylamino)-6-(2-methoxyphenylamino)-5-nitropyrimidine-4-carboxylate. Ethyl 2-chloro-6-(2-methoxyphenylamino)-5-nitropyrimidine-4-carboxylate (See Example 30.A) (0.250 g, 0.710 mmol), ethanolamine (0.052 g, 0.852 mmol) and diisopropylethylamine (0.137 g, 1.06 mmol) were reacted according to General Procedure C, except at room temperature and in dimethylformamide (5 mL). The crude reaction mixture was condensed and purified using Biotage chromatography (0-100% ethyl acetate in hexanes) to afford the title compound (0.250 g, 95%). MS (ESI) m/z 378.5 [M+1]$^+$.

B. Ethyl 5-amino-2-(2-hydroxyethylamino)-6-(2-methoxyphenylamino)pyrimidine-4-carboxylate. Ethyl 2-(2-hydroxyethylamino)-6-(2-methoxyphenylamino)-5-nitropyrimidine-4-carboxylate r. (0.250 g, 0.663 mmol) was dissolved in ethanol (20 mL) and 10% palladium on carbon (0.050 g) were added to the flask and flushed with fresh hydrogen gas and allowed to stir at room temperature. After 16 h, the reaction was filtered through celite and the filtrate condensed under reduced pressure. The crude oil was purified using Biotage chromatography (5% methanol in ethyl acetate) to afford the title compound (0.200 g, 87%). MS (ESI) m/z 348.1 [M+1]$^+$.

C. Ethyl 2-(2-hydroxyethylamino)-9-(2-methoxyphenyl)-8-oxo-8,9-dihydro-7H-purine-6-carboxylater. Ethyl 5-amino-2-(2-hydroxyethylamino)-6-(2-methoxyphenylamino)pyrimidine-4-carboxylate (0.200 g, 0.576 mmol) and carbonyldiimidiazole (0.939 g, 5.76 mmol) in dichloromethane (20 mL) were reacted according to General Procedure F and purified using Biotage chromatography (0-100% ethyl acetate in hexanes) to afford the title product and the imidazole carbamate as a mixture (0.240 g combined, 89%). MS (ESI) m/z 374.1 [M+1]$^+$ (title compound) and 468.1 [M+1]$^+$ (imidazole carbamate).

D. 2-(2-Hydroxyethylamino)-9-(2-methoxyphenyl)-8-oxo-8,9-dihydro-7H-purine-6-carboxamide Ethyl 2-(2-hydroxyethylamino)-9-(2-methoxyphenyl)-8-oxo-8,9-dihydro-7H-purine-6-carboxylate (0.400 g) and ammonia gas in methanol (10 mL) were reacted according to General Procedure G and purified using reverse-phase preparative HPLC (5-60% acetonitrile+0.1% TFA in H$_2$O+0.1% TFA, over 30 min) to afford the title compound (0.015 g, 8%). $^1$H NMR (400 MHz, DMSO-$d_6$) δ 10.49 (s, 1H), 7.86 (s, 1H), 7.81 (s, 1H), 7.48 (t, J=6.79, 1H), 7.36 (d, J=7.99, 1H), 7.20 (d, J=8.39, 1H), 7.07 (t, J=7.59, 1H), 6.78 (s, 1H), 4.50 (t, J=5.59, 1H), 3.72 (s, 3H), 3.44 (q, J=6.39, 2H), 3.31 (m, 2H); MS (ESI) m/z 345.2 [M+1]$^+$; mp 157-160° C.

5.1.110 Example 110

Synthesis of 9-(2-METHOXYPHENYL)-8-OXO-2-(2-(TRIFLUOROMETHYL)-1H-BENZO[D]IMIDAZOL-6-YL)-8,9-DIHYDRO-7H-PURINE-6-CARBOXAMIDE A. (2-(Trifluoromethyl)-1H-benzo[d]imidazol-6-yl)methanol. 2-(Trifluoromethyl)-1H-benzo[d]imidazole-6-carboxylic acid (1.38 g, 6.00 mmol) was suspended in anhydrous tetrahydrofuran (100 mL) and cooled to −78° C. A solution of lithium aluminum hydride (2.0M, 15.0 mL, 30.0 mmol) was added and the resulting solution was allowed to slowly warm to room temperature, with stirring, overnight. The reaction was quenched with methanol and the crude product adsorbed onto silica gel. Flash Chromatography (10% MeOH in EtOAc) afforded the title compound (1.20 g, 5.55 mmol, 93%) as a white solid. MS (ESI) m/z 217.1 [M+1]$^+$.

B. 2-(Trifluoromethyl)-1H-benzo[d]imidazole-6-carbaldehyde. (2-(Trifluoromethyl)-1H-benzo[d]imidazol-6-yl)methanol (1.08 mg, 4.99 mmol) was dissolved in anhydrous dimethylsulfoxide (5.0 mL) and methylenechloride (30.0 mL). Pyridiniumchlorochromate (4.31 g, 20.0 mmol) was added to the solution and stirred at room temperature overnight. The reaction mixture was filtered through silica gel and washed with ethyl acetate. Organics were poured into water (100 mL), extracted with EtOAc (3×100 mL), combined organic layers were dried with sodium sulfate, and concentrated under reduced pressure to afford the title compound (545 mg, 2.54 mmol, 51%) as a white solid. MS (ESI) m/z 215.1 [M+1]$^+$.

C. 9-(2-Methoxyphenyl)-8-oxo-2-(2-(trifluoromethyl)-1H-benzo[d]imidazol-6-yl)-8,9-dihydro-7H-purine-6-carboxamide. (Z)-1-(2-Amino-1,2-dicyanovinyl)-3-(2-methoxyphenyl)urea (See Example 2.A) (240 mg, 0.93 mmol), 2-(trifluoromethyl)-1H-benzo[d]imidazole-6-carbaldehyde (400 mg, 1.86 mmol), triethylamine (0.2 mL, 1.40 mmol) and methanol (6.0 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H$_2$O+0.1% TFA, over 30 min). The volatiles were removed under reduced pressure, the suspended solid treated with ammonium hydroxide with sonication, and filtered. The solid was washed with diethyl ether and dried in a vacuum oven at 60° C. overnight to afford the title compound (23 mg, 0.049 mmol, 5%) as a white solid. $^1$H NMR (400 MHz, DMSO-$d_6$) δ 11.75 (s, 1H), 8.59 (s, 1H), 8.50 (s, 1H), 8.00 (s, 1H), 7.57 (ddd, J=8.0, 7.6, 1.6, 1H), 7.53 (dd, J=8.0, 1.6, 1H), 7.32 (d, J=7.2, 1H), 7.18 (m, 1H), 3.76 (s, 3H); MS (ESI) m/z 470.1 [M+1]$^+$; mp 220-222° C.

5.1.111 Example 111

Synthesis of 2-(3-(1H-1,2,4-TRIAZOL-3-YL)PHENYL)-9-(2-METHOXYPHENYL)-8-OXO-7-HYDROPURINE-6-CARBOXAMIDE A. (3-(1H-1,2,4-Triazol-3-yl)phenyl)methanol. 3-(1H-1,2,4-Triazol-3-yl)benzoic acid (2.01 g, 10.62 mmol) was suspended in anhydrous tetrahydrofuran (100 mL) and cooled −78° C. A solution of lithium aluminum hydride (2.0M, 26.0 mL, 52.0 mmol) was added and the resulting solution was allowed to slowly warm to room temperature, with stirring, overnight. The reaction was quenched with methanol and the crude product adsorbed onto silica gel. Flash Chromatography (10% MeOH in EtOAc) afforded the title compound (1.0 g, 5.71 mmol, 54%) as a white solid. MS (ESI) m/z 176.1 [M+1]+.

B. 3-(1H-1,2,4-Triazol-3-yl)benzaldehyde. (3-(1H-1,2,4-Triazol-3-yl)phenyl)methanol (1.0 g, 5.71 mmol) was dissolved in anhydrous dimethylsulfoxide (4.0 mL) and methylenechloride (60.0 mL). Pyridiniumchlorochromate (4.92 g, 22.8 mmol) was added to the solution and stirred at room temperature overnight. The reaction mixture was filtered through silica gel and washed with ethyl acetate. Poured organics into water (100 mL), extracted with EtOAc (2×100 mL), dried combined organic layers with sodium sulfate, and concentrated under reduced pressure to afford the title compound (660 mg, 3.79 mmol, 66%) as a white solid. MS (ESI) m/z 174.1 [M+1]+.

C. 2-(3-(1H-1,2,4-Triazol-3-yl)phenyl)-9-(2-methoxyphenyl)-8-oxo-7-hydropurine-6-carboxamide. (Z)-1-(2-Amino-1,2-dicyanovinyl)-3-(2-methoxyphenyl)urea (See Example 2.A) (245 mg, 0.95 mmol), 3-(1H-1,2,4-triazol-3-yl)benzaldehyde (330 mg, 1.90 mmol), triethylamine (0.2 mL, 1.43 mmol) and methanol (8.0 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in $H_2O$+0.1% TFA, over 30 min). The volatiles were removed under reduced pressure, the suspended solid treated with ammonium hydroxide with sonication, and filtered. The solid was washed with diethyl ether and dried in a vacuum oven at 60° C. overnight to afford the title compound (72 mg, 0.15 mmol, 16%) as a white solid. $^1$H NMR (400 MHz, DMSO-$d_6$) δ 11.79 (s, 1H), 8.82 (s, 1H), 8.62 (s, 1H), 8.56 (d, J=8.0, 1H), 8.45 (s, 1H), 8.07 (m, 2H), 7.56 (m, 3H), 7.32 (dd, J=8.4, 0.8, 1H), 7.17 (m, 1H), 3.77 (s, 3H); MS (ESI) m/z 429.1 [M+1]+; mp 242-243° C.

5.1.112 Example 112

Synthesis of 9-(BIPHENYL-2-YL)-2-(3-HYDROXYPHENYL)-8-OXO-8,9-DIHYDRO-7H-PURINE-6-CARBOXAMIDE A. (Z)-1-(2-Amino-1,2-dicyanovinyl)-3-(biphenyl-2-yl) urea. In a round bottom flask, 2,3-diaminomaleonitrile (1.0 g, 9.25 mmol) was dissolved in acetonitrile (35 mL) and stirred at room temperature. 2-Biphenyl isocyanate (1.80 g, 9.25 mmol) in acetonitrile (5 mL) was added dropwise over 10 minutes and the reaction stirred at room temperature. After 16 hours, the solution was condensed under reduced pressure and the resultant solid purified using Biotage silica chromatography (0-100% ethyl acetate in hexanes) to afford the title compound (1.48 g, 53%). MS (ESI) m/z 304.3 [M+1]+.

B. 9-(Biphenyl-2-yl)-2-(3-hydroxyphenyl)-8-oxo-8,9-dihydro-7H-purine-6-carboxamide. (Z)-1-(2-Amino-1,2-dicyanovinyl)-3-(biphenyl-2-yl)urea (0.500 g, 1.65 mmol), 3-hydroxybenzaldehyde (0.403 g, 3.30 mmol) and triethylamine (0.6 ml) were reacted according to General Procedure B and triturated with dimethylformamide/water to afford the title compound (0.160 g, 23%). $^1$H NMR (400 MHz, DMSO-$d_6$) δ 11.63 (s, 1H), 9.49 (s, 1H), 8.34 (s, 1H), 7.95 (s, 1H), 7.84 (d, J=7.59, 1H), 7.67 (m, 1H), 7.63 (m, 4H), 7.20 (m, 5H), 7.17 (m, 1H), 6.80 (d, J=7.99, 1H); MS (ESI) m/z 424.2 [M+1]+; mp 293-296° C.

5.1.113 Example 113

Synthesis of 2-(4-(1H-1,2,4-TRIAZOL-3-YL)PHENYL)-9-(2-FLUOROPHENYL)-8-OXO-7-HYDROPURINE-6-CARBOXAMIDE A. 2-(4-(1H-1,2,4-Triazol-3-yl)phenyl)-9-(2-fluorophenyl)-8-oxo-7-hydropurine-6-carboxamide. N-((1Z)-2-Amino-1,2-dicyanovinyl)[(2-fluorophenyl)amino]carboxamide (See Example 9.A) (290 mg, 1.15 mmol), 4-(1H-1,2,4-triazol-3-yl)benzaldehyde (See 108.B) (440 mg, 2.54 mmol), triethylamine (0.24 mL, 1.73 mmol) and methanol (8.0 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in $H_2O$+0.1% TFA, over 30 min). The volatiles were removed under reduced pressure, the suspended solid treated with ammonium hydroxide with sonication, and filtered. The solid was washed with diethyl ether and dried in a vacuum oven at 60° C. overnight to afford the title compound (28 mg, 0.067 mmol, 6%) as a white solid. $^1$H NMR (400 MHz, DMSO-$d_6$) δ 11.95 (s, 1H), 8.65 (s, 1H), 8.57 (s, 1H), 8.48 (d, J=8.4, 1H), 8.08 (d, J=8.0, 1H), 8.05 (s, 1H), 7.73 (ddd, J=9.2, 7.6, 1.6, 1H), 7.64 (m, 2H), 7.56 (ddd, J=10.0, 8.4, 1.2, 1H), 7.47 (ddd, J=8.8, 7.6, 1.2, 1H); MS (ESI) m/z 417.1 [M+1]+; mp 358° C.

5.1.114 Example 114

Synthesis of 2-(4-(1H-1,2,4-TRIAZOL-3-YL)PHENYL)-9-(2-ISOPROPYLPHENYL)-8-OXO-8,9-DIHYDRO-7H-PURINE-6-CARBOXAMIDE A. 2-(4-(1H-1,2,4-Triazol-3-yl)phenyl)-9-(2-isopropylphenyl)-8-oxo-8,9-dihydro-7H-purine-6-carboxamide. (Z)-1-(2-amino-1,2-dicyanovinyl)-3-(2-isopropylphenyl)urea (See Example 56.A) (310 mg, 1.15 mmol), 4-(1H-1,2,4-triazol-3-yl)benzaldehyde (See 108.B) (440 mg, 2.54 mmol), triethylamine (0.24 mL, 1.73 mmol) and methanol (8.0 mL) were reacted according to General Procedure B. The solution was allowed to stir at room temperature overnight. The resultant heterogeneous mixture was filtered, washed with diethyl ether, and dried under reduced pressure to afford the title compound (225 mg, 0.51 mmol, 44%) as a white solid. $^1$H NMR (400 MHz, DMSO-$d_6$) δ 11.85 (s, 1H), 8.64 (s, 1H), 8.55 (s, 1H), 8.45 (d, J=7.6, 1H), 8.06 (d, J=8.0, 1H), 8.03 (s, 1H), 7.58 (m, 2H), 7.42 (m, 2H), 2.75 (hept, J=6.8, 1H), 1.14 (d, J=6.8, 3H), 1.12 (d, J=6.8, 1H); MS (ESI) m/z 441.1 [M+1]+; mp 368° C.

5.1.115 Example 115

Synthesis of 9-(2-METHOXYPHENYL)-2-(2-METHYL-1H-BENZO[D]IMIDAZOL-6-YL)-8-OXO-8,9-DIHYDRO-7H-PURINE-6-CARBOXAMIDE A. (2-Methyl-1H-benzo[d]imidazol-6-yl)methanol. 2-Methyl-1H-benzo[d]imidazole-6-carboxylic acid (2.0 g, 11.35 mmol) was suspended in anhydrous tetrahydrofuran (100 mL) and cooled –78° C. A solution of lithium aluminum hydride (2.0M, 22.7 mL, 45.4 mmol) was added and allowed to slowly warm to room temperature, with stirring, overnight. The reaction was quenched with methanol and the crude product adsorbed onto silica gel. Flash Chromatography (20% MeOH in EtOAc) afforded the title compound (1.11 g, 6.85 mmol, 60%) as a white solid. MS (ESI) m/z 163.1 [M+1]+.

B. 2-Methyl-1H-benzo[d]imidazole-6-carbaldehyde. (2-Methyl-1H-benzo[d]imidazol-6-yl)methanol (1.11 g, 6.85 mmol) was dissolved in anhydrous dimethylsulfoxide (6.0 mL) and methylenechloride (60.0 mL). Pyridiniumchlorochromate (5.90 g, 27.4 mmol) was added to the solution and stirred at room temperature overnight. The reaction mixture was filtered through silica gel and washed with ethyl acetate. Poured organics into water (100 mL), extracted with EtOAc (2×100 mL), dried combined organic layers with sodium sulfate, and concentrated under reduced pressure to afford the title compound (742 mg, 3.79 mmol, 67%) as a white solid. MS (ESI) m/z 161.1 [M+1]+.

C. 9-(2-Methoxyphenyl)-2-(2-methyl-1H-benzo[d]imidazol-6-yl)-8-oxo-8,9-dihydro-7H-purine-6-carboxamide. (Z)-1-(2-Amino-1,2-dicyanovinyl)-3-(2-methoxyphenyl)urea (See Example 2.A) (290 mg, 1.13 mmol), 2-methyl-1H-benzo[d]imidazole-6-carbaldehyde (400 mg, 2.49 mmol), triethylamine (0.24 mL, 1.70 mmol) and methanol (8.0 mL) were reacted according to General Procedure B. The solution was allowed to stir at room temperature overnight. The resultant heterogeneous mixture was filtered, washed with diethyl ether, and dried under reduced pressure to afford the title compound (265 mg, 0.64 mmol, 57%) as a white solid. $^1$H NMR (400 MHz, DMSO-$d_6$) δ 12.24 (s, 1H), 11.64 (s, 1H), 8.52 (m, 1H), 8.32 (s, 1H), 8.22 (m, 1H), 7.97 (s, 1H), 7.57 (ddd, J=9.2, 8.8, 1.6, 1H), 7.51 (dd, J=7.6, 1.6, 1H), 7.31 (dd, J=8.4, 0.8, 1H), 7.17 (ddd, J=8.8, 8.0, 1.6, 1H), 3.75 (s, 3H), 2.48 (s, 3H); MS (ESI) m/z 416.1 [M+1]+; mp 270° C.

5.1.116 Example 116

Synthesis of 2-(3-(HYDROXYMETHYL)PHENYLAMINO)-9-(2-METHOXYPHENYL)-8-OXO-8,9-DIHYDRO-7H-PURINE-6-CARBOXAMIDE A. Ethyl 5-nitro-2-(3-(hydroxymethyl)phenylamino)-6-(2-methoxyphenylamino)pyrimidine-4-carboxylate. Ethyl 2-chloro-6-(2-methoxyphenylamino)-5-nitropyrimidine-4-carboxylate (See Example 30.A) (0.300 g, 0.852 mmol), 3-aminobenzyl alcohol (0.125 g, 1.2 mmol) and diisopropylethylamine (0.219 g) were reacted according to General Procedure C, except at room temperature and in dimethylformamide (5 ml). The crude reaction mixture was condensed and purified using Biotage chromatography (60 to 100% EtOAc in hexanes) to afford the title compound (0.350 g., 93%). MS (ESI) m/z 440.5 [M+1]+.

B. Ethyl 5-amino-2-(3-(hydroxymethyl)phenylamino)-6-(2-methoxyphenylamino)pyrimidine-4-carboxylate. Ethyl-5-nitro-2-(3-(hydroxy(ethyl)phenylamino)-6-(2-methoxyphenylamino)pyrimidine-4-carboxylate (0.35 g, 0.797 mmol) was dissolved in ethanol (20 mL) and 10% palladium on carbon (0.087 g) was added to the flask and flushed with fresh hydrogen gas and allowed to stir at room temperature. After 16 h, the reaction was filtered through celite and the filtrate condensed under reduced pressure. The crude oil was purified using biotage chromatography (50-100% ethyl acetate in hexanes) to afford the title compound (0.277 g, 85%). MS (ESI) m/z 410.5 [M+1]+.

C. Ethyl 5-amino-2-(3-((tert-butyldimethylsilyloxy)methyl)phenylamino)-6-(2-methoxy-phenylamino)pyrimidine-4-carboxylate. Ethyl 5-amino-2-(3-(hydroxymethyl)phenylamino)-6-(2-methoxyphenylamino)pyrimidine-4-carboxylate (0.277 g, 0.677 mmol), tert-butyldimethylsilyl chloride (0.132 g, 0.880 mmol), imidazole (0.047 g, 0.693 mmol) were combined in methylene chloride (10 mL) and stirred for 16 h at room temperature. The solution was condensed under reduced pressure and purified using Biotage chromatography (0 to 100% EtOAc in hexanes) to afford the title compound (0.242 g, 68%). MS (ESI) m/z 524.7 [M+1]+.

D. Ethyl 2-(3-((tert-butyldimethylsilyloxy)methyl)phenylamino)-9-(2-methoxyphenyl)-8-oxo-8,9-dihydro-7H-purine-6-carboxylate. Ethyl 5-amino-2-(3-((tert-butyldimethylsilyloxy)methyl)phenylamino)-6-(2-methoxyphenylamino)pyrimidine-4-carboxylate (0.242 g, 0.462 mmol) and 1,1'-1,1'-carbonyldiimidazole (0.525 g, 3.23 mmol) in dichloromethane (15 mL) were reacted according to General Procedure F and purified using biotage chromatography (10 to 90% EtOAc in hexanes) to afford the title compound (0.180 g, 71%). MS (ESI) m/z 550.5 [M+1]+.

E. 2-(3-((tert-Butyldimethylsilyloxy)methyl)phenylamino)-9-(2-methoxyphenyl)-8-oxo-8,9-dihydro-7H-purine-6-carboxamide. Ethyl 2-(3-((tert-butyldimethylsilyloxy)methyl)phenyl-amino)-9-(2-methoxyphenyl)-8-oxo-8,9-dihydro-7H-purine-6-carboxylate. (0.180 g, 3.97 mmol) was dissolved in methanol (10 mL), saturated with ammonia gas, and reacted according to General Procedure G. After 16 h, the solution was condensed under reduced pressure to afford the title compound (0.153 g, 91%). MS (ESI) m/z 521.6. [M+1]+.

F. 2-(3-(Hydroxymethyl)phenylamino)-9-(2-methoxyphenyl)-8-oxo-8,9-dihydro-7H-purine-6-carboxamide. 2-(3-((tert-Butyldimethylsilyloxy)methyl)phenylamino)-9-(2-methoxyphenyl)-8-oxo-8,9-dihydro-7H-purine-6-carboxamide (0.153 g, 0.294 mmol) was dissolved in 4N HCl in dioxane (5 ml) and stirred at room temperature. After 30 min, the solution was condensed under reduced pressure to give the HCl salt. The salt was diluted with methanol and ran through a Strata-XC ion exchange column to afford the title compound as the free base (0.083 g, 69%). $^1$H NMR (400 MHz, DMSO-$d_6$) δ 11.27 (s, 1H), 9.43 (s, 1H), 8.00 (s, 1H), 7.78 (s, 1H), 7.54 (bs, 1H), 7.50 (m, 1H), 7.45 (d, J=6.39, 1H), 7.42 (d, J=8.79, 1H), 7.24 (d, J=8.39, 1H), 7.15 (t, J=7.59, 1H), 7.11 (t, J=7.99, 1H), 6.82 (d, J=7.19, 1H), 5.13 (t, J=5.59, 1H), 4.41 (d, J=5.59, 2H), 3.75 (s, 3H); MS (ESI) m/z 407.4 [M+1]+; mp 237-239° C.

5.1.117 Example 117

Synthesis of 2-(2-(HYDROXYMETHYL)PHENYLAMINO)-9-(2-METHOXYPHENYL)-8-OXO-8,9-DIHYDRO-7H-PURINE-6-CARBOXAMIDE A. Ethyl 5-nitro-2-(2-(hydroxymethyl)phenylamino)-6-(2-methoxyphenylamino)pyrimidine-4-carboxylate. Ethyl 2-chloro-6-(2-methoxyphenylamino)-5-nitropyrimidine-4-carboxylate (See Example 30.A) (0.300 g, 0.852 mmol), 2-aminobenzyl alcohol (0.125 g, 1.2 mmol) and diisopropylethylamine (0.296 g) were reacted according to General Procedure C, except at room temperature and in dimethylformamide (5 ml). The crude reaction mixture was condensed and purified using Biotage chromatography (60 to 100% EtOAc in hexanes) to afford the title compound (0.323 g, 86%). MS (ESI) m/z 440.5 [M+1]+.

B. Ethyl 5-amino-2-(2-(hydroxymethyl)phenylamino)-6-(2-methoxyphenylamino)pyrimidine-4-carboxylate. Ethyl-5-nitro-2-(2-(hydroxymethyl)phenylamino)-6-(2-methoxyphenylamino)pyrimidine-4-carboxylate (0.325 g, 0.740 mmol) was dissolved in ethanol (20 mL) and 10% palladium on carbon (0.081 g) were added to the flask and flushed with fresh hydrogen gas and allowed to stir at room temperature.

After 16 h, the reaction was filtered through celite and the filtrate condensed under reduced pressure. The crude oil was purified using biotage chromatography (50-100% ethyl acetate in hexanes) to afford the title compound (0.270 g., 89%). MS (ESI) m/z 410.5 [M+1]+.

C. Ethyl 5-amino-2-(2-((tert-butyldimethylsilyloxy)methyl)phenylamino)-6-(2-methoxy-phenylamino)pyrimidine-4-carboxylate. Ethyl 5-amino-2-(2-(hydroxymethyl)phenylamino)-6-(2-methoxyphenylamino)pyrimidine-4-carboxylate (0.227 g, 0.555 mmol), tert-butyldimethylsilyl chloride (0.104 g, 0.693 mmol), imidazole (0.047 g, 0.693 mmol) were combined in methylene chloride (10 mL) and stirred for 16 h at room temperature. The solution was condensed under reduced pressure and purified using Biotage chromatography (0 to 100% EtOAc in hexanes) to afford the title compound (0.200 g, 69%). MS (ESI) m/z 524.7 [M+1]+.

D. Ethyl 2-(2-((tert-butyldimethylsilyloxy)methyl)phenylamino)-9-(2-methoxyphenyl)-8-oxo-8,9-dihydro-7H-purine-6-carboxylate. Ethyl 5-amino-2-(3-((tert-butyldimethylsilyloxy)methyl)phenylamino)-6-(2-methoxyphenylamino)pyrimidine-4-carboxylate (0.200 g, 0.382 mmol) and 1,1'-1,1'-carbonyldiimidazole (0.433 g, 2.67 mmol) in dichloromethane (20 mL) were reacted according to General Procedure F and purified using biotage chromatography (10 to 90% EtOAc in hexanes) to afford the title compound (0.190 g, 91%). MS (ESI) m/z 550.5 [M+1]+.

E. 2-(2-((tert-Butyldimethylsilyloxy)methyl)phenylamino)-9-(2-methoxyphenyl)-8-oxo-8,9-dihydro-7H-purine-6-carboxamide. Ethyl 2-(2-((tert-butyldimethylsilyloxy)methyl)phenyl-amino)-9-(2-methoxyphenyl)-8-oxo-8,9-dihydro-7H-purine-6-carboxylate (0.190 g, 3.97 mmol) was dissolved in methanol (15 mL) and saturated with ammonia gas according to General Procedure G. After 16 h, the solution was condensed under reduced pressure to afford the title compound (0.150 g, 90%). MS (ESI) m/z 521.6. [M+1]+.

F. 2-(2-(Hydroxymethyl)phenylamino)-9-(2-methoxyphenyl)-8-oxo-8,9-dihydro-7H-purine-6-carboxamide. 2-(2-((tert-Butyldimethylsilyloxy)methyl)phenylamino)-9-(2-methoxyphenyl)-8-oxo-8,9-dihydro-7H-purine-6-carboxamide (0.150 g, 0.294 mmol) was dissolved in 4N HCl in dioxane (5 ml) and stirred at room temperature. After 30 min, the solution was condensed under reduced pressure to give the HCl salt. The salt was diluted with methanol and ran through a Strata-XC ion exchange syringe to afford the title compound as the free base (0.049 g, 41%). $^1$H NMR (400 MHz, DMSO-d$_6$) δ 11.26 (s, 1H), 8.63 (s, 1H), 7.89 (s, 1H), 7.83 (d, J=7.99, 1H) 7.57 (s, 1H), 7.50 (t, 8.39, 1H), 7.44 (dd, J=7.59, 1.59, 1H), 7.27 (t, J=7.19, 1H), 7.24 (d, J=8.39, 1H), 7.19 (t, J=7.59, 1H), 7.11 (t, J=7.59, 1H), 7.97 (t, J=7.99, 1H); MS (ESI) m/z 407.4 [M+1]+; mp 159-162° C.

5.1.118 Example 118

Synthesis of 9-(2-TERT-BUTYLPHENYL)-2-(3-HYDROXYPHENYL)-8-OXO-8,9-DIHYDRO-7H-PURINE-6-CARBOXAMIDE A. (Z)-1-(2-Amino-1,2-dicyanovinyl)-3-(2-tert-butylphenyl)urea. 2,3-Diaminomaleonitrile (3.0 g, 27.75 mmol) and 2-tertbutylphenyl isocyanate (1.61 g, 9.25 mmol) were reacted according to General Procedure A. The resulting precipitate was filtered and washed with acetonitrile and dried to afford the title compound (0.391 g, 15%). MS (ESI) m/z 284.3 [M+1]+.

B. 9-(2-tert-Butylphenyl)-2-(3-hydroxyphenyl)-8-oxo-8,9-dihydro-7H-purine-6-carboxamide. (Z)-1-(2-Amino-1,2-dicyanovinyl)-3-(2-tert-butylphenyl)urea (0.391 g, 1.38 mmol), 3-hydroxybenzaldehyde (0.337 g, 2.76 mmol) and triethylamine (0.6 ml) were reacted according to General Procedure B and purified using reverse-phase preparative HPLC (10-100% acetonitrile+0.1% TFA in H$_2$O+0.1% TFA, over 30 min) to afford the title compound (0.097 g, 17%). $^1$H NMR (400 MHz, DMSO-d$_6$) δ 8.40 (s, 1H), 8.00 (s, 1H), 7.85 (d, J=7.99, 1H), 7.718 (dd, J=8.39, 1.19, 1H), 7.62 (t, J=1.99, 1H), 7.53 (t, J=7.99, 1H), 7.40 (t, J=8.79, 1H), 7.30 (dd, J=7.59, 1.59, 1H), 7.21 (t, J=7.99, 1H), 6.80 (dd, J=7.99, 1.59, 1H), 3.37 (s, 9H); MS (ESI) m/z 404.1 [M+1]+; mp 294-297° C.

5.1.119 Example 119

Synthesis of 2-(3-HYDROXYPHENYL)-8-OXO-9-(2-PHENOXYPHENYL)-8,9-DIHYDRO-7H-PURINE-6-CARBOXAMIDE A. (Z)-1-(2-Amino-1,2-dicyanovinyl)-3-(2-phenoxyphenyl)urea. 2,3-Diaminomaleonitrile (3.0 g, 27.75 mmol) and 2-phenoxyphenyl isocyanate (1.95 g, 9.25 mmol) in acetonitrile (40 mL) were reacted according to General Procedure A. The precipitate was filtered and washed with acetonitrile and dried to afford the title compound (0.573 g, 19%). MS (ESI) m/z 320.1 [M+1]+.

B. 2-(3-Hydroxyphenyl)-8-oxo-9-(2-phenoxyphenyl)-8,9-dihydro-7H-purine-6-carboxamide. (Z)-1-(2-Amino-1,2-dicyanovinyl)-3-(2-phenoxyphenyl)urea (0.573 g, 1.79 mmol), 3-hydroxybenzaldehyde (0.438 g, 3.59 mmol) and triethylamine (0.6 ml) were reacted according to General Procedure B to afford the title compound (0.436 g, 55%). $^1$H NMR (400 MHz, DMSO-d$_6$) δ 8.36 (s, 1H), 7.96 (s, 1H), 7.91 (d, J=7.99, 1H), 7.74 (t, J=1.99, 1H), 7.66 (dd, J=7.99, 1.59, 1H), 7.57 (td, J=7.59, 1.59, 1H), 7.37 (td, J=7.99, 1.19, 1H), 7.23 (t, 3H), 7.11 (dd, J=8.39, 1.19, 1H), 7.02 (t, J=7.19, 1H), 6.97 (d, J=7.59, 2H), 6.82 (dd, J=7.99, 1.99, 1H); MS (ESI) m/z 440.1 [M+1]+; mp 329-331° C.

5.1.120 Example 120

Synthesis of 2-(1H-BENZO[D]IMIDAZOL-6-YL)-9-(2-ISOPROPYLPHENYL)-8-OXO-8,9-DIHYDRO-7H-PURINE-6-CARBOXAMIDE A. 2-(1H-Benzo[d]imidazol-6-yl)-9-(2-isopropylphenyl)-8-oxo-8,9-dihydro-7H-purine-6-carboxamide. (Z)-1-(2-amino-1,2-dicyanovinyl)-3-(2-isopropylphenyl)urea (See Example 56.A) (370 mg, 1.37 mmol), 1H-benzo[d]imidazole-6-carbaldehyde (See Example 84.B) (400 mg, 2.73 mmol), triethylamine (0.30 mL, 2.10 mmol) and methanol (6.0 mL) were reacted according to General Procedure B. The solution was allowed to stir at room temperature overnight. The resultant heterogeneous mixture was filtered, washed with diethyl ether, and dried under reduced pressure to afford the title compound (185 mg, 0.45 mmol, 33%) as a white solid. $^1$H NMR (400 MHz, DMSO-d$_6$) δ 12.48 (s, 1H), 11.71 (s, 1H), 8.72 (s, 1H), 8.52 (m, 1H), 8.41 (s, 1H), 8.24 (m, 1H), 7.95 (d, J=8.0, 1H), 7.59 (m, 3H), 7.42 (m, 2H), 2.75 (hept, J=5.7, 1H), 1.14 (d, J=5.7, 3H), 1.12 (d, J=5.7, 3H); MS (ESI) m/z 414.1 [M+1]+; mp 275° C. dec.

5.1.121 Example 121

Synthesis of 2-(1H-INDAZOL-4-YL)-9-(2-METHOXYPHENYL)-8-OXO-8,9-DIHYDRO-7H-PURINE-6-CARBOXAMIDE A. 4-Bromo-1-(tetrahydro-2H-pyran-2-yl)-1H-indazole. 4-Bromo-1H-indazole (1.0 g, 5.07 mmol) was dissolved in anhydrous tetrahydrofuran (50 mL). To this solution was added dihydropyran (0.93 mL, 10.14 mmol) and toluenesulfonic acid (144 mg, 0.76 mmol). The reaction mixture was refluxed over night. Saturated bicarbonate was added and the aqueous layer was extracted with ethyl acetate (3×50 mL). Organic fractions were pooled, dried over sodium sulfate and adsorbed onto silica gel. Flash chromatography (10% EtOAc in Hex) afforded a white solid (1.3 g, 4.62 mmol, 91%). MS (ESI) m/z 282.1 [M+1]$^+$.

B. 1-(Tetrahydro-2H-pyran-2-yl)-1H-indazole-4-carbaldehyde. 4-Bromo-1-(tetrahydro-2H-pyran-2-yl)-1H-indazole (816 mg, 2.90 mmol) was dissolved in anhydrous tetrahydrofuran (10 mL) and cooled to −78° C. n-Butyl lithium (1.6M, 4.0 mL, 6.38 mmol) was added and the reaction stirred for 30 min. Dimethylformamide (0.53 mL) was added and the solution was allowed to warm to room temperature. The reaction was quenched with saturated sodium bicarbonate, extracted with diethyl ether (2×75 mL), and dried with sodium sulfate. Product was used in next reaction without further purification or characterization. MS (ESI) m/z 231.2 [M+1]$^+$.

C. 2-(1H-Indazol-4-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (See Example 2.A) (340 mg, 1.31 mmol), 1-(tetrahydro-2H-pyran-2-yl)-1H-indazole-4-carbaldehyde (2.90 mmol), triethylamine (0.33 mL, 2.36 mmol) and methanol (8 mL) were reacted according to General Procedure B. The solution was allowed to stir at room temperature overnight. The precipitate was filtered and dissolved in a 4.0 M HCl/dioxane solution (0.2 mL) and anhydrous dioxane (3 mL). The reaction was heated to 55° C. overnight. The crude was poured into saturated sodium bicarbonate solution and extracted with ethyl acetate (3×75 mL), dried with sodium sulfate and concentrated under reduced pressure to afford the title compound (45 mg, 0.11 mmol) as a white solid. $^1$H NMR (400 MHz, DMSO-d$_6$) δ 13.16 (s, 1H), 11.80 (s, 1H), 8.42 (m, 2H), 8.40 (s, 1H), 8.35 (s, 1H), 7.59 (m, 3H), 7.35 (dd, J=8.4, 7.2, 1H), 7.35 (dd, J=8.4, 0.8, 1H), 7.20 (ddd, J=8.8, 7.6, 1.2, 1H), 3.75 (s, 3H); MS (ESI) m/z 402.1 [M+1]$^+$; mp 280° C.

5.1.122 Example 122

Synthesis of 2-(2-HYDROXYPYRIDIN-3-YL)-8-OXO-9-(2-(TRIFLUOROMETHYL)PHENYL)-8,9-DIHYDRO-7H-PURINE-6-CARBOXAMIDE A. 2-(2-Hydroxypyridin-3-yl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl)urea (See Example 50.A) (0.140 g, 0.474 mmol), 2-oxo-1,2-dihydropyridine-3-carboxaldehyde (0.130 g, 0.948 mmol) and triethylamine (0.1 ml) were reacted according to General Procedure B and purified using Biotage chromatography (5 to 20% MeOH in dichloromethane) to afford the title compound (0.078 g, 39%). $^1$H NMR (400 MHz, DMSO-d$_6$) δ 9.127 (s, 1H), 9.10 (s, 1H), 8.73 (dd, J=7.59, 1.59, 1H), 7.98 (m, 4H), 7.79 (m, 3H), 7.68 (d, J=7.59, 1H), 6.77 (t, J=6.39, 1H); MS (ESI) m/z 417.0 [M+1]$^+$; mp 331-335° C.

5.1.123 Example 123

Synthesis of 2-(1H-IMIDAZO[4,5-B]PYRIDIN-6-YL)-9-(2-METHOXYPHENYL)-8-OXO-8,9-DIHYDRO-7H-PURINE-6-CARBOXAMIDE A. (1H-Imidazo[4,5-b]pyridin-6-yl)methanol. Imidazo[4,5-b]pyridine-6-carboxylic acid (2.02 g, 12.38 mmol) was suspended in anhydrous tetrahydrofuran (100 mL) and cooled −78° C. A solution of lithium aluminum hydride (2.0M, 24.7 mL, 49.5 mmol) was added and the reaction was allowed to slowly warm to room temperature, with stirring, overnight. The reaction was quenched with methanol and the crude product adsorbed onto silica gel. Flash Chromatography (30% MeOH in EtOAc) afforded the title compound (0.29 g, 1.95 mmol, 15%) as a white solid. MS (ESI) m/z 150.1 [M+1]$^+$.

B. 1H-Imidazo[4,5-b]pyridine-6-carbaldehyde. (1H-Imidazo[4,5-b]pyridin-6-yl)methanol (290 mg, 1.95 mmol) was dissolved in anhydrous dimethylsulfoxide (4.0 mL) and methylenechloride (30 mL). Pyridiniumchlorochromate (1.68 g, 7.80 mmol) was added to the solution and stirred at room temperature overnight. The reaction mixture was filtered through silica gel and washed with ethyl acetate. Organics were poured into water (100 mL), extracted with EtOAc (3×100 mL), dried combined organic layers with sodium sulfate, and concentrated under reduced pressure to afford the title compound (133 mg, 0.89 mmol, 46%) as a white solid. MS (ESI) m/z 148.1 [M+1]$^+$.

C. 2-(1H-Imidazo[4,5-b]pyridin-6-yl)-9-(2-methoxyphenyl)-8-oxo-8,9-dihydro-7H-purine-6-carboxamide. (Z)-1-(2-Amino-1,2-dicyanovinyl)-3-(2-methoxyphenyl)urea (See Example 2.A) (162 mg, 0.63 mmol), 1H-imidazo[4,5-b]pyridine-6-carbaldehyde (133 mg, 0.89 mmol), triethylamine (0.14 mL, 0.94 mmol) and methanol (5 mL) were reacted according to General Procedure B. The solution was allowed to stir at room temperature overnight. The resultant heterogeneous mixture was filtered, washed with diethyl ether, and dried under reduced pressure to afford the title compound (7 mg, 0.017 mmol, 3%) as a white solid. $^1$H NMR (400 MHz, DMSO-d$_6$) δ 11.77 (s, 1H), 9.43 (s, 1H), 8.90 (s, 1H), 8.69 (s, 1H), 8.57 (s, 1H), 7.98 (s, 1H), 7.57 (ddd, J=9.2, 8.0, 1.6, 1H), 7.53 (dd, J=8.0, 1.6, 1H), 7.31 (dd, J=7.6, 1.2, 1H), 7.17 (ddd, J=8.8, 7.6, 1.2, 1H), 3.76 (s, 3H); MS (ESI) m/z 403.0 [M+1]$^+$; mp 358° C. dec.

5.1.124 Example 124

Synthesis of 2-(4-(1H-IMIDAZOL-1-YL)PHENYL)-9-(2-ISOPROPYLPHENYL)-8-OXO-8,9-DIHYDRO-7H-PURINE-6-CARBOXAMIDE A. 2-(4-(1H-Imidazol-1-yl)phenyl)-9-(2-isopropylphenyl)-8-oxo-8,9-dihydro-7H-purine-6-carboxamide. (Z)-1-(2-amino-1,2-dicyanovinyl)-3-(2-isopropylphenyl)urea (See Example 56.A) (360 mg, 1.32 mmol), 4-(1H-imidazol-1-yl)benzaldehyde (500 mg, 2.90 mmol), triethylamine (0.28 mL, 1.98 mmol) and methanol (10.0 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H$_2$O+0.1% TFA, over 30 min). The volatiles were removed under reduced pressure, the suspended solid treated with ammonium hydroxide with sonication, and filtered. The solid was washed with diethyl ether and dried in a vacuum oven at 60° C. overnight to afford the title compound (150 mg, 0.34 mmol, 26%) as a white solid. $^1$H NMR (400 MHz, CD$_3$OD) δ 10.77 (s, 1H), 10.64 (s, 1H), 10.62 (s, 1H), 10.16 (s, 1H), 9.96 (m, 1H), 9.87 (m, 2H), 9.74 (m, 2H), 9.56 (m, 2H), 9.28 (s, 1H), 4.90 (hept, J=6.8, 1H), 3.29 (d, J=6.8, 3H), 3.27 (d, J=6.8, 3H); MS (ESI) m/z 440.1 [M+1]$^+$; mp 232° C.

5.1.125 Example 125

Synthesis of 9-(2-CYCLOHEXYLPHENYL)-2-(3-HYDROXYPHENYL)-8-OXO-8,9-DIHYDRO-7H-PURINE-6-CARBOXAMIDE A. 1-Cyclohexyl-2-isocyanatobenzene. To a solution of 2-cyclohexylbenzoic acid (0.97 g, 4.75 mmol) in $CH_2Cl_2$ was added oxalyl chloride (0.62 mL, 7.13 mmol) at rt. The mixture was then refluxed for 15 min, cooled to rt, concentrated, and then dissolved in dioxane (10 mL). To this solution was added sodium azide (0.34 g, 5.23 mmol) in dioxane/water (10 mL, 1:1 v/v). The mixture was stirred for 5 min, diluted with EtOAc (50 mL) and washed with water (50 mL). The organic layer was dried over sodium sulfate, filtered, and concentrated. The crude residue was purified using silica gel chromatography (90% Hexanes in EtOAc) to afford the intermediate acyl azide in quantitative yield (1.13 g). The intermediate acyl azide was dissolved in toluene (50 mL) and stirred at 100° C. for 1 h. The mixture was concentrated to afford the title compound in quantitative yield (0.96 g). $^1$H NMR (400 MHz, DMSO) δ 7.23 (m, 2H), 7.15 (m, 2H), 2.81 (t, J=7.2, 1H), 1.80 (m, 5H), 1.40 (m, 5H).

B. 9-(2-Cyclohexylphenyl)-2-(3-hydroxyphenyl)-8-oxo-8,9-dihydro-7H-purine-6-carboxamide. 1-Cyclohexyl-2-isocyanatobenzene (0.96 g, 4.75 mmol) and diaminomaleonitrile (0.51 g, 4.75 mmol) were combined together in acetonitrile (30 mL). The mixture was stirred 3 d, after which the intermediate urea was seen by LCMS. The solution was concentrated. To the crude urea was added 3-hydroxybenzaldehyde (1.45 g, 11.88 mmol) in MeOH (20 mL) and triethyl amine (1 mL). The mixture was stirred for 11 h. The precipitate was filtered to afford the title compound (0.559 g, 27% over two steps). $^1$H NMR (400 MHz, DMSO) δ 11.78 (s, 1H), 9.48 (s, 1H), 8.41 (s, 1H), 8.00 (s, 1H), 7.87 (d, J=8.0, 1H), 7.65 (t, J=2.0, 1H), 7.54 (m, 2H), 7.39 (dd, J=4.4, 1.2, 2H), 7.22 (t, J=7.6, 1H), 6.81 (dd, J=8.0, 1.6, 1H), 2.32 (t, J=12.0, 1H), 1.71 (m, 3H), 1.56 (m, 2H), 1.44 (q, J=9.2, 2H), 1.17 (q, J=10.0, 2H), 0.95 (m, 1H); MS (ESI) m/z 430.1 [M+1]$^+$; mp>270° C.

5.1.126 Example 126

Synthesis of 2-(4-(1H-IMIDAZOL-2-YL)PHENYL)-9-(2-ISOPROPYLPHENYL)-8-OXO-8,9-DIHYDRO-7H-PURINE-6-CARBOXAMIDE A. (4-(1H-Imidazol-2-yl)phenyl)methanol. 4-(1H-Imidazol-2-yl)benzoic acid (2.05 g, 10.9 mmol) was suspended in anhydrous tetrahydrofuran (60 mL) and cooled to −78° C. A solution of lithium aluminum hydride (2.0M, 21.8 mL, 43.6 mmol) was added and the reaction was allowed to slowly warm to room temperature with stirring overnight. The reaction was quenched with methanol and the crude product adsorbed onto silica gel. Flash Chromatography (20% MeOH in EtOAc) afforded the title compound (1.6 g, 9.19 mmol, 84%) as a white solid. MS (ESI) m/z 175.1 [M+1]$^+$.

B. 4-(1H-Imidazol-2-yl)benzaldehyde. (4-(1H-Imidazol-2-yl)phenyl)methanol (1.6 g, 9.19 mmol) was dissolved in anhydrous dimethylsulfoxide (5.0 mL) and methylenechloride (50 mL). Pyridiniumchlorochromate (4.31 g, 20.0 mmol) was added to the solution and the reaction was stirred at room temperature overnight. The reaction mixture was filtered through silica gel and washed with ethyl acetate. Organics were poured into water (150 mL), extracted with EtOAc (4×100 mL), dried combined organic layers with sodium sulfate, and concentrated under reduced pressure to afford the title compound (1.10 g, 6.39 mmol, 70%) as a white solid. MS (ESI) m/z 173.1 [M+1]$^+$.

C. 2-(4-(1H-Imidazol-2-yl)phenyl)-9-(2-isopropylphenyl)-8-oxo-8,9-dihydro-7H-purine-6-carboxamide. (Z)-1-(2-Amino-1,2-dicyanovinyl)-3-(2-isopropylphenyl)urea (See example 56.A) (363 mg, 1.35 mmol), 4-(1H-imidazol-2-yl)benzaldehyde (420 mg, 2.44 mmol), triethylamine (0.28 mL, 2.03 mmol) and methanol (10 mL) were reacted according to General Procedure B. The solution was allowed to stir at room temperature overnight. The resultant heterogeneous mixture was filtered and purified using reverse-phase semipreparatory HPLC (20-100% acetonitrile+0.1% TFA in $H_2O+0.1$% TFA, over 30 min). The volatiles were removed under reduced pressure, the suspended solid treated with ammonium hydroxide with sonication, and filtered. The solid was washed with diethyl ether and dried in a vacuum oven at 60° C. overnight to afford the title compound (19 mg, 0.043 mmol, 3.2%) as a white solid. $^1$H NMR (400 MHz, DMSO-$d_6$) δ 11.94 (s, 1H), 8.63 (s, 1H), 8.57 (d, J=8.4, 1H), 8.04 (m, 2H), 7.76 (s, 1H), 7.59 (m, 2H), 7.42 (m, 2H), 2.75 (hept, J=7.2, 1H), 1.13 (d, J=6.8, 3H), 1.11 (d, J=6.8, 3H); MS (ESI) m/z 440.1 [M+1]$^+$; mp 340° C. dec.

5.1.127 Example 127

2-(1H-BENZO[D]IMIDAZOL-1-YL)-9-(2-METHOXYPHENYL)-8-OXO-8,9-DIHYDRO-7H-PURINE-6-CARBOXAMIDE

A. Methyl-2-(1H-benzo[d]imidazol-1-yl)-6-(2-methoxyphenylamino)-5-nitropyrimidine-4-carboxylate. To a solution of 1H-benzo[d]imidazole (0.354 g, 3.0 mmol) in tetrahydrofuran (20 mL) was added sodium hydride (0.120 g, 60% in mineral oil, 30 mmol). The reaction mixture was stirred at 60° C. for 15 min. Methyl 2-chloro-6-(2-methoxyphenylamino)-5-nitropyrimidine-4-carboxylate (See Example 30.A) (1.014 g, 3 mmol) was added and the resulting solution was stirred for 4 h. The reaction mixture was extracted with EtOAc (3×25 mL) and washed with brine (3×25 mL). The organic layers were combined, dried over sodium sulfate, filtered, and concentrated. The crude material was subjected to silica gel chromatography (25%-40% EtOAc in hexanes). Concentration of the desired fractions afforded the titled compound as yellow solid (1.0 g). MS (ESI) m/z 421.4 [M+1]$^+$.

B. Methyl 5-amino-2-(1H-benzo[d]imidazol-1-yl)-6-(2-methoxyphenylamino)pyrimidine-4-carboxylate. To a solution of methyl-2-(1H-benzo[d]imidazol-1-yl)-6-(2-methoxyphenylamino)-5-nitropyrimidine-4-carboxylate (0.500 g, 1.19 mmol) in methanol (20 mL) was added palladium on carbon (0.025 g, 10%). The reaction mixture was treated with hydrogen gas at 25° C. for 16 h. The reaction mixture was filtered through celite. Concentration of the filtrate afforded the titled compound (0.300 g, 60%). MS (ESI) m/z 417.5 [M+1]$^+$.

C. Methyl-2-(1H-benzo[d]imidazol-1-yl)-9-(2-methoxyphenyl)-8-oxo-8,9-dihydro-7H-purine-6-carboxylate. A solution of methyl 5-amino-2-(1H-benzo[d]imidazol-1-yl)-6-(2-methoxyphenylamino)pyrimidine-4-carboxylate (0.300 g, 0.769 mmol), 1,1'-carbonyldiimidazole (0.311 g, 1.922 mmol), and dichloromethane (10 mL) was reacted as described in General Procedure F. The reaction mixture was filtered to give the titled compound as white solid (0.200 g, 62%). $^1$H NMR (300 MHz, DMSO-$d_6$) δ 8.78 (s, 1H), 8.44-8.41 (m, 1H), 7.76-7.73 (m, 1H), 7.64-7.55 (m, 2H), 7.38-7.29 (m, 3H), 6.22-7.16 (m, 1H), 4.02 (s, 3H), 3.79 (s, 3H); MS (ESI) m/z 417.5 [M+1]$^+$.

D. 2-(1H-Benzo[d]imidazol-1-yl)-9-(2-methoxyphenyl)-8-oxo-8,9-dihydro-7H-purine-6-carboxamide. A solution of methyl-2-(1H-benzo[d]imidazol-1-yl)-9-(2-methoxyphenyl)-8-oxo-8,9-dihydro-7H-purine-6-carboxylate (0.200 g, 0.48 mmol) in methanol (10 mL) was saturated with ammonia and reacted as described in General Procedure G. The reaction mixture was poured onto ice-cold water. Collection of the resulting solid by filtration afford titled compound as white solid, 97.5% pure (188 mg, 94%). $^1$H NMR (400 MHz, DMSO-d$_6$) δ 11.91 (s, 1H), 9.54 (s, 1H), 8.67 (s, 1H), 8.08-8.04 (m, 2H), 7.74-7.72 (m, 1H), 7.64-7.56 (m, 2H), 7.37-7.35 (m, 1H), 7.30-7.25 (m, 1H), 7.22-7.19 (m, 2H), 3.78 (s, 3H); MS (ESI) m/z 401.9 [M+1]$^+$; mp 318-319° C.

5.1.128 Example 128

Synthesis of 2-(1H-IMIDAZO[4,5-B]PYRIDIN-6-YL)-9-(2-ISOPROPYLPHENYL)-8-OXO-8,9-DI-HYDRO-7H-PURINE-6-CARBOXAMIDE A. 2-(1H-Imidazo[4,5-b]pyridin-6-yl)-9-(2-isopropylphenyl)-8-oxo-8,9-dihydro-7H-purine-6-carboxamide. (Z)-1-(2-Amino-1,2-dicyanovinyl)-3-(2-isopropylphenyl)urea (See example 56.A) (455 mg, 1.69 mmol), 1H-imidazo[4,5-b]pyridine-6-carbaldehyde (See example 123.B) (300 mg, 2.03 mmol), triethylamine (0.35 mL, 2.54 mmol) and methanol (10 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (4×75 mL). Pooled organic layers were dried over sodium sulfate and concentrated under reduced pressure. The resulting solid was washed with diethyl ether and dried in a vacuum oven at 60° C. overnight to afford the title compound (19 mg, 0.045 mmol, 2.7%) as a white solid. $^1$H NMR (400 MHz, DMSO-d$_6$) δ 13.23 (s, 1H), 12.68 (s, 1H), 11.83 (m, 1H), 9.30 (m, 1H), 8.70 (m, 1H), 8.48 (m, 1H), 7.98 (m, 1H), 7.61 (m, 2H), 7.43 (m, 2H), 2.77 (hept, J=7.6, 1H), 1.14 (d, J=7.6, 3H), 1.12 (d, J=7.6, 3H); MS (ESI) m/z 415.0 [M+1]$^+$; mp 320° C. dec.

5.1.129 Example 129

Synthesis of 9-(2-ISOPROPYLPHENYL)-8-OXO-2-(1H-PYRROLO[2,3-B]PYRIDIN-5-YL)-8,9-DIHYDRO-7H-PURINE-6-CARBOXAMIDE A. (1H-Pyrrolo[2,3-b]pyridin-5-yl)methanol. 1H-Pyrrolo[2,3-b]pyridine-5-carboxylic acid (1.0 g, 5.67 mmol) was suspended in anhydrous tetrahydrofuran (75 mL) and cooled −78° C. A solution of lithium aluminum hydride (2.0M, 10.6 mL, 17.0 mmol) was added and the reaction was allowed to slowly warm to room temperature with stirring overnight. The reaction was quenched with methanol and the volatiles removed under reduced pressure. Crude material was taken on to the next step without further purification or characterization. MS (ESI) m/z 175.1 [M+1]$^+$.

B. 1H-Pyrrolo[2,3-b]pyridine-5-carbaldehyde. (1H-Pyrrolo[2,3-b]pyridin-5-yl)methanol (crude from previous reaction) was dissolved in anhydrous methylenechloride (50 mL). Pyridiniumchlorochromate (3.70 g, 17.0 mmol) was added to the solution and stirred at room temperature overnight. The reaction mixture was filtered through silica gel and washed with ethyl acetate. Organics were poured into water (150 mL), extracted with EtOAc (4×100 mL), combined organic layers were dried with sodium sulfate, and concentrated under reduced pressure to afford the title compound (0.72 g, 4.93 mmol, 87% over 2 steps) as a white solid. MS (ESI) m/z 147.1 [M+1]$^+$.

C. 9-(2-Isopropylphenyl)-8-oxo-2-(1H-pyrrolo[2,3-b]pyridin-5-yl)-8,9-dihydro-7H-purine-6-carboxamide. (Z)-1-(2-Amino-1,2-dicyanovinyl)-3-(2-isopropylphenyl)urea (See example 56.A) (762 mg, 2.83 mmol), 1H-pyrrolo[2,3-b]pyridine-5-carbaldehyde (0.72 mg, 4.93 mmol), triethylamine (0.60 mL, 4.24 mmol) and methanol (10 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×75 mL). The pooled organic layers were dried with sodium sulfate and concentrated under reduced pressure. The resulting solid was washed with diethyl ether and dried in a vacuum oven at 60° C. overnight to afford the title compound (358 mg, 0.87 mmol, 31%) as a white solid. $^1$H NMR (400 MHz, DMSO-d$_6$) δ 11.62 (s, 1H), 9.15 (m, 1H), 9.05 (d, J=2.0, 1H), 8.61 (d, J=1.6, 1H), 7.56 (m, 1H), 7.51 (dd, J=8.0, 1.6, 1H), 7.45 (m, 1H), 7.42 (m, 1H), 7.33 (ddd, J=9.2, 7.6, 1.6, 1H), 7.19 (m, 1H), 6.47 (dd, J=3.2, 1.2, 1H), 2.78 (hept, J=7.2, 1H), 1.11 (d, J=6.4, 3H), 1.10 (d, J=6.4, 3H); MS (ESI) m/z 414.1 [M+1]$^+$; mp 380° C. dec.

5.1.130 Example 130

Synthesis of 2-(1H-IMIDAZO[4,5-B]PYRIDIN-6-YL)-8-OXO-9-(2-(TRIFLUOROMETHYL)PHENYL)-8,9-DIHYDRO-7H-PURINE-6-CARBOXAMIDE A. Ethyl 1-(tetrahydro-2H-pyran-2-yl)-1H-imidazo[4,5-b]pyridine-6-carboxylate. Ethyl 1H-imidazo[4,5-b]pyridine-6-carboxylate (2.0 g, 10.4 mmol), dihydropyran (1.9 mL, 10.9 mmol), and toluenesulfonic acid (400 mg, 2.10 mmol) was dissolved in anhydrous tetrahydrofuran (100 mL) and refluxed overnight. The crude reaction mixture was adsorbed onto silica gel and purified using flash chromatography (60% EtOAc in hex) to give (2.75 g, 10.0 mmol) as a white solid. MS (ESI) m/z 276.1 [M+1]$^+$.

B. (1-(Tetrahydro-2H-pyran-2-yl)-1H-imidazo[4,5-b]pyridin-6-yl)methanol. Ethyl 1-(tetrahydro-2H-pyran-2-yl)-1H-imidazo[4,5-b]pyridine-6-carboxylate (2.75 g, 10.0 mmol) was suspended in anhydrous tetrahydrofuran (75 mL) and cooled −78° C. A solution of lithium aluminum hydride (2.0M, 18.8 mL, 30.0 mmol) was added and allowed to slowly warm to room temperature with stirring overnight. The reaction was quenched with methanol and the volatiles removed under reduced pressure. The crude product was taken on to the next step without further purification or characterization. MS (ESI) m/z 234.1 [M+1]$^+$.

C. 1-(Tetrahydro-2H-pyran-2-yl)-1H-imidazo[4,5-b]pyridine-6-carbaldehyde. (1-(Tetrahydro-2H-pyran-2-yl)-1H-imidazo[4,5-b]pyridin-6-yl)methanol (crude from previous reaction) was dissolved in anhydrous methylene chloride (50 mL). Pyridiniumchlorochromate (6.46 g, 30.0 mmol) was added and the solution stirred at room temperature overnight. The reaction mixture was filtered through silica gel and washed with ethyl acetate. The filtrate was poured into water (150 mL) and extracted with EtOAc (4×250 mL). Combined organic layers were dried over sodium sulfate and concen- D. 2-(1H-Imidazo[4,5-b]pyridin-6-yl)-8-oxo-9-(2-(trifluoromethyl)phenyl)-8,9-dihydro-7H-purine-6-carboxamide. (Z)-1-(2-Amino-1,2-dicyanovinyl)-3-(2-(trifluoromethyl)phenyl)urea (See example 50.A) (580 mg, 1.99 mmol), 1-(tetrahydro-2H-pyran-2-yl)-1H-imidazo[4,5-b]pyridine-6-carbaldehyde (690 mg, 2.98 mmol), triethylamine (0.50 mL, 3.0 mmol) and methanol (10 mL) were reacted according to General Procedure B. The solution was allowed to stir at room temperature overnight and precipitate collected by filtration. 8-Oxo-2-(1-(tetrahydro-2H-pyran-2-yl)-1H-imidazo[4,5-b]pyridin-6-yl)-9-(2-(trifluoromethyl)phenyl)-8,9-dihydro-7H-purine-6-carboxamide (120 mg, 0.23 mmol) was dissolved in dioxane (2 mL), a 4.0 M HCl/dioxane solution (4.0 mL) and water (0.3 mL) were added and the resulting solution was stirred at room temp overnight. The reaction was neutralized with saturated NaHCO$_3$, extracted with EtOAc (3×50 mL), and dried over sodium sulfate. The crude product was purified using reverse-phase semi-preparatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×75 mL). Combined organic layers were dried over sodium sulfate and concentrated under reduced pressure. The resulting solid was washed with diethyl ether and dried in a vacuum oven at 60° C. overnight to afford the title compound (40 mg, 0.091 mmol, 40%) as a white solid. $^1$H NMR (400 MHz, DMSO-d$_6$) δ 11.95 (s, 1H), 9.41 (s, 1H), 8.86 (s, 1H), 8.72 (s, 1H), 8.73 (s, 1H), 8.59 (s, 1H), 8.05 (m, 2H), 7.98 (m, 1H), 7.86 (m, 2H); MS (ESI) m/z 441.0 [M+1]$^+$; mp 320° C.

5.1.131 Example 131

Synthesis of 8-OXO-9-PHENYL-2-(PYRIDIN-2-YL)-8,9-DIHYDRO-7H-PURINE-6-CARBOXAMIDE A. (Z)-1-(2-Amino-1,2-dicyanovinyl)-3-phenylurea. Phenyl isocyanate (0.700 g, 5.88 mmol) and 2,3-diaminomaleonitrile (0.600 g, 5.55 mmol) were reacted in acetonitrile according to General Procedure A. The material was triturated from acetonitrile and diethyl ether. The resultant solid was filtered and dried to give the title compound as an orange solid (0.95 g, 4.2 mmol, 76% yield) which was used directly in the next step.

B. 8-Oxo-9-phenyl-2-(pyridin-2-yl)-8,9-dihydro-7H-purine-6-carboxamide. (Z)-1-(2-Amino-1,2-dicyanovinyl)-3-phenylurea (0.400 g, 1.76 mmol) and 2-pyridine carboxaldehyde (0.414 g, 3.87 mmol) were reacted according to General Procedure B. Product was purified using reverse-phase semi-preparatory HPLC (10-60% acetonitrile+0.1% TFA in H$_2$O+0.1% TFA, over 30 min). Fractions containing the desired material were neutralized with aqueous sodium carbonate solution and then concentrated to a smaller volume. The resulting precipitate was filtered and washed with water. The resulting solid was dried under high vacuum at 60° C. to afford the title compound as a white solid (0.129 g, 0.39 mmol, 22% yield). $^1$H NMR (400 MHz, DMSO-d$_6$) δ 11.87 (s, 1H), 8.65 (d, J=4.0, 1H), 8.56 (bs, 2H), 7.98 (bs, 1H), 7.94-7.88 (m, 1H), 7.71 (s, 1H), 7.69 (s, 1H), 7.59 (t, J=7.6, 2H), 7.52-7.41 (m, 2H); MS (ESI) m/z 333.2 [M+1]$^+$; mp 347-349° C.

5.1.132 Example 132

Synthesis of 9-(2-METHOXYPHENYL)-2-(2-(METHYLTHIO)-1H-BENZO[D]IMIDAZOL-5-YL)-8-OXO-8,9-DIHYDRO-7H-PURINE-6-CARBOXAMIDE A. (2-(Methylthio)-1H-benzo[d]imidazol-5-yl)methanol. Ethyl 2-(methylthio)-1H-benzo[d]imidazole-5-carboxylate (4.72 g, 20.0 mmol) was suspended in anhydrous tetrahydrofuran (100 mL) and cooled −78° C. A solution of lithium aluminum hydride (2.0 M, 37.5 mL, 60.0 mmol) was added and allowed to slowly warm to room temperature with stirring overnight. The reaction was quenched with methanol and the crude product adsorbed onto silica gel. Flash chromatography (20% MeOH in EtOAc) afforded the title compound (4.36 g, 22.5 mmol, 95%) as a white solid. MS (ESI) m/z 195.1 [M+1]$^+$.

B. 2-Methylthiobenzimidazole-5-carbaldehyde. (2-(Methylthio)-1H-benzo[d]imidazol-5-yl)methanol (4.36 g, 22.5 mmol) was dissolved in anhydrous methylene chloride (150 mL). Pyridiniumchlorochromate (9.68 g, 44.9 mmol) was added and the solution was stirred at room temperature overnight. The reaction mixture was filtered through silica gel and washed with ethyl acetate. Water (150 mL) was added and the solution extracted with EtOAc (4×250 mL). Pooled organic layers were dried over sodium sulfate and concentrated under reduced pressure to afford the title compound (2.10 g, 10.9 mmol, 48%) as a white solid. MS (ESI) m/z 193.1 [M+1]$^+$.

C. 9-(2-Methoxyphenyl)-2-(2-(methylthio)-1H-benzo[d]imidazol-5-yl)-8-oxo-8,9-dihydro-7H-purine-6-carboxamide. (Z)-1-(2-Amino-1,2-dicyanovinyl)-3-(2-methoxyphenyl)urea (See Example 2.A) (1.87 g, 7.29 mmol), 2-methylthiobenzimidazole-5-carbaldehyde (2.10 g, 10.93 mmol), triethylamine (1.52 mL, 10.9 mmol) and methanol (40 mL) were reacted according to General Procedure B. The solution was allowed to stir at room temperature overnight. The resultant heterogeneous mixture was filtered and 120 mg of crude product purified using reverse-phase semi-preparatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×50 mL). Organic layers were pooled, dried over sodium sulfate and concentrated under reduced pressure. The resulting solid was washed with diethyl ether and dried in a vacuum oven at 60° C. overnight to afford the title compound (70 mg, 0.16 mmol, 58%) as a white solid. $^1$H NMR (400 MHz, DMSO-d$_6$) δ 11.65 (s, 1H), 8.52 (s, 1H), 8.25 (m, 1H), 7.96 (s, 1H), 7.56 (m, 1H), 7.51 (dd, J=10.0, 2.0, 1H), 7.44 (m, 1H), 7.31 (d, J=11.2, 1H), 7.17 (m, 1H), 3.75 (s, 3H), 2.69 (s, 3H); MS (ESI) m/z 448.0 [M+1]$^+$; mp 244-245° C.

5.1.133 Example 133

Synthesis of 2-(1H-INDOL-5-YL)-9-(2-ISOPROPYLPHENYL)-8-OXO-8,9-DIHYDRO-7H-PURINE-6-CARBOXAMIDE A. 2-(1H-Indol-5-yl)-9-(2-isopropylphenyl)-8-oxo-8,9-dihydro-7H-purine-6-carboxamide. (Z)-1-(2-Amino-1,2-dicyanovinyl)-3-(2-isopropylphenyl)urea (See example 56.A) (400 mg, 1.48 mmol), 1H-indole-5-carbaldehyde (431 mg, 2.97 mmol), triethylamine (0.50 mL, 3.70 mmol) and methanol (10 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×50 mL). Organics were dried over sodium sulfate and concentrated under reduced pressure. The resulting solid was washed with diethyl ether and dried in a vacuum oven at 60° C. overnight to afford the title compound (75 mg, 0.18 mmol, 12%) as a white solid. $^1$H NMR (400 MHz, DMSO-d$_6$) δ 11.68 (s, 1H), 11.20 (s, 1H), 8.60 (s, 1H), 8.48 (m, 1H), 8.13 (dd, J=10.0, 2.0, 1H), 7.98 (m, 1H), 7.59 (m, 2H), 7.41 (d, J=3.6, 1H), 7.35 (m, 3H), 6.48 (m, 1H), 2.75 (hept, J=7.2, 1H), 1.13 (d, J=6.4, 3H), 1.11 (d, J=6.4, 3H); MS (ESI) m/z 413.1 [M+1]$^+$; mp 310° C. dec.

5.1.134 Example 134

Synthesis of 9-(CYCLOHEXYLMETHYL)-2-(3-HYDROXYPHENYL)-8-OXO-8,9-DIHYDRO-7H-PURINE-6-CARBOXAMIDE A. (Isocyanatomethyl)cyclohexane. Cyclohexylacetic acid (1.5 g, 10.54 mmol) and N-methylmorpholine (1.06 g, 10.54 mmol) were dissolved in tetrahydrofuran (30 mL) and cooled to −10° C. Ethyl chloroformate (1.25 g, 11.60 mmol) was added dropwise and stirred at −10° C. Sodium azide (1.02 g, 15.85 mmol) was then added and allowed to stir for an additional 30 min. The solution was then diluted with dichloromethane, partitioned with water, dried over magnesium sulfate, filtered and solvent removed under reduced pressure. The resulting oil was purified using Biotage chromatography (0-20% EtOAc in hexanes) to afford the title compound (0.450 g, 26%).

B. (Z)-1-(2-Amino-1,2-dicyanovinyl)-3-(cyclohexylmethyl)urea. 2,3-Diaminomaleonitrile (0.119 g, 1.10 mmol) and (isocyanatomethyl)cyclohexane (0.140 g, 1.00 mmol) in tetrahydrofuran (2 mL) were reacted according to General Procedure A. Dichloromethane and hexanes were added to the solution and the resultant precipitate was filtered and dried to afford the title compound (0.200 g, 47%). MS (ESI) m/z 248.2 [M+1]$^+$.

C. 9-(Cyclohexylmethyl)-2-(3-hydroxyphenyl)-8-oxo-8,9-dihydro-7H-purine-6-carboxamide. (Z)-1-(2-Amino-1,2-dicyanovinyl)-3-(cyclohexylmethyl)urea (0.200 g, 0.809 mmol), 3-hydroxybenzaldehyde (0.197 g, 1.62 mmol) and triethylamine (0.4 ml) were reacted according to General Procedure B and purified using reverse-phase preparative HPLC (5-60% acetonitrile+0.1% TFA in H$_2$O+0.1% TFA, over 30 min) to afford the title compound (0.011 g, 3.7%). $^1$H NMR (400 MHz, DMSO-d$_6$) δ 11.53 (s, 1H), 9.53 (s, 1H), 8.33 (s, 1H), 8.00 (d, J=7.99, 1H), 7.93 (s, 1H), 7.89 (s, 1H), 7.28 (t, J=7.59, 1H), 6.87 (d, J=7.99, 1H), 3.74 (d, J=7.19, 2H), 1.90 (bs, 1H), 1.64 (m, 5H), 1.16 (m, 3H), 1.02 (m, 2H); MS (ESI) m/z 368.2 [M+1]$^+$; mp 368-370° C.

5.1.135 Example 135

Synthesis of 9-(2,3-DIHYDRO-1H-INDEN-1-YL)-2-(3-HYDROXYPHENYL)-8-OXO-8,9-DIHYDRO-7H-PURINE-6-CARBOXAMIDE A. Methyl 2-chloro-6-(2,3-dihydro-1H-inden-1-ylamino)-5-nitropyrimidine-4-carboxylate. Methyl 2,6-dichloro-5-nitroprimidine (1.3 g, 5.23 mmol), diisopropylethylamine (1.68 g, 13.07 mmol) and 1-aminoindane (0.734 g, 5.49 mmol) were reacted according to General Procedure C and purified using Biotage chromatography (0 to 60% EtOAc in hexanes) to afford the title compound (0.595 g, 33%). MS (ESI) m/z 349.3 [M+1]$^+$.

B. Methyl 5-amino-2-chloro-6-(2,3-dihydro-1H-inden-1-ylamino)pyrimidine-4-carboxylate. 2-Chloro-6-(2,3-dihydro-1H-inden-1-ylamino)-5-nitropyrimidine-4-carboxylate (0.595 g, 1.71 mmol), iron (s) (0.477 g, 8.55 mmol) and acetic acid (20 mL) were reacted according to General Procedure D2 to afford the title compound (0.205 g, 38%). MS (ESI) m/z 319.3 [M+1]$^+$.

C. Methyl 5-amino-6-(2,3-dihydro-1H-inden-1-ylamino)-2-(3-(triisopropylsilyloxy)phenyl)pyrimidine-4-carboxylate. Methyl 5-amino-2-chloro-6-(2,3-dihydro-1H-inden-1-ylamino)pyrimidine-4-carboxylate (0.205 g, 0.604 mmol) triisopropyl(3-(trimethylstannyl)phenoxy)silane (0.400 g, 0.966 mmol) and bisdichloro(triphenylphosphine)palladium (0) (0.135 g, 0.193 mmol) were combined in dimethyl formamide (4 mL) and heated to 100° C. The reaction was monitored via thin layer chromatography. Once starting materials were consumed, the solution was condensed under reduced pressure and purified using Biotage chromatography (0 to 40% EtOAc in hexanes) to afford the title compound (0.192 g, 56%). MS (ESI) m/z 533.2 [M+1]$^+$.

D. Methyl 9-(2,3-dihydro-1H-inden-1-yl)-8-oxo-2-(3-(triisopropylsilyloxy)phenyl)-8,9-dihydro-7H-purine-6-carboxylate. Methyl 5-amino-6-(2,3-dihydro-1H-inden-1-ylamino)-2-(3-(triisopropylsilyloxy)phenyl)pyrimidine-4-carboxylate (0.192 g, 0.360 mmol) and 1,1'-1,1'-carbonyldiimidazole (0.467 g, 2.88 mmol) in dichloromethane (15 mL) were reacted according to General Procedure F and purified using biotage chromatography (0 to 45% EtOAc in hexanes) to afford the title compound (0.171 g, 85%). $^1$H NMR (400 MHz, DMSO-d$_6$) δ 11.85 (s, 1H), 7.76 (d, J=7.99, 1H), 7.64 (s, 1H), 7.36 (d, J=7.59, 1H), 7.32 (t, J=7.99, 1H), 7.24 (m, 1H), 7.12 (s, 1H), 7.11 (s, 1H), 6.92 (dd, J=7.99, 2.39, 1H), 6.05 (t, J=7.19, 1H), 3.94 (s, 3H), 3.33 (s, 9H), 3.06 (m, 1H), 2.67 (m, 1H), 1.23 (m, 3H), 1.08 (m, 18H).

E. 9-(2,3-Dihydro-1H-inden-1-yl)-2-(3-hydroxyphenyl)-8-oxo-8,9-dihydro-7H-purine-6-carboxamide. Methyl 9-(2,3-dihydro-1H-inden-1-yl)-8-oxo-2-(3-(triisopropylsilyloxy)phenyl)-8,9-dihydro-7H-purine-6-carboxylate (0.180 g, 3.97 mmol) and ammonia gas were reacted in methanol (10 mL) according to General Procedure G. After 16 h, the solution was condensed under reduced pressure and the resultant crude product diluted with tetrahydrofuran (10 mL) and 1.0 M tetrabutylammonium fluoride in tetrahydrofuran (0.76 mL) was added. After two h, the resulting precipitate was filtered and washed with tetrahydrofuran followed by hexanes. Purification using reverse-phase preparative HPLC (10 to 100% acetonitrile+0.1% TFA in H$_2$O+0.1% TFA, over 30 min) gave the title compound (0.052 g, 3%). $^1$H NMR (400 MHz, DMSO-d$_6$) δ 11.60 (s, 1H), 9.45 (s, 1H), 8.31 (s, 1H), 7.92 (s, 1H), 7.98 (d, J=7.99, 1H), 7.71 (s, 1H), 7.38 (d, J=7.59, 1H), 7.23 (m, 2H), 7.10 (s, 2H), 6.83 (dd, J=7.99, 1.99, 1H), 6.06 (t, J=6.39, 1H), 3.40 (m, 1H), 3.05 (m, 1H), 2.61 (m, 2H); MS (ESI) m/z 388.0. [M+1]$^+$; mp 341-343° C.

5.1.136 Example 136

Synthesis of 2-(3-HYDROXYPHENYL)-9-ISOBUTYL-8-OXO-8,9-DIHYDRO-7H-PURINE-6-CARBOXAMIDE A. Methyl 2-chloro-6-(isobutylamino)-5-nitropyrimidine-4-carboxylate. Methyl 2,6-dichloro-5-nitroprimidine (1.3 g, 5.23 mmol), diisopropylethylamine (2.3 g, 17.85 mmol) and isobutylamine (0.457 g, 6.24 mmol) were reacted according to General Procedure C and purified using Biotage chromatography (0 to 40% EtOAc in hexanes) to afford the title compound (1.10 g, 64%). MS (ESI) m/z 289.2 [M+1]$^+$.

B. Methyl 5-amino-2-chloro-6-(isobutylamino)pyrimidine-4-carboxylate. Methyl 2-chloro-6-(isobutylamino)-5-nitropyrimidine-4-carboxylate (1.10 g, 3.80 mmol), iron (s) (1.06 g, 19.0 mmol) and acetic acid (25 mL) were reacted according to General Procedure D2 to afford the title compound (0.726 g, 74%). MS (ESI) m/z 259.1 [M+1]$^+$, 260.1 [M+2]$^+$.

C. Methyl 5-amino-6-(2,3-dihydro-1H-inden-1-ylamino)-2-(3-(triisopropylsilyloxy)phenyl)pyrimidine-4-carboxylate. Methyl 5-amino-2-chloro-6-(isobutylamino)pyrimidine-4-carboxylate. (0.285 g, 1.11 mmol) triisopropyl(3-(trimethylstannyl)phenoxy)silane (0.691 g, 1.67 mmol) and bisdichloro(triphenylphosphine) palladium (0) (0.311 g, 0.444 mmol) were combined in dimethyl formamide (4 mL) and heated to 100° C. The reaction was monitored via thin layer chromatography. Once starting materials were consumed, the solution was condensed under reduced pressure and purified using Biotage chromatography (0 to 40% EtOAc in hexanes) to afford the title compound (0.300 g, 58%). MS (ESI) m/z 473.6 [M+1]$^+$.

D. Methyl 9-isobutyl-8-oxo-2-(3-(triisopropylsilyloxy)phenyl)-8,9-dihydro-7H-purine-6-carboxylate. Methyl 5-amino-6-(2,3-dihydro-1H-inden-1-ylamino)-2-(3-(triisopropylsilyloxy)phenyl)pyrimidine-4-carboxylate (0.300 g, 0.635 mmol) and 1,1'-1,1'-carbonyldiimidazole (0.411 g, 2.54 mmol) in dichloromethane (25 mL) were reacted according to General Procedure F. The solution was condensed under reduced pressure and partitioned between water and ethyl acetate (3×). Organic fractions were combined and dried over magnesium sulfate, filtered and solvent removed under reduced pressure. The crude solid was diluted with methanol (15 mL) and sonicated. The resulting precipitate was filtered to afford the title compound (0.185 g, 85%). MS (ESI) m/z 268.2 [M+1]$^+$.

E. 2-(3-Hydroxyphenyl)-9-isobutyl-8-oxo-8,9-dihydro-7H-purine-6-carboxamide. Methyl 9-isobutyl-8-oxo-2-(3-(triisopropylsilyloxy)phenyl)-8,9-dihydro-7H-purine-6-carboxylate (0.185 g, 3.97 mmol) was dissolved in methanol (10 mL) and was reacted with ammonia gas according to General Procedure G. After 16 h, the solution was condensed under reduced pressure and the resultant crude product diluted with tetrahydrofuran (10 mL) and 1.0M tetrabutylammonium fluoride in tetrahydrofuran (0.94 mL) was added. After two h, the resultant precipitate was filtered and washed with tetrahydrofuran followed by hexanes. The precipitate was triturated with methanol and dichloromethane to afford the title compound (0.061 g, 50%). $^1$H NMR (400 MHz, DMSO-d$_6$) δ 11.54 (s, 1H), 9.52 (s, 1H), 8.33 (s, 1H), 8.0 (d, J=7.59, 1H), 7.93 (s, 1H), 7.89 (s, 1H), 7.28 (t, J=7.59, 1H), 6.86 (dd, J=7.99, 2.39, 1H). 3.72 (d, J=7.59, 2H), 2.26 (m, 1H), 0.923 (d, J=6.39, 6H); MS (ESI) m/z 328.1. [M+1]$^+$; mp 374-376° C.

5.1.137 Example 137

Synthesis of 9-(TRANS-4-HYDROXYCYCLOHEXYL)-2-(3-HYDROXYPHENYL)-8-OXO-8,9-DIHYDRO-7H-PURINE-6-CARBOXAMIDE A. Methyl 2-chloro-6-(trans-4-methoxycyclohexylamino)-5-nitropyrimidine-4-carboxylate. Methyl 2,6-dichloro-5-nitroprimidine (0.934 g, 3.71 mmol), diisopropylethylamine (1.43 g, 11.13 mmol) and trans-4-methoxycyclohexanamine (0.613 g, 3.71 mmol) were reacted according to General Procedure C and purified using Biotage chromatography (0 to 60% EtOAc in hexanes) to afford the title compound (0.880 g, 69%). MS (ESI) m/z 345.3[M+1]$^+$, 346.3 [M+2]$^+$.

B. Methyl 5-amino-2-chloro-6-(trans-4-methoxycyclohexylamino)pyrimidine-4-carboxylate. Methyl 2-chloro-6-(trans-4-methoxycyclohexylamino)-5-nitropyrimidine-4-carboxylate (0.880 g, 2.55 mmol), iron (s) (0.712 g, 12.75 mmol) and acetic acid (20 mL) were reacted according to General Procedure D2 to afford the title compound (0.719 g, 90%). MS (ESI) m/z 315.3 [M+1]$^+$, 316.3 [M+2]$^+$.

C. Methyl 5-amino-6-(trans-4-methoxycyclohexylamino)-2-(3-(triisopropylsilyloxy)phenyl)pyrimidine-4-carboxylate. Methyl 5-amino-2-chloro-6-(trans-4-methoxycyclohexylamino)pyrimidine-4-carboxylate (0.300 g, 0.955 mmol) triisopropyl(3-(trimethylstannyl)phenoxy)silane (0.591 g, 1.43 mmol) and bisdichloro(triphenylphosphine) palladium (0) (0.200 g, 0.286 mmol) were combined in dimethyl formamide (6 mL) and heated to 100° C. The reaction was monitored via thin layer chromatography. Once starting materials were consumed, the solution was condensed under reduced pressure and purified using Biotage chromatography (0 to 60% EtOAc in hexanes) to afford the title compound (0.261 g, 56%). MS (ESI) m/z 529.6 [M+1]$^+$.

D. Methyl 9-((trans-4-methoxycyclohexyl)-8-oxo-2-(3-(triisopropylsilyloxy)phenyl)-8,9-dihydro-7H-purine-6-carboxylate. Methyl 5-amino-6-(trans-4-methoxycyclohexylamino)-2-(3-(triisopropylsilyloxy)phenyl)pyrimidine-4-carboxylate (0.261 g, 0.494 mmol) and 1,1'-1,1'-carbonyldiimidazole (0.640 g, 3.95 mmol) in dichloromethane (20 mL) were reacted according to General Procedure F and purified using biotage chromatography (0 to 65% EtOAc in hexanes) to afford the title compound (0.206 g, 88%). MS (ESI) m/z 555.0 [M+1]$^+$.

E. 9-(trans-4-Methoxycyclohexyl)-2-(3-hydroxyphenyl)-8-oxo-8,9-dihydro-7H-purine-6-carboxamide. Methyl 9-(trans-4-methoxycyclohexyl)-8-oxo-2-(3-(triisopropylsilyloxy)phenyl)-8,9-dihydro-7H-purine-6-carboxylate (0.205 g, 370 mmol) was dissolved in methanol (15 mL) reacted with ammonia gas according to General Procedure G. After 16 h, the solution was condensed under reduced pressure and the resultant crude product diluted with tetrahydrofuran (15 mL) and 1.0M tetrabutylammonium fluoride in tetrahydrofuran (0.92 mL) was added. After two h, the resulting precipitate was filtered and washed with tetrahydrofuran followed by hexanes. The product was purified using reverse-phase preparative HPLC (20 to 100% acetonitrile+0.1% TFA in H$_2$O+ 0.1% TFA, over 30 min) to afford the title compound (0.093 g, 66%). $^1$H NMR (400 MHz, DMSO-d$_6$) δ 11.51 (s, 1H), 9.55 (s, 1H), 8.33 (s, 1H), 8.01 (d, J=7.59, 1H), 7.91 (s, 1H), 7.89 (s, 1H), 7.29 (t, J=7.99, 1H), 6.7 (dd, J=7.59, 1.59, 1H), 4.27 (m, 1H), 3.34 (s, 3H), 3.31 (s, 1H), 2.18 (d, J=10.79, 2H), 1.82 (d, J=11.19, 2H), 1.31 (q, J=12.39, 2H); MS (ESI) m/z 384.4 [M+1]$^+$; mp 355-357° C.

5.1.138 Example 138

Synthesis of 9-(CIS-4-HYDROXYCYCLOHEXYL)-2-(3-HYDROXYPHENYL)-8-OXO-8,9-DIHYDRO-7H-PURINE-6-CARBOXAMIDE A. Methyl 2-chloro-6-(cis-4-methoxycyclohexylamino)-5-nitropyrimidine-4-carboxylate. Methyl 2,6-dichloro-5-nitroprimidine (1.14 g, 4.54 mmol), diisopropylethylamine (1.75 g, 13.62 mmol) and cis-4-methoxycyclohexanamine (0.750 g, 4.54 mmol) were reacted according to General Procedure C and purified using Biotage chromatography (0 to 60% ethyl acetate in hexanes) to afford the title compound (0.712 g, 46%). MS (ESI) m/z 345.3 [M+1]⁺, 346.3 [M+2]⁺.

B. Methyl 5-amino-2-chloro-6-(cis-4-methoxycyclohexylamino)pyrimidine-4-carboxylate. Methyl 2-chloro-6-(cis-4-methoxycyclohexylamino)-5-nitropyrimidine-4-carboxylate (0.712 g, 2.06 mmol), iron (s) (0.577 g, 10.34 mmol) and acetic acid (25 mL) were reacted according to General Procedure D2 to afford the title compound (0.567 g, 87%). MS (ESI) m/z 315.3 [M+1]⁺, 316.3 [M+2]⁺.

C. Methyl 5-amino-6-(cis-4-methoxycyclohexylamino)-2-(3-(triisopropylsilyloxy)phenyl)pyrimidine-4-carboxylate. Methyl 5-amino-2-chloro-6-(cis-4-methoxycyclohexylamino)pyrimidine-4-carboxylate (0.300 g, 0.955 mmol) triisopropyl(3-(trimethylstannyl)phenoxy)silane (0.591 g, 1.43 mmol) and bisdichloro(triphenylphosphine)palladium (0) (0.200 g, 0.286 mmol) were combined in dimethyl formamide (6 mL) and heated to 100° C. The reaction was monitored via thin layer chromatography. Once the starting materials were consumed, the solution was condensed under reduced pressure and purified using Biotage chromatography (0 to 60% EtOAc in hexanes) to afford the title compound (0.223 g, 44%). MS (ESI) m/z 529.6 [M+1]⁺.

D. Methyl 9-(cis-4-methoxycyclohexyl)-8-oxo-2-(3-(triisopropylsilyloxy)phenyl)-8,9-dihydro-7H-purine-6-carboxylate. Methyl 5-amino-6-(cis-4-methoxycyclohexylamino)-2-(3-(triisopropylsilyloxy)phenyl)pyrimidine-4-carboxylate (0.223 g, 0.422 mmol) and 1,1'-1,1'-carbonyldiimidazole (0.547 g, 3.38 mmol) in dichloromethane (20 mL) were reacted according to General Procedure F and purified using biotage chromatography (0 to 65% EtOAc in hexanes) to afford the title compound (0.210 g, 90%). MS (ESI) m/z 555.5 [M+1]⁺.

E. 9-(cis-4-Methoxycyclohexyl)-2-(3-hydroxyphenyl)-8-oxo-8,9-dihydro-7H-purine-6-carboxamide. Methyl 9-(cis-4-methoxycyclohexyl)-8-oxo-2-(3-(triisopropylsilyloxy)phenyl)-8,9-dihydro-7H-purine-6-carboxylate (0.210 g, 377 mmol) was dissolved in methanol (15 mL) reacted with ammonia gas according to General Procedure G. After 16 h, the solution was condensed under reduced pressure and the resultant crude product diluted with tetrahydrofuran (15 mL) and 1.0M tetrabutylammonium fluoride in tetrahydrofuran (0.92 mL) was added. After two h, the resultant precipitate was filtered and washed with tetrahydrofuran followed by hexanes. The product was purified using reverse-phase preparative HPLC (20 to 100% acetonitrile+0.1% TFA in H₂O+0.1% TFA, over 30 min) to afford the title compound (0.093 g, 64%). ¹H NMR (400 MHz, DMSO-d₆) δ 11.48 (s, 1H), 9.47 (s, 1H), 8.32 (s, 1H), 8.03 (d, J=7.59, 1H), 7.92 (s, 2H), 7.28 (t, J=7.59, 1H), 6.86 (dd, J=7.99, 2.39, 1H), 4.30 (m, 1H), 3.49 (s, 1H), 3.34 (s, 3H), 2.71 (m, 2H), 2.06 (s, 1H), 2.03 (s, 1H), 1.53 (m, 4H); MS (ESI) m/z 384.4. [M+1]⁺; mp 345-347° C.

5.1.139 Example 139

Synthesis of 2-(3-HYDROXYPHENYL)-8-OXO-9-(5,6,7,8-TETRAHYDRONAPHTHALEN-1-YL)-8,9-DIHYDRO-7H-PURINE-6-CARBOXAMIDE A. (Z)-1-(2-Amino-1,2-dicyanovinyl)-3-(5,6,7,8-tetrahydronaphthalen-1-yl)urea. 5-Isocyanato-1,2,3,4-tetrahydronaphthalene (0.34 mL, 2.16 mmol) and 2,3-diaminomaleonitrile (0.234 g, 2.16 mmol) were stirred together in acetonitrile (10 mL). The title compound precipitated from solution and was collected by filtration. MS (ESI) m/z 321.4 [M+1]⁺.

B. 2-(3-Hydroxyphenyl)-8-oxo-9-(5,6,7,8-tetrahydronaphthalen-1-yl)-8,9-dihydro-7H-purine-6-carboxamide. (Z)-1-(2-Amino-1,2-dicyanovinyl)-3-(5,6,7,8-tetrahydronaphthalen-1-yl)urea (0.59 g, 2.16 mmol) was mixed together with 3-hydroxybenzaldehyde (0.55 g, 5.4 mmol) in methanol/triethylamine (9:1 v/v, 15 mL). After 24 h, the mixture was concentrated and then subjected to preparatory HPLC (30-80% acetonitrile+0.1% TFA in H₂O+0.1% TFA, over 30 min). The desired fractions were combined and concentrated to afford the title compound. The resulting material was dried under vacuum overnight to afford the title compound as an off white solid, 97.5% pure, (15 mg, 2%). ¹H NMR (400 MHz, DMSO-d₆) δ 11.77 (s, 1H), 9.50 (s, 1H), 8.39 (s, 1H), 7.98 (s, 1H), 7.89 (d, J=4.8, 1H), 7.67 (t, J=2.0, 2H), 7.26 (m, 4H), 6.81 (dd, J=8.0, 2.0, 1H), 2.86 (t, J=5.6, 2H), 2.45 (m, 2H), 1.75 (m, 2H), 1.67 (m, 2H); MS (ESI) m/z 402.3 [M+1]⁺; mp>250° C.

5.1.140 Example 140

Synthesis of 2-(4-(1H-1,2,4-TRIAZOL-3-YL)PHENYL)-9-CYCLOHEXYL-8-OXO-8,9-DIHYDRO-7H-PURINE-6-CARBOXAMIDE A. 2-(4-(1H-1,2,4-Triazol-3-yl)phenyl)-9-cyclohexyl-8-oxo-8,9-dihydro-7H-purine-6-carboxamide. (Z)-1-(2-Amino-1,2-dicyanovinyl)-3-cyclohexylurea (See Example 26.A) (200 mg, 0.86 mmol), 4-(1H-1,2,4-triazol-3-yl)benzaldehyde (See 108.B) (300 mg, 1.72 mmol), triethylamine (0.18 mL, 1.29 mmol) and methanol (10 mL) were reacted according to General Procedure B. The solution was allowed to stir at room temperature overnight. The resultant heterogeneous mixture was filtered and purified using reverse-phase semi-preparatory HPLC (20-100% acetonitrile+0.1% TFA in H₂O+0.1% TFA, over 30 min). The volatiles were removed under reduced pressure, treated with saturated NaHCO₃ and extracted with ethyl acetate (3×50 mL). Pooled organic fractions were dried over sodium sulfate and concentrated under reduced pressure. The resulting solid was washed with diethyl ether and dried in a vacuum oven at 60° C. overnight to afford the title compound (75 mg, 0.18 mmol, 12%) as a white solid. ¹H NMR (400 MHz, DMSO-d₆) δ 11.56 (s, 1H), 8.66 (m, 2H), 8.49 (m, 1H), 8.14 (d, J=8.0, 1H), 7.95 (m, 1H), 4.30 (m, 1H), 2.67 (m, 1H), 2.37 (m, 2H), 2.32 (m, 1H), 1.88 (m, 2H), 1.78 (m, 2H), 1.42 (m, 2H); MS (ESI) m/z 404.1 [M+1]⁺; mp 375° C. dec.

5.1.141 Example 141

Synthesis of 2-(3-HYDROXYPHENYL)-9-(1H-INDOL-4-YL)-8-OXO-8,9-DIHYDRO-7H-PURINE-6-CARBOXAMIDE A. 1-Benzenesulfonyl-1H-indol-4-ylamine. 4-Nitroindole (1.07 g, 6.6 mmol) was dissolved in acetonitrile (12 mL) and diisopropylethylamine (1.2 mL, 7.92 mmol) was added. The solution was heated to 80° C. and the benzenesulfonyl chloride (0.93 mL, 7.26 mmol) was then added. The mixture was stirred at 80° C. for 1.5 h. The reaction was cooled, diluted with water (20 mL), and filtered. The crude 1-benzenesulfonyl-4-nitro-1H-indole was washed with water (10 mL) and then with methanol (5 mL). Crude 1-benzenesulfonyl-4-nitro-1H-indole was then taken up in methanol (50 mL). To this suspension was added 10% Pd/C (0.5 g) and ammonium formate (1.0 g, 15.6 mmol). The mixture was stirred at reflux for 1.5 h, after which the reaction was complete as indicated by LCMS (MS (ESI) m/z 273.1[M+1]⁺). The reaction was concentrated and the crude residue was subjected to silica gel chromatography (90% hexanes in EtOAc). Concentration of the desired fractions afforded the title compound (1.42 g, 5.22 mmol, 79%).

B. Methyl 5-amino-2-chloro-6-(1-(phenylsulfonyl)-1H-indol-4-ylamino)pyrimidine-4-carboxylate. To a solution of methyl-2,4-dichloro-5-nitro-pyrimidine-6-carboxylate (2.0 g, 7.9 mmol) in tetrahydrofuran (20 mL) and diisopropylamine (2.3 mL, 13.05 mmol) was added amine (1.42 g, 5.22 mmol) in TETRAHYDROFURAN (5 mL) at −78° C. After warming to rt, only desired adduct was seen (MS (ESI) m/z 487.9[M+1]$^+$). The reaction was diluted with EtOAc (100 mL) and washed with 5% HCl (aq, 100 mL). The EtOAc layer was separated, dried ($Na_2SO_4$), filtered, and concentrated. The crude 6-(1-benzenesulfonyl-1H-indol-4-ylamino)-2-chloro-5-nitro-pyrimidine-4-carboxylic acid methyl ester was subjected to silica gel chromatography (9:1 Hex in EtOAc) to afford 1.32 g (2.71 mmol, 52%) after concentration of the desired fractions. 6-(1-Benzenesulfonyl-1H-indol-4-ylamino)-2-chloro-5-nitro-pyrimidine-4-carboxylic acid methyl ester (1.32 g, 2.71 mmol) was then dissolved in AcOH (15 mL). To this solution was added Fe (s, 1.4 g). The mixture was stirred at 60° C. for 1H, after which LCMS showed the desired reduced product (MS (ESI) m/z 458.1 [M+1]$^+$). The reaction was filtered and then concentrated. The crude residue was subjected to silica gel chromatography (4:1 Hex in EtOAc). Concentration of the desired fractions afforded the title compound (0.85 g, 1.86 mmol, 69%).

C. Methyl 5-amino-2-(3-hydroxyphenyl)-6-(1-(phenylsulfonyl)-1H-indol-4-ylamino)pyrimidine-4-carboxylate. Methyl 5-amino-2-chloro-6-(1-(phenylsulfonyl)-1H-indol-4-ylamino)pyrimidine-4-carboxylate (0.31 g, 0.68 mmol), 3-hydroxyphenyboronic acid (0.14 g, 1.0 mmol), palladium (II) acetate (30 mg, 0.14 mmol), dicyclohexyl(2',6'-dimethoxybiphenyl-2-yl)phosphine (60 mg, 0.14 mmol), and potassium phosphate (0.36 g, 2.1 mmol) were reacted together according to General Procedure E. The reaction was diluted with EtOAc (40 mL) and washed with 5% HCl (aq, 40 mL). The organic layer was separated, dried over sodium sulfate, filtered, and concentrated. The crude residue was subjected to silica gel chromatography (50% Hexanes in EtOAc). Concentration of the desired fractions afforded the title compound (0.1 g, 0.19 mmol, 28%). MS (ESI) m/z 516.5[M+1]$^+$.

D. 5-Amino-2-(3-hydroxyphenyl)-6-(1-(phenylsulfonyl)-1H-indol-4-ylamino)pyrimidine-4-carboxamide. Methyl 5-amino-2-(3-hydroxyphenyl)-6-(1-(phenylsulfonyl)-1H-indol-4-ylamino)pyrimidine-4-carboxylate (0.1 g, 0.19 mmol) was stirred in 7N $NH_3$/MeOH (20 mL) at 55° C. for 24 h. LCMS shows only the desired product. The mixture was concentrated to afford the title compound, 50 mg, 0.1 mmol, 50%. MS (ESI) m/z 501.5[M+1]$^+$.

E. 2-(3-Hydroxyphenyl)-9-(1H-indol-4-yl)-8-oxo-8,9-dihydro-7H-purine-6-carboxamide. To a solution of 5-amino-2-(3-hydroxyphenyl)-6-(1-(phenylsulfonyl)-1H-indol-4-ylamino)pyrimidine-4-carboxamide (50 mg, 0.1 mmol) in $CH_2Cl_2$ (4 mL) and EtOAc (1 mL) was added 1,1'-1,1'-carbonyldiimidazole (0.1 g, 0.6 mmol). The mixture was stirred at 55° C. for 1.5 h, after which LCMS showed the desired mass, MS (ESI) m/z 527.1[M+1]$^+$. The reaction was then concentrated and the resulting residue was taken up in methanol (3 mL). Sodium methoxide (25% in MeOH, 0.5 mL) was added. The mixture was stirred at 70° C. for 1 h, after which time LCMS indicated complete reaction. AcOH was added to neutralize the mixture. The mixture was then subjected to semi-preparatory HPLC (10-70% acetonitrile+0.1% TFA in $H_2O$+0.1% TFA, over 30 min). Clean fractions were concentrated to afford the title compound, 98.3% pure (15 mg, 39% over 2 steps). $^1$H NMR (400 MHz, DMSO-$d_6$) δ 11.75 (s, 1H), 11.41 (s, 1H), 9.41 (s, 1H), 8.34 (s, 1H), 7.98 (s, 1H), 7.84 (dt, J=8.0, 1.2, 1H), 7.61 (t, J=2.4, 1H), 7.58 (d, J=8.0, 1H), 7.41 (t, J=2.8, 1H), 7.28 (t, J=8.0, 1H), 7.18 (m, 2H), 6.78 (dq, J=7.6, 1.2, 1H), 6.23 (m, 1H); MS (ESI) m/z 387.3 [M+1]$^+$; mp>260° C.

5.1.142 Example 142

Synthesis of 9-(2-FLUORO-3-METHOXYPHE-NYL)-2-(3-HYDROXYPHENYL)-8-OXO-8,9-DI-HYDRO-7H-PURINE-6-CARBOXAMIDE A. 2-Fluoro-1-isocyanato-3-methoxybenzene. 2-Fluoro-3-methoxybenzoic acid (0.61 g, 3.59 mmol) was dissolved in $CH_2Cl_2$ (10 mL) and DMF (0.5 mL). Oxalyl chloride (0.41 mL, 4.7 mmol) was added slowly. The mixture was stirred at rt for 15 min. The mixture was then concentrated and then reconstituted in dioxane (10 mL). Sodium azide (0.26 g, 4.0 mmol) in water/dioxane (1:1 v/v, 10 mL) was added to the acid chloride at 0° C. The mixture was allowed to warm to rt over 1 h. The reaction was then diluted with EtOAc (50 mL) and water (50 mL). The mixture was shaken and separated. The organic layer was dried, filtered, and concentrated. The crude acyl azide was filtered through a silica gel plug (90% Hex in EtOAc). The filtrate was concentrated to afford the intermediate 2-fluoro-3-methoxybenzoyl azide. 2-Fluoro-3-methoxybenzoyl azide was dissolved in toluene (50 mL) and stirred at 100° C. for 1 h. The mixture was concentrated to afford the title compound in quantitative yield.

B. 9-(2-Fluoro-3-methoxyphenyl)-2-(3-hydroxyphenyl)-8-oxo-8,9-dihydro-7H-purine-6-carboxamide. 2-Fluoro-1-isocyanato-3-methoxybenzene (0.6 g, 3.59 mmol) was reacted with 2,3-diaminomaleonitrile (0.39 g, 3.59 mmol) according to General Procedure A. The urea intermediate precipitated from solution and was filtered. The urea intermediate was reacted with 3-hydroxybenzaldehyde according to General Procedure B. The title compound precipitated from solution and was filtered to give 0.184 g (13% over 2 steps, 98.9% pure). $^1$H NMR (400 MHz, DMSO-$d_6$) δ 11.89 (s, 1H), 9.50 (s, 1H), 8.38 (s, 1H), 8.42 (s, 1H), 8.01 (s, 1H), 7.90 (d, J=7.6, 1H), 7.70 (t, J=1.8, 1H), 7.40 (d, J=4.8, 1H), 7.38 (d, J=5.2, 1H), 7.25 (m, 2H), 6.84 (dd, J=8.0, 1.6, 1H), 3.95 (s, 3H); MS (ESI) m/z 396.4 [M+1]$^+$; mp>260° C.

5.1.143 Example 143

Synthesis of 9-(2-FLUORO-5-METHOXYPHE-NYL)-2-(3-HYDROXYPHENYL)-8-OXO-8,9-DI-HYDRO-7H-PURINE-6-CARBOXAMIDE A. (Z)-1-(2-Amino-1,2-dicyanovinyl)-3-(2-fluoro-5-methoxyphenyl)urea. 2-Fluoro-5-methoxybenzoic acid (0.62 g, 3.62 mmol) was dissolved in $CH_2Cl_2$ (15 mL) and DMF (0.5 mL). Oxalyl chloride (0.38 mL, 4.32 mmol) was added dropwise. The mixture was stirred for another 15 min. The reaction was concentrated and then taken up in dioxane (10 mL). Sodium azide (0.26 g, 3.96 mmol) in water/dioxane (1:1 v/v, 10 mL) was added to the acid chloride at 0° C. The mixture was stirred for 10 min. The reaction was partitioned between EtOAc and water. The layers were shaken and separated. The organic layer was dried over sodium sulfate, filtered, and concentrated. The crude acyl azide was filtered through a silica gel plug (90% Hexanes in EtOAc. The filtrate was concentrated. The purified acyl azide was dissolved in toluene and stirred at 100° C. for 1 h. The toluene solution was concentrated to afford 1-fluoro-2-isocyanato-4-methoxybenzene in quantitative yield. 1-Fluoro-2-isocyanato-4-methoxybenzene (0.6 g, 3.62 mmol) was reacted with 2,3-diaminomaleonitrile (0.39 g, 3.62 mmol) according to General Procedure A to afford the title compound. MS (ESI) m/z 276.4 [M+1]+.

B. 9-(2-Fluoro-5-methoxyphenyl)-2-(3-hydroxyphenyl)-8-oxo-8,9-dihydro-7H-purine-6-carboxamide. (Z)-1-(2-Amino-1,2-dicyanovinyl)-3-(2-fluoro-5-methoxyphenyl) urea was reacted with 3-hydroxybenzaldehyde according to General Procedure B to afford the title compound, 98.6% pure. (94 mg, 0.24 mmol, 7% over two steps). $^1$H NMR (400 MHz, DMSO-$d_6$) δ 9.50 (s, 1H), 8.46 (s, 1H), 7.99 (s, 1H), 7.90 (d, J=7.6, 1H), 7.72 (s, 1H), 7.46 (t, J=9.2, 1H), 7.29 (m, 1H), 7.24 (t, J=8.0, 1H), 7.18 (m, 1H), 6.83 (d, J=8.0, 1H), 3.80 (s, 3H); MS (ESI) m/z 396.4 [M+1]+; mp>260° C.

5.1.144 Example 144

Synthesis of 9-CYCLOHEXYL-2-(1H-IMIDAZO[4,5-B]PYRIDIN-6-YL)-8-OXO-8,9-DIHYDRO-7H-PURINE-6-CARBOXAMIDE A. 9-Cyclohexyl-2-(1H-imidazo[4,5-b]pyridin-6-yl)-8-oxo-8,9-dihydro-7H-purine-6-carboxamide. (Z)-1-(2-Amino-1,2-dicyanovinyl)-3-cyclohexylurea (See example 26.A) (215 mg, 0.93 mmol), 1-(tetrahydro-2H-pyran-2-yl)-1H-imidazo[4,5-b]pyridine-6-carbaldehyde (See example 130.C) (322 mg, 1.39 mmol), and triethylamine (0.20 mL, 1.39 mmol) were reacted according to General Procedure B. The solution was allowed to stir at room temperature overnight and the resulting precipitate was collected by filtration. A solution of 5-(1-(2H-3,4,5,6-tetrahydropyran-2-yl)imidazo[4,5-b]pyridin-6-yl)-3-cyclohexyl-2-oxo-4-imidazolino[4,5-b]pyridine-7-carboxamide (316 mg, 0.68 mmol) in dioxane (2 mL) was treated with 4.0 M HCl/dioxane solution (4.0 mL) and water (0.3 mL) and stirred at room temp overnight. The reaction was neutralized with saturated NaHCO$_3$, extracted with EtOAc (3×50 mL), and dried over sodium sulfate. The crude product was purified using reverse-phase semi-preparatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×75 mL). Pooled organic layers were dried over sodium sulfate and concentrated under reduced pressure. The resulting solid was washed with diethyl ether and dried in a vacuum oven at 60° C. overnight to afford the title compound (40 mg, 0.091 mmol, 40%) as a white solid. $^1$H NMR (400 MHz, DMSO-$d_6$) δ 9.49 (s, 1H), 8.97 (s, 1H), 8.83 (s, 1H), 8.49 (s, 1H), 7.74 (m, 1H), 4.26 (m, 1H), 2.67 (m, 1H), 2.37 (m, 2H), 2.32 (m, 1H), 1.88 (m, 2H), 1.72 (m, 2H), 1.41 (m, 2H); MS (ESI) m/z 378.0 [M+1]+; mp 320° C. dec.

5.1.145 Example 145

Synthesis of 2-(3-HYDROXYPHENYL)-8-OXO-9-(TETRAHYDRO-2H-PYRAN-4-YL)-8,9-DIHYDRO-7H-PURINE-6-CARBOXAMIDE A. Methyl 2-chloro-5-nitro-6-(tetrahydro-2H-pyran-4-ylamino)pyrimidine-4-carboxylate. Methyl 2,6-dichloro-5-nitroyprimidine (2.49 g, 9.89 mmol), diisopropylethylamine (3.18 g, 24.72 mmol) and tetrahydro-2H-pyran-4-amine (1.00 g, 9.89 mmol) were reacted according to General Procedure C and purified via Biotage chromatography (0 to 50% EtOAc in hexanes) to afford the title compound (2.01 g, 33%). MS (ESI) m/z 317.2 [M+1]+.

B. Methyl 5-amino-2-chloro-6-(tetrahydro-2H-pyran-4-ylamino)pyrimidine-4-carboxylate. Methyl 2-chloro-5-nitro-6-(tetrahydro-2H-pyran-4-ylamino)pyrimidine-4-carboxylate (2.01 g, 6.36 mmol), iron (s) (2.48 g, 44.52 mmol) and acetic acid (35 mL) were reacted according to General Procedure D2 and partitioned between sodium bicarbonate and ethyl acetate (3×) to afford the title compound (1.60 g, 88%). MS (ESI) m/z 287.3 [M+1]+.

C. Methyl 5-amino-2-(3-(tert-butyldiphenylsilyloxy)phenyl)-6-(tetrahydro-2H-pyran-4-ylamino)pyrimidine-4-carboxylate. Methyl 5-amino-2-chloro-6-(tetrahydro-2H-pyran-4-ylamino)pyrimidine-4-carboxylate. (0.400 g, 1.39 mmol) triisopropyl(3-(trimethylstannyl)phenoxy)silane (0.810 g, 1.95 mmol) and bisdichloro(triphenylphosphine) palladium (0) (0.292 g, 0.410 mmol) were combined in dimethyl formamide (6 mL) and heated to 100° C. The reaction was monitored via thin layer chromatography. Once starting materials were consumed, the solution was condensed under reduced pressure and purified via Biotage chromatography (0 to 50% EtOAc in hexanes) to afford the title compound (0.361 g, 51%). MS (ESI) m/z 501.5 [M+1]+.

D. Methyl 2-(3-(tert-butyldiphenylsilyloxy)phenyl)-8-oxo-9-(tetrahydro-2H-pyran-4-yl)-8,9-dihydro-7H-purine-6-carboxylate. Methyl 5-amino-2-(3-(tert-butyldiphenylsilyloxy)phenyl)-6-(tetrahydro-2H-pyran-4-ylamino) pyrimidine-4-carboxylate (0.361 g, 0.722 mmol) and 1,1'-1,1'-carbonyldiimidazole (0.702 g, 4.33 mmol) in dichloromethane (15 mL) were reacted according to General Procedure F and purified via biotage chromatography (0 to 75% EtOAc in hexanes) to afford the title compound (0.270 g, 71%). $^1$H NMR (400 MHz, DMSO-$d_6$) δ 11.80 (s, 1H), 7.96 (s, 2H), 7.41 (t, J=8.39, 1H), 7.00 (dd, J=7.99 2.39, 1H), 4.51 (m, 1H), 4.01 (dd, J=11.19, 3.59, 2H), 3.94 (s, 3H), 3.48 (t, J=11.99, 2H), 2.65 (m, 2H), 1.75 (d, 9.59, 2H), 1.33 (m, 3H), 1.10 (d, J=3.59, 18H).

E. Methyl 2-(3-hydroxyphenyl)-8-oxo-9-(tetrahydro-2H-pyran-4-yl)-8,9-dihydro-7H-purine-6-carboxylate. Methyl 2-(3-(tert-butyldiphenylsilyloxy)phenyl)-8-oxo-9-(tetrahydro-2H-pyran-4-yl)-8,9-dihydro-7H-purine-6-carboxylate (0.270 g, 0.513 mmol) was dissolved in tetrahyrdofuran (10 mL) and tetrabutylammonium fluoride on silica gel (0.410 g, 0.615 mmol) was added to the solution. The solution stirred at ambient temperature for two hours. LCMS confirms product and no starting materials. The solution was filtered and condensed to give the crude title compound (0.110 g, 58%) which is used in the next step without further purification or characterization.

F. 2-(3-Hydroxyphenyl)-8-oxo-9-(tetrahydro-2H-pyran-4-yl)-8,9-dihydro-7H-purine-6-carboxamide. Methyl 2-(3-hydroxyphenyl)-8-oxo-9-(tetrahydro-2H-pyran-4-yl)-8,9-dihydro-7H-purine-6-carboxylate (0.103 g, 0.277 mmol) and ammonia gas were reacted in methanol according to General Procedure G. After 16 h, LCMS confirms product and the solution was condensed under reduced pressure to afford the title compound (0.080 g, 81%). $^1$H NMR (300 MHz, DMSO-$d_6$) δ 11.54 (s, 1H), 9.57 (s, 1H), 8.35 (s, 1H), 7.99 (d, J=8.4, 2H), 7.92 (s, 1H), 7.88 (s, 1H), 7.29 (t, J=7.8, 2H), 6.87 (d, J=7.8, 1H), 4.51 (m, 1H), 4.02 (d, J=7.8, 2H), 3.4 (t, J=12.00, 2H), 1.72 (d, J=9.9, 2H), MS (ESI) m/z 356.5 [M+1]+; mp 361-363° C.

5.1.146 Example 146

Synthesis of 2-(3-HYDROXYPHENYL)-8-OXO-9-((TETRAHYDRO-2H-PYRAN-4-YL)METHYL)-8,9-DIHYDRO-7H-PURINE-6-CARBOXAMIDE A. Methyl 2-chloro-5-nitro-6-((tetrahydro-2H-pyran-4-yl)methylamino)pyrimidine-4-carboxylate. Methyl 2,6- dichloro-5-nitroyprimidine (2.18 g, 8.68 mmol), diisopropylethylamine (2.8 g, 21.7 mmol) and (tetrahydro-2H-pyran-4-yl)methanamine (1.00 g, 8.68 mmol) were reacted according to General Procedure C and purified via Biotage chromatography (0-50% EtOAc in hexanes) to afford the title compound (2.14 g, 75%). MS (ESI) m/z 331.3 [M+1]$^+$.

B. Methyl 5-amino-2-chloro-6-((tetrahydro-2H-pyran-4-yl)methylamino)pyrimidine-4-carboxylate. Methyl 2-chloro-5-nitro-6-((tetrahydro-2H-pyran-4-yl)methylamino)pyrimidine-4-carboxylate (2.14 g, 6.45 mmol), iron (s) (2.50 g, 45.39 mmol) and acetic acid (35 mL) were reacted according to General Procedure D2 and partitioned between sodium bicarbonate and ethyl acetate (3×) to afford the title compound (1.69 g, 87%) which is used in the next step without further purification or characterization. MS (ESI) m/z 301.4 [M+1]$^+$.

C. Methyl 5-amino-2-(3-(tert-butyldiphenylsilyloxy)phenyl)-6-((tetrahydro-2H-pyran-4-yl)methylamino)pyrimidine-4-carboxylate. Methyl 5-amino-2-chloro-6-((tetrahydro-2H-pyran-4-yl)methylamino)pyrimidine-4-carboxylate. (0.400 g, 1.33 mmol) triisopropyl(3-(trimethyl-stannyl)phenoxy)silane (0.772 g, 1.86 mmol) and bisdichloro(triphenylphosphine)palladium (0) (0.280 g, 0.400 mmol) were combined in dimethyl formamide (6 mL) and heated to 100° C. The reaction was monitored via thin layer chromatography. Once starting materials were consumed, the solution was condensed under reduced pressure and purified via Biotage chromatography (0-50% EtOAc in hexanes) to afford the title compound (0.276 g, 40%). MS (ESI) m/z 515.6 [M+1]$^+$.

D. Methyl 2-(3-(tert-butyldiphenylsilyloxy)phenyl)-8-oxo-9-((tetrahydro-2H-pyran-4-yl)methyl)-8,9-dihydro-7H-purine-6-carboxylate. Methyl 5-amino-2-(3-(tert-butyl-diphenyl-silyloxy)phenyl)-6-((tetrahydro-2H-pyran-4-yl)methylamino)pyrimidine-4-carboxylate (0.276 g, 0.536 mmol) and 1,1'-1,1'-carbonyldiimidazole (0.522 g, 3.22 mmol) in dichloromethane (15 mL) were reacted according to General Procedure F and purified via biotage chromatography (0-75% EtOAc in hexanes) to afford the title compound (0.202 g, 70%). $^1$H NMR (400 MHz, DMSO-d$_6$) δ 11.79 (s, 1H), 7.98 (s, 1H), 7.96 (s, 1H), 7.40 (t, J=8.39, 1H), 7.00 (d, J=7.99, 1H), 3.94 (s, 3H), 3.8 (m, 4H), 3.24 (t, J=10.79, 3H), 2.15 (m, 1H), 1.57 (d, J=12.39, 2H), 1.31 (m, 5H), 1.11 (d, J=7.59, 18H).

E. Methyl 2-(3-hydroxyphenyl)-8-oxo-9-((tetrahydro-2H-pyran-4-yl)methyl)-8,9-dihydro-7H-purine-6-carboxylate. Methyl 2-(3-(tert-butyldiphenylsilyloxy)phenyl)-8-oxo-9-((tetrahydro-2H-pyran-4-yl)methyl)-8,9-dihydro-7H-purine-6-carboxylate (0.202 g, 0.367 mmol) was dissolved in tetrahyrdrofuran (10 mL) and tetrabutylammonium fluoride on silica gel (0.294 g, 0.404 mmol) was added to the solution. The solution stirred at ambient temperature for two h. LCMS confirms product and no starting materials. The solution was filtered and condensed to give the crude title compound (0.110 g, 58%).

F. 2-(3-Hydroxyphenyl)-8-oxo-9-((tetrahydro-2H-pyran-4-yl)methyl)-8,9-dihydro-7H-purine-6-carboxamide. Methyl 2-(3-hydroxyphenyl)-8-oxo-9-((tetrahydro-2H-pyran-4-yl)methyl)-8,9-dihydro-7H-purine-6-carboxylate (0.083 g, 0.215 mmol) and ammonia gas were reacted in methanol according to General Procedure G. After 16 h, LCMS confirms product and the solution was condensed under reduced pressure to afford the title compound (0.063 g, 81%). $^1$H NMR (300 MHz, DMSO-d$_6$) δ 11.53 (s, 1H), 9.51 (s, 1H), 8.31 (s, 1H), 8.02 (d, J=7.8, 1H), 7.90 (s, 2H), 7.28 (t, J=8.10, 1H), 6.84 (d, J=8.10, 1H), 3.81 (m, 4H), 3.31 (s, 1H), 3.25 (m, 3H), 2.15 (m, 1H), 1.55 (d, J=10.8, 2H), 1.33 (m, 2H); MS (ESI) m/z 356.5 [M+1]$^+$; mp 363-365° C.

5.1.147 Example 147

Synthesis of 9-(2-CYCLOPENTYLPHENYL)-2-(3-HYDROXYPHENYL)-8-OXO-8,9-DIHYDRO-7H-PURINE-6-CARBOXAMIDE A. N-(2-(Cyclopent-2-enyl)phenyl)acetamide. 2-Iodoaniline (3.07 g, 14 mmol), acetic anhydride (1.46 mL, 15.4 mmol), and triethyl amine (5.9 mL) were combined in chloroform (20 mL). The mixture was stirred overnight at rt. The mixture was concentrated and purified on a silica gel column (15% ethyl acetate in hexanes) to afford the acylated aniline (2.91 g, 11.1 mmol, 80%), which was carried on into the next reaction. N-Acetyl-2-iodoaniline (2.91 g, 11.1 mmol) was combined with cyclopentene (4.9 mL, 55 mmol), palladium (II)acetate (0.5 g), tetrabutylammonium chloride (3.06 g), triphenylphosphine (0.58 g) and potassium acetate (3.25 g) in DMF (25 mL). The mixture was purged with nitrogen and then stirred at 100° C. for 2 h. The mixture was diluted with ethyl acetate and water and the layers were shaken. The organic layer was dried over sodium sulfate, filtered, and concentrated. The crude residue was purified using silica gel chromatography (20% ethyl acetate in hexanes). Concentration of the desired fractions afforded the title compound (1.45 g, 65%). $^1$H NMR (300 MHz, CDCl$_3$) δ 7.83 (d, J=6.6, 1H), 7.41 (br s, 1H), 7.07-7.26 (m, 3H), 6.07 (m, 1H), 5.85 (m, 1H), 4.00 (m, 1H), 2.38-2.54 (m, 4H), 2.15 (s, 3H); MS (ESI) m/z 202.3[M+1]$^+$.

B. 2-Cyclopentylaniline. N-(2-(Cyclopent-2-enyl)phenyl)acetamide (1.45 g, 7.2 mmol), ammonium bicarbonate (1.36 g, 21 mmol), and palladium on carbon (0.4 g) were combined in methanol (20 mL). The mixture was stirred at reflux for 2 h. The mixture was filtered and then concentrated. The crude residue was dissolved in ethanol (20 mL) and potassium hydroxide (aq. 4.5M, 20 mL). The mixture was stirred at 100° C. for 24 h. The mixture was concentrated and diluted with water (100 mL). The mixture was washed with ethyl acetate (2×100 mL). The combined organic layers were dried over sodium sulfate, filtered, and concentrated. The crude residue was purified on silica gel chromatography (25% ethyl acetate in hexanes). Concentration of the desired fractions afforded the title compound (0.3 g, 1.86 mmol, 25%). MS (ESI) m/z 204.4[M+1]$^+$.

C. 2-Cyclopentylbenzoic acid. 2-Cyclopentylaniline (0.64 g, 3.98 mmol) was dissolved in conc. hydrochloric acid (aq). To this solution was added sodium nitrite (0.27 g, 4.37 mmol) in water (3 mL) at 0° C. The mixture was stirred 15 min, followed by addition of potassium iodine (4.62 g, 27.8 mmol) in water (10 mL). The mixture was allowed to warm to rt. The reaction was then diluted with ethyl acetate (100 mL) and sodium metabisulfite (10% aq, 50 mL). The layers were shaken and separated. The organic layer was dried over sodium sulfate, filtered, and concentrated to afford 2-cyclopentyliodobenzene (0.62 g, 2.3 mmol, 57%). The aryl iodide (0.62 g, 2.3 mmol) was dissolved in tetrahydrofuran. n-Butyl lithium (2.2 mL, 1.6 M in hex, 3.45 mmol) was added at −78° C. After stirring for 10 min, crushed dry ice (1 g) was added to the solution. The mixture was warmed to rt. The reaction was diluted with 5% hydrochloric acid (aq, 50 mL) and ethyl acetate (50 mL). The layers were shaken and separated. The organic layer was dried over sodium sulfate, filtered, and concentrated to afford the title compound (0.19 g, 43%). $^1$H NMR (300 MHz, CDCl$_3$) δ 9.6-10.2 (br s, 1H), 7.90 (d, J=7.8, 1H), 7.46 (m, 2H), 7.24 (m, 1H), 2.12 (m, 2H), 1.71 (m, 7H).

D. 1-Cyclopentyl-2-isocyanatobenzene. 2-Cyclopentylbenzoic acid (0.19 g, 1 mmol) was dissolved in methylene chloride (10 mL) and DMF (0.5 mL). Oxalyl chloride (0.11 mL, 1.3 mmol) was added dropwise. After 15 min, the mixture was concentrated and the resulting residue was diluted with dioxane (5 mL). Sodium azide (72 mg, 1.1 mmol) in water/dioxane (5 mL, 1:1 v/v) was added at 0° C. The mixture was stirred for 15 min, followed by dilution with ethyl acetate (50 mL) and water (50 mL). The organic layer was dried over sodium sulfate, filtered, and concentrated. The crude acyl azide was passed through a silica gel plug (10% ethyl acetate in hexanes). The eluent was concentrated and then dissolved in toluene (20 mL). The solution was stirred for 1 h at 100° C. Concentration of the reaction mixture afforded the title compound (0.19 g, quant).

E. (Z)-1-(2-Amino-1,2-dicyanovinyl)-3-(2-cyclopentylphenyl)urea. The title compound was prepared according to General Procedure A using 1-cyclopentyl-2-isocyanatobenzene (0.19 g, 1 mmol) and 2,3-diaminomaleonitrile (0.11 g, 1 mmol). The mixture was concentrated to afford the title compound (0.29 g, quant). MS (ESI) m/z 296.3[M+1]$^+$.

F. 9-(2-Cyclopentylphenyl)-2-(3-hydroxyphenyl)-8-oxo-8,9-dihydro-7H-purine-6-carboxamide. The title compound was prepared according to General Procedure B using 3-hydroxybenzaldehyde (0.31 g, 2.5 mmol) and (Z)-1-(2-amino-1,2-dicyanovinyl)-3-(2-cyclopentylphenyl)urea (0.29 g, 1 mmol). The crude reaction mixture was concentrated. The crude residue was purified by semi-preparatory HPLC (10-70% acetonitrile+0.1% TFA in H$_2$O+0.1% TFA, over 30 min). Clean fractions were concentrated to afford the title compound (20 mg, 5%) as a white solid, 100% pure. $^1$H NMR (400 MHz, DMSO-d$_6$) δ 9.57 (s, 1H), 8.49 (s, 1H), 8.07 (s, 1H), 7.96 (d, J=7.2, 1H), 7.48 (m, 1H), 7.30 (t, J=7.8, 2H), 6.89 (dd, J=7.8, 2.4, 1H), 2.91 (q, J=7.5, 1H), 1.44-2.00 (m, 7H); MS (ESI) m/z 416.1 [M+1]$^+$; mp>260° C.

5.1.148 Example 148

Synthesis of 2-(3-HYDROXYPHENYL)-8-OXO-9-(PIPERIDIN-4-YL)-8,9-DIHYDRO-7H-PURINE-6-CARBOXAMIDE A. Ethyl 6-(1-(tert-butoxycarbonyl)piperidin-4-ylamino)-2-chloro-5-nitropyrimidine-4-carboxylate. Ethyl 2,6-dichloro-5-nitropyrimidine (3.0 g, 11.28 mmol), diisopropylethylamine (1.46 g, 11.28 mmol) and tert-butyl 4-aminopiperidine-1-carboxylate (2.03 g, 10.15 mmol) were reacted according to General Procedure C, filtered and solvent removed under reduced pressure to afford the title compound (5.25 g, 75%). MS (ESI) m/z 430.1 [M+1]$^+$.

B. Ethyl 5-amino-6-(1-(tert-butoxycarbonyl)piperidin-4-ylamino)-2-chloropyrimidine-4-carboxylate. Ethyl 6-(1-(tert-butoxycarbonyl)piperidin-4-ylamino)-2-chloro-5-nitropyrimidine-4-carboxylate (1.5 g, 3.49 mmol) was combined with tin(II)chloride dihydrate (2.36 g, 10.47 mmol) and ethanol (50 mL). After 16 h, the solution was filtered and the filtrate condensed and purified via Biotage chromatography (0 to 60% EtOAc in hexanes) (0.788 g, 56%). MS (ESI) m/z 400.1 [M+1]$^+$.

C. Ethyl 5-amino-6-(1-(tert-butoxycarbonyl)piperidin-4-ylamino)-2-(3-hydroxyphenyl)pyrimidine-4-carboxylate. Ethyl 5-amino-6-(1-(tert-butoxycarbonyl)piperidin-4-ylamino)-2-chloropyrimidine-4-carboxylate. (0.400 g, 1.00 mmol) 3-hydroxyphenyl boronic acid (0.207 g, 1.5 mmol), palladium(II)acetate (0.034 g, 0.15 mmol), potassium phosphate (0.430 g, 2.0 mmol) and dicyclohexyl(2,6-dimethoxyphenyl)phosphine (0.062 g, 0.15 mmol) were combined in tetrahydrofuran (6 mL) and water (0.6 ml) and reacted in the microwave at 120° C. for 30 min. The reaction was monitored via thin layer chromatography for consumption of starting materials. The solution was filtered and concentrated and the residue purified via Biotage chromatography (0-60% EtOAc in hexanes) to afford the title compound (0.120 g, 40%). MS (ESI) m/z 458.5 [M+1]$^+$.

D. Ethyl 9-(1-(tert-butoxycarbonyl)piperidin-4-yl)-2-(3-hydroxyphenyl)-8-oxo-8,9-dihydro-7H-purine-6-carboxylate. Ethyl 5-amino-6-(1-(tert-butoxycarbonyl)piperidin-4-ylamino)-2-(3-hydroxyphenyl)pyrimidine-4-carboxylate (0.120 g, 0.260 mmol) and 1,1'-1,1'-carbonyldiimidazole (0.425 g, 2.62 mmol) in dichloromethane (10 mL) were reacted according to General Procedure F and purified via biotage chromatography (0-70% EtOAc in hexanes) to afford the title compound (0.050 g, 19%). MS (ESI) m/z 484.3 [M+1]$^+$.

E. 2-(3-Hydroxyphenyl)-8-oxo-9-(piperidin-4-yl)-8,9-dihydro-7H-purine-6-carboxamide. Ethyl 9-(1-(tert-Butoxycarbonyl)piperidin-4-yl)-2-(3-hydroxyphenyl)-8-oxo-8,9-dihydro-7H-purine-6-carboxylate (0.050 g, 0.103 mmol) was reacted according to General Procedure G. After 16 h, LCMS confirms product and the solution was condensed under reduced pressure to afford the protected product. The solid was taken up in HCl (4N in dioxanes, 4 mL) and stirred at room temperature. After two h, LCMS confirms product. Solution was condensed under reduced pressure and diluted with methanol, sonicated and filtered to afford the title compound as the HCl salt (0.011 g, 28%). $^1$H NMR (400 MHz, DMSO-d$_6$) δ 9.49 (s, 2H), 8.34 (s, 1H), 8.07 (d, J=7.59, 2H), 8.04 (s, 1H), 7.95 (s, 1H), 7.28 (t, J=7.99, 2H), 6.89 (dd, J=7.99, 1.59, 2H), 4.63 (m, 3H), 3.45 (m, 4H), 3.16 (m, 4H), 2.75 (m, 3H), 2.32 (s, 1H), 1.99 (d, J=13.19, 3H); MS (ESI) m/z 355.2 [M+1]$^+$.

5.1.149 Example 149

Synthesis of 9-(2-FLUORO-4-METHOXYPHENYL)-2-(3-HYDROXYPHENYL)-8-OXO-8,9-DIHYDRO-7H-PURINE-6-CARBOXAMIDE A. (Z)-1-(2-Amino-1,2-dicyanovinyl)-3-(2-fluoro-4-methoxyphenyl)urea. In a 100 mL round-bottomed flask was added 2-fluoro-4-methoxyaniline (0.79 g, 5.60 mmol) and trichloromethyl carbonochloridate (0.68 mL, 5.60 mmol) in toluene (6 mL) to give a purple suspension. The mixture was then stirred at 110° C. for 3 h. Upon heating, the suspension becomes a homogeneous solution. After 3 h, no starting material remained (TLC, 3:1 hex/EtOAc). The reaction mixture was concentrated to afford 2-fluoro-1-isocyanato-4-methoxybenzene (0.936 g, 5.6 mmol, quant.) as a green oil. The intermediate 2-fluoro-1-isocyanato-4-methoxybenzene (0.936 g, 5.6 mmol) was then dissolved in acetonitrile (20 ml) and reacted with 2,3-diaminomaleonitrile (0.605 g, 5.60 mmol) according to General Procedure A. The product was filtered to give the title compound (1.36 g, 88%). MS (ESI) m/z 276.3[M+1]$^+$.

B. 9-(2-Fluoro-4-methoxyphenyl)-2-(3-hydroxyphenyl)-8-oxo-8,9-dihydro-7H-purine-6-carboxamide. (Z)-1-(2-Amino-1,2-dicyanovinyl)-3-(2-fluoro-4-methoxyphenyl)urea (1.36 g, 4.94 mmol) and 3-hydroxybenzaldehyde (1.509 g, 12.35 mmol) were combined together in methanol (20 mL) and triethylamine (4 mL, 4.94 mmol) according to General Procedure B. The product was filtered, washed with methanol, and dried (1.08 g, 55%, 97.6% pure). $^1$H NMR (400 MHz, DMSO-d$_6$) δ 11.83 (s, 1H), 9.49 (s, 1H), 8.42 (s, 1H), 8.00 (s, 1H), 7.91 (d, 8.0, 1H), 7.71 (t, J=2.0, 1H), 7.59 (t, J=8.8, 1H), 7.24 (t, J=8.0, 1H), 7.17 (dd, J=12, 2.4, 1H), 7.10

(dd, J=9.2, 2.4, 1H), 6.83 (dd, J=8.0, 1.6, 1H), 3.88 (s, 3H); MS (ESI) m/z 396.3 [M+1]$^+$; mp>260° C.

5.1.150 Example 150

Synthesis of 2-(1H-BENZO[D]IMIDAZOL-6-YL)-9-CYCLOHEXYL-8-OXO-8,9-DIHYDRO-7H-PURINE-6-CARBOXAMIDE A. 2-(1H-benzo[d]imidazol-6-yl)-9-cyclohexyl-8-oxo-8,9-dihydro-7H-purine-6-carboxamide. (Z)-1-(2-Amino-1,2-dicyanovinyl)-3-cyclohexylurea (See Example 26.A) (520 mg, 2.23 mmol), 1H-benzo[d]imidazole-6-carbaldehyde (See Example 84.B) (652 mg, 4.46 mmol), triethylamine (0.34 mL, 3.34 mmol) and methanol (20 mL) were reacted according to General Procedure B. The solution was allowed to stir at ambient temperature overnight. The resultant heterogeneous mixture was filtered and purified via reverse-phase semi-prepatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×50 mL). Pooled organic layers were dried over sodium sulfate, filtered and concentrated under reduced pressure. The solid was washed with diethyl ether and dried in a vacuum oven at 60° C. overnight to afford the title compound (103 mg, 0.27 mmol, 12.2%) as a white solid. $^1$H NMR (400 MHz, DMSO-d$_6$) δ 11.47 (s, 1H), 8.79 (s, 1H), 8.52 (m, 1H), 8.50 (m, 1H), 8.39 (s, 1H), 7.92 (s, 1H), 7.69 (d, J=8.0, 1H), 4.30 (m, 1H), 2.41 (m, 2H), 1.85 (m, 5H), 1.36 (m, 4H); MS (ESI) m/z 378.1 [M+1]$^+$; mp 280° C. dec.

5.1.151 Example 151

Synthesis of 2-BENZIMIDAZOL-6-YL-9-(TRANS-4-METHOXYCYCLOHEXYL)-8-OXO-7-HYDRO-PURINE-6-CARBOXAMIDE A. trans-4-Methoxycyclohexanisocyanate. A suspension of trans-4-methoxycyclohexylamine (243 mg, 1.46 mmol) in toluene (5 mL) was treated with diphosgene (0.18 mL, 1.46 mmol) and the resulting solution was heated to 100° C. for 3 h. Solvent was removed under reduced pressure and the resulting material was dried under high vacuum overnight.

B. N-((1Z)-2-Amino-1,2-dicyanovinyl)[trans-(4-methoxycyclohexyl)amino]carboxamide. A solution of trans-4-methoxycyclohexanisocyanate (200 mg, 1.29 mmol) and (1Z)-1,2-diaminoethene-1,2-dicarbonitrile (139 mg, 1.29 mmol) in anhydrous tetrahydrofuran (13 mL) was stirred at room temperature overnight. Volatiles were removed under reduced pressure and purified via reverse-phase semi-prepatory HPLC (20-100% acetonitrile+0.1% TFA in H$_2$O+0.1% TFA, over 30 min). Product containing fractions were combined and concentrated. The resulting material was treated with saturated NaHCO$_3$ and extracted with EtOAc (4×25 mL). The organics were dried with sodium sulfate and concentrated to afford the title compound (200 mg, 0.76 mmol, 59%) as a yellow solid.

C. 2-Benzimidazol-6-yl-9-(trans-4-methoxycyclohexyl)-8-oxo-7-hydropurine-6-carboxamide. N-((1Z)-2-Amino-1,2-dicyanovinyl)[(4-methoxycyclohexyl)amino]carboxamide (200 mg, 0.76 mmol), benzimidazole-6-carbaldehyde (167 mg, 1.14 mmol), triethylamine (0.16 mL, 1.14 mmol) and methanol (8 mL) were reacted according to General Procedure B. The solution was allowed to stir at room temperature overnight. The resultant heterogeneous mixture was filtered and purified via reverse-phase semi-prepatory HPLC (20-100% acetonitrile+0.1% TFA in H$_2$O+0.1% TFA, over 30 min). The volatiles were removed under reduced pressure, treated with saturated NaHCO$_3$ and extracted with ethyl acetate (3×50 mL). Pooled organic fractions were dried over sodium sulfate and concentrated under reduced pressure. The resulting solid was washed with diethyl ether and dried in a vacuum oven at 60° C. overnight to afford the title compound (0.018 mg, 0.044 mmol, 5.8%) as a white solid. $^1$H NMR (400 MHz, DMSO-d$_6$) δ 11.42 (s, 1H), 8.74 (s, 1H), 8.65 (m, 1H), 8.54 (m, 1H), 8.39 (s, 1H), 7.92 (s, 1H), 7.69 (d, J=8.0, 1H), 4.30 (m, 1H), 3.80 (m, 1H), 3.39 (s, 3H), 2.41 (m, 2H), 1.85 (m, 4H), 1.36 (m, 4H); MS (ESI) m/z 408.1 [M+1]$^+$; mp 298° C. dec.

5.1.152 Example 152

Synthesis of 2-(4-(AMINOMETHYL)PHENYL)-9-(2-METHOXYPHENYL)-8-OXO-8,9-DIHYDRO-7H-PURINE-6-CARBOXAMIDE A. tert-butyl 4-(6-Carbamoyl-9-(2-methoxyphenyl)-8-oxo-8,9-dihydro-7H-purin-2-yl)benzylcarbamate. (Z)-1-(2-Amino-1,2-dicyanovinyl)-3-(2-methoxyphenyl)urea (See Example 2.A) (0.2 g, 0.777 mmol), tert-butyl 4-formylbenzylcarbamate (0.366 g, 1.555 mmol), and triethylamine (0.163 ml, 1.166 mmol) were combined in methanol (15 ml) and stirred at room temperature overnight. Excess solvent was removed under reduced pressure and the resulting solid was purified was purified by silica gel Biotage chromatography (0-10% methanol in dichloromethane). Clean fractions were combined and solvent removed under reduced pressure. The resulting material was dried under house vacuum to provide the product (0.145 g, 0.296 mmol, 38.0% yield) as a yellow solid. MS (ESI) m/z 491.5 [M+1]$^+$.

B. 2-(4-(Aminomethyl)phenyl)-9-(2-methoxyphenyl)-8-oxo-8,9-dihydro-7H-purine-6-carboxamide. A solution of tert-butyl 4-(6-carbamoyl-9-(2-methoxyphenyl)-8-oxo-8,9-dihydro-7H-purin-2-yl)benzylcarbamate (0.14 g, 0.285 mmol) and HCl (3.0 mL, 3.00 mmol, 1M in ethyl ether) in dichloromethane (10 mL) was stirred at room temperature 2.5 h. Solvent was removed under reduced pressure and the material was taken up in methanol/dicholoromethane, and DMSO. The solution was filtered through a Strata-XC ion exchange column. Product was released with ammonium hydroxide (5% in methanol) and solvent removed under reduced pressure to give the title compound (0.045 g, 115 mmol, 40% yield) after drying on house vac. $^1$H NMR (400 MHz, DMSO-d$_6$) δ 8.62 (bs, 1H), 8.28 (AA'XX', J$_{AX}$=8.20, 2H), 7.90 (s, 1H), 7.53 (td, J=7.13, 1.56, 1H), 7.46 (dd, J=7.71, 1.46, 1H), 7.39 (AA'XX', J$_{AX}$=8.20, 2H), 7.28 (m, 1H), 7.14 (td, J=7.61, 1.17, 1H), 2H) 3.74 (s, 3H); MS (ESI) m/z 391.3 [M+1]$^+$.

5.1.153 Example 153

Synthesis of 2-(3-HYDROXYPHENYL)-9-(CIS-4-(METHOXYMETHYL)CYCLOHEXYL)-8-OXO-8,9-DIHYDRO-7H-PURINE-6-CARBOXAMIDE A. tert-Butyl cis-4-(hydroxymethyl)cyclohexylcarbamate. tert-Butyl-cis-4-aminocyclohexanecarboxylic acid (2.0 g, 8.23 mmol) was diluted with tetrahydrofuran (20 mL) and cooled to −10° C. N-Methylmorpholine (0.31 g, 8.23 mmol) and isobutylchloroformate (1.12 g, 8.23 mmol) were added and stirred for ten min. Sodium borohydride (0.938 g, 24.69 mmol) was then added in one portion. After two min, methanol (5 mL) was added dropwise and the reaction was then stirred at 0° C. an additional thirty min. The solution was then diluted with dichloromethane and partitioned with 5% sodium hydroxide solution (3×), dried over magnesium sulfate, filtered and solvent removed under reduced pressure to afford the title compound without purification (2.2 g, quantitative).

B. tert-Butyl cis-4-(methoxymethyl)cyclohexylcarbamate. Sodium hydride (0.216 g, 8.98 mmol) was suspended in tetrahydrofuran (30 mL) and stirred at 0° C. cis-4-(Hydroxymethyl)cyclohexylcarbamate (1.0 g, 5.99 mmol) and 15-crown-5-ether (1.385 g, 6.29 mmol) were then added the reaction was stirred for 30 min. Methyl iodide (0.393 mL, 8.98 mmol) was then added and the solution stirred at room temperature for 16 h. Additional sodium hydride (1.0 equiv.) was added and stirring continued. Upon starting material was consumption (monitored by thin layer chromatography) the solution was condensed under reduced pressure and partitioned between ethyl acetate and water (3×). The organics were combined, dried over magnesium sulfate, filtered and solvent removed under reduced pressure. The resulting oil was purified via Biotage chromatography (0 to 50% EtOAc in hexanes) to afford the title compound (0.498 g, 45%). MS (ESI) m/z 188.3 [M+1]+.

C. cis-4-(Methoxymethyl)cyclohexanamine hydrochloride. tert-Butyl cis-4-(methoxymethyl)cyclohexylcarbamate (1.0 g, 4.11 mmol) was dissolved in 1,4-dioxane (5 mL), 4.0 N HCl in dioxane (2 mL) was added and the solution stirred at room temperature for 16 h. The solution was condensed under reduced pressure to afford the title compound (0.573 g, 78%). MS (ESI) m/z 144.3 [M+1]+.

D. cis-1-Isocyanato-4-(methoxymethyl)cyclohexane. cis-4-(Methoxymethyl)cyclohexanamine hydrochloride (0.423 g, 2.36 mmol) was diluted with toluene (8 mL) and trichloromethyl carbonchloridate (0.207 g, 1.05 mmol) in toluene (5 mL) was added to the solution. The mixture was stirred at 100° C. for three hours. The solution was condensed to give an oil and used without purification (quantitative yield).

E. 1-((Z)-2-Amino-1,2-dicyanovinyl)-3-(cis-4-(methoxymethyl)cyclohexyl)urea. cis-1-Isocyanato-4-(methoxymethyl)cyclohexane (0.398 g, 2.35 mmol) was dissolved in tetrahydrofuran (10 mL), followed by the addition of diaminomaleonitrile (0.508 g, 4.70 mmol). The solution was allowed to stir at room temperature for 16 h. LCMS confirms product. Solution was purified via reverse-phase preparative HPLC (20-100% acetonitrile+0.1% TFA in H2O+0.1% TFA, over 30 min) to afford the title compound (0.405 g, 62%). MS (ESI) m/z 278.5 [M+1]+.

F. 2-(3-Hydroxyphenyl)-9-(cis-4-(methoxymethyl)cyclohexyl)-8-oxo-8,9-dihydro-7H-purine-6-carboxamide. 1-((Z)-2-Amino-1,2-dicyanovinyl)-3-(cis-4-(methoxymethyl)cyclohexyl)urea (0.405 g, 1.46 mmol), 3-hydroxybenzaldehyde (0.268 g, 2.19 mmol) and triethyl amine (0.611 mL, 4.38 mmol) were combined in methanol (10 mL). The solution was stirred at ambient temperature for 16 h. The resulting precipitate was filtered and washed with acetonitrile and dried under reduced pressure to afford the title compound (0.089 g, 15%). $^1$H NMR (400 MHz, DMSO-$d_6$) δ 11.52 (s, 1H), 9.50 (s, 1H), 8.32 (s, 1H), 7.99 (d, J=7.99, 1H), 7.90 (m, 2), 7.27 (t, J=7.59, 1H), 6.89 (dd, J=6.79, 1.59), 4.26 (m, 1H), 3.63 (d, J=7.59, 2H), 3.79 (s, 3H), 1.98 (s, 1H), 1.85 (m, 2H), 1.59 (m, 4H); MS (ESI) m/z 398.1 [M+1]+; mp 324-326° C.

5.1.154 Example 154

Synthesis of 9-(TRANS-4-AMINOCYCLOHEXYL)-2-(3-HYDROXYPHENYL)-8-OXO-8,9-DIHYDRO-7H-PURINE-6-CARBOXAMIDE A. Ethyl 6-(trans-4-(tert-butoxycarbonylamino)cyclohexylamino)-2-chloro-5-nitro-pyrimidine-4-carboxylate. Ethyl 2,6-dichloro-5-nitroyprimidine (1.5 g, 5.64 mmol), diisopropylethylamine (0.729 g, 5.64 mmol) and tert-butyl trans-4-aminocyclohexylcarbamate (1.09 g, 5.07 mmol) were reacted according to General Procedure C to afford the title compound (3.08 g, quantitative). MS (ESI) m/z 444 [M+1]+.

B. Ethyl 5-amino-6-(trans-4-(tert-butoxycarbonylamino)cyclohexylamino)-2-chloro-pyrimidine-4-carboxylate. Ethyl 6-(trans-4-(tert-butoxycarbonylamino)cyclohexylamino)-2-chloro-5-nitropyrimidine-4-carboxylate (2.5 g, 5.63 mmol) was dissolved in ethanol (25 mL) and dimethylformamide (6 mL). Tinchloride dihydrate (2.52 g, 11.16 mmol) was added and the solution stirred at room temperature for 16 h. The reaction was filtered and concentrated. The residue purified via Biotage chromatography (0 to 55% EtOAc in hexanes) (1.83 g, 78%). MS (ESI) m/z 414 [M+1]+.

C. Ethyl 5-amino-6-(trans-4-(tert-butoxycarbonylamino)cyclohexylamino)-2-(3-hydroxyphenyl)pyrimidine-4-carboxylate. Ethyl 5-amino-6-(trans-4-(tert-butoxycarbonylamino)cyclohexylamino)-2-chloropyrimidine-4-carboxylate. (0.500 g, 1.21 mmol), 3-hydroxyphenylboronic acid (0.249 g, 1.81 mmol), dicyclohexyl(2',6'-dimethoxybiphenyl-2-yl)phosphine (0.075 g, 0.182 mmol), palladium acetate (0.041 g, 0.182 mmol) and potassium phosphate (0.52 g, 2.42 mmol) were combined in tetrahydrofuran (7 mL) and water (0.6 mL) and heated to 120° C. in a Biotage Emrys Optimizer microwave reactor for thirty min. The reaction solution was filtered and concentrated. The residue purified via Biotage chromatography (0 to 60% ethyl acetate in hexanes) to afford the title compound (0.150 g, 26%). MS (ESI) m/z 472[M+1]+.

D. Ethyl 9-(trans-4-(tert-butoxycarbonylamino)cyclohexyl)-2-(3-hydroxyphenyl)-8-oxo-8,9-dihydro-7H-purine-6-carboxylate. Ethyl 5-amino-6-(trans-4-(tert-butoxycarbonylamino)cyclohexylamino)-2-(3-hydroxyphenyl)pyrimidine-4-carboxylate (0.150 g, 0.317 mmol) and 1,1'-1,1'-carbonyldiimidazole (0.514 g, 3.17 mmol) in dichloromethane (10 mL) were reacted according to General Procedure F and purified via biotage chromatography (0 to 60% EtOAc in hexanes) to afford the title compound (0.070 g, 44%). MS (ESI) m/z 498[M+1]+.

F. tert-Butyl trans-4-(6-carbamoyl-2-(3-hydroxyphenyl)-8-oxo-7H-purin-9(8H)-yl)cyclohexylcarbamate. Ethyl 9-(trans-4-(tert-butoxycarbonylamino)cyclohexyl)-2-(3-hydroxyphenyl)-8-oxo-8,9-dihydro-7H-purine-6-carboxylate (0.070 g, 0.140 mmol) and ammonia in methanol were reacted according to General Procedure G. After 16 h, LCMS confirms product and the solution was condensed under reduced pressure to afford the title compound (0.040 g, 60%). MS (ESI) m/z 469 [M+1]+.

G. 9-(trans-4-Aminocyclohexyl)-2-(3-hydroxyphenyl)-8-oxo-8,9-dihydro-7H-purine-6-carboxamide. tert-Butyl trans-4-(6-carbamoyl-2-(3-hydroxyphenyl)-8-oxo-7H-purin-9(8H)-yl)cyclohexylcarbamate (0.090 g, 0.212 mmol) was diluted with dichloromethane (10 ml) followed by trifluoroacetic acid (1 mL). The solution was concentrated and purified via reverse-phase preparative HPLC (10-40% acetonitrile+0.1% TFA in H2O+0.1% TFA, over 35 min) to afford the title compound (0.030 g, 38%). $^1$H NMR (400 MHz, DMSO-$d_6$) δ 8.4 (bs, 1H), 8.00 (d, J=7.99, 1H), 7.90 (s, 1H), 7.87 (s, 1H), 7.26 (t, J=7.59, 1H), 6.86 (d, J=7.59, 1H), 4.24 (m, 1H), 3.2 (s, 1H), 2.75 (m, 2H), 1.73 (m, 4H), 1.53 (s, 1H), 1.52 (s, 1H); MS (ESI) m/z 398.1 [M+1]+; mp 299-301° C.

5.1.155 Example 155

Synthesis of 2-(3-HYDROXYPHENYL)-9-(2-ISOBUTYLPHENYL)-8-OXO-8,9-DIHYDRO-7H-PURINE-6-CARBOXAMIDE A. 1-(2-Methylprop-1-enyl)-2-nitrobenzene. A solution of isopropyltriphenylphosphonium bromide (1.405 g, 4.6 mmol) in tetrahyrdofuran (20 mL) was cooled in an ice bath. nButyl lithium (3.2 mL, 5.1 mmol as 1.6M in hex) was added dropwise. The mixture was stirred 5 min, and then 2-nitrobenzaldehyde was added in tetrahydrofuran (10 mL). The reaction was monitored for consumption of starting material. After 1 h, the reaction was quenched with water (100 mL) and extracted with EtOAc (100 mL). The organic layer was washed with brine (50 mL), dried over sodium sulfate, filtered, and concentrated. The resulting residue was purified via Biotage (95% hexanes in EtOAc; 40+S column). Concentration of the desired fractions afforded the desired product (0.48 g, 59%). $^1$H NMR (300 MHz, CDCl$_3$) δ 7.93 (dd, J=6.0, 0.9, 1H), 7.54 (td, J=5.4, 0.6, 1H), 7.26-7.38 (m, 2H), 6.49 (s, 1H), 1.93 (d, J=0.9, 3H), 1.70 (d, J=0.9, 3H).

B. 2-Isobutylaniline. To a solution of 1-(2-methylprop-1-enyl)-2-nitrobenzene (0.48 g, 2.71 mmol) in ethanol (15 mL), palladium on carbon (10%, 0.3 g) was added. The reaction was stirred under an atmosphere of hydrogen for 1-2 h. LCMS at 2 h (M+1=150.6) showed the reaction was complete. The mixture was filtered through a pad of celite, rinsed with ethanol, and concentrated. The residue was purified via Biotage (90% hexanes in EtOAc; 40+S column). Concentration of the desired fractions afforded the product (0.34 g, 85%). MS (ESI) m/z 150.6[M+1]$^+$.

C. (Z)-1-(2-Amino-1,2-dicyanovinyl)-3-(2-isobutylphenyl)urea. In a 50 mL round-bottomed flask 2-isobutylaniline (0.34 g, 2.300 mmol) and trichloromethyl carbonochloridate (0.28 mL, 2.32 mmol) were combined in toluene (3 mL). The mixture was stirred at reflux for 1 h. The solution was then concentrated. The residue was taken up in acetonitrile (10 mL). 2,3-Diaminomaleonitrile (0.249 g, 2.300 mmol) was added. The mixture was stirred at rt for 24 h. The reaction mixture was filtered to afford the title compound (0.6 g, 2.1 mmol, 90%). MS (ESI) m/z 284.5[M+1]$^+$.

D. 2-(3-Hydroxyphenyl)-9-(2-isobutylphenyl)-8-oxo-8,9-dihydro-7H-purine-6-carboxamide. (Z)-1-(2-Amino-1,2-dicyanovinyl)-3-(2-isobutylphenyl)urea (0.595 g, 2.100 mmol) and 3-hydroxybenzaldehyde (0.641 g, 5.25 mmol) were combined in methanol (10 mL) and triethylamine (1 mL) according to General Procedure B. The reaction mixture was concentrated and the resulting residue was purified via Biotage (50% hexanes in EtOAc; 40+S column). Concentration of the desired fractions afforded the title compound (0.22 g, 25%, 97.9% pure). $^1$H NMR (400 MHz, DMSO-d$_6$) δ 11.79 (s, 1H), 9.50 (s, 1H), 8.43 (s, 1H), 8.01 (s, 1H), 7.91 (d, J=8.0, 1H), 7.71 (t, J=2.0, 1H), 7.59 (t, J=8.8, 1H), 7.24 (t, J=8.0, 1H), 7.17 (dd, J=12, 2.4, 1H), 7.10 (dd, J=9.2, 2.4, 1H), 6.83 (dd, J=8.0, 1.6, 1H), 2.37 (d, J=7.2, 2H), 1.68 (sept, J=2.8, 1H), 0.72 (d, J=6.8, 3H), 0.67 (d, J=6.4, 3H); MS (ESI) m/z 404.3 [M+1]$^+$; mp>260° C.

5.1.156 Example 156

Synthesis of (R)-2-(3-HYDROXYPHENYL)-8-OXO-9-(TETRAHYDROFURAN-3-YL)-8,9-DIHYDRO-7H-PURINE-6-CARBOXAMIDE A. (R)-3-Isocyanatotetrahydrofuran toluene sulfonate salt. (R)-Tetrahydrofuran-3-amine toluene sulfonic acid salt (0.75 g, 2.91 mmol) was diluted with toluene (15 mL). Trichlormethyl carbonchloridate (0.577 g, 2.91 mmol) was added to the solution and the mixture heated to 100° C. After 3 h, the solution was condensed under reduced pressure and used without purification (quantitative).

B. (R,Z)-1-(2-Amino-1,2-dicyanovinyl)-3-(tetrahydrofuran-3-yl)urea. (R)-3-Isocyanatotetrahydrofuran toluene sulfonate salt (0.327 g, 2.89 mmol) and diaminomaleonitrile (0.625 g, 5.78 mmol) were reacted according to General Procedure A in tetrahydrofuran (10 mL) and purified via reverse-phase preparative HPLC (0-10% acetonitrile+0.1% TFA in H$_2$O+0.1% TFA, over 35 min) to afford the title compound (0.404 g, 63%). MS (ESI) m/z 222.2 [M+1]$^+$.

C. (R)-2-(3-Hydroxyphenyl)-8-oxo-9-(tetrahydrofuran-3-yl)-8,9-dihydro-7H-purine-6-carboxamide. (R,Z)-1-(2-Amino-1,2-dicyanovinyl)-3-(tetrahydrofuran-3-yl)urea (0.404 g, 2.26 mmol), 3-hydroxybenzaldehyde (0.554 g, 4.53 mmol) and triethylamine (0.63 mL, 4.53 mmol) in methanol (15 mL) were reacted according to General Procedure B to afford the title compound (0.094 g, 12%). $^1$H NMR (400 MHz, DMSO-d$_6$) δ 11.75 (s, 1H), 9.53 (s, 1H), 8.34 (s, 1H), 7.99 (d, J=9.19, 1H), 7.93 (s, 1H), 7.87 (s, 1H), 7.28 (t, J=7.99, 1H), 6.88 (d, J=7.99, 1H), 5.07 (m, 1H), 4.25 (q, J=7.99, 1H), 3.99 (m, 3H), 2.30 (m, 1H); MS (ESI) m/z 342.1 [M+1]$^+$; mp 353-355° C.

5.1.157 Example 157

Synthesis of (S)-2-(3-HYDROXYPHENYL)-8-OXO-9-(TETRAHYDROFURAN-3-YL)-8,9-DIHYDRO-7H-PURINE-6-CARBOXAMIDE A. (S)-3-Isocyanatotetrahydrofuran toluene sulfonate salt. (S)-Tetrahydrofuran-3-amine toluene sulfonic acid salt (0.75 g, 2.91 mmol) was diluted with toluene (15 mL). Trichloromethyl carbonchloridate (0.577 g, 2.91 mmol) was added to the solution and the mixture heated to 100° C. After 3 h, the solution was condensed under reduced pressure and used without purification (quantitative).

B. (S,Z)-1-(2-Amino-1,2-dicyanovinyl)-3-(tetrahydrofuran-3-yl)urea. (S)-3-Isocyanato tetrahydrofuran toluene sulfonate salt (0.825 g, 7.29 mmol) and diaminomaleonitrile (1.57 g, 14.59 mmol) were reacted according to General Procedure A in tetrahydrofuran (10 mL) and purified via reverse-phase preparative HPLC (0-10% acetonitrile+0.1% TFA in H$_2$O+0.1% TFA, over 35 min) to afford the title compound (0.636 g, 39%). MS (ESI) m/z 222.2 [M+1]$^+$.

C. (S)-2-(3-Hydroxyphenyl)-8-oxo-9-(tetrahydrofuran-3-yl)-8,9-dihydro-7H-purine-6-carboxamide. (S,Z)-1-(2-Amino-1,2-dicyanovinyl)-3-(tetrahydrofuran-3-yl)urea (0.636 g, 3.57 mmol), 3-hydroxybenzaldehyde (0.872 g, 7.14 mmol) and triethylamine (1.0 mL, 4.53 mmol) in methanol (15 mL) were reacted according to General Procedure B to afford the title compound (0.120 g, 10%). $^1$H NMR (400 MHz, DMSO-d$_6$) δ 11.75 (s, 1H), 9.53 (s, 1H), 8.34 (s, 1H), 7.99 (d, J=9.19, 1H), 7.93 (s, 1H), 7.87 (s, 1H), 7.28 (t, J=7.99, 1H), 6.88 (d, J=7.99, 1H), 5.07 (m, 1H), 4.25 (q, J=7.99, 1H), 3.99 (m, 3H), 2.30 (m, 1H); MS (ESI) m/z 342.1 [M+1]$^+$; mp 354-356° C.

5.1.158 Example 158

Synthesis of 2-(4-(1H-1,2,3-TRIAZOL-5-yl)Phenyl)-9-(2-ISOPROPYLPHENYL)-8-OXO-8,9-DIHYDRO-7H-Purine-6-CARBOXAMIDE A. ((4-(Diethoxymethyl)phenyl)ethynyl)trimethylsilane. A 20 mL microwave reaction vial was filled with DMF (10 mL). The solvent was degassed for 5 min before adding 1-bromo-4-(diethoxymethyl)benzene (3.89 g, 15.0 mmol), trimethylsilylacetylene (6.31 mL, 45.0 mmol), bis(triphenylphosphine)palladium (II) chloride (0.316 g, 0.450 mmol), copper (I) iodide (0.171 g, 0.900 mmol) and 1,1,3,3-tetramethylguanidine (5.65 mL, 45.0 mmol). The resulting mixture was degassed for another 2 min and then split between two 20 mL microwave reaction vials due to volume. The reaction mixtures were heated at 150° C. for 20 min in a Biotage Emrys Optimizer microwave reactor. The two reaction mixtures were combined and then filtered to remove any solids. The liquid volume was reduced by half under reduced pressure. Water (20 mL) was added to the remaining liquid and the resulting solution was extracted with methylene chloride (3×30 mL). The organic layers were combined, dried over magnesium sulfate and filtered through Celite. Solvent was removed under reduced pressure. The dark brown oil was carried to the next step without further purification. $^1$H NMR (300 MHz, CDCl$_3$) δ 7.46 (d, J=8.4, 2H), 7.40 (d, J=8.4, 2H), 5.50 (s, 1H), 3.60-3.50 (m, 4H), 1.25-1.20 (m, 6H), 0.25 (s, 9H).

B. 1-(Diethoxymethyl)-4-ethynylbenzene. To a 50 mL round-bottomed flask was added ((4-(diethoxymethyl)phenyl)ethynyl)trimethylsilane (4.15 g, 15.0 mmol) and tetrabutyl ammonium fluoride on silica gel (4.31 g, 16.5 mmol) in tetrahydrofuran (15 mL) to give a brown suspension. The mixture was stirred at room temperature for 5 h and then filtered to remove solids. Water (20 mL) was added to the reaction mixture, which was then extracted with methylene chloride (3×40 mL). The combined extracts were dried over magnesium sulfate and the solvent was removed under reduced pressure. The dark brown residue was purified using Biotage column chromatography (gradient 0-10% EtOAc in hexanes) leaving a clear, yellow oil (1.92 g, 63% over two steps). $^1$H NMR (300 MHz, CDCl$_3$) δ 7.49 (d, J=8.4, 2H), 7.44 (d, J=8.4, 2H), 5.50 (s, 1H), 3.61-3.51 (m, 4H), 3.08 (s, 1H), 1.24 (t, J=6.9, 6H).

C. 4-(4-(Diethoxymethyl)phenyl)-1H-1,2,3-triazole. A 35 mL sealed tube was filled with dimethylformamide (7.27 mL) and methanol (0.808 mL). 1-(Diethoxymethyl)-4-ethynylbenzene (0.825 g, 4.04 mmol), trimethylsilyl azide (0.804 mL, 6.06 mmol) and copper (I) iodide (0.038 g, 0.202 mmol) were added and the reaction was stirred at 100° C. for 24 h. Precipitates were removed and the filtrate was concentrated under reduced pressure. The oil was dissolved in ethyl acetate (20 mL) and rinsed with water (20 mL). The aqueous was extracted with ethyl acetate (2×20 mL). The organic layers were combined and dried over magnesium sulfate. The solvent was evaporated under reduced pressure leaving a light brown oil. Purification using Biotage column chromatography (gradient 0-20% MeOH in CH$_2$Cl$_2$) provided a white solid (0.600 g, 60%).

D. 4-(1H-1,2,3-Triazol-4-yl)benzaldehyde. 4-(4-(Diethoxymethyl)phenyl)-1H-1,2,3-triazole (0.600 g, 2.43 mmol) was stirred in a solution of 4 M HCl in dioxane (15 mL, 4.85 mmol). The pale yellow solid that precipitated was collected and rinsed with hexanes. The solid was added to water (10 mL) and 1 M NaOH was added until the pH was between 7-8. The solution was extracted with ethyl acetate (3×20 mL) and dried over magnesium sulfate. Solvents were removed under reduced pressure yielding a clear, pale yellow oil (0.250 g, 60%). The product was greater than 95% pure and was carried to the next step without further purification. $^1$H NMR (300 MHz, CDCl$_3$) δ 10.06 (s, 1H), 8.08 (s, 1H), 8.03 (d, J=6.6, 2H), 7.98 (d, J=6.6, 2H).

E. 2-(4-(1H-1,2,3-Triazol-5-yl)phenyl)-9-(2-isopropylphenyl)-8-oxo-8,9-dihydro-7H-purine-6-carboxamide. (Z)-1-(2-Amino-1,2-dicyanovinyl)-3-(2-isopropylphenyl)urea (0.311 mg, 1.16 mmol) was dissolved in methanol (7 mL) and stirred at room temperature until homogeneous. 4-(1H-1,2,3-Triazol-5-yl)benzaldehyde (0.100 g, 0.577 mmol) and triethylamine (0.121 ml, 0.866 mmol) were added sequentially. The reaction solution was stirred at room temperature for 24 h. The resulting heterogeneous mixture was filtered. The precipitate was collected and recrystallized by dissolving in warm DMF (1 mL) and adding water dropwise. The solid was collected and dried in a vacuum oven for 48 h yielding a pale yellow solid (0.080 g, 32% over two steps). $^1$H NMR (400 MHz, DMSO-d$_6$) δ 11.84 (s, 1H), 8.56 (s, 1H), 8.44 (d, J=6.3, 2H), 8.31 (s, 1H), 8.02 (s, 1H), 7.92 (d, J=6.3, 2H), 7.62-7.55 (m, 2H), 7.42-7.39 (m, 2H), 2.75 (septet, J=7.2, 1H), 1.13 (d, J=7.2, 3H), 1.12 (d, J=7.2, 3H); MS (ESI) m/z 441.1[M+1]$^+$.

5.1.159 Example 159

Synthesis of 2-(3-(AMINOMETHYL)PHENYL)-9-(2-METHOXYPHENYL)-8-OXO-8,9-DIHYDRO-7H-PURINE-6-CARBOXAMIDE A. tert-Butyl 3-(6-carbamoyl-9-(2-methoxyphenyl)-8-oxo-8,9-dihydro-7H-purin-2-yl)benzylcarbamate. (Z)-1-(2-Amino-1,2-dicyanovinyl)-3-(2-methoxyphenyl)urea (0.200 g, 0.777 mmol) was dissolved in methanol (5 mL) and stirred at room temperature until homogeneous. tert-Butyl 3-formylbenzylcarbamate (0.183 g, 0.777 mmol) and triethylamine (0.108 mL, 0.777 mmol) were added sequentially. The reaction solution was stirred at room temperature for 16 h. The resulting heterogeneous mixture was filtered and rinsed with cold methanol yielding a white solid (0.247 g, 65% yield). MS (ESI) m/z 491.6 [M+1]$^+$.

B. 2-(3-(Aminomethyl)phenyl)-9-(2-methoxyphenyl)-8-oxo-8,9-dihydro-7H-purine-6-carboxamide. tert-Butyl 3-(6-carbamoyl-9-(2-methoxyphenyl)-8-oxo-8,9-dihydro-7H-purin-2-yl)benzylcarbamate (0.100 g, 0.204 mmol) was stirred in a solution of 4 M HCl in dioxane (4.0 mL, 16 mmol) for 5 h. The resulting heterogeneous mixture was filtered and rinsed with methylene chloride. The resulting solid was added to water (1 mL) and neutralized with saturated sodium bicarbonate. The precipitate was collected and recrystallized by dissolving in warm DMF (1 mL) and adding water dropwise. The solid was dried in a vacuum oven for 48 h yielding a white solid (0.050 g, 63%). $^1$H NMR (400 MHz, DMSO-d$_6$) δ 8.62 (s, 1H), 8.36 (s, 1H), 8.14 (dt, J=7.3, 1.6, 1H), 7.95 (s, 1H), 7.56-7.52 (m, 1H), 7.46 (dd, J=7.8, 2.0, 1H), 7.41-7.34 (m, 2H), 7.28 (dd, J=8.6, 1.2, 1H), 7.14 (td, J=7.5, 1.4, 1H), 3.83 (s, 2H), 3.74 (s, 3H); MS (ESI) m/z 391.0 [M+1]$^+$.

5.1.160 Example 160

Synthesis of 2-(4-(1H-1,2,4-TRIAZOL-3-YL)PHENYL)-9-(CIS-4-METHOXYCYCLOHEXYL)-8-OXO-8,9-DIHYDRO-7H-PURINE-6-CARBOXAMIDE A. cis-(1-Isocyanato-4-methoxycyclohexane. A suspension of cis-4-methoxy-cyclohexanamine (1.89 g, 11.41 mmol) in toluene (50 mL) and diphos gene (2.25 g, 11.41 mmol) was heated to 100° C. for 5 h. Solvent was removed under reduced pressure and product was dried on high vacuum overnight. This material was used without further purification or characterization.

B. 1-((Z)-2-Amino-1,2-dicyanovinyl)-3-(cis-4-methoxycyclohexyl)urea. A solution of cis-1-isocyanato-4-methoxycyclohexane (1.77 g, 11.41 mmol) and (1Z)-1,2-diaminoethene-1,2-dicarbonitrile (1.23 g, 11.41 mmol) in anhydrous tetrahydrofuran (50 mL) was allowed to stir at room temperature overnight. Volatiles were removed under reduced pressure and the resulting solid was purified via reverse-phase semi-prepatory HPLC (20-100% acetonitrile+0.1% TFA in $H_2O$+0.1% TFA, over 30 min). Product containing fractions were combined and solvent removed. A solution of saturated sodium bicarbonate was added and product was extracted with EtOAc (4×25 mL). Pooled organics were dried over sodium sulfate and concentrated to afford the title compound (1.12 g, 4.25 mmol, 37%) as a yellow solid.

C. 2-(4-(1H-1,2,4-Triazol-3-yl)phenyl)-9-(cis-4-methoxycyclohexyl)-8-oxo-8,9-dihydro-7H-purine-6-carboxamide. 1-((Z)-2-Amino-1,2-dicyanovinyl)-3-(cis-4-methoxycyclohexyl)urea (375 mg, 1.42 mmol), 4-(1H-1,2,4-triazol-3-yl)benzaldehyde (See 108.B) (450 mg, 2.60 mmol), triethylamine (0.32 mL, 2.28 mmol) and methanol (8 mL) were reacted according to General Procedure B. The solution was allowed to stir at room temperature overnight. The resultant heterogeneous mixture was filtered and purified via reverse-phase semi-prepatory HPLC (20-100% acetonitrile+ 0.1% TFA in $H_2O$+0.1% TFA, over 30 min). The volatiles were removed under reduced pressure, treated with saturated sodium bicarbonate and extracted with ethyl acetate (3×50 mL), dried organics with sodium sulfate, and concentrated under reduced pressure. The solid was washed with diethyl ether and dried in a vacuum oven at 60° C. overnight to afford the title compound (0.037 mg, 0.085 mmol, 6.0%) as a white solid. $^1$H NMR (400 MHz, DMSO-$d_6$) δ 11.54 (s, 1H), 8.68 (m, 2H), 8.14 (d, J=8.0, 2H), 7.94 (m, 2H), 4.34 (m, 1H), 3.51 (m 1H), 3.38 (s, 3H), 2.74 (m, 2H), 2.06 (m, 4H), 1.55 (m 4H); MS (ESI) m/z 435.1 [M+1]$^+$; mp 350 dec.

5.1.161 Example 161

Synthesis of 2-(1H-BENZO[D]IMIDAZOL-6-YL)-9-((CIS-4-METHOXYCYCLOHEXYL)-8-OXO-8,9-DIHYDRO-7H-PURINE-6-CARBOXAMIDE A. 2-(1H-Benzo[d]imidazol-6-yl)-9-(cis-4-methoxycyclohexyl)-8-oxo-8,9-dihydro-7H-purine-6-carboxamide. 1-((Z)-2-Amino-1,2-dicyanovinyl)-3-(cis-4-methoxy cyclohexyl)urea (See example 160.B) (375 mg, 1.42 mmol), 1H-benzo[d]imidazole-6-carbaldehyde (See Example 84.B) (416 mg, 2.85 mmol), triethylamine (0.29 mL, 2.14 mmol) and methanol (20 mL) were reacted according to General Procedure B. The solution was allowed to stir at room temperature overnight. The resultant heterogeneous mixture was filtered and purified via reverse-phase semi-prepatory HPLC (20-100% acetonitrile+0.1% TFA in $H_2O$+0.1% TFA, over 30 min). The volatiles were removed under reduced pressure, treated with saturated sodium bicarbonate and extracted with ethyl acetate (3×50 mL). Pooled organics were dried over sodium sulfate and concentrated under reduced pressure. The solid was washed with diethyl ether and dried in a vacuum oven at 60° C. overnight to afford the title compound (0.039 mg, 0.095 mmol, 6.7%) as a white solid. $^1$H NMR (400 MHz, DMSO-$d_6$) δ 12.56 (s, 1H), 11.43 (s, 1H), 8.94 (s, 1H), 8.68 (s, 1H), 8.51 (m, 2H), 8.29 (m, 2H), 7.89 (m, 2H), 7.73 (d, J=8.0, 1H), 7.58 (d, J=8.0, 1H), 4.33 (m, 1H), 3.52 (m, 1H), 3.42 (s, 3H), 2.79 (m, 2H), 2.07 (m, 4H), 1.56 (m, 4H); MS (ESI) m/z 408.1 [M+1]$^+$; mp 345° C. dec.

5.1.162 Example 162

Synthesis of 2-(1H-IMIDAZO[4,5-b]PYRIDIN-6-YL)-9-(CIS-4-METHOXYCYCLOHEXYL)-8-OXO-8,9-DIHYDRO-7H-PURINE-6-CARBOXAMIDE A. 2-(1H-Imidazo[4,5-b]pyridin-6-yl)-9-(cis-4-methoxycyclohexyl)-8-oxo-8,9-dihydro-7H-purine-6-carboxamide. 1-((Z)-2-Amino-1,2-dicyanovinyl)-3-(cis-4-methoxycyclohexyl)urea (See example 160.B) (375 mg, 1.42 mmol), 1-(tetrahydro-2H-pyran-2-yl)-1H-imidazo[4,5-b]pyridine-6-carbaldehyde (See example 130.C) (644 mg, 2.80 mmol), triethylamine (0.4 mL, 2.80 mmol) and methanol (20 mL) were reacted according to General Procedure B. The solution was allowed to stir at room temperature overnight and the resulting precipitate was collected by filtration to give 9-(cis-4-methoxycyclohexyl)-8-oxo-2-(1-(tetrahydro-2H-pyran-2-yl)-1H-imidazo[4,5-b]pyridin-6-yl)-8,9-dihydro-7H-purine-6-carboxamide. This THP-protected intermediate (235 mg, 0.48 mmol) was dissolved in dioxane (2 mL) and a 4.0 M HCl/dioxane solution (4.0 mL) and water (0.3 mL) were added. The resulting solution was stirred at room temperature overnight. The reaction was neutralized with saturated sodium bicarbonate, extracted with EtOAc (3×50 mL), and pooled organics were dried over sodium sulfate. The crude product was purified via reverse-phase semi-prepatory HPLC (20-100% acetonitrile+0.1% TFA in H2O+0.1% TFA, over 30 min). The volatiles were removed under reduced pressure, treated with saturated sodium bicarbonate and extracted with ethyl acetate (3×75 mL). Organic layers were pooled, dried over sodium sulfate, filtered and concentrated under reduced pressure. The resulting solid was washed with diethyl ether and dried in a vacuum oven at 60° C. overnight to afford the title compound (15 mg, 0.036 mmol, 7.5%) as a white solid. $^1$H NMR (400 MHz, MeOD-$d_3$) δ 9.56 (s, 1H), 8.50 (m, 1H), 7.80 (m, 1H), 4.31 (m, 1H), 3.51 (m, 1H), 3.39 (s, 3H), 2.77 (m, 2H), 2.07 (m, 4H), 1.53 (m, 4H); MS (ESI) m/z 409.0 [M+1]$^+$; mp 360° C. dec.

5.1.163 Example 163

Synthesis of 2-(2-CHLOROPYRIDIN-3-YL)-8-OXO-9-PHENYL-8,9-DIHYDRO-7H-PURINE-6-CARBOXAMIDE A. 2-(2-Chloropyridin-3-yl)-8-oxo-9-phenyl-8,9-dihydro-7H-purine-6-carboxamide. (Z)-1-(2-Amino-1,2-dicyanovinyl)-3-phenylurea (See Example 131.A) (0.153 g, 0.67 mmol) and 2-chloronicotinaldehyde (0.191 g, 1.35 mmol) were reacted according to General Procedure B. Product was purified using reverse-phase semi-preparatory HPLC (0-50% acetonitrile+0.1% TFA in $H_2O$+0.1% TFA, over 30 min). Fractions containing the desired material were neutralized with aqueous sodium carbonate solution and then concentrated to a smaller volume. The resulting precipitate was filtered and washed with water. The resulting solid was dried under high vacuum at 60° C. to afford the title compound as a white solid (0.070 g, 0.19 mmol, 28% yield). $^1$H NMR (400 MHz, DMSO-$d_6$) δ 8.94 (dd, J=4.4, 2.0, 1H), 8.22-8.10 (m, 1H), 7.77 (d, J=7.6, 3H), 7.55-7.46 (m, 3H), 7.38-7.28 (m, 1H); MS (ESI) m/z 367.2 [M+1]$^+$; mp 283-286° C.

5.1.164 Example 164

Synthesis of 2-(2-METHOXYPYRIDIN-3-YL)-8-OXO-9-PHENYL-8,9-DIHYDRO-7H-PURINE-6-CARBOXAMIDE A. 2-(2-methoxypyridin-3-yl)-8-oxo-9-phenyl-8,9-dihydro-7H-purine-6-carboxamide. (Z)-1-(2-Amino-1,2-dicyanovinyl)-3-phenylurea (See Example 131.A) (0.400 g, 1.61 mmol) and 2-methoxynicotinaldehyde (0.44 g, 3.24 mmol) were reacted according to General Procedure B. Product was recrystallized from boiling ethanol, filtered and dried to afford a white solid (0.290 g, 0.8 mmol, 50% yield). $^1$H NMR (300 MHz, DMSO-$d_6$) δ 11.93 (s, 1H), 8.37-8.31 (m, 2H), 8.31-8.25 (brs, 1H), 8.09-8.03 (brs, 1H), 7.87-7.81 (m, 2H), 7.70-7.62 (m, 2H), 7.57-7.49 (m, 1H), 7.19 (dd, J=7.4, 4.9, 1H), 3.99 (s, 3H); MS (ESI) m/z 363.4 [M+1]$^+$; mp 279-281° C.

5.1.165 Example 165

Synthesis of N,N-DIMETHYL-8-OXO-9-PHENYL-2-(PYRIDIN-3-YL)-8,9-DIHYDRO-7H-PURINE-6-CARBOXAMIDE A. N,N-dimethyl-8-oxo-9-phenyl-2-(pyridin-3-yl)-8,9-dihydro-7H-purine-6-carboxamide. To a solution of 8-oxo-9-phenyl-2-(pyridin-3-yl)-8,9-dihydro-7H-purine-6-carboxylic acid (See Example 38.A) (0.290 g, 0.87 mmole) in DMSO (2 mL) was added diisopropylethylamine (1.6 g, 12.4 mmole), dimethylamine hydrochloride (0.633 g, 7.81 mmole) and benzotriazol-1-yloxy-tris(dimethylamino)-phosphonium hexafluorophosphate (0.580 g, 1.30 mmole). The mixture was sonicated for 5 min to dissolve all components of the mixture. After stirring 10 min starting material was consumed (monitored by LCMS). Solvent was removed and the product was purified using reverse-phase semi-preparatory HPLC (10-50% acetonitrile+0.1% TFA in H$_2$O+0.1% TFA, over 30 min). Fractions containing the desired material were combined and concentrated under reduced pressure before being passed through a Strata-XC ion exchange column with water, methanol, and 5% ammonium hydroxide in methanol. The resulting solid was dried under high vacuum at 60° C. to afford the title compound as a white solid (0.037 g, 0.10 mmol, 12% yield). $^1$H NMR (400 MHz, DMSO-$d_6$) δ 12.05 (s, 1H), 9.35 (d, J=2.1, 1H), 8.65 (dd, J=4.8, 1.8, 1H), 8.49 (dt, J=8.1, 2.1, 1H), 7.75 (d, J=7.8, 2H), 7.62 (t, J=7.5, 2H), 7.55-7.45 (m, 2H), 3.17 (s, 3H), 3.11 (s, 3H); MS (ESI) m/z 361.2 [M+1]$^+$; mp 250-252° C.

5.1.166 Example 166

Synthesis of 9-METHYL-8-OXO-2-(PYRIDIN-3-YL)-8,9-DIHYDRO-7H-PURINE-6-CARBOXAMIDE A. 9-Methyl-8-oxo-2-(pyridin-3-yl)-8,9-dihydro-7H-purine-6-carboxamide. (Z)-1-(2-Amino-1,2-dicyanovinyl)-3-methylurea (0.730 g, 4.42 mmol) and 3-pyridine carboxaldehyde (1.04 g, 9.73 mmol) were reacted according to General Procedure B. Product was purified using reverse-phase semi-preparatory HPLC (10-40% acetonitrile+0.1% TFA in H$_2$O+0.1% TFA, over 30 min). Fractions containing the desired material were neutralized with aqueous sodium carbonate solution and then concentrated to a smaller volume. The resulting precipitate was filtered and washed with water. The resulting solid was dried under high vacuum at 60° C. to afford the title compound as a solid (0.073 g, 0.268 mmol, 6% yield). $^1$H NMR (300 MHz, DMSO-$d_6$) δ 11.6 (s, 1H), 9.73 (d, J=1.9, 1H), 8.89 (dt, J=10.1, 2.0, 1H), 8.68 (dd, J=4.8, 1.7, 1H), 8.58 (brs, 1H), 7.96 (s, 1H), 7.53 (dd, J=7.8, 4.9, 1H), 3.41 (s, 3H); MS (ESI) m/z 271.5 [M+1]$^+$; mp>350° C.

5.1.167 Example 167

Synthesis of 2-(3-CYANOPHENYL)-8-OXO-9-PHENYL-8,9-DIHYDRO-7H-PURINE-6-CARBOXAMIDE A. 2-(3-Cyanophenyl)-8-oxo-9-phenyl-8,9-dihydro-7H-purine-6-carboxamide. (Z)-1-(2-amino-1,2-dicyanovinyl)-3-phenylurea (See Example 131.A) (0.25 g, 1.10 mmol) and 3-cyano carboxaldehyde (0.314 g, 2.4 mmol) were reacted according to General Procedure B. Product was purified using reverse-phase semi-preparatory HPLC (30-80% acetonitrile+0.1% TFA in H$_2$O+0.1% TFA, over 30 min). Fractions containing the desired material were neutralized with aqueous sodium carbonate solution and then concentrated to a smaller volume. The resulting precipitate was filtered and washed with water. The resulting solid was dried under high vacuum at 60° C. to afford the title compound as a white solid (0.078 g, 0.22 mmol, 20% yield). $^1$H NMR (400 MHz, DMSO-$d_6$) δ 11.92 (s, 1H), 8.88 (bs, 2H), 8.61 (d, J=8.0, 1H), 7.98-7.86 (m, 2H), 7.75 (d, J=7.6, 2H), 7.67 (t, J=8.0, 1H), 7.60 (t, J=8.0, 2H), 7.49-7.42 (m, 1H); MS (ESI) m/z 358.0 [M+1]$^+$; mp 328-330° C.

5.1.168 Example 168

Synthesis of 6-OXO-8-PHENYL-2-(PYRIDIN-4-YL)-5,6,7,8-TETRAHYDROPTERIDINE-4-CARBOXAMIDE A. Ethyl 2-chloro-6-((2-ethoxy-2-oxoethyl)(phenyl)amino)-5-nitropyrimidine-4-carboxylate. A solution of ethyl 2,6-dichloro-5-nitropyrimidine-4-carboxylate (1.5 g, 5.67 mmol) in anhydrous tetrahydrofuran (20 mL) was chilled to −78° C. under nitrogen. A solution of ethyl 2-(phenylamino)acetate (1.1 g, 6.22 mmol) and diisopropylethylamine (3.0 mL, 17.01 mmol) in anhydrous tetrahydrofuran (10 mL) was then added dropwise, with stirring, over 10 min. The reaction was stirred at −78° C. for 6 h, followed by addition of aqueous sodium bicarbonate solution (saturated, 10 mL). The mixture was extracted with ethyl acetate (3×10 mL). The organic phase was dried over sodium sulfate and concentrated to a residue which was purified by chromatography on a normal phase silica gel column (0-10% ethyl acetate in hexanes). Fractions containing product were combined and the solvent evaporated to provide the title compound (1.1 g, 2.89 mmol, 41% yield). MS (ESI) m/z 409.5 [M+1]$^+$.

B. Ethyl 2-chloro-6-oxo-8-phenyl-5,6,7,8-tetrahydropteridine-4-carboxylate. To a solution of ethyl 2-chloro-6-((2-ethoxy-2-oxoethyl)(phenyl)amino)-5-nitropyrimidine-4-carboxylate (1.7 g, 4.16 mmol) in glacial acetic acid (20.0 mL) was added iron powder (1.2 g, 20.8 mmole). The grey suspension was heated to 60° C. for 12 h. Additional iron powder (total of 3.4 g) was added over the next 24 h. The acetic acid was removed under reduced pressure and the residue was suspended in methanol, filtered through a short Celite pad and concentrated under reduced pressure to a residue. The resulting residue was purified by chromatography on a normal phase silica gel column (20-40% ethyl acetate in hexanes). Fractions containing product were combined and the solvent evaporated to provide the title compound (0.595 g, 1.78 mmol, 43% yield). MS (ESI) m/z 333.2 [M+1]$^+$.

C. Ethyl 6-oxo-8-phenyl-2-(pyridin-4-yl)-5,6,7,8-tetrahydropteridine-4-carboxylate. To a solution of ethyl 2-chloro-6-oxo-8-phenyl-5,6,7,8-tetrahydropteridine-4-carboxylate (0.160 g, 0.48 mmol) in anhydrous DMF (6.7 mL) was added 4-(tributylstannyl)pyridine (0.884 g, 2.40 mmol), and dichlorobis(triphenylphosphine)palladium(II) (0.170 g, 0.24 mmol). The solution was purged with nitrogen then heated in a Biotage Emrys Optimizer microwave reactor for 30 min at 120° C. The volatiles were evaporated and the resulting residue was purified by chromatography on a normal phase silica gel column (1-10% methanol in dichloromethane). Fractions containing product were combined and the solvent evaporated. The material was re-purified using reverse-phase preparatory HPLC (10-70% acetonitrile+0.1% TFA in H$_2$O+0.1% TFA, over 30 min). Fractions containing the desired material were combined and concentrated under reduced pressure to afford a residue. The residue was dissolved in methylene chloride (100 mL) which was washed with aqueous potassium carbonate solution (saturated, 10 mL) and dried over sodium sulfate. The organic phase was concentrated and the resulting solid was dried under high vacuum at 60° C. to afford the title compound (0.090 g, 0.24 mmol, 50% yield). MS (ESI) m/z 376.4 [M+1]$^+$.

D. 6-Oxo-8-phenyl-2-(pyridin-4-yl)-5,6,7,8-tetrahydropteridine-4-carboxamide. A solution of ethyl 6-oxo-8-phenyl-2-(pyridin-4-yl)-5,6,7,8-tetrahydropteridine-4-carboxylate (0.037 g, 0.098 mmol) in anhydrous methanol (15 mL) was chilled to −78° C. The solution was then saturated with ammonia gas. The reaction vessel was sealed at −78° C. and allowed to warm to room temperature. After 18 h the reaction was chilled to −78° C. and opened to atmosphere. The volatiles were evaporated and the resulting solids dried under vacuum to provide the title compound (0.029 g, 0.083 mmol, 85% yield). $^1$H NMR (400 MHz, DMSO-d$_6$) δ 11.4 (s, 1H), 8.83 (s, 1H), 8.62 (d, J=4.5, 2H), 8.25 (s, 1H), 8.11-8.09 (m, 2H), 7.55-7.50 (m, 4H), 7.39-7.35 (m, 1H), 4.67 (s, 2H); MS (ESI) m/z 347.2 [M+1]$^+$; mp 298-304° C.

5.1.169 Example 169

Synthesis of 2-(3-HYDROXYPHENYL)-9-((1R,4R)-4-(METHOXYMETHYL)CYCLOHEXYL)-8-OXO-8,9-DIHYDRO-7H-PURINE-6-CARBOXAMIDE A. tert-Butyl (1r,4r)-4-(hydroxymethyl)cyclohexylcarbamate. tert-Butyl-trans-4-aminocyclohexanecarboxylic acid (1.5 g, 6.17 mmol) was diluted with tetrahydrofuran (20 ml) and cooled to −10° C. N-Methylmorpholine (0.624 g, 6.17 mmol) and isobutylchloroformate (1.12 g, 8.23 mmol) were added and the reaction was stirred for ten min. Sodium borohydride (0.842 g, 6.17 mmol) was then added in one portion. After two min, methanol (5 mL) was added dropwise and the reaction was stirred at 0° C. for thirty min. The solution was then diluted with dichloromethane, partitioned with 5% sodium hydroxide solution (3×), dried over magnesium sulfate, filtered and solvent removed under reduced pressure to afford the title compound without purification (1.85 g, quantitative).

B. tert-Butyl (1r,4r)-4-(methoxymethyl)cyclohexylcarbamate. Sodium hydride (0.216 g, 8.98 mmol) was suspended in tetrahydrofuran (30 mL) and stirred at 0° C. (1r,4r)-4-(Hydroxymethyl)cyclohexylcarbamate (1.0 g, 5.99 mmol) and 15-crown-5-ether (1.385 g, 6.29 mmol) were then added the stirred for 30 min. Methyl iodide (0.393 mL, 8.98 mmol) was then added and the solution stirred at ambient temperature for 16 h. The reaction was not complete. Additional sodium hydride (1.0 equiv.) was added and stirring continued. Once starting material was consumed (monitored by TLC), the solution was condensed under reduced pressure and partitioned between ethyl acetate and water (3×). The organics were combined, dried over magnesium sulfate, filtered and solvent removed under reduced pressure. The resultant oil was purified via Biotage chromatography (0 to 50% ethyl acetate in hexanes) to afford the title compound (0.280 g, 26%). MS (ESI) m/z 188.3 [M+1]$^+$.

C. (1r,4r)-4-(Methoxymethyl)cyclohexanamine. Tert-butyl (1r,4r)-4-(methoxymethyl)cyclohexylcarbamate (0.28 g, 1.15 mmol) was dissolved in 1,4-dioxane (3 mL). 4.0N Hydrochloric acid in dioxane (2 mL) was added and the solution stirred at ambient temperature for 16 h. The solution was condensed under reduced pressure to afford the hydrochloride salt of the title compound (0.207 g, quantitative). MS (ESI) m/z 144.3 [M+1]$^+$.

D. (1r,4r)-1-Isocyanato-4-(methoxymethyl)cyclohexane. (1r,4r)-4-(methoxymethyl)cyclohexanamine hydrochloride (0.207 g, 1.15 mmol) was diluted with toluene (15 mL) and trichloromethyl carbonchloridate (0.228 g, 1.15 mmol) in toluene (5 mL) was added to the solution. The mixture was stirred at 105° C. for three h. The solution was condensed to give an oil and used without purification (quantitative yield).

E. 1-((Z)-2-Amino-1,2-dicyanovinyl)-3-((1r,4r)-4-(methoxymethyl)cyclohexyl)urea. (1r,4r)-1-Isocyanato-4-(methoxymethyl)cyclohexane (0.195 g, 1.15 mmol) was dissolved in tetrahydrofuran (10 mL) followed by the addition of diaminomaleonitrile (0.125 g, 1.15 mmol). The solution was allowed to stir at ambient temperature for 16 h. Solution was purified via reverse-phase-preparative HPLC (20-100% acetonitrile+0.1% TFA in H$_2$O+0.1% TFA, over 30 min) to afford the title compound (0.186 g, 62%). MS (ESI) m/z 278.5 [M+1]$^+$.

F. 2-(3-Hydroxyphenyl)-9-((1r,4r)-4-(methoxymethyl)cyclohexyl)-8-oxo-8,9-dihydro-7H-purine-6-carboxamide. 1-((Z)-2-Amino-1,2-dicyanovinyl)-3-((1r,4r)-4-(methoxymethyl)cyclohexyl)urea (0.180 g, 0.649 mmol), 3-hydroxybenzaldehyde (0.159 g, 1.29 mmol) and triethyl amine (0.2 mL, 1.43 mmol) were combined in methanol (10 mL). The solution stirred at ambient temperature for 16 h. The product precipitate was filtered and washed with acetonitrile and dried under reduced pressure to afford the title compound (0.042 g, 16%). $^1$H NMR (400 MHz, DMSO-d$_6$) δ 11.50 (s, 1H), 9.55 (s, 1H), 8.32 (s, 1H), 8.01 (d, J=7.99, 1H), 7.90 (m, 2H), 7.28 (t, J=7.59, 1H), 6.87 (dd, J=6.79, 1.59, 1H), 4.24 (m, 1H), 3.27 (s, 3H), 3.23 (d, J=6.39, 2H), 2.42 (m, 2H), 1.90 (d, J=11.59, 2H), 1.81 (d, J=11.59, 2H), 1.70 (s, 1H), 1.35 (q, J=14.79, 2H); MS (ESI) m/z 398.1 [M+1]$^+$; mp 354-356° C.

5.2 Biological Examples 5.2.1 MG63 pS6 MesoScale Assay

The following is an example of an assay that can be used to determine the anticancer activity of a test compound.

MG63 human osteosarcoma cells (ATCC: CRL-1427) (passage 7-15) are used in this assay. Cells are maintained using DMEM (high glucose with L-glutamine), 10% FBS and Pen/Strep. The following buffers are used: Complete Tris Lysis Buffer (for 10 ml use: 100 µl phosphatase inhibitor I (100× stock), 100 µl phosphatase inhibitor II (100× stock), 1 tablet Complete Mini (EDTA-free), 40 µl PMSF, all mixed thoroughly for 5 minutes at room temperature); 1×Tris wash Buffer (for 250 ml use: 25 ml 10×Tris wash buffer, 225 ml deionized water, store at room temperature); MSD blocking solution-A (for 20 ml use: 20 ml 1×tris wash buffer and 600 mg MSD blocker A, store on ice); Antibody dilution buffer (for 3 ml use: 1 ml blocking solution-A, 1.82 ml 1×tris wash buffer, 150 µl 2% MSD blocker D-M, 30 µl 10% MSD blocker D-R, store on ice).

On day one in the afternoon, cells are plated in 96-well flat bottom cell culture plates at 5000 cells/well in 100 µl of volume. On day 2 in the morning, test compounds are diluted to the desired concentration and added to the cells. Cells are treated with compound for 16-24 hours at 37° C., 0.5% $CO_2$.

Plates are blocked about 5 minutes before compound treatment is complete by adding 150 µl of MSD blocking solution-A to the plate and incubating with vigorous shaking at room temperature for 1 hour.

Cells are harvested and lysates are prepared by removing the medium with a multi-channel pipette, washing 1× with ice-cold PBS (Ca-free, Mg-free), adding 50 µl/well of Complete Tris Lysis Buffer and incubating with shaking at 4° C. for 1 hour.

Lysate samples are added to an MSD multi-spot plate by pipetting cell lysates up and down about 4-5 times, transferring 25 µl/well to an MSD multi-spot plate ($R_A$ for negative control and $R_B$ for positive control) (lysis buffer is only added to background wells) and incubating with vigorous shaking at room temperature for 2 hours.

Detection antibody is added by diluting anti-pS6 antibody (SULFO-TAG labeled, light sensitive) in 3 ml of cold antibody dilution buffer to a final concentration of 10 nM, adding 25 µl/well of 10 nM detection antibody to MSD plate, incubating with vigorous shaking at room temperature in the dark for 1 hour and washing the plate 4 times with 1×tris wash buffer.

The plate is read by adding 150 µl/well of 1× read buffer T (with surfactant) and using, for example, an MSD SECTOR plate reader and an appropriate program for data analysis.

5.2.2 mTOR HTR-FRET Assay

The following is an example of an assay that can be used to determine the mTOR inhibitory activity of a test compound. Reagents are prepared as follows:

"Simple TOR buffer" (used to dilute high glycerol TOR fraction): 10 mM Tris pH 7.4, 10 mM NaCl, 0.1% Tween-20, 1 mM DTT (from 1M stock frozen at −20° C. just prior to use). For convenience a large quantity of "Simple TOR buffer" w/o DTT can be stored at 4° C. It can be brought to room temperature and DTT added just prior to dilution of TOR fraction.

5×KB/5×Mn/5×ATP solution (used to dilute substrate GST-p70S6kin 81 a.a. just prior to use) (40 ml screen quantity shown):

| 0.075 mM ATP | 30 µL 0.1M ATP (made fresh from powder) |
| 12.5 mM $MnCl_2$ | 500 µL 1M $MnCl_2$ |
| 50 mM Hepes, pH 7.4 | 2 ml 1M Hepes, pH 7.4 |
| 50 mM β-GOP | 2 ml 1M β-GOP |
| 250 nM Microcystin LR | 500 µL 20 µM Microcystin LR (in DMSO) |
| 0.25 mM EDTA | 20 µL 0.5M EDTA |
| 5 mM DTT | 200 µL 1M DTT |
| dd$H_2O$ | 34.752 ml |

Enzyme solution: Dilute TOR fraction 1:14 in "Simple TOR Buffer". For current lot that is 640 µg/ml TOR fraction diluted 14× to yield 45.7 µg/ml TOR in buffer (i.e. 7.85 ml TOR pooled fraction+102.1 ml Simple TOR buffer=110 ml 14× diluted TOR fraction). Each Enzyme Lot must be QC'd prior to assay.

Substrate solution: This may be prepared just prior to assay if preferred. Dilute 5.3 mg/ml GST-p70S6kinase fragment stock to 3.5 µg/ml (97 nM) working stock in 5×KB/5×Mn/5× ATP solution (i.e. 26.41 µL (5.3 mg/ml) GST-p70S6+40 ml 5×KB/5×Mn/5×ATP=40 ml 3.5 µg/ml (97 nM)).

Assay Buffer (for dilution of Antibodies used in Antibody Detection Reagent):

| 50 mM Hepes, pH 7.4 | 12.5 ml 1M Hepes, pH 7.4 |
| 1 mM DTT | 250 µL 1M DTT |
| 0.01% Triton® X-100 | 250 µL 10% Triton® X-100 |
| 0.01% BSA | 25 mg BSA |
| 0.1 mM EDTA | 50 uL 0.5M EDTA |
| dd$H_2O$ | 236.5 ml |

Antibody Detection Reagent (this reagent should be made just prior to addition to Assay Plates):

| 3.056 ml | 1000 µg/ml Cy5-αGST Amersham Cat#PA92002V |
| 0.07661 ml | 1000 µg/ml α-phospho p70S6(Thr389) Cell Signalling Mouse Monoclonal #9206L |
| 0.223 ml | 690 µg/ml α-mouse Lance Eu Perkin Elmer Cat#AD0077 |
| 236.64 ml | Assay Buffer |

Using PlateTrak program (Screen) or Matrix Pipettor (SAR), 19.5 µL of diluted TOR fraction is added to assay plate in all test, reference or positive control wells. 19.5 µL of "Simple TOR buffer" is added to all negative control wells. If treating multiple plates with the same compounds, can increase volume of enzyme to multiples of 19.5 µL in a tall 384 well polypropylene plate.

Using EP3, 0.5 µl of test, reference or control DMSO is added to each well with mixing. Plates are incubated for 30 minutes at room temperature.

Using PlateTrak program (Screen) or Matrix Pipettor (SAR) 5 µL of 5×KB/5×Mn/5×ATP/5× substrate solution is added to each well of the assay plate to start the reaction. The solutions are mixed well and incubated for 2 hours at room temperature.

Using PlateTrak program (Screen) or Matrix Pipettor (SAR) 5 µL of 60 mM EDTA is added to stop the reaction. The solutions are mixed well and allowed to sit for 15-20 minutes before the next step.

Using PlateTrak program (Screen) or Matrix Pipettor (SAR) 10 µl of Antibody Detection Reagent is added. The solutions are mixes well and incubated for 5 hours to O/N to allow antibodies to form complexes with phosphorylated substrate.

Plates are read on AnalystHT using protocol Multi-Method protocol.

5.2.3 IKK2EE $^{33}P$ Assay Protocol

The following is an example of an assay that can be used to determine the IKK2EE inhibitory activity of a test compound.

A reaction buffer (pH 7.8) is prepared containing HEPES (20 mM), $MgCl_2$ (10 mM), EDTA (0.1 mM), DTT (1 mM) and Triton® X-100 (0.004%). IKK2EE (0.75 µg/ml is used.

GST-IKBα (50 µg/ml) is used as substrate. Adenosine 5'-triphosphate (1.5 µM with $^{33}$P-ATP 5 nCi/µl) is used. Reactions are stopped with trichloroacetic acid (6.25%).

Appropriate amounts of test compounds or controls in 100% DMSO are added to the assay plate. A peptide-substrate solution (PSS) is prepared by adding peptide stock to an appropriate volume of buffer (peptide concentration in the PSS will be about 100 µg/ml). An enzyme-peptide solution (EPS) is prepared by adding enzyme stock to an appropriate volume of PSS (the enzyme concentration in the EPS will be about 1 µg/ml). An ATP solution is prepared by adding ATP stock to an appropriate volume of buffer (the ATP concentration will be 15 µM).

85 µl of EPS is added to the assay wells (or PSS to positive control wells) of 96 well polypropylene plates. The ATP solution is then completed by adding $^{33}$P-ATP (to a final concentration of 50 µCi/ml).

The reaction is initiated by adding 10 µl ATP solution to each well. Plates are shaken from about 12 seconds and allowed to incubate at room temperature for 1 hours. 100 µl of trichloroacetic acid solution (12.5%) is added to stop the reaction and the plates are incubated at room temperature for at least 10 minutes. The assay plates are harvested onto a Millipore Multiscreen harvest Plate FC using an appropriate harvester and the harvest plates are washed with 1×PBS solution for about 10 seconds (continuous flow). Harvest plates are allowed to dry thoroughly and the bottoms of the plates are sealed. 20-50 µl of Microscint20 is added to each well, tops are sealed and plates are read using an appropriate scintillation counter.

5.2.4 IKK2EE NEMO HTRF Assay Protocol

The following is an example of an assay that can be used to determine the IKK2EE inhibitory activity of a test compound.

A reaction buffer (pH 7.6) is prepared containing HEPES (20 mM), MgCl$_2$ (10 mM), EDTA (0.05 mM), DTT (1 mM) and Triton® X-100 (0.004%). IKK2EE-NEMO (0.7 µg/ml is used. GST-IKBα (0.5 µg/ml) is used as substrate. Adenosine 5'-triphosphate (1.5 µM) is used. Detection reagents used are mouse anti-P-IKBα (30 ng/ml), Eu anti-mouse (300 ng/ml) and Cy5 anti-GST (11.5 µg/ml). Reactions are stopped with EDTA (20 mM).

An enzyme solution (ES) is prepared by adding enzyme stock to an appropriate volume of buffer (enzyme concentration in the ES will be about 1.7 ng/ml). A detection mixture (DM) is prepared by adding ATP (final conc. 3.75 µM), mouse anti-P-IKBα (final conc. 75 ng/ml), GST-IKBα (final conc. 1.26 µg/ml), Eu anti-mouse in buffer (final conc. 750 ng/ml).

5 µl of compound (solvated in 10% DMSO) is added to assay wells (or 10% DMSO to control wells) of low binding reaction plates. 10 µl ES is added to assay wells (or buffer to control wells) and the reaction is initiated by adding 10 µl DM to all wells. Plates are incubated at room temperature for 45 minutes. Stop mixture is prepared by adding EDTA (final conc. 70 mM) and Cy5 anti-GST (final conc. 40 µg/ml) to an appropriate volume of buffer. Stop mixture is added and plates are shaken for 20 seconds and incubated at room temperature for at least 3 hours (preferably in the dark). Plates are read on an Analyst HT using Multi-Method HTRF.

5.2.5 Tyk2 HTRF Assay Protocol (with ATP Shift Option)

The following is an example of an assay that can be used to determine the Tyk2 inhibitory activity of a test compound.

25 µl/well DMSO is added to Columns 2 and 14 (except 28.5 µl is added to well P14 of Greiner 384-well polypropylene plate). 20 µl/well DMSO is added to all remaining wells.

5 mM compound solutions are added by addition of 5 µl of 30 mM compound to 25 µl DMSO in Columns 2 and 14 of plate. 1.5 mM reference control is prepared by addition of 1.5 µl of 30 mM JAK3 Inhibitor VI to 28.5 µl DMSO in Well P14.

Serial dilution is then performed by the following steps: (i) Compounds in Column 2 are mixed by pipetting 20 µl up and down 6×; (ii) 10 µl/well compounds in DMSO are transferred from one column to the next column for Columns 2-11; (iii) wells are mixed by pipetting 20 µl up and down 6×; (iv) tips are washed 3×25 µl DMSO, 2×25 µl next DMSO; (v) steps i-iv repeated for Columns 14-23.

The following buffers are prepared:
Assay Buffer: 50 mM HEPES pH 7.6; 1 mM DTT; 10 mM MgCl$_2$; 0.01% Triton® X-100; 0.01% BSA; and 0.1 mM EDTA.

Kinase in Assay Buffer: 450 ng/ml TYK2 KD (Cama Biosciences 08-147 Lot 06CBS-3022D).

Substrate/Detection Mixture (1×ATP) in Assay Buffer: 188 nM DyLight 647-Streptavidin (Pierce 21824); 5 µM Biotin-EQEDEPEGDYFEWLE (Lyn Substrate Peptide); 750 ng/ml Eu-anti-phospho-Tyrosine (PerkinElmer AD0069); 62.5 µM ATP; 80 nM Substrate Peptide (American Peptide Company 332722).

Substrate/Detection Mixture (20×ATP) in Assay Buffer: 188 nM DyLight 647-Streptavidin; 5 µM Biotin-EQEDE-PEGDYFEWLE; 750 ng/ml Eu-anti-phospho-Tyrosine; 1250 µM ATP; 80 nM Substrate Peptide.

14.5 µl/well Enzyme Mix or Dilution Buffer (Background Controls) is added to Costar 384 well black plates.

Compound addition and mixture is performed by the following steps: (i) 0.5 µl/well DMSO/compounds in DMSO is transferred from Greiner 384-well polypropylene plate to a plate containing 14.5 µl/well Enzyme Mix and Dilution Buffer; (ii) mixed by pipetting 10 µl up and down 4×; (iii) tips are washed 4×10 µl in DMSO, 2×20 µl in other DMSO; (iv) steps i-iii are repeated until all plates are completed.

10 µl/well Substrate/Detection Mixtures is added and incubated at room temperature 2 hours (on shaker for first 2+ minutes).

10 µl/well 50 mM EDTA/0.01% Triton® X-100 is added and incubated >15 minutes at room temperature (on shaker for first 2+ minutes).

Plates are read at 665 nm and 620 nm emission on Analyst GT protocol HTRF_SP_A (Counts=665/620×10000).

5.2.6 Syk HTRF Assay Protocol

5 µl/well DMSO is added to Column 2 Wells A-O and 29.5 µl to well P2 of Greiner 384-well polypropylene plate. 20 µl/well DMSO is added to Columns 1 and 3-12.

25 mM compound solutions are prepared by the addition of 25 µl of 30 mM compound to Column 2 and 0.5 µl 30 mM reference control to well P2.

Serial dilution is then performed by the following steps: (i) compounds in Column 2 are mixed by pipetting 20 µl up and down 6×; (ii) 10 µl/well compounds in DMSO are transferred from one column to the next column for Columns 2-11; (iii) wells are mixed by pipetting 20 µl up and down 6×; (iv) tips washed 3×25 µl DMSO, 2×25 µl next DMSO.

The following buffers are prepared:
Dilution Buffer: 50 mM HEPES pH 7.6; 1 mM DTT; 10 mM MgCl$_2$; 0.01% Triton® X-100; 0.01% BSA; 0.1 mM EDTA.

Enzyme Mix in Dilution Buffer: 8.621 ng/ml Syk (Cama Biosciences 08-176).

Start Mix in Dilution Buffer: 87.5 µM ATP; 80 nM Substrate Peptide (American Peptide Company 332722).

14.5 µl/well Enzyme Mix or Dilution Buffer (Background Controls) is added to Costar 384-well black plates.

Compound addition and mixture is performed by the following steps: (i) 0.5 µl/well DMSO/compounds in DMSO transferred from Greiner 384-well polypropylene plate to left half of assay plate containing 14.5 µl/well Enzyme Mix and Dilution Buffer; (ii) Mix by pipetting 10 µl up and down 4×; (iii) tips are washed 4×10 µl in DMSO, 2×20 µl in other DMSO; (iv) steps i-iii are repeated with transfer to right half of assay plate; (v) steps i-iv are repeated with each compound/assay plate until all plates are completed.

10 µl/well Start Mix is added and incubated at room temperature on shaker for 2 minutes (1 hour total reaction time).

The following buffers are prepared:

Stop Solution in Dilution Buffer: 120 mM EDTA

Antibody Mix in Dilution Buffer: 4.86 µg/ml DyLight 647 Streptavidin (Pierce 21824); 1 µg/ml Lance Eu-Anti-Phosphotyrosine (PerkinElmer AD0069).

5 µl/well/in Dilution Buffer is added and incubated at room temperature on shaker for 2 minutes.

10 ml/well Antibody Mix is added and Incubated at room temperature on shaker for 2 minutes (4 hours to overnight total time).

Plates are read at 665 nm and 620 nm emission on Analyst GT protocol HTRF_SP_A or EnVision protocol Steve's TR-FRET.

5.2.7 Syk Functional Assay Protocol (CD69 Expression in Anti-IgM Stimulated Primary B-cells)

Cells: Primary B-cells are purified from Buffy coat cell preparations obtained from healthy human donors at San Diego Blood Bank (SDBB). Cells are maintained in RPIM/10% FBS.

Reagents: AffiniPure F(ab') fragment goat anti-human IgM (Jackson, cat. 109-006-129, 1.3 mg/ml); PE labeled anti-human CD69 (BD Pharmingen, cat. 555531, 2 mls); 7AAD (BD Pharmingen, cat. 559925, 2 mls); ROSETTESEP® B-cell enrichment Reagent (Stem Cell Technologies, cat. 15064, 10 mls); FICOLL-PAQUE™ Plus (Amersham, cat. 17-440-02); FBS Stain Buffer (BD Pharmingen).

Protocol: (i) Buffy coat cell preparation is ordered in advance from SDBB (two are typically ordered in case difficulty is encountered with one of them); (ii) B-cells are purified using the RosetteSep negative selection procedure, as follows:

a. 2.0 mL of RosetteSep reagent is added to 40 mL of buffy coat. Each buffy coat is typically 80-100 mL. The mixture is gently mixed and allowed to sit at room temperature for 20 minutes (some settling may occur).

b. In a tissue culture flask, 40 ml buffy coat is mixed with an equal volume of sterile filtered 2% FBS in PBS (no calcium/magnesium).

c. 35 mL of this diluted buffy coat is added to each of five 50 mL polypropylene conical tubes. 14 mL of Ficoll Paque is slowly added under buffy coat and bottom of each tube (being careful not to mix with buffy coat).

d. Tubes are spun at 2200 rpm for 20 minutes in Sorvall tabletop centrifuge with brake off.

e. After spin, cells should be visible at serum/Ficoll interface. The serum is gently aspirated off to a point near the interface. With a Pasteur pipette and pipetteman, cell layer is removed from the interface taking care to remove as little Ficoll as possible.

f. Recovered cells are diluted (approx. 10 mls) in 100 mL 2% FBS in PBS, spun at 1200 rpm from 5 minutes and the cell pellet is resuspended in 5-10 mL RPMI growth media, depending on anticipated cells recovery.

Cells are counted and cell density is adjusted to 1 mln/ml in RPMI growth media. Compound pretreatment plate in 96 well round-bottom format is prepared with enough cell volume to cover the desired number of wells, assuming 50 µl cells/well in the treatment plate. In a separate 96 well plate, compounds are diluted 1:50 into RPMI growth media. 22 µL of diluted compound is added to 200 µL cells in compound pretreatment plate. The mixture is placed in tissue culture incubator for 30-60 minutes.

20 µg/ml anti-IgM solution in RPMI growth media is prepared. 50 µL of anti-IgM solution per well is added into a new 96 well round bottom plate (cell stimulation plate). Controls spent culture media only are included. 50 µL of compound pretreated cells are added to the anti-IgM containing plate using a multichannel pipettor. The mixture is placed back in tissue culture incubator for 12-14 hours.

Plate is spun at 1200 rpm for 5 minutes. Media is dumped and the plate is gently blotted dry. Enough antibody solution to cover plate is prepared, assuming 100 µL Stain Buffer containing 5 µL of CD69 antibody/well. 100 µL of antibody solution per well is added, plate is gently tapped to mix, plate is covered with aluminum foil and placed in drawer at room temperature for 30 minutes.

Plate is spun, dumped and blotted. Plate is washed once with 250 µL Stain buffer, spun, dumped, and blotted. Final cell pellet is resuspended in 100 µL Stain buffer and read on cytometer.

5.2.8 Syk Functional Assay S.O.P. (IgE-dependent beta-hexosaminidase Secretion from the LAD2 Human Mast Cell Line)

Overview: LAD2 cells are plated into 96 well format, sensitized through FcepsilonR with NP-IgE, and degranulated by crosslinking with $NP_{16}$-BSA. The supernatants are collected and secretory granule components including beta-hexosaminidase measured in various colorimetric assays.

Cells: LAD2 cells are provided by Metcalf lab at NIH. For detailed description of the derivation, characteristics, and growth/storage of these cells refer to original publication (Kirshenbaum, et al., *Leukemia Research* 27:677-682, 2003). The cells grow quite slowly, doubling every 10-14 days, and so need to feed by hemidepletion every week and split infrequently. Growth media: StemPro®-34 plus serum supplement (Invitrogen) with 100 ng/ml recombinant human SCF (BioSource). The cells can be maintained in culture for approximately 15 passages before morphology and functionality changes.

Reagents: chimeric human nitrophenyl-IgE (Serotec, MCA333S, 20 ug/ml stock solution); $NP_{16}$-BSA (Biosearch Technologies, N5050-10 mg, 10 mg/ml stock solution); PNAG substrate (p-Nitrophenyl N-acetyl-β-D-Glucosaminide; Sigma N-9376) 0.004 M=1.37 mg/ml; prepare 1.37 mg/mL1 in citrate/phosphate buffer, 150 µL/sample (will take 30-60 min at 37° C. with frequent vortexing)); Citrate/Phosphate Buffer (0.04 M Anhydrous Citric acid (FW 192 g/mol); 2 mL of 1M Citric Acid (Hampton Research); 0.02 M $Na_2HPO_4$; 2 mL of 0.5 M $Na_2HPO_4$ (SIGMA), use 5N NaOH to pH to 4.6 (approx 1 mL) per 50 mls soln); Modified Tyrode's Buffer (Tyrode's Buffer Powder (SIGMA, T2145) one vial into 1 L distilled water; allow powder to dissolve and then add the following: 1 M HEPES buffer pH 7.8 to 20 mM final (1:50), 0.5M NA2HPO4 to 0.5 mM final (1:1000), 0.04% BSA (400 mg/L), pH should be 7.4); Glycine Stop Solution (0.32 M glycine, 2.4 g/100 ml; 0.2 M Sodium Carbonate (FW 106 g/mol), 2.5 g/100 ml).

Protocol: LAD2 is gently dislodged from culture flask, collected, and spun down at 1200 rpm for 5 minutes. Spent culture media is removed and saved. Cells are resuspended at 0.8-1 million/ml in spent culture media. 100 μL of 0.5 ug/ml NP-IgE is plated in spent culture media into a round bottom 96 well plate. Note: IgE solution needs to be clarified to remove aggregates by spinning at >10000 rpm for 10 minutes at 4° C. 100 μL cells is added to plate and placed back in tissue culture incubator for 12-14 hours to sensitize cells and load FcepsilonR receptors. Cold Modified Tyrode's Buffer is allowed to warm to room temp overnight.

The next morning, plate is spun at 1200 rpm for 5 minutes. Media is removed with multichannel pipettor. Cell pellets are resuspended in 100 ul Modified Tyrode's buffer with GENTLE trituration (5 strokes). Cells are allowed torest for 3.5 hours in tissue culture incubator. Note: During this time, it will be necessary to warm the Citrate/Phosphate buffer to 37° C. and then resuspend the PNAG substrate to 1.3 mg/ml with periodic vortexing. Compound series are diluted 1:50 in Modified Tyrode's buffer and then 11 μL of compound, without further mixing, is added to each well (giving a 0.2% dmso final concentration). Compound is pre-incubated for 30-60 minutes in tissue culture incubator.

12 μL of 1.0 μg/ml NP$_{16}$-BSA diluted in Modified Tyrode's is added. Total volume is now 123 μL. Ionomycin at 100 nM final can be added instead of NP-BSA as a Syk-independent control for stimulation. Incubated in tissue culture incubator for 90 minutes.

Plate is spun at 1200 rpm for 5 minutes, 75 μL of supernatant (SN) is transferred to empty 96 well plate for storage. Remaining SN is removed from cell plate and discarded. 125 μL 0.1% Triton® X-100 in Modified Tyrode's buffer is added to cell pellet, pipetted up/down to lyse cells and mixture is Incubated on ice for 15 min.

30 μL supernatant from storage plate or 5 μL cell pellet lysate plus 25 μL 0.1% Triton® solution is added to a new 96 well flat-bottom plates in identical layout for the final plate read. 150 μL PNAG substrate is added to all wells. Plate is incubated in 37° C. bacterial incubator for 1 hour.

50 μL stop solution is added to each well. Wells with most activity will be brightest yellow. The plate is read immediately at 405 nm.

% release per well is calculated (after subtracting background from all wells)=100×(SN/(SN+6×cell lysate)). Net % release=100×(SN stim−SN PBS)/(SN stim+cell lysate stim− SN PBS).]

Assay Quality Control criteria: 3 primary parameters of assay performance: 1) Percent release values should be between 10-20% in IgE- and DMSO-treated wells (40% release with 100 nM Ionomycin); 2) IC$_{50}$ values with Syk tool compounds should be in the range of 50-200 nM; 3) Z' for assay should be >0.55.

5.2.9 Syk Biomarker Assay Protocol (phosphoBLNK Measurement by PhosFlow in Anti-IgM Stimulated Ramos)

Cells: Ramos B-cell lymphoma (clone RA1, CRL1596™) from ATCC grow rapidly and need to be split 1:20 every 3-4 days for maintenance. The cells grow in RPMI/10% FBS.

Reagents: AffiniPure F(ab') fragment goat anti-human IgM (Jackson, cat. 109-006-129, 1.3 mg/ml); PE mouse anti-phos-phoBLNK (pY84, BD Pharmingen, cat. 558442); CytoFix® Reagent (BD Pharmingen, cat. 554655); Perm/Wash Buffer I (BD Pharmingen, cat. 557885, 10× solution); BSA Stain Buffer (BD Pharmingen, cat 554657).

Protocol: Ramos cells are split 1:1 with fresh growth media the day before experiment. On the day of the experiment, cells are spun down at 1200 rpm for 5 minutes. All spent culture media is saved. Cells are resuspended at 1 mln/ml in spent culture media. Compound pretreatment plate is prepared in 96 well round-bottom format with enough cell volume to cover the desired number of wells, assuming 50 L cells/ well in the treatment plate, e.g. for 4 wells 200 μL cells is added. In a separate 96 well plate, compounds are diluted 1:50 into spent culture media. 22 μL of diluted compound is added to 200 L cells in compound pretreatment plate. Plated is placed back in tissue culture incubator for 30-60 minutes. CytoFix® reagent is pre-warmed in 37° C. waterbath prior to stimulating cells.

40 μg/ml anti-IgM solution in spent culture media is prepared. 50 μL of anti-IgM solution per well is added into a new 96 well round bottom plate (cell stimulation plate). Controls of spent culture media only are included. Using a multichannel pipettor, 50 μL of compound pretreated cells are quickly added to the anti-IgM containing plate, and the plate is placed back in tissue culture incubator for 10 minutes.

An equal volume (100 μL) of prewarmed CytoFix® reagent is added to all wells of cell stimulation plate. Plate is placed back into tissue culture incubator for 10 minutes, spun at 1200 rpm for 5 minutes, and media is gently dumped out and the plate is blotted dry.

100 μL of Perm/Wash Buffer I is added to all wells. Plate is left at room temperature for 10 minutes, spun at 1200 rpm for 5 minutes, and media is gently dumped out and plate is blotted dry. Cells are washed three times with 200 μL BSA Stain Buffer. Plate is spun plate, dumped, and blotted.

Enough antibody solution to cover plate is prepared, assuming 100 μL Stain Buffer containing 5 μL of pBLNK antibody/well. 100 μL of antibody solution per well is added, plate is gently tapped to mix, and covered with aluminum foil and placed in drawer at room temperature for 30 minutes.

Plate is spun plate, dumped, and blotted. Plate is washed once with 200 μL Stain buffer. Plate is spun plate, dumped, and blotted. Final cell pellet is resuspended in 100 μL Stain buffer and read on cytometer.

Compounds of Table 1 were found to have the following values in the mTOR and IKK-2 screening assays.

| Compound | mTOR IC$_{50}$ (μM) | IKK-2 IC$_{50}$ (μM) | Tyk2 IC$_{50}$ (μM) | Syk IC$_{50}$ (μM) |
|---|---|---|---|---|
| 1 | *** | * | ND | ND |
| 2 | * | * | ND | ND |
| 3 | ND | ** | ND | ND |
| 4 | * | * | ND | ND |
| 5 | * | * | ND | ND |
| 6 | * | * | ND | ND |
| 7 | ND | * | ND | ND |
| 8 | **** | * | ND | * |
| 9 | **** | * | ND | ND |
| 10 | **** | * | ND | ND |
| 11 | *** | * | ND | ND |
| 12 | ***** | ** | ND | ND |
| 13 | * | * | ND | * |
| 14 | ***** | * | ND | ND |
| 15 | ***** | * | ND | ND |
| 16 | ***** | ND | ND | ND |
| 17 | ***** | ND | ND | ND |
| 18 | * | ND | ND | ND |
| 19 | * | ND | ND | ND |
| 20 | * | ND | ND | ND |
| 21 | *** | ND | ND | ND |
| 22 | * | ND | ND | ND |
| 23 | * | ND | ND | ND |

| Compound | mTOR IC₅₀ (μM) | IKK-2 IC₅₀ (μM) | Tyk2 IC₅₀ (μM) | Syk IC₅₀ (μM) |
|---|---|---|---|---|
| 24 | **** | ND | ND | ND |
| 25 | **** | ND | ND | ND |
| 26 | * | ND | ND | ND |
| 27 | *** | * | ND | ND |
| 28 | * | ND | ND | ND |
| 29 | * | ND | ND | ND |
| 30 | **** | ND | ND | ND |
| 31 | * | ND | ND | ND |
| 32 | ***** | *** | ND | ND |
| 33 | ***** | * | ND | ND |
| 34 | * | ND | ND | ND |
| 35 | ** | **** | ND | ND |
| 36 | * | * | ND | ND |
| 37 | *** | * | ND | ND |
| 38 | ND | ND | ND | * |
| 39 | *** | ND | ND | ND |
| 42 | * | ND | * | ND |
| 47 | ***** | ND | *** | ND |
| 50 | ***** | ***** | ** | ND |
| 54 | ***** | ND | ND | ***** |
| 69 | ***** | ND | ***** | ND |
| 77 | ***** | ND | ***** | ND |
| 99 | * | ND | ***** | ND |
| 101 | ***** | ND | ND | *** |

In the table set forth above, the following system is used: ***=0.1-5 μM, =5.1-10 μM, *=10.1-20 μM, **=20.1-30 μM, *=>30 μM. "ND" means that the compound was not tested against that particular enzyme.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A method of inhibiting mTOR in a cell expressing mTOR, comprising contacting said cell in vivo with an effective amount of a compound, wherein the compound is:
   9-benzyl-8-oxo-2-(pyridin-3-yl)-8,9-dihydro-7H-purine-6-carboxamide;
   2-(4-hydroxyphenyl)-9-(2-methoxyphenyl)-8-oxo-8,9-dihydro-7H-purine-6-carboxamide;
   2-(3-hydroxyphenyl)-8-oxo-9-o-tolyl-8,9-dihydro-7H-purine-6-carboxamide;
   2-(1H-indol-4-yl)-9-(2-methoxyphenyl)-8-oxo-8,9-dihydro-7H-purine-6-carboxamide;
   2-(1H-indol-6-yl)-9-(2-methoxyphenyl)-8-oxo-8,9-dihydro-7H-purine-6-carboxamide;
   2-(3-hydroxyphenyl)-9-(4-methoxyphenyl)-8-oxo-8,9-dihydro-7H-purine-6-carboxamide;
   9-(2-chlorophenyl)-2-(3-hydroxyphenyl)-8-oxo-8,9-dihydro-7H-purine-6-carboxamide;
   9-(2-fluorophenyl)-2-(3-hydroxyphenyl)-8-oxo-8,9-dihydro-7H-purine-6-carboxamide;
   9-(2,6-difluorophenyl)-2-(3-hydroxyphenyl)-8-oxo-8,9-dihydro-7H-purine-6-carboxamide;
   9-cycloheptyl-8-oxo-2-(pyridin-3-yl)-8,9-dihydro-7H-purine-6-carboxamide;
   9-(2-methoxyphenyl)-2-(6-methoxypyridin-3-yl)-8-oxo-8,9-dihydro-7H-purine-6-carboxamide;
   2-(3-hydroxyphenyl)-8-oxo-9-(2-(trifluoromethoxy)phenyl)-8,9-dihydro-7H-purine-6-carboxamide;
   9-(2,4-dichlorophenyl)-2-(3-hydroxyphenyl)-8-oxo-8,9-dihydro-7H-purine-6-carboxamide;
   2-(3-cyanophenyl)-8-oxo-9-phenyl-8,9-dihydro-7H-purine-6-carboxamide;
   2-(5-fluoropyridin-3-yl)-9-(2-methoxyphenyl)-8-oxo-8,9-dihydro-7H-purine-6-carboxamide;
   benzyl 4-(6-carbamoyl-8-oxo-2-(pyridin-3-yl)-7H-purin-9(8H)-yl)piperidine-1-carboxylate;
   9-cyclohexyl-2-(3-hydroxyphenyl)-8-oxo-8,9-dihydro-7H-purine-6-carboxamide;
   9-phenyl-2-(pyridin-3-yl)-9H-purine-6-carboxamide;
   6-oxo-8-phenyl-2-(pyridin-4-yl)-5,6,7,8-tetrahydropteridine-4-carboxamide;
   2-(3-hydroxyphenyl)-9-(2-methoxyphenyl)-9H-purine-6-carboxamide;
   9-(trans-4-Hydroxycyclohexyl)-2-(3-hydroxyphenyl)-8-oxo-8,9-dihydro-7H-purine-6-carboxamide;
   9-(trans-4-Hydroxycyclohexyl)-8-oxo-2-(pyridin-3-yl)-8,9-dihydro-7H-purine-6-carboxamide;
   2-(2-Chloro-3-hydroxyphenyl)-9-(2-methoxyphenyl)-8-oxo-7-hydropurine-6-carbox amide;
   9-(2,6-Dichlorophenyl)-2-(3-hydroxyphenyl)-8-oxo-7-hydropurine-6-carboxamide;
   2-(2-Fluoro-3-hydroxyphenyl)-9-(2-methoxyphenyl)-8-oxo-7-hydropurine-6-carbox-amide;
   2-(1H-benzo[d]imidazol-6-yl)-9-(2-fluorophenyl)-8-oxo-8,9-dihydro-7H-purine-6-carboxamide;
   or a pharmaceutically acceptable salt thereof.

2. A method of inhibiting IKK-2 in a cell expressing IKK-2, comprising contacting said cell in vivo with an effective amount of a compound, wherein the compound is:
   8-oxo-9-phenyl-2-(pyridin-2-yl)-8,9-dihydro-7H-purine-6-carboxamide;
   2-(3-hydroxyphenyl)-9-(4-methoxyphenyl)-8-oxo-8,9-dihydro-7H-purine-6-carboxamide;
   benzyl 4-(6-carbamoyl-8-oxo-2-(pyridin-3-yl)-7H-purin-9(8H)-yl)piperidine-1-carboxylate;
   9-phenyl-2-(pyridin-3-yl)-9H-purine-6-carboxamide;
   9-(trans-4-hydroxycyclohexyl)-8-oxo-2-(pyridin-3-yl)-8,9-dihydro-7H-purine-6-carboxamide;
   or a pharmaceutically acceptable salt thereof.

3. A method of inhibiting Tyk2 in a cell expressing Tyk2, comprising contacting said cell in vivo with an effective amount of a compound, wherein the compound is:
   9-(trans-4-Hydroxycyclohexyl)-2-(3-hydroxyphenyl)-8-oxo-8,9-dihydro-7H-purine-6-carboxamide;
   9-(trans-4-Hydroxycyclohexyl)-8-oxo-2-(pyridin-3-yl)-8,9-dihydro-7H-purine-6-carboxamide;
   9-(2,6-Dichlorophenyl)-2-(3-hydroxyphenyl)-8-oxo-7-hydropurine-6-carboxamide;
   2-(2-Fluoro-3-hydroxyphenyl)-9-(2-methoxyphenyl)-8-oxo-7-hydropurine-6-carbox-amide;
   2-(1H-benzo[d]imidazol-4-yl)-9-(2-methoxyphenyl)-8-oxo-8,9-dihydro-7H-purine-6-carboxamide;
   or a pharmaceutically acceptable salt thereof.

4. A method of inhibiting Syk in a cell expressing Syk, comprising contacting said cell in vivo with an effective amount of a compound, wherein the compound is:
   2-(2-Chloro-3-hydroxyphenyl)-9-(2-methoxyphenyl)-8-oxo-7-hydropurine-6-carbox amide;
   2-(1H-benzo[d]imidazol-6-yl)-9-(2-fluorophenyl)-8-oxo-8,9-dihydro-7H-purine-6-carboxamide;
   or a pharmaceutically acceptable salt thereof.

* * * * *